US012128227B2

(12) United States Patent
Tuval et al.

(10) Patent No.: US 12,128,227 B2
(45) Date of Patent: Oct. 29, 2024

(54) MANUFACTURE OF AN IMPELLER

(71) Applicant: MAGENTA MEDICAL LTD., Kadima (IL)

(72) Inventors: Yosi Tuval, Even Yehuda (IL); Yinnon Elisha, Kffar Hess (IL); David Israeli, Tel Aviv (IL); Gad Lubinsky, Ein Vered (IL); Victor Troshin, Hodhasharon (IL); Shaul Mustacchi, Raanana (IL); Yuval Zipory, Modiin (IL); Avi Rozenfeld, Haifa (IL); Aurelie Benaddi, Netanya (IL); Gilad Moiseyev, Givataim (IL); Yuri Sudin, Modi'in-Makkabbim-Re'ut (IL)

(73) Assignee: MAGENTA MEDICAL LTD., Kadima (IL)

( * ) Notice: Subject to any disclaimer, the term of this patent is extended or adjusted under 35 U.S.C. 154(b) by 333 days.

(21) Appl. No.: 17/528,807

(22) Filed: Nov. 17, 2021

(65) Prior Publication Data

US 2022/0072297 A1    Mar. 10, 2022

Related U.S. Application Data

(63) Continuation of application No. 17/609,589, filed as application No. PCT/IB2021/052857 on Apr. 6, 2021.
(Continued)

(51) Int. Cl.
*A61M 60/237*  (2021.01)
*A61B 5/021*   (2006.01)
(Continued)

(52) U.S. Cl.
CPC ....... *A61M 60/237* (2021.01); *A61B 5/02141* (2013.01); *A61B 5/0215* (2013.01);
(Continued)

(58) Field of Classification Search
None
See application file for complete search history.

(56) References Cited

U.S. PATENT DOCUMENTS

| 3,592,183 A | 7/1971 | Watkins et al. |
| 3,932,068 A | 1/1976 | Zimmermann |

(Continued)

FOREIGN PATENT DOCUMENTS

| AU | 2013205145 A1 | 5/2013 |
| CA | 2701809 A1 | 4/2009 |

(Continued)

OTHER PUBLICATIONS

Corrected Notice of Allowability for U.S. Appl. No. 16/810,121 mailed Sep. 20, 2022.
(Continued)

*Primary Examiner* — Jacob T Minskey
*Assistant Examiner* — Adrianna N Konves
(74) *Attorney, Agent, or Firm* — Dorsey & Whitney LLP

(57) ABSTRACT

Apparatus and methods are described including manufacturing an impeller by forming a structure having first and second bushings at proximal and distal ends of the structure, the first and second bushings being connected to one another by at least one elongate element. The elongate element is caused to radially expand and form at least one helical elongate element, at least partially by axially compressing the structure. The helical elongate element is coated with a coupling agent configured to enhance bonding between the helical elongate element and an elastomeric layer. The coated helical elongate element is coated with the elastomeric layer. Subsequently, an elastomeric film is coupled to the helical elongate element, such that the helical elongate element with the elastomeric film coupled thereto defines a blade of the impeller. Other applications are also described.

13 Claims, 58 Drawing Sheets

Related U.S. Application Data

(60) Provisional application No. 63/129,983, filed on Dec. 23, 2020, provisional application No. 63/114,136, filed on Nov. 16, 2020, provisional application No. 63/006,122, filed on Apr. 7, 2020.

(51) Int. Cl.
| | |
|---|---|
| *A61B 5/0215* | (2006.01) |
| *A61M 60/13* | (2021.01) |
| *A61M 60/135* | (2021.01) |
| *A61M 60/174* | (2021.01) |
| *A61M 60/178* | (2021.01) |
| *A61M 60/216* | (2021.01) |
| *A61M 60/226* | (2021.01) |
| *A61M 60/414* | (2021.01) |
| *A61M 60/419* | (2021.01) |
| *A61M 60/422* | (2021.01) |
| *A61M 60/523* | (2021.01) |
| *A61M 60/531* | (2021.01) |
| *A61M 60/538* | (2021.01) |
| *A61M 60/546* | (2021.01) |
| *A61M 60/808* | (2021.01) |
| *A61M 60/816* | (2021.01) |
| *A61M 60/818* | (2021.01) |
| *A61M 60/825* | (2021.01) |
| *A61M 60/857* | (2021.01) |
| *A61M 60/865* | (2021.01) |
| *A61M 60/804* | (2021.01) |
| *A61M 60/829* | (2021.01) |

(52) U.S. Cl.
CPC .......... *A61M 60/13* (2021.01); *A61M 60/135* (2021.01); *A61M 60/174* (2021.01); *A61M 60/178* (2021.01); *A61M 60/216* (2021.01); *A61M 60/226* (2021.01); *A61M 60/414* (2021.01); *A61M 60/419* (2021.01); *A61M 60/422* (2021.01); *A61M 60/523* (2021.01); *A61M 60/531* (2021.01); *A61M 60/538* (2021.01); *A61M 60/546* (2021.01); *A61M 60/808* (2021.01); *A61M 60/816* (2021.01); *A61M 60/818* (2021.01); *A61M 60/825* (2021.01); *A61M 60/857* (2021.01); *A61M 60/865* (2021.01); *A61B 2562/0223* (2013.01); *A61M 60/804* (2021.01); *A61M 60/829* (2021.01); *A61M 2205/3327* (2013.01); *A61M 2207/00* (2013.01)

(56) References Cited

U.S. PATENT DOCUMENTS

| | | |
|---|---|---|
| 4,625,712 A | 12/1986 | Wampler |
| 4,753,221 A | 6/1988 | Kensey et al. |
| 4,919,647 A | 4/1990 | Nash |
| 4,944,722 A | 7/1990 | Carriker et al. |
| 4,954,055 A | 9/1990 | Raible et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 5,011,469 A | 4/1991 | Buckberg et al. |
| 5,037,403 A | 8/1991 | Garcia |
| 5,061,256 A | 10/1991 | Wampler |
| 5,169,378 A | 12/1992 | Figuera |
| 5,275,580 A | 1/1994 | Yamazaki |
| 5,330,484 A | 7/1994 | Guenther et al. |
| 5,348,545 A | 9/1994 | Shani et al. |
| 5,507,629 A | 4/1996 | Jarvik |
| 5,531,789 A | 7/1996 | Yamazaki et al. |
| 5,569,275 A | 10/1996 | Kotula et al. |
| 5,613,935 A | 3/1997 | Jarvik |
| 5,692,882 A | 12/1997 | Bozeman et al. |
| 5,713,730 A | 2/1998 | Nose et al. |
| 5,749,855 A | 5/1998 | Reitan |
| 5,772,693 A | 6/1998 | Brownlee |
| 5,843,158 A | 12/1998 | Lenker et al. |
| 5,863,179 A | 1/1999 | Westphal et al. |
| 5,876,385 A | 3/1999 | Ikari et al. |
| 5,879,499 A | 3/1999 | Corvi |
| 5,911,685 A | 6/1999 | Siess et al. |
| 5,928,132 A | 7/1999 | Leschinsky |
| 5,947,892 A | 9/1999 | Benkowski et al. |
| 5,964,694 A | 10/1999 | Siess et al. |
| 6,007,478 A | 12/1999 | Siess et al. |
| 6,086,527 A | 7/2000 | Talpade |
| 6,116,862 A | 9/2000 | Rau et al. |
| 6,135,729 A | 10/2000 | Aber |
| 6,136,025 A | 10/2000 | Barbut et al. |
| 6,162,017 A | 12/2000 | Raible |
| 6,176,848 B1 | 1/2001 | Rau et al. |
| 6,183,220 B1 | 2/2001 | Ohara et al. |
| 6,217,541 B1 | 4/2001 | Yu |
| 6,247,892 B1 | 6/2001 | Kazatchkov et al. |
| 6,355,001 B1 | 3/2002 | Quinn et al. |
| 6,413,222 B1 | 7/2002 | Pantages et al. |
| 6,482,228 B1 | 11/2002 | Norred |
| 6,506,146 B1 | 1/2003 | Mohl |
| 6,533,716 B1 | 3/2003 | Schmutz-Rode et al. |
| 6,537,315 B2 | 3/2003 | Yamazaki et al. |
| 6,544,216 B1 | 4/2003 | Sammler et al. |
| 6,592,567 B1 | 7/2003 | Levin et al. |
| 6,616,624 B1 | 9/2003 | Kieval |
| 6,884,210 B2 | 4/2005 | Nose et al. |
| 6,949,066 B2 | 9/2005 | Bearnson et al. |
| 6,974,436 B1 | 12/2005 | Aboul-Hosn et al. |
| 7,004,925 B2 | 2/2006 | Navia et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,070,555 B2 | 7/2006 | Siess |
| 7,144,364 B2 | 12/2006 | Barbut et al. |
| 7,159,593 B2 | 1/2007 | McCarthy et al. |
| 7,201,772 B2 | 4/2007 | Schwammenthal et al. |
| 7,258,679 B2 | 8/2007 | Moore et al. |
| 7,335,192 B2 | 2/2008 | Keren et al. |
| 7,338,521 B2 | 3/2008 | Antaki et al. |
| 7,341,570 B2 | 3/2008 | Keren et al. |
| 7,393,181 B2 | 7/2008 | Mcbride et al. |
| 7,485,104 B2 | 2/2009 | Kieval |
| 7,717,952 B2 | 5/2010 | Case et al. |
| 7,744,642 B2 | 6/2010 | Rittgers et al. |
| 7,762,941 B2 | 7/2010 | Jarvik |
| 7,766,853 B2 | 8/2010 | Lane |
| 7,766,892 B2 | 8/2010 | Keren et al. |
| 7,766,961 B2 | 8/2010 | Patel et al. |
| 7,780,628 B1 | 8/2010 | Keren et al. |
| 7,811,221 B2 | 10/2010 | Gross |
| 7,841,976 B2 | 11/2010 | Mcbride et al. |
| 7,878,967 B1 | 2/2011 | Khanal |
| 7,914,436 B1 | 3/2011 | Kung |
| 7,914,503 B2 | 3/2011 | Goodson et al. |
| 7,927,068 B2 | 4/2011 | Mcbride et al. |
| 8,012,121 B2 | 9/2011 | Goodson et al. |
| 8,079,948 B2 | 12/2011 | Shifflette |
| 8,118,723 B2 | 2/2012 | Richardson et al. |
| 8,123,669 B2 | 2/2012 | Siess et al. |
| 8,157,758 B2 | 4/2012 | Pecor et al. |
| 8,192,451 B2 | 6/2012 | Cambronne et al. |
| 8,216,122 B2 | 7/2012 | Kung |
| 8,221,492 B2 | 7/2012 | Case et al. |
| 8,235,933 B2 | 8/2012 | Keren et al. |
| 8,277,470 B2 | 10/2012 | Demarais et al. |
| 8,376,707 B2 | 2/2013 | Mcbride et al. |
| 8,439,859 B2 | 5/2013 | Pfeffer et al. |
| 8,449,443 B2 | 5/2013 | Rodefeld et al. |
| 8,485,961 B2 | 7/2013 | Campbell et al. |
| 8,489,190 B2 | 7/2013 | Pfeffer et al. |
| 8,512,262 B2 | 8/2013 | Gertner |

(56) References Cited

U.S. PATENT DOCUMENTS

| | | |
|---|---|---|
| 8,535,211 B2 | 9/2013 | Walters et al. |
| 8,538,535 B2 | 9/2013 | Ariav et al. |
| 8,579,858 B2 | 11/2013 | Reitan et al. |
| 8,591,393 B2 | 11/2013 | Walters et al. |
| 8,591,539 B2 | 11/2013 | Gellman |
| 8,597,170 B2 | 12/2013 | Walters et al. |
| 8,617,239 B2 | 12/2013 | Reitan |
| 8,672,868 B2 | 3/2014 | Simons |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,734,508 B2 | 5/2014 | Hastings et al. |
| 8,777,832 B1 | 7/2014 | Wang et al. |
| 8,814,543 B2 | 8/2014 | Liebing |
| 8,814,776 B2 | 8/2014 | Hastie et al. |
| 8,814,933 B2 | 8/2014 | Siess |
| 8,827,887 B2 | 9/2014 | Curtis et al. |
| 8,849,398 B2 | 9/2014 | Evans |
| 8,864,642 B2 | 10/2014 | Scheckel |
| 8,888,728 B2 | 11/2014 | Aboul-Hosn et al. |
| 8,900,060 B2 | 12/2014 | Liebing |
| 8,926,492 B2 | 1/2015 | Scheckel |
| 8,932,141 B2 | 1/2015 | Liebing |
| 8,944,748 B2 | 2/2015 | Liebing |
| 8,979,493 B2 | 3/2015 | Roehn |
| 8,992,163 B2 | 3/2015 | Mcbride et al. |
| 8,998,792 B2 | 4/2015 | Scheckel |
| 9,028,216 B2 | 5/2015 | Schumacher et al. |
| 9,067,006 B2 | 6/2015 | Toellner |
| 9,072,825 B2 | 7/2015 | Pfeffer et al. |
| 9,089,634 B2 | 7/2015 | Schumacher et al. |
| 9,138,518 B2 | 9/2015 | Campbell et al. |
| 9,162,017 B2 | 10/2015 | Evans et al. |
| 9,162,019 B2 | 10/2015 | Horvath et al. |
| 9,217,442 B2 | 12/2015 | Wiessler et al. |
| 9,259,521 B2 | 2/2016 | Simons |
| 9,278,189 B2 | 3/2016 | Corbett |
| 9,314,558 B2 | 4/2016 | Er |
| 9,327,067 B2 | 5/2016 | Zeng et al. |
| 9,328,741 B2 | 5/2016 | Liebing |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,592 B2 | 6/2016 | Mcbride et al. |
| 9,364,593 B2 | 6/2016 | Mcbride et al. |
| 9,370,613 B2 | 6/2016 | Hsu et al. |
| 9,381,288 B2 | 7/2016 | Schenck et al. |
| 9,393,384 B1 | 7/2016 | Kapur et al. |
| 9,402,942 B2 | 8/2016 | Hastie et al. |
| 9,404,505 B2 | 8/2016 | Scheckel |
| 9,416,783 B2 | 8/2016 | Schumacher et al. |
| 9,416,791 B2 | 8/2016 | Toellner |
| 9,421,311 B2 | 8/2016 | Tanner et al. |
| 9,446,179 B2 | 9/2016 | Keenan et al. |
| 9,474,840 B2 | 10/2016 | Siess |
| 9,512,839 B2 | 12/2016 | Liebing |
| 9,533,082 B2 | 1/2017 | Reichenbach et al. |
| 9,533,084 B2 | 1/2017 | Siess et al. |
| 9,545,468 B2 | 1/2017 | Aboul-Hosn et al. |
| 9,550,017 B2 | 1/2017 | Spanier et al. |
| 9,561,314 B2 | 2/2017 | Aboul-Hosn et al. |
| 9,572,915 B2 | 2/2017 | Heuring et al. |
| 9,597,205 B2 | 3/2017 | Tuval |
| 9,597,437 B2 | 3/2017 | Aboul-Hosn et al. |
| 9,603,983 B2 | 3/2017 | Roehn et al. |
| 9,611,743 B2 | 4/2017 | Toellner et al. |
| 9,616,159 B2 | 4/2017 | Anderson et al. |
| 9,623,161 B2 | 4/2017 | Medvedev et al. |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,675,740 B2 | 6/2017 | Zeng et al. |
| 9,713,663 B2 | 7/2017 | Medvedev et al. |
| 9,717,833 B2 | 8/2017 | Mcbride et al. |
| 9,750,860 B2 | 9/2017 | Schumacher |
| 9,750,861 B2 | 9/2017 | Hastie et al. |
| 9,759,237 B2 | 9/2017 | Liebing |
| 9,764,113 B2 | 9/2017 | Tuval et al. |
| 9,771,801 B2 | 9/2017 | Schumacher et al. |
| 9,789,238 B2 | 10/2017 | Aboul-Hosn et al. |
| 9,795,727 B2 | 10/2017 | Schumacher |
| 9,814,814 B2 | 11/2017 | Corbett et al. |
| 9,821,146 B2 | 11/2017 | Tao et al. |
| 9,827,356 B2 | 11/2017 | Muller et al. |
| 9,833,550 B2 | 12/2017 | Siess |
| 9,835,550 B2 | 12/2017 | Kakuno et al. |
| 9,850,906 B2 | 12/2017 | Ozaki et al. |
| 9,872,947 B2 | 1/2018 | Keenan et al. |
| 9,872,948 B2 | 1/2018 | Siess |
| 9,878,079 B2 | 1/2018 | Pfeffer et al. |
| 9,889,242 B2 | 2/2018 | Pfeffer et al. |
| 9,895,475 B2 | 2/2018 | Toellner et al. |
| 9,903,384 B2 | 2/2018 | Roehn |
| 9,907,890 B2 | 3/2018 | Muller |
| 9,907,891 B2 | 3/2018 | Wiessler et al. |
| 9,919,087 B2 | 3/2018 | Pfeffer et al. |
| 9,962,475 B2 | 5/2018 | Campbell et al. |
| 9,964,115 B2 | 5/2018 | Scheckel |
| 9,974,893 B2 | 5/2018 | Toellner |
| 9,999,714 B2 | 6/2018 | Spanier et al. |
| 10,029,037 B2 | 7/2018 | Muller et al. |
| 10,029,040 B2 | 7/2018 | Taskin |
| 10,039,872 B2 | 8/2018 | Zeng et al. |
| 10,039,874 B2 | 8/2018 | Schwammenthal et al. |
| 10,052,419 B2 | 8/2018 | Er |
| 10,052,420 B2 | 8/2018 | Medvedev et al. |
| 10,071,192 B2 | 9/2018 | Zeng |
| 10,086,121 B2 | 10/2018 | Fitzgerald et al. |
| 10,105,475 B2 | 10/2018 | Muller |
| 10,107,299 B2 | 10/2018 | Scheckel |
| 10,117,980 B2 | 11/2018 | Keenan et al. |
| 10,119,550 B2 | 11/2018 | Bredenbreuker et al. |
| 10,149,932 B2 | 12/2018 | Mcbride et al. |
| 10,172,985 B2 | 1/2019 | Simon et al. |
| 10,179,197 B2 | 1/2019 | Kaiser et al. |
| 10,183,104 B2 | 1/2019 | Anderson et al. |
| 10,196,899 B2 | 2/2019 | Toellner et al. |
| 10,207,037 B2 | 2/2019 | Corbett et al. |
| 10,208,763 B2 | 2/2019 | Schumacher et al. |
| 10,215,187 B2 | 2/2019 | Mcbride et al. |
| 10,221,866 B2 | 3/2019 | Liebing |
| 10,231,838 B2 | 3/2019 | Chin et al. |
| 10,238,783 B2 | 3/2019 | Aboul-Hosn et al. |
| 10,245,363 B1 | 4/2019 | Rowe |
| 10,265,447 B2 | 4/2019 | Campbell et al. |
| 10,265,448 B2 | 4/2019 | Liebing |
| 10,279,095 B2 | 5/2019 | Aboul-Hosn et al. |
| 10,300,185 B2 | 5/2019 | Aboul-Hosn et al. |
| 10,300,186 B2 | 5/2019 | Aboul-Hosn et al. |
| 10,316,853 B2 | 6/2019 | Toellner |
| 10,330,101 B2 | 6/2019 | Toellner |
| 10,342,904 B2 | 7/2019 | Schumacher |
| 10,342,906 B2 | 7/2019 | D'Ambrosio et al. |
| 10,363,349 B2 | 7/2019 | Muller et al. |
| 10,369,260 B2 | 8/2019 | Smith et al. |
| 10,376,162 B2 | 8/2019 | Edelman et al. |
| 10,413,646 B2 | 9/2019 | Wiessler et al. |
| 10,449,276 B2 | 10/2019 | Pfeffer et al. |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,540 B2 | 11/2019 | Scheckel et al. |
| 10,495,101 B2 | 12/2019 | Scheckel |
| 10,557,475 B2 | 2/2020 | Roehn |
| 10,583,231 B2 | 3/2020 | Schwammenthal et al. |
| 10,584,589 B2 | 3/2020 | Schumacher et al. |
| 10,589,012 B2 | 3/2020 | Toellner et al. |
| 10,617,808 B2 | 4/2020 | Hastie et al. |
| 10,662,967 B2 | 5/2020 | Scheckel |
| 10,669,855 B2 | 6/2020 | Toellner et al. |

(56) References Cited

U.S. PATENT DOCUMENTS

| | | |
|---|---|---|
| 10,765,789 B2 | 9/2020 | Zeng et al. |
| 10,792,406 B2 | 10/2020 | Roehn et al. |
| 10,799,624 B2 | 10/2020 | Pfeffer et al. |
| 10,799,626 B2 | 10/2020 | Siess et al. |
| 10,801,511 B2 | 10/2020 | Siess et al. |
| 10,806,838 B2 | 10/2020 | Er |
| 10,835,653 B2 | 11/2020 | Liebing |
| 10,857,272 B2 | 12/2020 | Liebing |
| 10,864,309 B2 | 12/2020 | Mcbride et al. |
| 10,865,801 B2 | 12/2020 | Mcbride et al. |
| 10,874,783 B2 | 12/2020 | Pfeffer et al. |
| 10,881,770 B2 | 1/2021 | Tuval et al. |
| 10,881,845 B2 | 1/2021 | Siess et al. |
| 10,894,115 B2 | 1/2021 | Pfeffer et al. |
| 10,898,629 B2 | 1/2021 | Siess et al. |
| 10,907,646 B2 | 2/2021 | Bredenbreuker et al. |
| 10,920,596 B2 | 2/2021 | Toellner et al. |
| 10,926,013 B2 | 2/2021 | Schumacher et al. |
| 10,935,038 B2 | 3/2021 | Siess |
| 10,980,927 B2 | 4/2021 | Pfeffer et al. |
| 10,994,120 B2 | 5/2021 | Tuval et al. |
| 11,007,350 B2 | 5/2021 | Tao et al. |
| 11,020,584 B2 | 6/2021 | Siess et al. |
| 11,027,114 B2 | 6/2021 | D'Ambrosio et al. |
| 11,033,729 B2 | 6/2021 | Scheckel et al. |
| 11,040,187 B2 | 6/2021 | Wiessler et al. |
| RE48,649 E | 7/2021 | Siess |
| 11,077,294 B2 | 8/2021 | Keenan et al. |
| 11,116,960 B2 | 9/2021 | Simon et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,168,705 B2 | 11/2021 | Liebing |
| 11,185,680 B2 | 11/2021 | Tuval et al. |
| 11,191,944 B2 | 12/2021 | Tuval et al. |
| 11,197,690 B2 | 12/2021 | Fantuzzi et al. |
| 11,219,755 B2 | 1/2022 | Siess et al. |
| 11,229,786 B2 | 1/2022 | Zeng et al. |
| 11,253,692 B2 | 2/2022 | Schumacher |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,266,824 B2 | 3/2022 | Er |
| 11,268,521 B2 | 3/2022 | Toellner |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,291,825 B2 | 4/2022 | Tuval et al. |
| 11,298,525 B2 | 4/2022 | Jahangir |
| 11,305,105 B2 | 4/2022 | Corbett et al. |
| 11,313,228 B2 | 4/2022 | Schumacher et al. |
| 11,338,124 B2 | 5/2022 | Pfeffer et al. |
| 11,351,358 B2 | 6/2022 | Nix et al. |
| 11,364,373 B2 | 6/2022 | Corbett et al. |
| 11,421,701 B2 | 8/2022 | Schumacher et al. |
| 11,434,922 B2 | 9/2022 | Roehn |
| 11,708,833 B2 | 7/2023 | Mcbride et al. |
| 11,833,278 B2 | 12/2023 | Siess et al. |
| 2001/0031210 A1 | 10/2001 | Antaki et al. |
| 2001/0031981 A1 | 10/2001 | Evans et al. |
| 2001/0041934 A1 | 11/2001 | Yamazaki et al. |
| 2002/0107536 A1 | 8/2002 | Hussein |
| 2002/0151799 A1 | 10/2002 | Pantages et al. |
| 2003/0055486 A1 | 3/2003 | Adams et al. |
| 2003/0088310 A1 | 5/2003 | Hansen et al. |
| 2003/0100816 A1 | 5/2003 | Siess |
| 2003/0135086 A1 | 7/2003 | Khaw et al. |
| 2003/0149473 A1 | 8/2003 | Chouinard et al. |
| 2003/0208097 A1 | 11/2003 | Aboul-Hosn et al. |
| 2004/0064090 A1 | 4/2004 | Keren et al. |
| 2004/0064091 A1 | 4/2004 | Keren et al. |
| 2004/0111006 A1 | 6/2004 | Alferness et al. |
| 2004/0116769 A1 | 6/2004 | Jassawalla et al. |
| 2004/0167415 A1 | 8/2004 | Gelfand et al. |
| 2004/0210236 A1 | 10/2004 | Allers et al. |
| 2004/0260389 A1 | 12/2004 | Case et al. |
| 2005/0033406 A1 | 2/2005 | Barnhart et al. |
| 2005/0049692 A1 | 3/2005 | Numamoto et al. |
| 2005/0079274 A1 | 4/2005 | Palasis et al. |
| 2005/0085848 A1 | 4/2005 | Johnson et al. |
| 2005/0119682 A1 | 6/2005 | Nguyen et al. |
| 2005/0137680 A1 | 6/2005 | Ortiz et al. |
| 2005/0180854 A1 | 8/2005 | Grabau et al. |
| 2006/0062672 A1 | 3/2006 | Mcbride et al. |
| 2006/0064059 A1 | 3/2006 | Gelfand et al. |
| 2006/0106449 A1 | 5/2006 | Ben |
| 2006/0135961 A1 | 6/2006 | Rosenman et al. |
| 2006/0155322 A1 | 7/2006 | Sater et al. |
| 2006/0265051 A1 | 11/2006 | Caro et al. |
| 2007/0100415 A1 | 5/2007 | Licata et al. |
| 2007/0100435 A1 | 5/2007 | Case et al. |
| 2007/0142729 A1 | 6/2007 | Pfeiffer et al. |
| 2007/0162103 A1 | 7/2007 | Case et al. |
| 2007/0208291 A1 | 9/2007 | Patel |
| 2007/0260327 A1 | 11/2007 | Case et al. |
| 2007/0282243 A1 | 12/2007 | Pini et al. |
| 2007/0293808 A1 | 12/2007 | Williams et al. |
| 2008/0009668 A1 | 1/2008 | Cohn |
| 2008/0086027 A1 | 4/2008 | Siess et al. |
| 2008/0103591 A1 | 5/2008 | Siess |
| 2008/0114339 A1 | 5/2008 | Mcbride et al. |
| 2008/0132747 A1 | 6/2008 | Shifflette |
| 2008/0132748 A1 | 6/2008 | Shifflette |
| 2008/0140189 A1 | 6/2008 | Nguyen et al. |
| 2008/0154236 A1 | 6/2008 | Elkins et al. |
| 2008/0183280 A1 | 7/2008 | Agnew et al. |
| 2008/0306327 A1 | 12/2008 | Shifflette |
| 2009/0024157 A1 | 1/2009 | Anukhin |
| 2009/0024195 A1 | 1/2009 | Rezai et al. |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2009/0264991 A1 | 10/2009 | Paul et al. |
| 2009/0287299 A1 | 11/2009 | Tabor et al. |
| 2009/0318857 A1 | 12/2009 | Goodson et al. |
| 2010/0030098 A1 | 2/2010 | Fojtik |
| 2010/0048793 A1* | 2/2010 | Baekelandt ............ C09J 5/06 524/439 |
| 2010/0049313 A1 | 2/2010 | Alon et al. |
| 2010/0076247 A1 | 3/2010 | Zilbershlag et al. |
| 2010/0130810 A1 | 5/2010 | Mohl |
| 2010/0152523 A1 | 6/2010 | Macdonald et al. |
| 2010/0185043 A1 | 7/2010 | Woodard et al. |
| 2010/0268017 A1 | 10/2010 | Siess |
| 2011/0004046 A1 | 1/2011 | Campbell et al. |
| 2011/0034874 A1 | 2/2011 | Reitan et al. |
| 2011/0106244 A1 | 5/2011 | Ferrari et al. |
| 2011/0112567 A1 | 5/2011 | Lenker et al. |
| 2011/0152999 A1 | 6/2011 | Hastings et al. |
| 2011/0190874 A1 | 8/2011 | Celermajer et al. |
| 2011/0213408 A1 | 9/2011 | Gross et al. |
| 2011/0230949 A1 | 9/2011 | Haverkost et al. |
| 2011/0257462 A1 | 10/2011 | Rodefeld et al. |
| 2011/0264075 A1 | 10/2011 | Leung et al. |
| 2011/0282128 A1 | 11/2011 | Reitan et al. |
| 2011/0282274 A1 | 11/2011 | Fulton |
| 2011/0301662 A1 | 12/2011 | Bar-Yoseph et al. |
| 2012/0022579 A1 | 1/2012 | Fulton |
| 2012/0059460 A1 | 3/2012 | Reitan |
| 2012/0089047 A1 | 4/2012 | Ryba et al. |
| 2012/0089225 A1 | 4/2012 | Akkerman et al. |
| 2012/0116382 A1 | 5/2012 | Ku et al. |
| 2012/0130469 A1 | 5/2012 | Cragg et al. |
| 2012/0143141 A1 | 6/2012 | Verkaik et al. |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |

(56) References Cited

U.S. PATENT DOCUMENTS

| | | |
|---|---|---|
| 2012/0245680 A1 | 9/2012 | Masuzawa et al. |
| 2012/0303112 A1 | 11/2012 | Armstrong et al. |
| 2012/0316586 A1 | 12/2012 | Demarais et al. |
| 2012/0328460 A1 | 12/2012 | Horvath et al. |
| 2013/0053623 A1 | 2/2013 | Evans et al. |
| 2013/0053732 A1 | 2/2013 | Heuser |
| 2013/0060077 A1 | 3/2013 | Liebing |
| 2013/0066140 A1 | 3/2013 | Mcbride et al. |
| 2013/0079874 A1 | 3/2013 | Doss et al. |
| 2013/0085318 A1 | 4/2013 | Toellner |
| 2013/0085319 A1 | 4/2013 | Evans et al. |
| 2013/0177407 A1 | 7/2013 | Farineau et al. |
| 2013/0177409 A1 | 7/2013 | Schumacher et al. |
| 2013/0177432 A1 | 7/2013 | Toellner et al. |
| 2013/0237744 A1 | 9/2013 | Pfeffer et al. |
| 2013/0245360 A1 | 9/2013 | Schumacher |
| 2013/0253328 A1 | 9/2013 | Zelenka et al. |
| 2013/0303831 A1 | 11/2013 | Evans |
| 2013/0303969 A1 | 11/2013 | Keenan et al. |
| 2014/0018840 A1 | 1/2014 | Morgan et al. |
| 2014/0025041 A1 | 1/2014 | Fukuoka et al. |
| 2014/0128659 A1 | 5/2014 | Heuring et al. |
| 2014/0255176 A1 | 9/2014 | Bredenbreuker et al. |
| 2014/0275720 A1 | 9/2014 | Ferrari |
| 2014/0275722 A1 | 9/2014 | Zimmermann et al. |
| 2014/0350523 A1 | 11/2014 | Dehdashtian et al. |
| 2015/0005570 A1 | 1/2015 | Fritz et al. |
| 2015/0018597 A1 | 1/2015 | Fierens et al. |
| 2015/0119633 A1 | 4/2015 | Haselby et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0258262 A1 | 9/2015 | Pfeffer et al. |
| 2015/0290372 A1 | 10/2015 | Muller et al. |
| 2015/0328382 A1 | 11/2015 | Corbett et al. |
| 2015/0343136 A1 | 12/2015 | Nitzan et al. |
| 2015/0343179 A1 | 12/2015 | Schumacher et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |
| 2016/0106896 A1 | 4/2016 | Pfeffer et al. |
| 2016/0129170 A1 | 5/2016 | Siess |
| 2016/0136341 A1 | 5/2016 | Pfeffer et al. |
| 2016/0136342 A1 | 5/2016 | Pfeffer et al. |
| 2016/0136343 A1 | 5/2016 | Anagnostopoulos |
| 2016/0144089 A1 | 5/2016 | Woo et al. |
| 2016/0184500 A1 | 6/2016 | Zeng |
| 2016/0256620 A1 | 9/2016 | Scheckel et al. |
| 2016/0279310 A1 | 9/2016 | Scheckel et al. |
| 2016/0331378 A1 | 11/2016 | Nitzan et al. |
| 2016/0354525 A1 | 12/2016 | Mcbride et al. |
| 2017/0007403 A1 | 1/2017 | Wildhirt et al. |
| 2017/0014562 A1 | 1/2017 | Liebing |
| 2017/0028115 A1 | 2/2017 | Muller |
| 2017/0035954 A1 | 2/2017 | Muller et al. |
| 2017/0049946 A1 | 2/2017 | Kapur et al. |
| 2017/0071769 A1 | 3/2017 | Mangiardi |
| 2017/0087286 A1 | 3/2017 | Spanier et al. |
| 2017/0087288 A1 | 3/2017 | Gross-Hardt et al. |
| 2017/0100527 A1 | 4/2017 | Schwammenthal et al. |
| 2017/0173237 A1 | 6/2017 | Pfeifer et al. |
| 2017/0197021 A1 | 7/2017 | Nitzan et al. |
| 2017/0215918 A1 | 8/2017 | Tao et al. |
| 2017/0232168 A1 | 8/2017 | Reichenbach et al. |
| 2017/0232171 A1 | 8/2017 | Roehn et al. |
| 2017/0290964 A1 | 10/2017 | Barry |
| 2017/0333067 A1 | 11/2017 | Wilson |
| 2017/0333607 A1 | 11/2017 | Zarins |
| 2017/0340791 A1 | 11/2017 | Aboul-Hosn et al. |
| 2017/0348470 A1 | 12/2017 | D'Ambrosio et al. |
| 2018/0050142 A1 | 2/2018 | Siess et al. |
| 2018/0055979 A1 | 3/2018 | Corbett et al. |
| 2018/0064861 A1 | 3/2018 | Dur et al. |
| 2018/0080326 A1 | 3/2018 | Schumacher et al. |
| 2018/0100507 A1 | 4/2018 | Wu et al. |
| 2018/0104453 A1 | 4/2018 | Tao et al. |
| 2018/0149164 A1 | 5/2018 | Siess |
| 2018/0149165 A1 | 5/2018 | Siess et al. |
| 2018/0169312 A1 | 6/2018 | Barry |
| 2018/0169313 A1 | 6/2018 | Schwammenthal et al. |
| 2018/0207334 A1 | 7/2018 | Siess |
| 2018/0228952 A1 | 8/2018 | Pfeffer et al. |
| 2018/0228953 A1 | 8/2018 | Siess et al. |
| 2018/0264182 A1 | 9/2018 | Spanier et al. |
| 2018/0264183 A1 | 9/2018 | Jahangir |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0303992 A1 | 10/2018 | Taskin |
| 2018/0303993 A1 | 10/2018 | Schwammenthal et al. |
| 2018/0353667 A1 | 12/2018 | Moyer et al. |
| 2019/0015570 A1 | 1/2019 | Muller |
| 2019/0030228 A1 | 1/2019 | Keenan et al. |
| 2019/0046702 A1 | 2/2019 | Siess et al. |
| 2019/0060539 A1 | 2/2019 | Siess et al. |
| 2019/0070345 A1 | 3/2019 | Mcbride et al. |
| 2019/0076167 A1 | 3/2019 | Fantuzzi et al. |
| 2019/0083690 A1 | 3/2019 | Siess et al. |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0134287 A1 | 5/2019 | Demou |
| 2019/0143018 A1 | 5/2019 | Salahieh et al. |
| 2019/0143019 A1 | 5/2019 | Mehaffey et al. |
| 2019/0170153 A1 | 6/2019 | Scheckel |
| 2019/0175802 A1 | 6/2019 | Tuval et al. |
| 2019/0175803 A1 | 6/2019 | Pfeffer et al. |
| 2019/0175805 A1 | 6/2019 | Tuval et al. |
| 2019/0175806 A1 | 6/2019 | Tuval et al. |
| 2019/0209753 A1 | 7/2019 | Tuval et al. |
| 2019/0209755 A1 | 7/2019 | Nix et al. |
| 2019/0209757 A1 | 7/2019 | Tuval et al. |
| 2019/0209758 A1 | 7/2019 | Tuval et al. |
| 2019/0211836 A1 | 7/2019 | Schumacher et al. |
| 2019/0216994 A1 | 7/2019 | Pfeffer et al. |
| 2019/0224391 A1 | 7/2019 | Liebing |
| 2019/0224392 A1 | 7/2019 | Pfeffer et al. |
| 2019/0224393 A1 | 7/2019 | Pfeffer et al. |
| 2019/0239998 A1 | 8/2019 | Tuval et al. |
| 2019/0262518 A1 | 8/2019 | Molteni et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0290817 A1 | 9/2019 | Guo et al. |
| 2019/0307561 A1 | 10/2019 | Gosal et al. |
| 2019/0316591 A1 | 10/2019 | Toellner |
| 2019/0321527 A1 | 10/2019 | King et al. |
| 2019/0321530 A1 | 10/2019 | Cambronne et al. |
| 2019/0321531 A1 | 10/2019 | Cambronne et al. |
| 2019/0328948 A1 | 10/2019 | Salahieh et al. |
| 2019/0336664 A1 | 11/2019 | Liebing |
| 2019/0344001 A1 | 11/2019 | Salahieh et al. |
| 2019/0351118 A1 | 11/2019 | Graichen et al. |
| 2019/0365975 A1 | 12/2019 | Muller et al. |
| 2020/0038567 A1 | 2/2020 | Siess et al. |
| 2020/0078506 A1 | 3/2020 | Schwammenthal et al. |
| 2020/0087199 A1* | 3/2020 | Gimblet ............... C03C 25/143 |
| 2020/0093973 A1 | 3/2020 | Gandhi et al. |
| 2020/0114053 A1 | 4/2020 | Salahieh et al. |
| 2020/0155739 A1 | 5/2020 | Siess et al. |
| 2020/0197585 A1 | 6/2020 | Scheckel et al. |
| 2020/0237981 A1 | 7/2020 | Tuval et al. |
| 2020/0237982 A1 | 7/2020 | Tuval et al. |
| 2020/0237984 A1 | 7/2020 | Tuval et al. |
| 2020/0237985 A1 | 7/2020 | Tuval et al. |
| 2020/0237986 A1 | 7/2020 | Tuval et al. |
| 2020/0246527 A1 | 8/2020 | Hildebrand et al. |
| 2020/0268952 A1 | 8/2020 | Nitzan et al. |
| 2020/0276369 A1 | 9/2020 | Nitzan et al. |
| 2020/0288988 A1 | 9/2020 | Goldvasser |
| 2020/0405926 A1 | 12/2020 | Alexander et al. |
| 2021/0023285 A1 | 1/2021 | Brandt |
| 2021/0023286 A1 | 1/2021 | Tuval et al. |

(56) References Cited

U.S. PATENT DOCUMENTS

| | | |
|---|---|---|
| 2021/0069394 A1 | 3/2021 | Tuval et al. |
| 2021/0069395 A1 | 3/2021 | Tuval et al. |
| 2021/0077692 A1 | 3/2021 | Tanner et al. |
| 2021/0145475 A1 | 5/2021 | Tao et al. |
| 2021/0170081 A1 | 6/2021 | Kanz |
| 2021/0178145 A1 | 6/2021 | Tuval et al. |
| 2021/0236797 A1 | 8/2021 | D'Ambrosio et al. |
| 2021/0299433 A1 | 9/2021 | Siess et al. |
| 2022/0072297 A1 | 3/2022 | Tuval et al. |
| 2022/0079457 A1 | 3/2022 | Tuval et al. |
| 2022/0088368 A1 | 3/2022 | Tuval et al. |
| 2022/0134085 A1 | 5/2022 | Siess et al. |
| 2022/0184376 A1 | 6/2022 | Tuval et al. |
| 2022/0226632 A1 | 7/2022 | Tuval et al. |
| 2023/0071248 A1 | 3/2023 | Keenan et al. |
| 2023/0137473 A1 | 5/2023 | Zipory et al. |
| 2023/0226342 A1 | 7/2023 | Tuval et al. |

FOREIGN PATENT DOCUMENTS

| | | |
|---|---|---|
| CA | 2927346 A1 | 4/2009 |
| CN | 101448535 A | 6/2009 |
| CN | 102805885 A | 12/2012 |
| CN | 113457006 A | 10/2021 |
| DE | 1033690 B | 7/1958 |
| DE | 10336902 B3 | 8/2004 |
| EP | 0916359 A1 | 5/1999 |
| EP | 1339443 A1 | 9/2003 |
| EP | 1651290 A1 | 5/2006 |
| EP | 1827531 A1 | 9/2007 |
| EP | 1871441 A2 | 1/2008 |
| EP | 2047872 A1 | 4/2009 |
| EP | 2047873 A1 | 4/2009 |
| EP | 2217300 A1 | 8/2010 |
| EP | 2218469 A1 | 8/2010 |
| EP | 2234658 A2 | 10/2010 |
| EP | 2282070 B | 2/2011 |
| EP | 2298374 A1 | 3/2011 |
| EP | 2299119 A1 | 3/2011 |
| EP | 2301598 A1 | 3/2011 |
| EP | 2308524 A1 | 4/2011 |
| EP | 2314331 A1 | 4/2011 |
| EP | 2345440 A1 | 7/2011 |
| EP | 2366412 A2 | 9/2011 |
| EP | 2376788 A1 | 10/2011 |
| EP | 2408489 A1 | 1/2012 |
| EP | 2424587 A1 | 3/2012 |
| EP | 2475415 A1 | 7/2012 |
| EP | 2607712 A1 | 6/2013 |
| EP | 2040639 B1 | 2/2014 |
| EP | 1207934 B1 | 8/2014 |
| EP | 2662099 B1 | 9/2014 |
| EP | 2427230 B1 | 12/2014 |
| EP | 2396050 B1 | 1/2015 |
| EP | 2835141 A1 | 2/2015 |
| EP | 2840954 A1 | 3/2015 |
| EP | 2841122 A1 | 3/2015 |
| EP | 2841124 A1 | 3/2015 |
| EP | 2860849 A1 | 4/2015 |
| EP | 2868331 A2 | 5/2015 |
| EP | 2868332 A1 | 5/2015 |
| EP | 2999496 A2 | 3/2016 |
| EP | 3000492 A1 | 3/2016 |
| EP | 3000493 A1 | 3/2016 |
| EP | 3055922 A1 | 8/2016 |
| EP | 3062730 A1 | 9/2016 |
| EP | 3115070 A1 | 1/2017 |
| EP | 3127562 A1 | 2/2017 |
| EP | 2922486 B1 | 5/2017 |
| EP | 3216467 A1 | 9/2017 |
| EP | 3222302 A1 | 9/2017 |
| EP | 3236079 A1 | 10/2017 |
| EP | 3287154 A1 | 2/2018 |
| EP | 3287155 A1 | 2/2018 |
| EP | 3326567 A1 | 5/2018 |
| EP | 3329951 A1 | 6/2018 |
| EP | 3338825 A1 | 6/2018 |
| EP | 3205360 B1 | 8/2018 |
| EP | 3359214 A1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| EP | 3545983 A1 | 10/2019 |
| EP | 3606575 A1 | 2/2020 |
| EP | 3737436 A1 | 11/2020 |
| EP | 3858421 A1 | 8/2021 |
| EP | 3897814 A1 | 10/2021 |
| EP | 4218899 A1 | 8/2023 |
| GB | 2239675 A | 7/1991 |
| GB | 2451161 A | 1/2009 |
| GB | 2504175 A | 1/2014 |
| GB | 2504177 A | 1/2014 |
| JP | 2003504091 A | 2/2003 |
| JP | 2009530041 A | 8/2009 |
| JP | 2012505038 A | 3/2012 |
| JP | 2012527269 A | 11/2012 |
| JP | 2015500666 A | 1/2015 |
| JP | 2016509950 A | 4/2016 |
| JP | 2018535727 A | 12/2018 |
| WO | 9001972 A1 | 3/1990 |
| WO | 90/13321 | 11/1990 |
| WO | 1994/01148 A1 | 1/1994 |
| WO | 99/34847 | 7/1999 |
| WO | 2001/083016 A2 | 5/2000 |
| WO | 2000043053 A1 | 7/2000 |
| WO | 0062838 A2 | 10/2000 |
| WO | 2002/070039 A2 | 3/2001 |
| WO | 2002/038085 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007081818 A2 | 7/2007 |
| WO | 2007112033 A2 | 10/2007 |
| WO | 2007127477 A2 | 11/2007 |
| WO | 2008005747 A2 | 1/2008 |
| WO | 2008005990 A2 | 1/2008 |
| WO | 2008055301 A1 | 5/2008 |
| WO | 2008104858 A2 | 9/2008 |
| WO | 2009010963 A1 | 1/2009 |
| WO | 2009046096 A1 | 4/2009 |
| WO | 2009064879 A2 | 5/2009 |
| WO | 2009129481 A1 | 10/2009 |
| WO | 2010042546 | 4/2010 |
| WO | 2010063494 A1 | 6/2010 |
| WO | 2010105854 A1 | 9/2010 |
| WO | 2010127871 A1 | 11/2010 |
| WO | 2010133567 A1 | 11/2010 |
| WO | 2010150208 A2 | 12/2010 |
| WO | 2011035926 A1 | 3/2011 |
| WO | 2011047884 A1 | 4/2011 |
| WO | 2011076441 A1 | 6/2011 |
| WO | 2011089022 A1 | 7/2011 |
| WO | 2012007141 A1 | 1/2012 |
| WO | 2012094535 A2 | 7/2012 |
| WO | 2013032849 A1 | 3/2013 |
| WO | 2013070186 A1 | 5/2013 |
| WO | 2013093001 A2 | 6/2013 |
| WO | 2013148697 A1 | 10/2013 |
| WO | 2013183060 A2 | 12/2013 |
| WO | 2014141284 A2 | 9/2014 |
| WO | 2015063277 A2 | 5/2015 |
| WO | 2015160943 A1 | 10/2015 |
| WO | 2015177793 A2 | 11/2015 |
| WO | 2016001218 A1 | 1/2016 |
| WO | 2016005803 A2 | 1/2016 |
| WO | 2016185473 A1 | 11/2016 |
| WO | 2016207293 A1 | 12/2016 |
| WO | 2017053361 A1 | 3/2017 |
| WO | 2017060254 A1 | 4/2017 |
| WO | 2017081561 A1 | 5/2017 |

(56) References Cited

FOREIGN PATENT DOCUMENTS

| | | |
|---|---|---|
| WO | 2017137604 A1 | 8/2017 |
| WO | 2017147291 A1 | 8/2017 |
| WO | 2018033920 A1 | 2/2018 |
| WO | 2018061001 A2 | 4/2018 |
| WO | 2018061002 A1 | 4/2018 |
| WO | 2018067410 A1 | 4/2018 |
| WO | 2018078615 A1 | 5/2018 |
| WO | 2018096531 A1 | 5/2018 |
| WO | 2018158636 A1 | 9/2018 |
| WO | 2018172848 A2 | 9/2018 |
| WO | 2018220589 A1 | 12/2018 |
| WO | 2018226991 A1 | 12/2018 |
| WO | 2018234454 A1 | 12/2018 |
| WO | 2019094963 A1 | 5/2019 |
| WO | 2019125899 A1 | 6/2019 |
| WO | 2019138350 A2 | 7/2019 |
| WO | 2019152875 A1 | 8/2019 |
| WO | 2019158996 A1 | 8/2019 |
| WO | 2019229223 A1 | 12/2019 |
| WO | 2020152611 A2 | 7/2020 |
| WO | 2021152012 A1 | 8/2021 |
| WO | 2021159147 A1 | 8/2021 |
| WO | 2021198881 A1 | 10/2021 |
| WO | 2021205346 A2 | 10/2021 |
| WO | 2022189932 A1 | 9/2022 |
| WO | 2023062453 A1 | 4/2023 |
| WO | 2024057252 A2 | 3/2024 |
| WO | 2024057253 A2 | 3/2024 |
| WO | 2024057254 A1 | 3/2024 |
| WO | 2024057255 A2 | 3/2024 |
| WO | 2024057256 A2 | 3/2024 |
| WO | 2024057257 A2 | 3/2024 |

OTHER PUBLICATIONS

Corrected Notice of Allowability for U.S. Appl. No. 17/182,482 mailed Feb. 7, 2023.
Examination Report for Australian Patent Application No. 2017349920 mailed Nov. 4, 2022.
Extended European Search Report for European Application No. 22155936.2 mailed Jul. 8, 2022.
Extended European Search Report for European Application No. 22163648.3 mailed Aug. 10, 2022.
Extended European Search Report for European Application No. 22163648.3 mailed Jul. 1, 2022.
Final Office Action for U.S. Appl. No. 17/176,344 mailed Oct. 12, 2022.
International Search Report and Written Opinion from International Application No. PCT/IB2022/051990 mailed Aug. 10, 2022.
Invitation to Pay Additional Fees for International Application No. PCT/IB2022/051990 mailed May 13, 2022.
Issue Notification for U.S. Appl. No. 16/810,270 mailed Oct. 12, 2022.
Non-Final Office Action for U.S. Appl. No. 16/275,559 mailed Jan. 19, 2023.
Non-Final Office Action for U.S. Appl. No. 16/952,327 mailed Nov. 8, 2022.
Non-Final Office Action for U.S. Appl. No. 16/952,389 mailed Dec. 21, 2022.
Non-Final Office Action for U.S. Appl. No. 16/952,444 mailed Jan. 6, 2023.
Non-Final Office Action for U.S. Appl. No. 17/069,064 mailed Nov. 7, 2022.
Non-Final Office Action for U.S. Appl. No. 17/069,570 mailed Oct. 6, 2022.
Non-Final Office Action for U.S. Appl. No. 17/070,323 mailed Oct. 6, 2022.
Non-Final Office Action for U.S. Appl. No. 17/070,670 mailed Oct. 5, 2022.
Non-Final Office Action for U.S. Appl. No. 17/077,769 mailed Oct. 5, 2022.
Non-Final Office Action for U.S. Appl. No. 17/180,041 mailed Jan. 31, 2023.
Notice of Allowance for U.S. Appl. No. 16/810,121 mailed Aug. 19, 2022.
Notice of Allowance for U.S. Appl. No. 16/810,270 mailed Jul. 22, 2022.
Notice of Allowance for U.S. Appl. No. 17/182,482 mailed Jan. 5, 2023.
Office Action for Japanese Application No. 2019-521643 mailed May 10, 2022.
Office Action for Japanese Application No. 2019-521643 mailed Oct. 27, 2022.
Third Party Submission received during the prosecution of U.S. Appl. No. 17/078,439 on Sep. 28, 2022.
U.S. Appl. No. 63/003,955, filed Apr. 2, 2020.
"Compendium of Technical and Scientific Information for the Hemopump Temporary Cardiac Assist System", Johnson & Johnson Interventional Systems, 1988, pp. 1-15.
Achour, et al., "Mechanical Left Ventricular Unloading Prior to Reperfusion Reduces Infarct Size in a Canine Infarction Model", Catheterization and Cardiovascular Interventions 64, 2005, pp. 182-192.
Butler, et al., "The Hemopump—A New Cardiac Prothesis Device", Reprinted from IEEE Transactions on Biomedical Engineering, vol. 37, No. 2, Feb. 1990, pp. 192-195.
Chan, et al., "Rapid manufacturing techniques in the development of an axial blood pump impeller", Proc. Instn Mech. Engrs vol. 217 Part H: J. Engineering in Medicine, 2003, pp. 469-475.
Dekker, et al., "Efficacy of a New Intraaortic Propeller Pump vs the Intraaortic Balloon Pump", CHEST, vol. 123, Issue 6, Jun. 2003, pp. 2089-2095.
Flameng, "Temporary Cardiac Assist with an Axial Pump System", Steinkopff Verlag Darmstadt, 1991, 79 pages.
Frazier, et al., "Treatment of Cardiac Allograft Failure by use of an IntraAortic Axial Flow Pump", Journal of Heart Transplantation, St. Louis, vol. 9, No. 4, pp. 408-414, Jul. 1990.
Gunther, et al., "Experimentelle Radiologie", Life Sciences, Berichte Aus Der Rheinischwestfälischen Technischen Hochschule Aachen Ausgabe Feb. 2002, 9 pages.
Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.
Merhige, et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.
Roundtree, et al., "The Hemopump Cardiac Assist System: Nursing Care of the Patient", Reprinted from Critical Care Nurse, Apr. 1991.
Scholz, et al., "Mechanical left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.
Siess, "System Analysis and Development of Intravascular Rotation Pumps for Cardiac Assist", Helmholtz-Institute—Chapter 3, Jun. 1998, 17 pages.
Smalling, et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.
Smalling, et al., "The Hemopump: A transvalvular, axial flow, left ventricular assist device", Coronary Artery Disease, Circulatory support devices in clinical cardiology, vol. 2 No. 6, pp. 666-671, Aug. 1991.
Smalling, et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.

(56) References Cited

OTHER PUBLICATIONS

Tamareille, et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.
Wampler, "Newspaper Articles", Captain Hemo, 1988, 6 pages.
Wampler, "Newsweek", Captain Hemo, May 16, 1988, 3 pages.
Wampler, "THI Today", Captain Hemo, Summer 1988, 2 pages.
Wampler, "Time Magazine", Captain Hemo, May 1988, 2 pages.
Wampler, et al., "Treatment of Cardiogenic Shock With the Hemopump Left Ventricular Assist Device", Annual of Thoracic Surgery, vol. 52, pp. 560-513, 1991.
Wampler, "U.S. News & World Report", Captain Hemo, pp. 1-2, May 16, 1988.
Corrected Notice of Allowability for U.S. Appl. No. 16/810,121 mailed Jun. 28, 2022.
Corrected Notice of Allowability for U.S. Appl. No. 16/810,172 mailed Feb. 2, 2022.
Examination Report for Australian Patent Application No. 2017349920 issued on Jun. 2, 2022.
Examination Report for Indian Patent Application No. 202047017397 issued on May 4, 2022.
Extended European Search Report for European Application No. 21208803.3 issued on Apr. 13, 2022.
Extended European Search Report for European Application No. 21209256.3 issued on Mar. 2, 2022.
Final Office Action for U.S. Appl. No. 16/275,559 mailed May 17, 2022.
Final Office Action for U.S. Appl. No. 17/069,064 mailed May 25, 2022.
Issue Notification for U.S. Appl. No. 16/276,965 mailed Mar. 16, 2022.
Issue Notification for U.S. Appl. No. 16/277,411 mailed Feb. 9, 2022.
Issue Notification for U.S. Appl. No. 16/750,354 mailed Nov. 17, 2021.
Issue Notification for U.S. Appl. No. 16/810,086 mailed Mar. 9, 2022.
Issue Notification for U.S. Appl. No. 16/810,172 mailed Mar. 23, 2022.
Issue Notification for U.S. Appl. No. 17/069,321 mailed Mar. 16, 2022.
Non-Final Office Action for U.S. Appl. No. 16/275,559 mailed Jan. 26, 2022.
Non-Final Office Action for U.S. Appl. No. 16/810,121 mailed Mar. 9, 2022.
Non-Final Office Action for U.S. Appl. No. 17/069,064 mailed Dec. 9, 2021.
Non-Final Office Action for U.S. Appl. No. 17/069,321 mailed Nov. 18, 2021.
Non-Final Office Action for U.S. Appl. No. 17/176,344 mailed Apr. 20, 2022.
Notice of Allowance for U.S. Appl. No. 16/276,965 mailed Jan. 26, 2022.
Notice of Allowance for U.S. Appl. No. 16/277,411 mailed Dec. 8, 2021.
Notice of Allowance for U.S. Appl. No. 16/810,086 mailed Jan. 7, 2022.
Notice of Allowance for U.S. Appl. No. 16/810,121 mailed Jun. 1, 2022.
Notice of Allowance for U.S. Appl. No. 16/810,172 mailed Jan. 10, 2022.
Notice of Allowance for U.S. Appl. No. 16/810,270 mailed Apr. 14, 2022.
Notice of Allowance for U.S. Appl. No. 17/069,321 mailed Feb. 2, 2022.
Restriction Requirement for U.S. Appl. No. 16/810,116 mailed Jun. 29, 2022.
Supplemental Notice of Allowability for U.S. Appl. No. 16/276,965 mailed Mar. 10, 2022.
Supplemental Notice of Allowability for U.S. Appl. No. 16/276,965 mailed Mar. 2, 2022.
U.S. Appl. No. 16/810,086, filed Mar. 5, 2020.
U.S. Appl. No. 16/810,121, filed Mar. 5, 2020.
U.S. Appl. No. 17/528,015, filed Nov. 16, 2021.
U.S. Appl. No. 17/528,807, filed Nov. 17, 2021.
U.S. Appl. No. 17/532,318, filed Nov. 22, 2021.
U.S. Appl. No. 17/574,701, filed Jan. 13, 2022.
U.S. Appl. No. 17/677,571, filed Feb. 22, 2022.
U.S. Appl. No. 17/678,122, filed Feb. 23, 2022.
U.S. Appl. No. 17/857,402, filed Jul. 5, 2022.
Agarwal, et al., "Newer-generation ventricular assist devices.", Best Practice & Research Clinical Anaesthesiology, 2012, pp. 117-130.
Corrected Notice of Allowability for U.S. Appl. No. 16/279,352 mailed Nov. 3, 2021.
Corrected Notice of Allowability for U.S. Appl. No. 16/281,237 mailed Mar. 31, 2021.
Final Office Action for U.S. Appl. No. 16/275,559 mailed Jan. 4, 2021.
Final Office Action for U.S. Appl. No. 16/275,559 mailed Oct. 20, 2021.
Final Office Action for U.S. Appl. No. 16/276,965 mailed Apr. 13, 2021.
Final Office Action for U.S. Appl. No. 16/277,411 mailed Jun. 21, 2021.
Final Office Action for U.S. Appl. No. 16/279,352 mailed May 3, 2021.
Issue Notification for U.S. Appl. No. 16/278,482 mailed Jan. 13, 2021.
Issue Notification for U.S. Appl. No. 16/279,352 mailed Nov. 10, 2021.
Issue Notification for U.S. Appl. No. 16/280,566 mailed Nov. 10, 2021.
Issue Notification for U.S. Appl. No. 16/281,237 mailed Apr. 14, 2021.
Issue Notification for U.S. Appl. No. 16/281,264 mailed Dec. 16, 2020.
Non-Final Office Action for U.S. Appl. No. 16/275,559 mailed May 26, 2021.
Non-Final Office Action for U.S. Appl. No. 16/275,559 mailed Sep. 4, 2020.
Non-Final Office Action for U.S. Appl. No. 16/276,965 mailed Jul. 26, 2021.
Non-Final Office Action for U.S. Appl. No. 16/276,965 mailed Jun. 19, 2020.
Non-Final Office Action for U.S. Appl. No. 16/276,965 mailed Nov. 30, 2020.
Non-Final Office Action for U.S. Appl. No. 16/277,411 mailed Feb. 9, 2021.
Non-Final Office Action for U.S. Appl. No. 16/278,482 mailed Jun. 23, 2020.
Non-Final Office Action for U.S. Appl. No. 16/279,352 mailed Nov. 10, 2020.
Non-Final Office Action for U.S. Appl. No. 16/280,566 mailed Dec. 21, 2020.
Non-Final Office Action for U.S. Appl. No. 16/281,237 mailed Aug. 21, 2020.
Non-Final Office Action for U.S. Appl. No. 16/281,264 mailed Jun. 29, 2020.
Notice of Allowance for U.S. Appl. No. 16/278,482 mailed Dec. 2, 2020.
Notice of Allowance for U.S. Appl. No. 16/279,352 mailed Oct. 1, 2021.
Notice of Allowance for U.S. Appl. No. 16/280,566 mailed Aug. 31, 2021.
Notice of Allowance for U.S. Appl. No. 16/281,237 mailed Feb. 1, 2021.
Notice of Allowance for U.S. Appl. No. 16/281,264 mailed Nov. 12, 2020.

(56) References Cited

OTHER PUBLICATIONS

Notice of Allowance for U.S. Appl. No. 16/750,354 mailed Oct. 18, 2021.
Restriction Requirement for U.S. Appl. No. 16/275,559 mailed Jun. 2, 2020.
Restriction Requirement for U.S. Appl. No. 16/279,352 mailed Aug. 11, 2020.
Restriction Requirement for U.S. Appl. No. 16/280,566 mailed Aug. 11, 2020.
Supplemental Notice of Allowability for U.S. Appl. No. 16/278,482 mailed Dec. 24, 2020.
Supplemental Notice of Allowability for U.S. Appl. No. 16/279,352 mailed Oct. 21, 2021.
Alba, et al., "The future is here: ventricular assist devices for the failing heart", Expert review of cardiovascular therapy, 2009, pp. 1067-1077.
Bai, et al., "A Split-Array, C-2C Switched-Capacitor Power Amplifier in 65 nm CMOS", IEEE Radio Frequency Integrated Circuits Symposium, 2017, pp. 336-339.
Burnett, et al., "Renal Interstitial Pressure And Sodium Excretion During Renal Vein Constriction", American Physiological Society, 1980, pp. F279-F282.
Cassidy, et al., "The Conductance Volume Catheter Technique for Measurement of Left Ventricular Volume in Young Piglets", Pediatric Research, 1992, pp. 85-90.
Coxworth, "Artificial Vein Valve Could Replace Drugs For Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion And The Association With Renal Impairment In Patients With Cardiac Dysfunction", European Journal of Heart Failure, 2007, pp. 872-878.
Damman, et al., "Increased Central Venous Pressure Is Associated With Impaired Renal Function And Mortality In A Broad Spectrum Of Patients With Cardiovascular Disease", Journal of American College of Cardiology, 2009, pp. 582-588.
Doty, et al., "The Effect Of Increased Renal Venous Pressure On Renal Function", The Journal of Trauma,, Dec. 1999, pp. 1000-1003.
Felker, et al., "Anemia As A Risk Factor And Therapeutic Target In Heart Failure", Journal of the American College of Cardiology, 2004, pp. 959-966.
Firth, et al., "Raised Venous Pressure: A Direct Cause Of Sodium Retention In Oedema?", The Lancet, May 7, 1988, pp. 1033-1036.
Forman, et al., "Incidence, Predictors At Admission, And Impact Of Worsening Renal Function Among Patients Hospitalized With Heart Failure", Journal of American College of Cardiology, 2004, pp. 61-67.
Fraser, et al., "The use of computational fluid dynamics in the development of ventricular assist devices", Medical engineering & physics, 2011, pp. 263-280.
Frazier, et al., "First Human Use of the Hemopump, a CatheterMounted Ventricular Assist Device", Ann Thorac Surg, 1990, pp. 299-304.
Gomes, et al., "Heterologous Valve Implantation In The Infra-Renal Vena Cava For Treatment Of The Iliac Venous Valve Regurgitation Disease: Experimental Study", Rev Bras Cir Cardiovasc, 2002, pp. 367-369.
Haddy, et al., "Effect Of Elevation Of Intraluminal Pressure On Renal Vascular Resistance", Circulation Research Journal Of The American Heart Association, 1956, pp. 659-663.
Heywood, et al., "High Prevalence Of Renal Dysfunction And Its Impact On Outcome In 118,465 Patients Hospitalized With Acute Decompensated Heart Failure: A Report From The ADHERE Database", Journal of Cardiac Failure, 2007, pp. 422-430.
Hillege, et al., "Renal Function As A Predictor Of Outcome In A Broad Spectrum Of Patients With Heart Failure", Circulation Journal of the American Heart Association, 2006, pp. 671-678.
Hillege, et al., "Renal Function, Neurohormonal Activation, And Survival In Patients With Chronic Heart Failure", Circulation Journal of the American Heart Association, 2000, pp. 203-210.
Hsu, et al., "Review of recent patents on foldable ventricular assist devices", Recent Patents on Biomedical Engineering, 2012, pp. 208-222.
IKARI, "The Physics Of Guiding Catheter; The IKARI Guiding Catheter In TRI", available at http:i /www.docstoc.com/docs/148136553/The-[KARI-catheter---anovel-guide-for-TRI--.
Kafagy, et al., "Design of axial blood pumps for patients with dysfunctional fontan physiology: computational studies and performance testing", Artificial organs, 2015, pp. 34-42.
Kang, et al., "Fluid dynamics aspects of miniaturized axial-flow blood pump", Bio-medical materials and engineering, 2014, pp. 723-729.
Koochaki, et al., "A new design and computational fluid dynamics study of an implantable axial blood pump", Australasian Physical & Engineering Sciences in Medicine, 2013, pp. 417-422.
Lauten, et al., "Heterotopic Transcatheter Tricuspid Valve Implantation: First-In-Man Application Of A Novel Approach To Tricuspid Regurgitation", European Heart Journal, Feb. 15, 2011, pp. 1207-1213.
McAlister, et al., "Renal Insufficiency And Heart Failure: Prognostic And Therapeutic Implications From A Prospective Cohort Study", Circulation Journal of the American Heart Association, 2004, pp. 1004-1009.
Meyns, et al., "The Heart-Hemopump Interaction: A Study of Hemopump Flow as a Function of Cardiac Activity", Artificial Organs, 1996, pp. 641-649.
Mullens, et al., "Elevated Intra-Abdominal Pressure In Acute Decompensated Heart Failure. A Potential Contributor To Worsening Renal Function", Journal of the American College of Cardiology, 2008, pp. 300-306.
Mullens, et al., "Importance Of Venous Congestion For Worsening Of Renal Function In Advanced Decompensated Heart Failure", Journal of American College of Cardiology, 2009, pp. 589-596.
Mullens, et al., "Prompt Reduction In Intra-Abdominal Pressure Following Large-Volume Mechanical Fluid Removal Improves Renal Insufficiency In Refractory Decompensated Heart Failure", Journal of Cardiac Failure, 2008, pp. 508-514.
Notarius, et al., "Central Venous Pressure During Exercise: Role Of Muscle Pump", Canadian Journal of Physiology and Pharmacology, 1996, pp. 647-651.
Park, et al., "Nutcracker Syndrome: Intravascular Stenting Approach", Nephrol Dial Transplant, 2000, pp. 99-101.
Reul, et al., "Blood pumps for circulatory support", PERFUSION-SEVENOAKS, 2000, pp. 295-312.
Reul, et al., "Rotary blood pumps in circulatory assist", Perfusion, May 1995, pp. 153-158.
Roefeld, "Cavopulmonary assist for the univentricular Fontan circulation: von Karman viscous impeller pump", The Journal of Thoracic and Cardiovascular Surgery, 2010, pp. 529-536.
Schmitz-Rode, et al., "An Expandable Percutaneous Catheter Pump For Left Ventricular Support", Journal of the American College of Cardiology, 2005, pp. 1856-1861.
Schmitz-Rode, et al., "Axial flow catheter pump for circulatory support", Biomed Tech (Berl), 2002, pp. 142-143.
Semple, et al., "Effect Of Increased Renal Venous Pressure On Circulatory "Autoregulation" Of Isolated Dog Kidneys", Circulation Research Journal of The American Heart Association, 1959, pp. 643-648.
Sianos, et al., "The Recover® LP 2.5 catheter-mounted left ventricular assist device", EuroIntervention, 2006, pp. 116-119.
Siess, et al., "Concept, realization, and first in vitro testing of an intraarterial microaxial blood pump", Artificial Organs, 1995, pp. 644-652.
Siess, et al., "Hemodynamic system analysis of intraarterial microaxial pumps in vitro and in vivo", Artificial Organs, Jun. 1996, pp. 650-661.
Siess, "PhD Chapter 3—English translation", https://www.shaker.eu/en/content/catalogue/index.asp?lang=en&ID=8&ISBN=978-3-8265-6150-4&search=yes.

(56) References Cited

OTHER PUBLICATIONS

Song, et al., "Axial flow blood pumps", ASAIO journal, 2003, pp. 355-364.
Tang, et al., "Anemia In Chronic Heart Failure: Prevalence, Etiology, Clinical Correlates, And Treatment Options", Circulation Journal of the American Heart Association, 2006, pp. 2454-2461.
Throckmorton, et al., "Design of a protective cage for an intra vascular axial flow blood pump to mechanically assist the failing Fontan", Artificial organs, 2009, pp. 611-621.
Throckmorton, et al., "Mechanical Cavopulmonary Assist for the Univentricular Fontan Circulation Using a Novel Folding Propeller Blood Pump", ASAIO Journal, 2007, pp. 734-741.
Thunberg, et al., "Ventricular assist devices today and tomorrow", Journal of cardiothoracic and vascular anesthesia, 2010, pp. 656-680.
Timms, "A review of clinical ventricular assist devices", Medical engineering & physics, 2011, pp. 1041-1047.
Triep, et al., "Computational Fluid Dynamics and Digital Particle Image Velocimetry Study of the Flow Through an Optimized Micro-axial Blood Pump", Artificial Organs, May 2006, pp. 384-391.
Uthoff, et al., "Central venous pressure at emergency room presentation predicts cardiac rehospitalization in patients with decompensated heart failure", European Journal of Heart Failure, 2010, pp. 469-476.
U.S. Appl. No. 14/567,439, filed Dec. 11, 2014.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,482, filed Feb. 18, 2019.
U.S. Appl. No. 16/279,352, filed Feb. 19, 2019.
U.S. Appl. No. 16/280,566, filed Feb. 20, 2019.
U.S. Appl. No. 16/281,237, filed Feb. 21, 2019.
U.S. Appl. No. 16/281,264, filed Feb. 21, 2019.
U.S. Appl. No. 16/750,354, filed Jan. 23, 2020.
U.S. Appl. No. 16/952,327, filed Nov. 19, 2020.
U.S. Appl. No. 16/952,389, filed Nov. 19, 2020.
U.S. Appl. No. 16/952,444, filed Nov. 19, 2020.
U.S. Appl. No. 17/069,064, filed Oct. 13, 2020.
U.S. Appl. No. 17/069,321, filed Oct. 13, 2020.
U.S. Appl. No. 17/069,570, filed Oct. 13, 2020.
U.S. Appl. No. 17/070,323, filed Oct. 14, 2020.
U.S. Appl. No. 17/070,670, filed Oct. 14, 2020.
U.S. Appl. No. 17/077,769, filed Oct. 22, 2020.
U.S. Appl. No. 17/078,439, filed Oct. 23, 2020.
U.S. Appl. No. 17/078,472, filed Oct. 23, 2020.
U.S. Appl. No. 17/176,344, filed Feb. 16, 2021.
U.S. Appl. No. 17/177,296, filed Feb. 17, 2021.
U.S. Appl. No. 17/180,041, filed Feb. 19, 2021.
U.S. Appl. No. 17/182,482, filed Feb. 23, 2021.
U.S. Appl. No. 17/609,589, filed Nov. 8, 2021.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,718, filed May 2, 2018.
U.S. Appl. No. 62/681,868, filed Jun. 7, 2018.
U.S. Appl. No. 62/727,605, filed Sep. 6, 2018.
U.S. Appl. No. 62/796,138, filed Jan. 24, 2019.
U.S. Appl. No. 62/851,716, filed May 23, 2019.
U.S. Appl. No. 62/870,821, filed Jul. 5, 2019.
U.S. Appl. No. 62/896,026, filed Sep. 5, 2019.
U.S. Appl. No. 63/006,122, filed Apr. 7, 2020.
U.S. Appl. No. 63/114,136, filed Nov. 16, 2020.
U.S. Appl. No. 63/129,983, filed Dec. 23, 2020.
Examination Report for Indian Patent Application No. 201917018651 mailed Jun. 30, 2021.
Extended Search Report for European Application No. 19172327.9 mailed Aug. 23, 2019.
Extended Search Report for European Application No. 20159714.3 mailed Jul. 3, 2020.
Extended Search Report for European Application No. 20159716.8 mailed Jul. 3, 2020.
Extended Search Report for European Application No. 20159718.4 mailed Jul. 9, 2020.
Extended Search Report for European Application No. 20195082.1 mailed Nov. 5, 2020.
Extended Search Report for European Application No. 20195084.7 mailed Nov. 5, 2020.
Extended Search Report for European Application No. 20195085.4 mailed Nov. 4, 2020.
Extended Search Report for European Application No. 20195987.1 mailed Nov. 5, 2020.
Extended Search Report for European Application No. 21156647.6 mailed May 21, 2021.
Extended Search Report for European Application No. 21158196.2 mailed Apr. 8, 2021.
Extended Search Report for European Application No. 21158902.3 mailed Apr. 29, 2021.
Extended Search Report for European Application No. 21158903.1 mailed Apr. 9, 2021.
International Search Report and Written Opinion from International Application No. PCT/IB2020/050515 mailed Sep. 9, 2020.
International Search Report and Written Opinion from International Application No. PCT/IB2021/052590 mailed Sep. 14, 2021.
International Search Report and Written Opinion from International Application No. PCT/IB2021/052857 mailed Oct. 5, 2021.
International Search Report and Written Opinion from International Application No. PCT/IL2017/051158 mailed Jan. 17, 2018.
International Search Report and Written Opinion from International Application No. PT/IB2019/050186 mailed Jul. 18, 2019.
Invitation to Pay Additional Fees for International Application No. PCT/IB2020/050515 mailed Mar. 31, 2020.
Invitation to Pay Additional Fees for International Application No. PCT/IB2021/052590 mailed Jul. 23, 2021.
Invitation to Pay Additional Fees for International Application No. PCT/IB2021/052857 mailed Jul. 7, 2021.
Invitation to Pay Additional Fees in International Application No. PCT/IB2020/050515 mailed Mar. 31, 2020.
Office Action for Chinese Application No. 201780066201.3 mailed Jun. 29, 2021.
Office Action for Japanese Patent Application No. 2019-521643 mailed Sep. 28, 2021.
"Tanslation of decision of Board 4 (Nullity Board) of the German Federal Patent Court re German patent 10336902", pronounced Nov. 15, 2016, and appendices to decision, 62 pages.
Van Mieghem, et al., "Design and Principle of Operation of the HeartMate PHPTM (Percutaneous Heart Pump)", EuroIntervention, 2016.
Vercaemst, et al., "Impella: A Miniaturized Cardiac Support System in an Era of Minimal Invasive Cardiac Surgery", Presented at the 39th International Conference of the American Society of Extra-Corporeal Technology, Mar. 22-25, 2001.
Wampler, "The first co-axial flow pump for human use: the Hemopump", Flameng W. (eds) Temporary Cardiac Assist with an Axial Pump System, 1991.
Wencker, "Acute Cardio-Renal Syndrome: Progression From Congestive Heart Failure To Congestive Kidney Failure", Current Heart Failure Reports, 2007, pp. 134-138.
Winton, "The Control Of Glomerular Pressure By Vascular Changes Within The Mammalian Kidney, Demonstrated By The Actions Of Adrenaline", Journal of Physiology, Nov. 1931, pp. 151-162.
Winton, "The Influence Of Venous Pressure On The Isolated Mammalian Kidney", Journal of Physiology, Jun. 6, 1931, pp. 49-61.

(56) References Cited

OTHER PUBLICATIONS

Wood, "The Mechanism Of The Increased Venous Pressure With Exercise In Congestive Heart Failure", Journal of Clinical Investigation, 1962, pp. 2020-2024.
Wu, et al., "Design and simulation of axial flow maglev blood pump", International Journal of Information Engineering and Electronic Business, 2011, p. 42.
Yancy et al., "Clinical Presentation, Management, And In-Hospital Outcomes Of Patients Admitted With Acute Decompensated Heart Failure With Preserved Systolic Function. A Report From The Acute Decompensated Heart Failure National Registry (ADHERE) Database", Journal of the American College of Cardiology, 2006, pp. 76-84.
Corrected Notice of Allowability for U.S. Appl. No. 16/810,116 mailed Apr. 7, 2023.
Corrected Notice of Allowability for U.S. Appl. No. 17/070,323 mailed Jun. 1, 2023.
Corrected Notice of Allowability for U.S. Appl. No. 17/180,041 mailed Jun. 30, 2023.
Examination Report for Indian Patent Application No. 202147033522 mailed May 24, 2023.
Extended Search Report and Preliminary Opinion for European Application No. 23159720.4 mailed Jun. 27, 2023.
Extended Search Report for European Application No. 22197511.3 mailed Dec. 5, 2022.
Extended Search Report for European Application No. 23159721.2 mailed Jun. 26, 2023.
Extended Search Report for European Application No. 23159724.6 mailed Jun. 26, 2023.
Extended Search Report for European Application No. 23159725.3 mailed Jun. 28, 2023.
Final Office Action for U.S. Appl. No. 16/952,327 mailed Jun. 8, 2023.
Final Office Action for U.S. Appl. No. 16/952,389 mailed Jul. 18, 2023.
Final Office Action for U.S. Appl. No. 16/952,444 mailed Jul. 5, 2023.
Final Office Action for U.S. Appl. No. 17/069,570 mailed Apr. 28, 2023.
Final Office Action for U.S. Appl. No. 17/070,670 mailed Jun. 2, 2023.
Final Office Action for U.S. Appl. No. 17/077,769 mailed Jun. 7, 2023.
International Search Report and Written Opinion from International Application No. PCT/IB2022/058101 mailed Feb. 20, 2023.
Issue Notification for U.S. Appl. No. 16/810,116 mailed May 17, 2023.
Non-Final Office Action for U.S. Appl. No. 17/078,439 mailed Jun. 1, 2023.
Non-Final Office Action for U.S. Appl. No. 17/078,472 mailed May 4, 2023.
Non-Final Office Action for U.S. Appl. No. 17/574,701 mailed Sep. 27, 2023.
Notice of Allowance for U.S. Appl. No. 16/275,559 mailed Jul. 27, 2023.
Notice of Allowance for U.S. Appl. No. 16/810,116 mailed Mar. 13, 2023.
Notice of Allowance for U.S. Appl. No. 17/069,064 mailed Mar. 8, 2023.
Notice of Allowance for U.S. Appl. No. 17/070,323 mailed Aug. 30, 2023.
Notice of Allowance for U.S. Appl. No. 17/070,323 mailed May 15, 2023.
Notice of Allowance for U.S. Appl. No. 17/077,769 mailed Sep. 27, 2023.
Notice of Allowance for U.S. Appl. No. 17/173,944 mailed Jul. 10, 2023.
Notice of Allowance for U.S. Appl. No. 17/180,041 mailed Jun. 13, 2023.
Notice of Allowance for U.S. Appl. No. 17/180,041 mailed Sep. 18, 2023.
Notice of Allowance for U.S. Appl. No. 17/182,482 mailed Apr. 21, 2023.
Office Action for Canadian Application No. 3,039,285 mailed Mar. 24, 2023.
Office Action for Canadian Application No. 3,080,800 mailed Sep. 12, 2023.
Office Action for Canadian Application No. 3,122,415 mailed Mar. 31, 2023.
Office Action for Chinese Application No. 201980007116.9 mailed Nov. 28, 2022.
Office Action for Japanese Application No. 2019-521643 mailed Apr. 11, 2023.
Office Action for Japanese Application No. 2020-537746 mailed Feb. 21, 2023.
U.S. Appl. No. 18/121,995, filed Mar. 15, 2023.
U.S. Appl. No. 18/122,456, filed Mar. 16, 2023.
U.S. Appl. No. 18/122,486, filed Mar. 16, 2023.
U.S. Appl. No. 18/122,504, filed Mar. 16, 2023.
U.S. Appl. No. 18/447,025, filed Aug. 9, 2023.
U.S. Appl. No. 18/447,050, filed Aug. 9, 2023.
U.S. Appl. No. 18/447,064, filed Aug. 9, 2023.
U.S. Appl. No. 18/447,074, filed Aug. 9, 2023.
U.S. Appl. No. 18/447,086, filed Aug. 9, 2023.
U.S. Appl. No. 63/158,708, filed Mar. 9, 2021.
U.S. Appl. No. 63/254,321, filed Oct. 11, 2021.
U.S. Appl. No. 63/317,199, filed Mar. 7, 2022.
Extended European Search Report for EP Patent Application No. 22163640.0 mailed Jun. 29, 2022.
Corrected Notice of Allowance for U.S. Appl. No. 16/275,559 mailed Nov. 8, 2023.
Corrected Notice of Allowance for U.S. Appl. No. 17/070,323 mailed Oct. 4, 2023.
Corrected Notice of Allowance for U.S. Appl. No. 17/077,769 mailed Nov. 15, 2023.
Corrected Notice of Allowance for U.S. Appl. No. 17/077,769 mailed Nov. 6, 2023.
Corrected Notice of Allowance for U.S. Appl. No. 17/077,769 mailed Oct. 4, 2023.
Corrected Notice of Allowance for U.S. Appl. No. 17/180,041 mailed Oct. 4, 2023.
Examination Report for Australian Patent Application No. 2019206421 mailed Sep. 29, 2023.
Extended Search Report for European Application No. 23189145.8 mailed Nov. 27, 2023.
Extended Search Report for European Application No. 23189147.4 mailed Dec. 13, 2023.
Extended Search Report for European Application No. 23189148.2 mailed Dec. 13, 2023.
Extended Search Report for European Application No. 23189149.0 mailed Dec. 13, 2023.
Final Office Action for U.S. Appl. No. 17/078,472 mailed Oct. 23, 2023.
Hearing Notice for Indian Patent Application No. 201917018651 mailed Dec. 11, 2023.
Issue Notification for U.S. Appl. No. 16/275,559 mailed Nov. 22, 2023.
Issue Notification for U.S. Appl. No. 17/070,323 mailed Oct. 18, 2023.
Issue Notification for U.S. Appl. No. 17/077,769 mailed Nov. 29, 2023.
Issue Notification for U.S. Appl. No. 17/180,041 mailed Oct. 18, 2023.
Non-Final Office Action for U.S. Appl. No. 16/952,327 mailed Oct. 13, 2023.
Non-Final Office Action for U.S. Appl. No. 17/069,570 mailed Oct. 2, 2023.
Non-Final Office Action for U.S. Appl. No. 17/070,670 mailed Oct. 30, 2023.
Non-Final Office Action for U.S. Appl. No. 17/176,344 mailed Oct. 31, 2023.

(56) References Cited

OTHER PUBLICATIONS

Notice of Allowance for U.S. Appl. No. 16/275,559 mailed Oct. 4, 2023.
Notice of Allowance for U.S. Appl. No. 17/078,439 mailed Dec. 5, 2023.
Notice of Allowance for U.S. Appl. No. 17/173,944 mailed Nov. 8, 2023.
Notice of Allowance for U.S. Appl. No. 17/177,296 mailed Nov. 17, 2023.
Office Action for Canadian Application No. 3,176,272 mailed Jan. 2, 2024.
Office Action for Chinese Application No. 202080017728.9 mailed Nov. 6, 2023.
Office Action for Japanese Application No. 2021-533242 mailed Nov. 8, 2023.
U.S. Appl. No. 18/511,532, filed Nov. 16, 2023.
Corrected Notice of Allowance for U.S. Appl. No. 16/952,389 mailed Feb. 20, 2024.
Corrected Notice of Allowance for U.S. Appl. No. 16/952,389 mailed Mar. 4, 2024.
Corrected Notice of Allowance for U.S. Appl. No. 16/952,444 mailed Mar. 13, 2024.
Examination Report for European Application No. 21718229.4 mailed Mar. 17, 2022.
Final Office Action for U.S. Appl. No. 17/176,344 mailed Apr. 12, 2024.
Final Office Action for U.S. Appl. No. 17/574,701 mailed Feb. 8, 2024.
International Search Report and Written Opinion from International Application No. PCT/IB2023/059136 mailed Jan. 2, 2024.
International Search Report and Written Opinion from International Application No. PCT/IB2023/059137 mailed Mar. 21, 2024.
International Search Report and Written Opinion from International Application No. PCT/IB2023/059138 mailed Feb. 7, 2024.
International Search Report and Written Opinion from International Application No. PCT/IB2023/059141 mailed Mar. 22, 2024.
International Search Report and Written Opinion from International Application No. PCT/IB2023/059143 mailed Mar. 14, 2024.
Invitation to Pay Additional Fees for International Application No. PCT/IB2023/059134 mailed Dec. 21, 2023.
Invitation to Pay Additional Fees for International Application No. PCT/IB2023/059137 mailed Jan. 2, 2024.
Invitation to Pay Additional Fees for International Application No. PCT/IB2023/059138 mailed Dec. 8, 2023.
Invitation to Pay Additional Fees for International Application No. PCT/IB2023/059141 mailed Dec. 22, 2023.
Invitation to Pay Additional Fees for International Application No. PCT/IB2023/059142 mailed Jan. 2, 2024.
Issue Notification for U.S. Appl. No. 16/952,389 mailed Mar. 13, 2024.
Issue Notification for U.S. Appl. No. 16/952,444 mailed Mar. 20, 2024.
Issue Notification for U.S. Appl. No. 17/078,439 mailed Apr. 3, 2024.
Issue Notification for U.S. Appl. No. 17/177,296 mailed Mar. 13, 2024.
Non-Final Office Action for U.S. Appl. No. 17/078,472 mailed Feb. 14, 2024.
Notice of Allowance for U.S. Appl. No. 16/952,389 mailed Feb. 7, 2024.
Notice of Allowance for U.S. Appl. No. 16/952,444 mailed Feb. 15, 2024.
Notice of Allowance for U.S. Appl. No. 17/069,570 mailed Mar. 13, 2024.
Notice of Allowance for U.S. Appl. No. 17/078,439 mailed Feb. 27, 2024.
Notice of Allowance for U.S. Appl. No. 17/173,944 mailed Mar. 6, 2024.
Notice of Allowance for U.S. Appl. No. 17/177,296 mailed Feb. 14, 2024.
Notice of Missing Requirements for U.S. Appl. No. 18/447,025 mailed Feb. 1, 2024.
U.S. Appl. No. 18/444,972, filed Feb. 19, 2024.
U.S. Appl. No. 18/632,533, filed Apr. 11, 2024.
U.S. Appl. No. 18/632,545, filed Apr. 11, 2024.
U.S. Appl. No. 18/632,557, filed Apr. 11, 2024.
U.S. Appl. No. 18/632,569, filed Apr. 11, 2024.
U.S. Appl. No. 63/406,427, filed Sep. 14, 2022.
U.S. Appl. No. 63/432,496, filed Dec. 14, 2022.
U.S. Appl. No. 63/443,519, filed Feb. 6, 2023.
U.S. Appl. No. 63/470,259, filed Jun. 1, 2023.
Chang, et al., "Leveraging Device-Arterial Coupling to Determine Cardiac and Vascular State", IEEE Transactions On Biomedical Engineering, vol. 66, No. 10, Oct. 2019, pp. 2800-2808.
Keller, et al., "Dynamic Modulation of Device-Arterial Coupling to Determine Cardiac Output and Vascular Resistance", Annals of Biomedical Engineering, vol. 48, No. 9, Sep. 2020, pp. 2333-2342.
Corrected Notice of Allowance for U.S. Appl. No. 17/069,570 mailed Apr. 10, 2024.
Corrected Notice of Allowance for U.S. Appl. No. 17/069,570 mailed Jul. 16, 2024.
Examination Report for European Application No. 21158196.2 mailed May 28, 2024.
Examination Report for European Application No. 21158903.1 mailed Jul. 9, 2024.
Extended Search Report for European Application No. 24170573.0 mailed Jul. 29, 2024.
Final Office Action for U.S. Appl. No. 17/078,472 mailed Aug. 9, 2024.
Hearing Notice for Indian Application No. 202147033522 mailed Jul. 24, 2024.
International Search Report and Written Opinion from International Application No. PCT/IB2023/059142 mailed Apr. 16, 2024.
Issue Notification for U.S. Appl. No. 17/173,944 mailed Jun. 12, 2024.
Non-Final Office Action for U.S. Appl. No. 17/532,318 mailed Jul. 18, 2024.
Non-Final Office Action for U.S. Appl. No. 17/609,589 mailed Jul. 1, 2024.
Non-Final Office Action for U.S. Appl. No. 17/677,571 mailed Aug. 15, 2024.
Notice of Allowance for U.S. Appl. No. 16/952,327 mailed Apr. 29, 2024.
Notice of Allowance for U.S. Appl. No. 16/952,327 mailed Aug. 6, 2024.
Notice of Allowance for U.S. Appl. No. 17/069,570 mailed Jun. 24, 2024.
Notice of Allowance for U.S. Appl. No. 17/070,670 mailed Jun. 13, 2024.
Notice of Allowance for U.S. Appl. No. 17/574,701 mailed Jun. 26, 2024.
Office Action for Japanese Application No. 2023-156391 mailed Jun. 3, 2024.
U.S. Appl. No. 18/635,275, filed Apr. 15, 2024.
U.S. Appl. No. 18/635,286, filed Apr. 15, 2024.
U.S. Appl. No. 18/635,292, filed Apr. 15, 2024.
U.S. Appl. No. 18/637,653, filed Apr. 17, 2024.
U.S. Appl. No. 18/637,655, filed Apr. 17, 2024.
U.S. Appl. No. 18/637,667, filed Apr. 17, 2024.
U.S. Appl. No. 18/639,079, filed Apr. 18, 2024.
U.S. Appl. No. 18/639,087, filed Apr. 18, 2024.
U.S. Appl. No. 18/639,094, filed Apr. 18, 2024.
U.S. Appl. No. 18/639,098, filed Apr. 18, 2024.
U.S. Appl. No. 18/640,222, filed Apr. 19, 2024.
U.S. Appl. No. 18/640,260, filed Apr. 19, 2024.
U.S. Appl. No. 18/640,285, filed Apr. 19, 2024.
U.S. Appl. No. 18/640,303, filed Apr. 19, 2024.
U.S. Appl. No. 18/652,930, filed May 2, 2024.
U.S. Appl. No. 18/652,956, filed May 2, 2024.
U.S. Appl. No. 18/652,959, filed May 2, 2024.
U.S. Appl. No. 18/652,962, filed May 2, 2024.
U.S. Appl. No. 18/654,336, filed May 3, 2024.

(56) References Cited

OTHER PUBLICATIONS

"Peripheral Interventions 2015 Product Catalog", Boston Scientific, 2015, 7 pages.
Alsafarr, et al., "Hydrodynamic Effects on Flow Through Screens at Intakes", Water Research vol. 8, Issue 9, Sep. 1974, pp. 617-622.
Brückler, et al., "Flow Design and Optimization of a Percutaneously Implantable Miniature Blood Pump", Medical technology in cardiology, 2002, 11 pages.
Fox, et al., "Introduction to Fluid Mechanics", Sixth Edition, pp. 341-343.
Kapur, et al., "Mechanical Left Ventricular Unloading to Reduce Infarct Size During Acute Myocardial Infarction: Insight from Preclinical and Clinical Studies", Journal of Cardiovascular Translational Research, Apr. 23, 2019, pp. 1-8.
Kaufman, "Invasive Vascular Diagnosis", Radiology Key Fastest Radiology Insight Engine, Chapter 3, Dec. 23, 2015, 12 pages.
Schmitz-Rode, "Percutaneously implantable, self-expanding left heart support pump", Clinic for Radiological Diagnostics, 2001, 19 Pages.
Siess, et al., "Basic Design Criteria for Rotary Blood Pumps", Rotary Blood Pumps, 2000, pp. 69-83.
US 9,427,507, Jul. 2004, Siess (withdrawn).
US 9,399,088, Apr. 2013, Siess (withdrawn).

\* cited by examiner

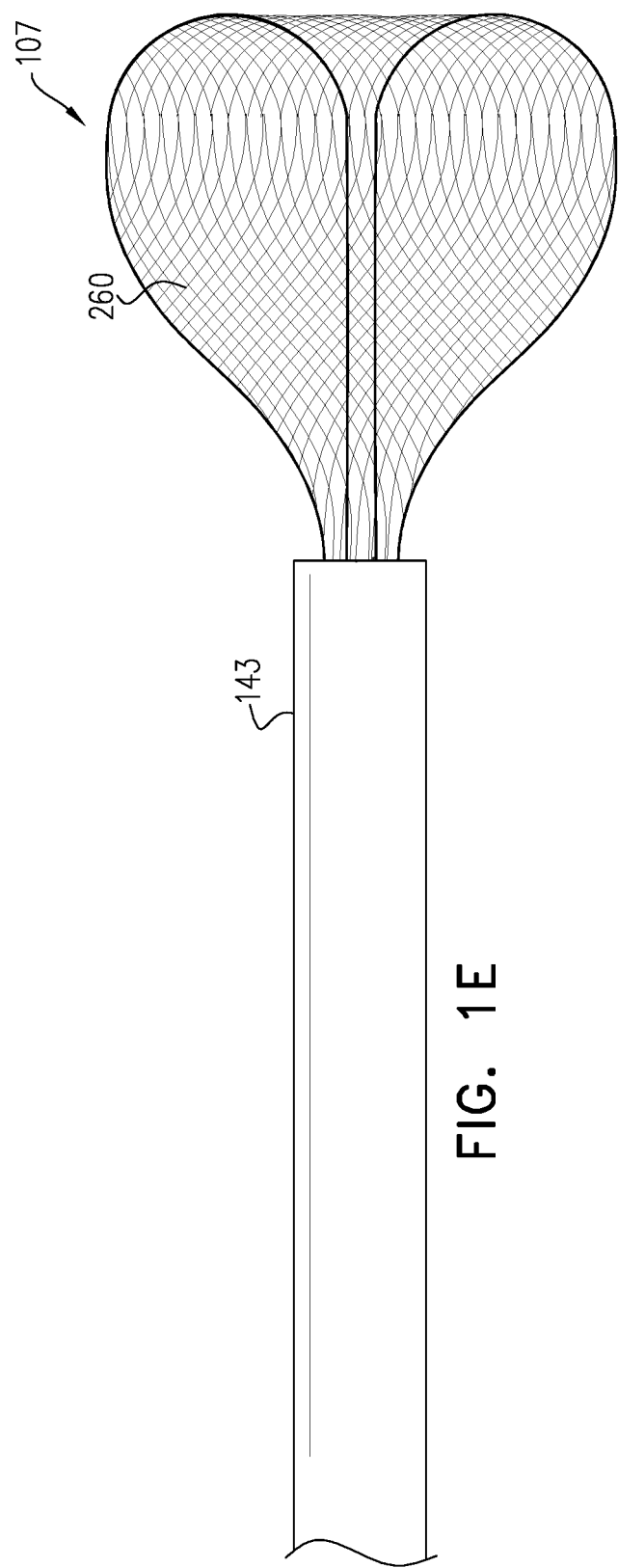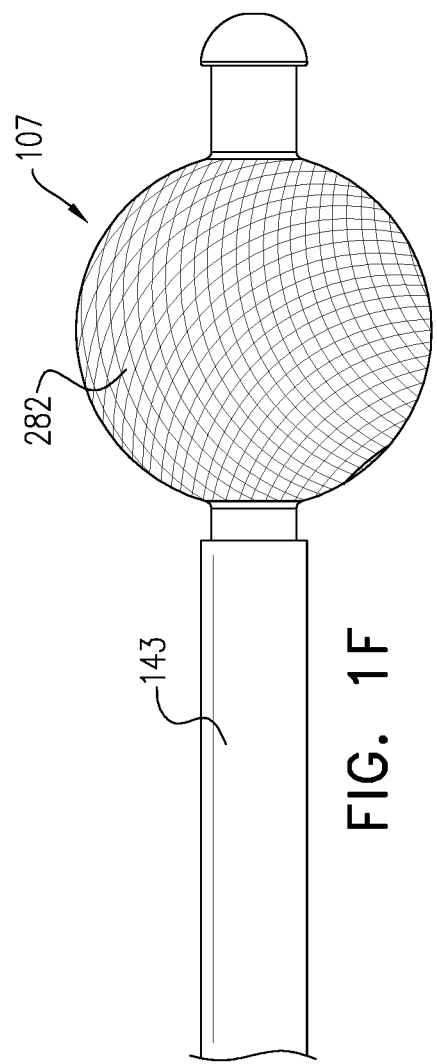

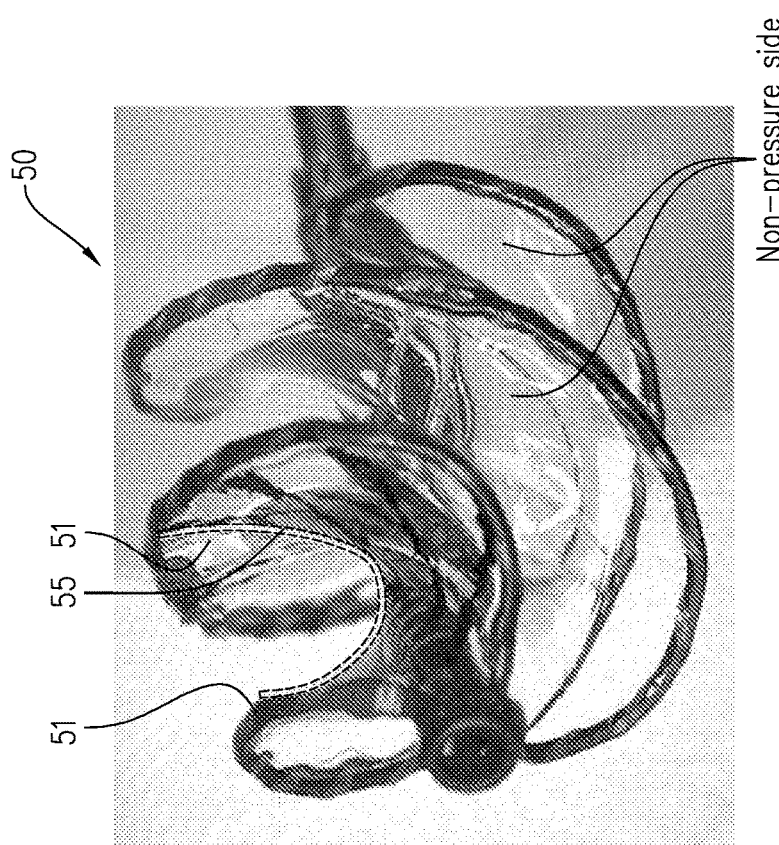
FIG. 3Gii
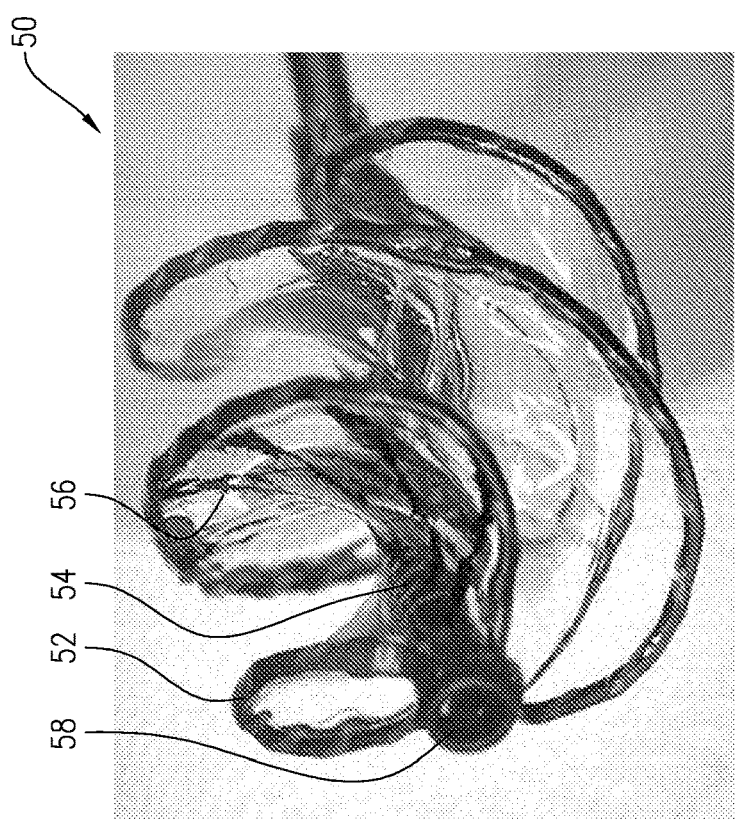
FIG. 3Gi

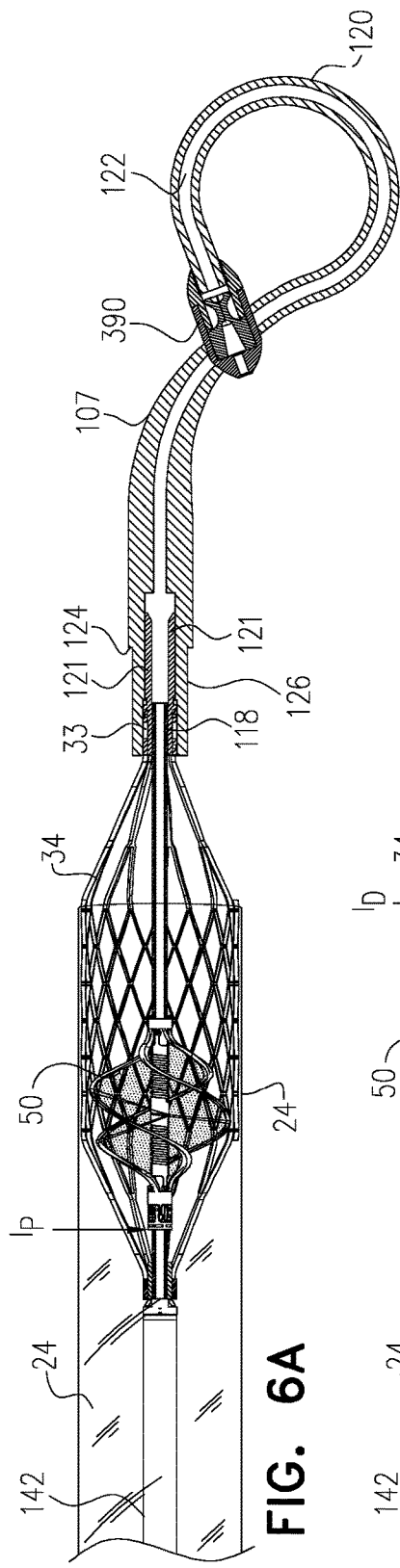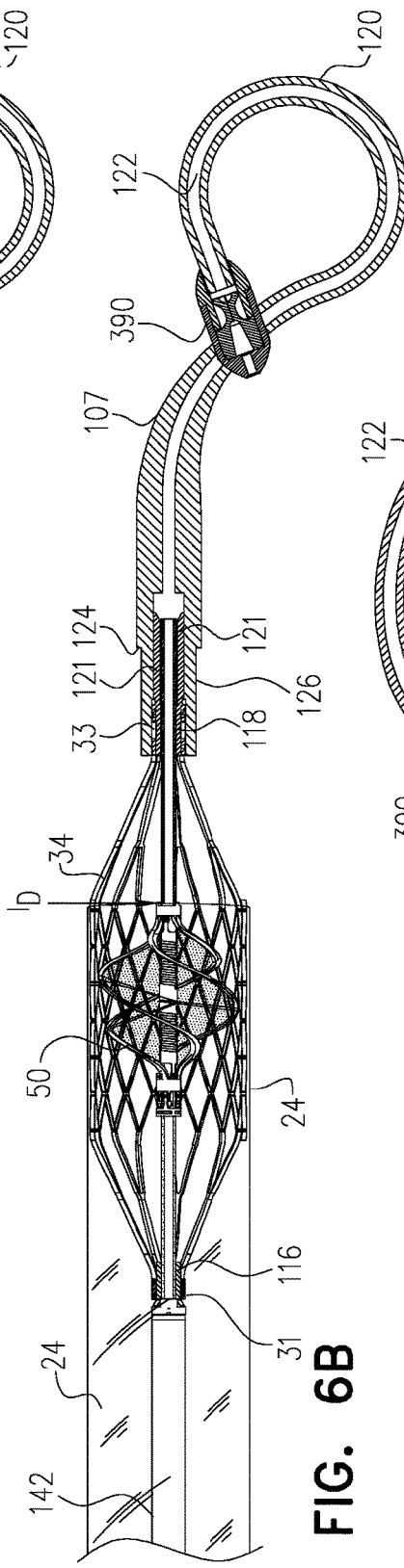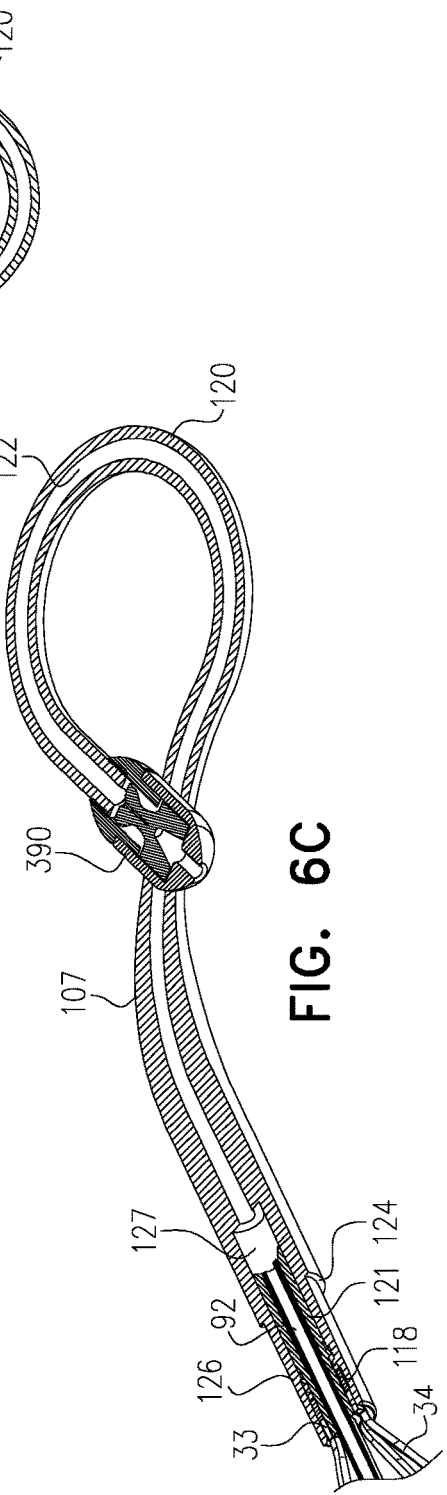

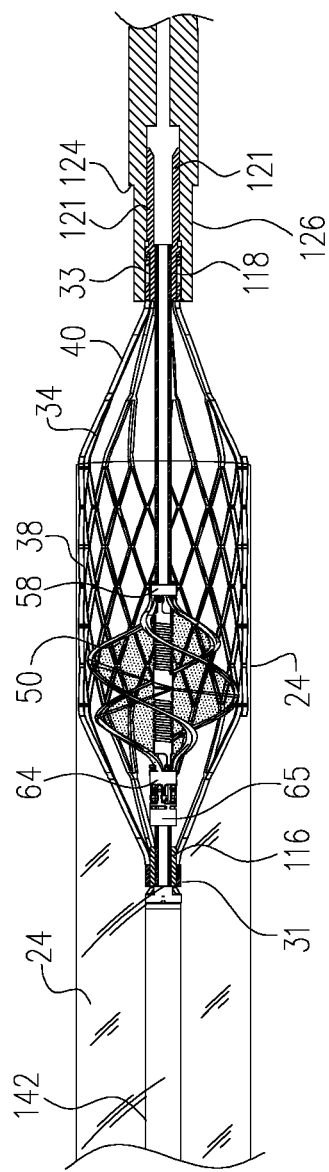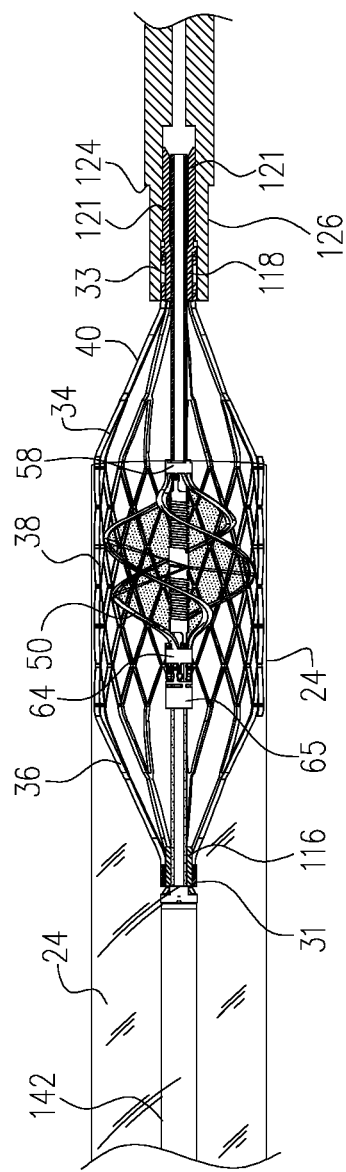

FIG. 7Bii

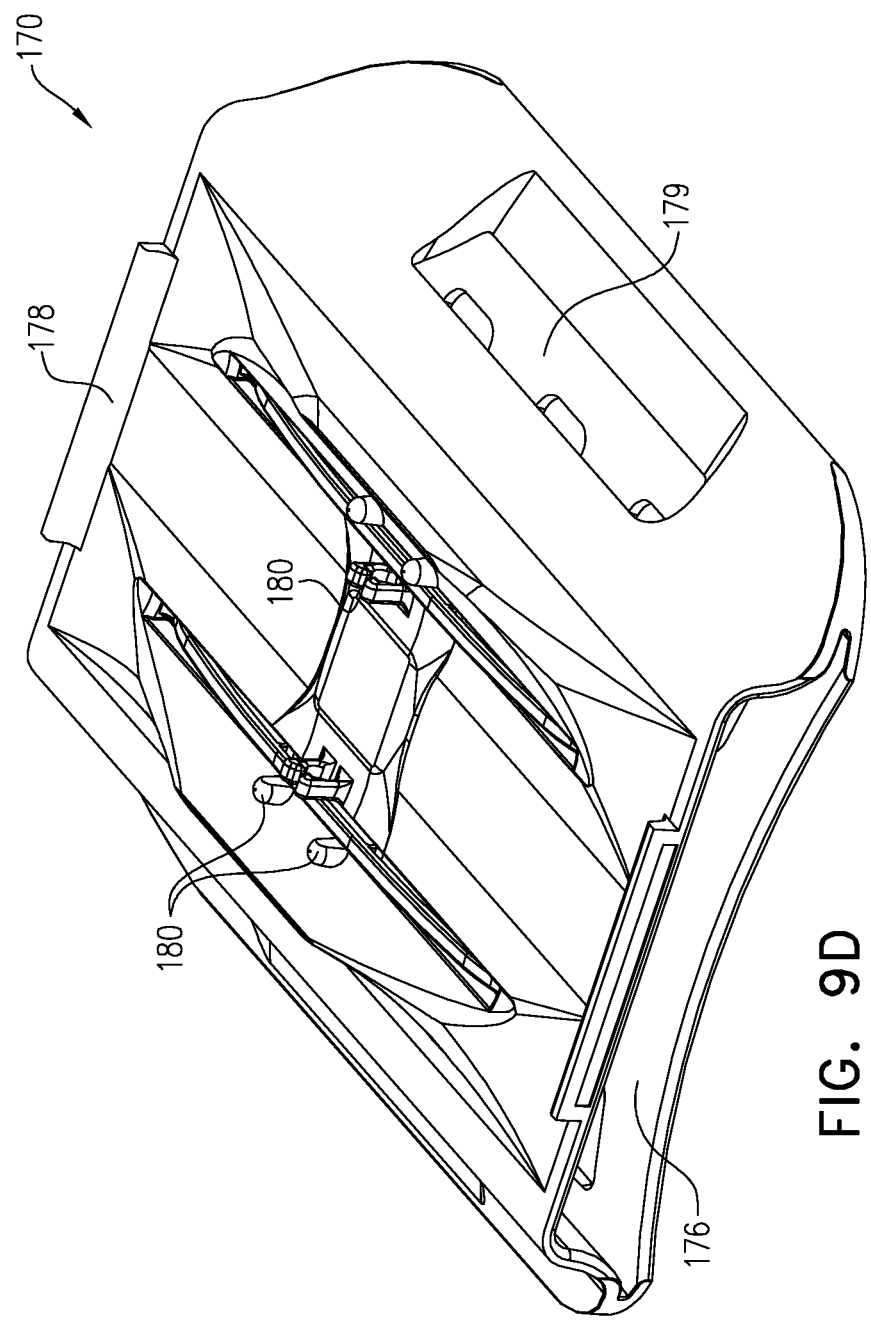

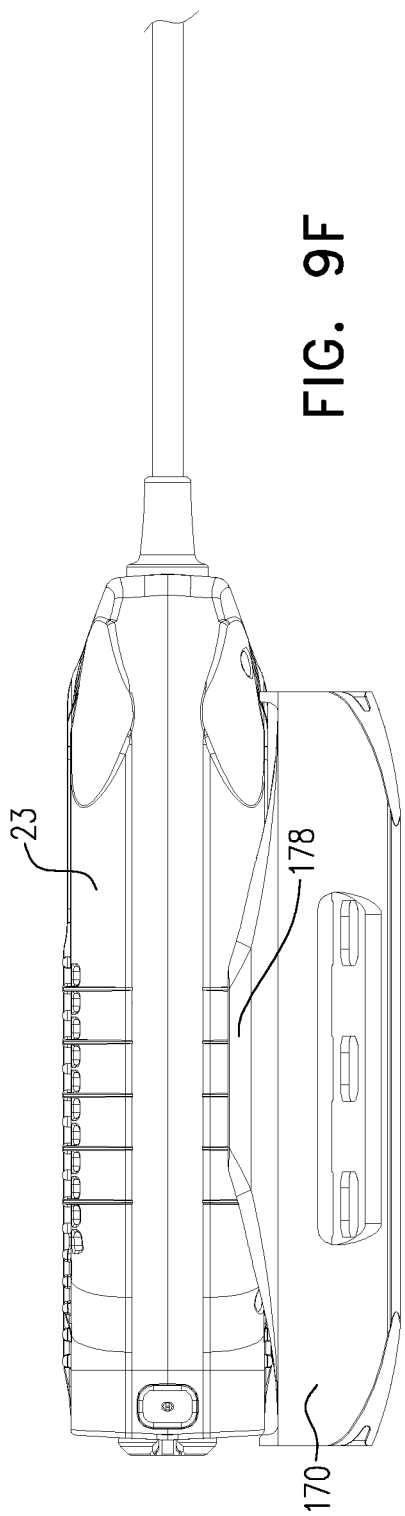
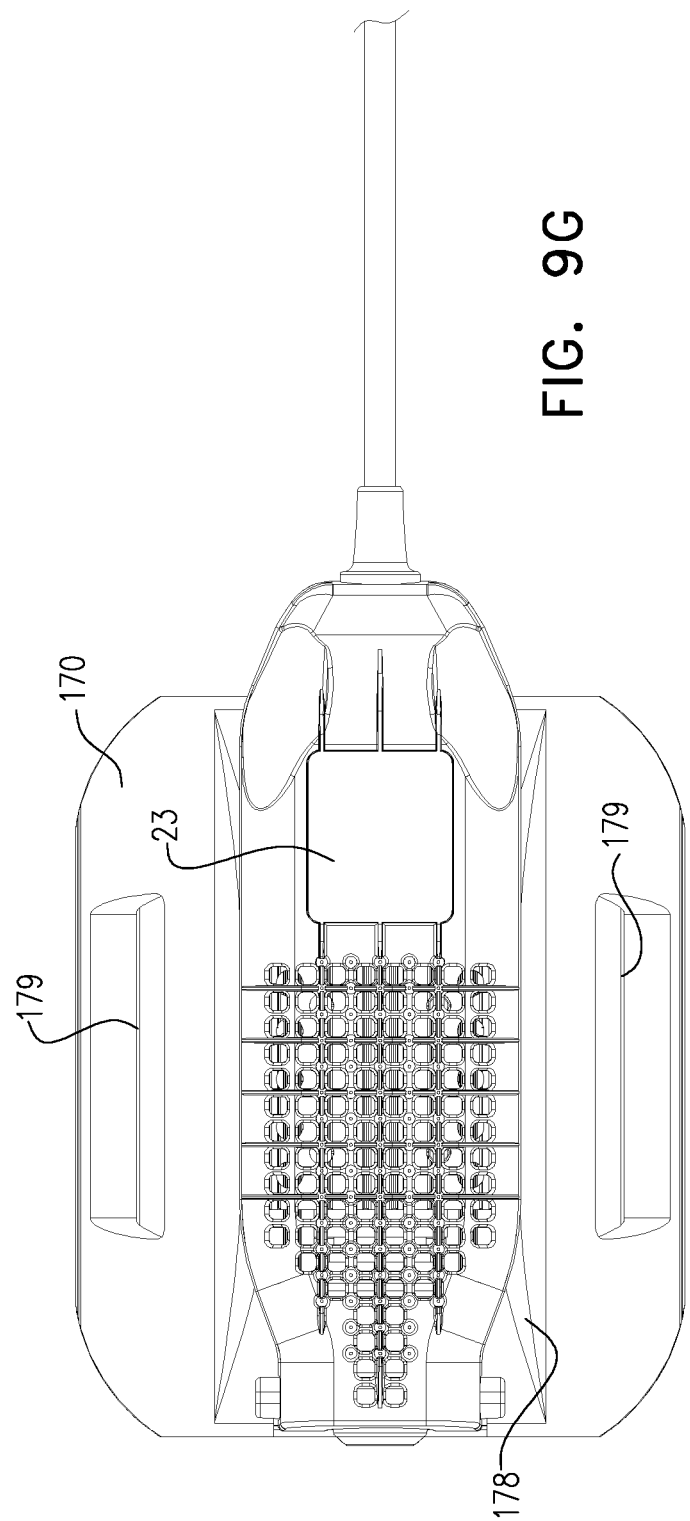

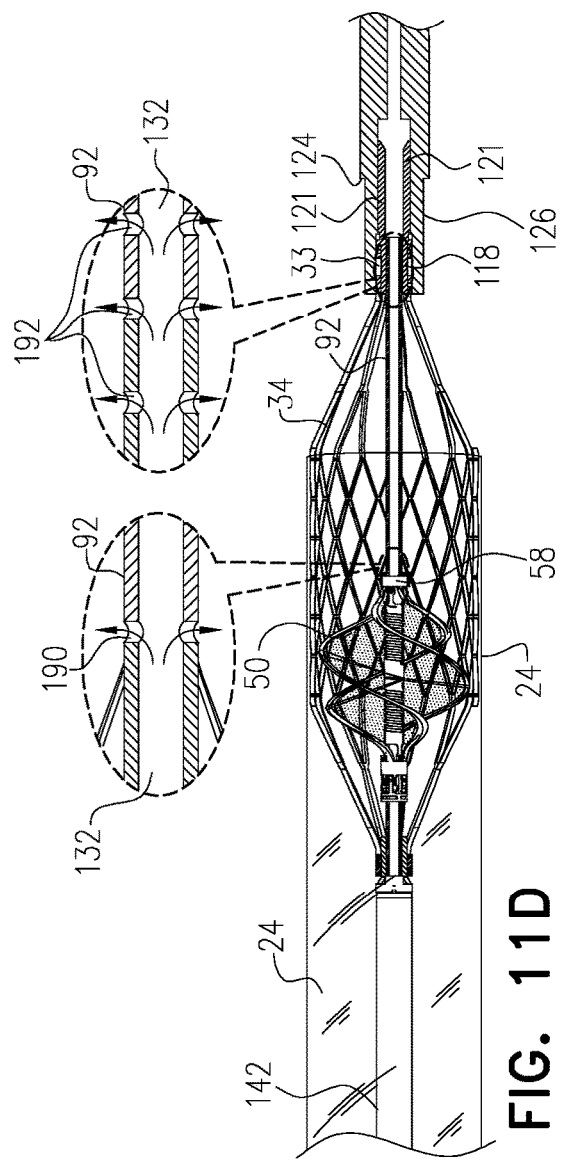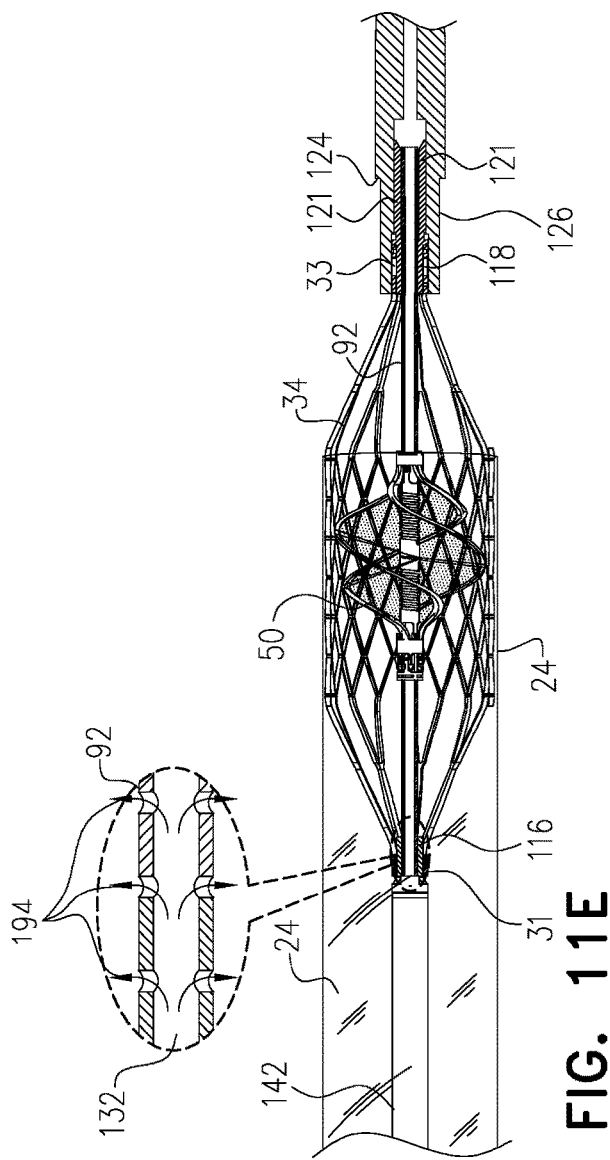

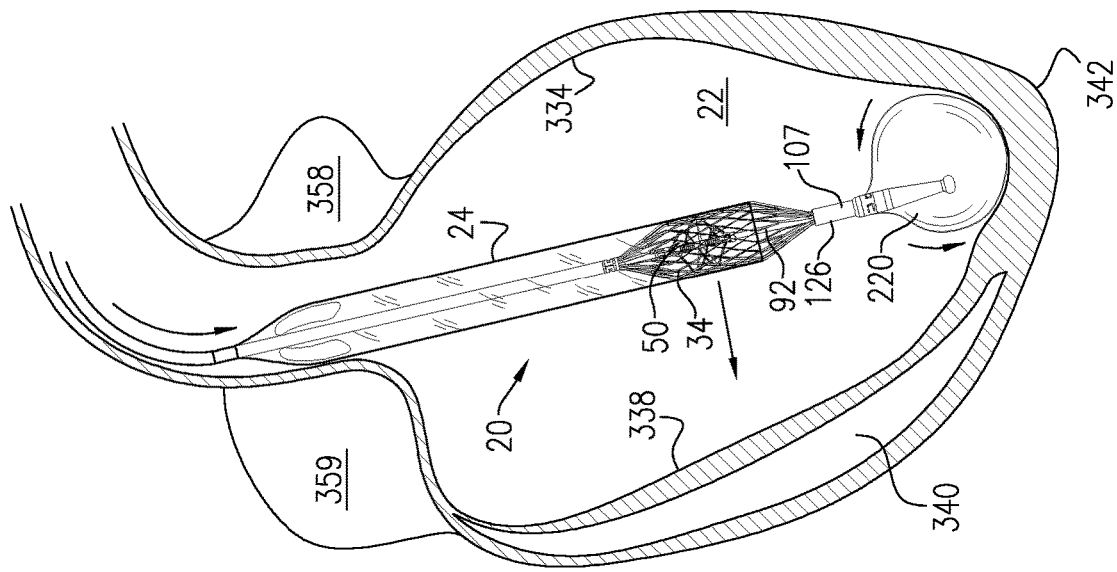
FIG. 17Aii
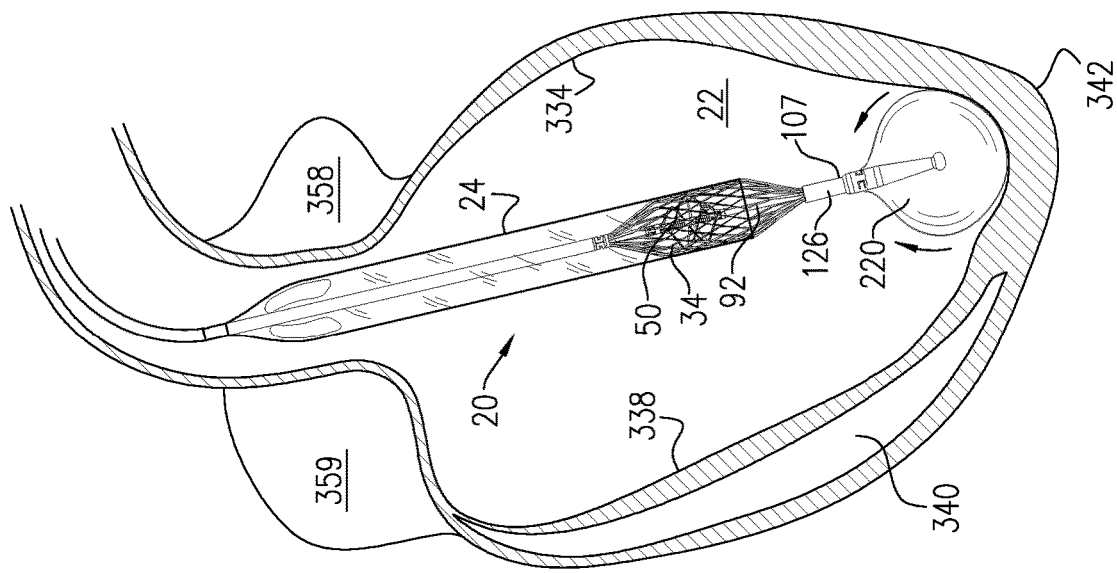
FIG. 17Ai

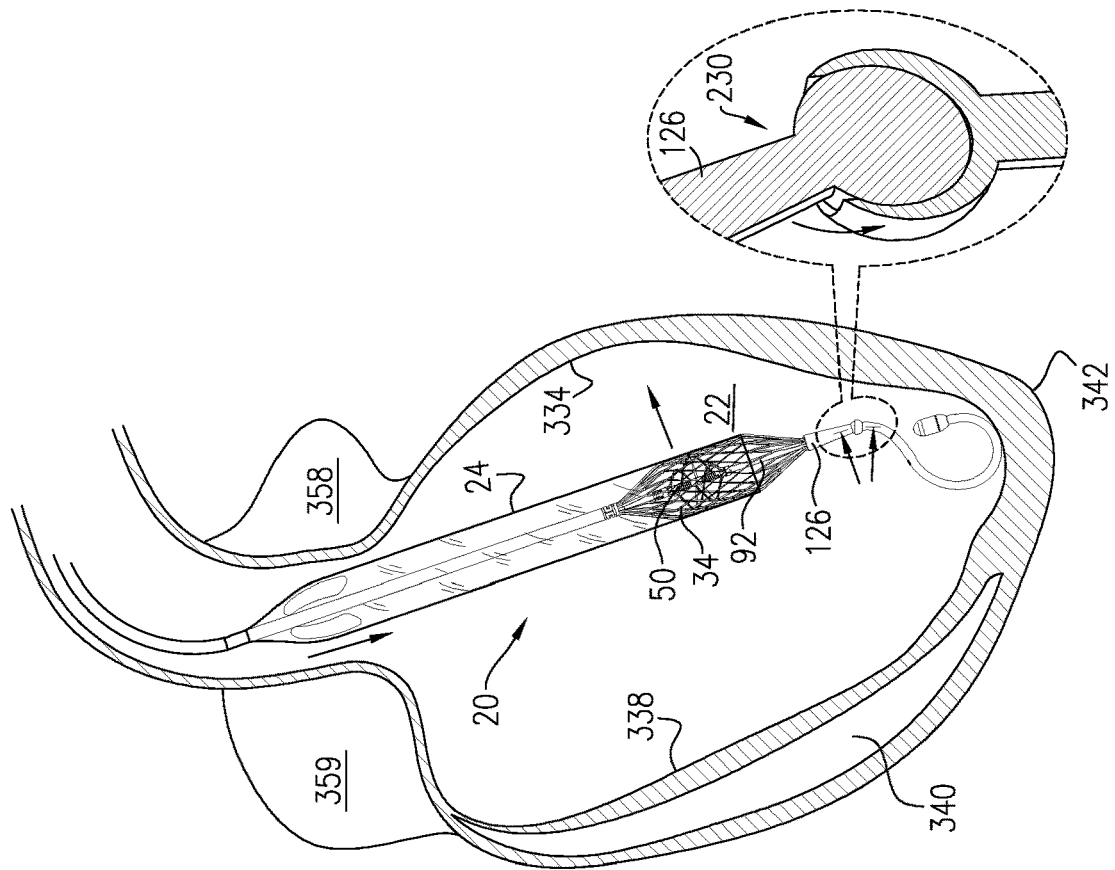
FIG. 17Bii
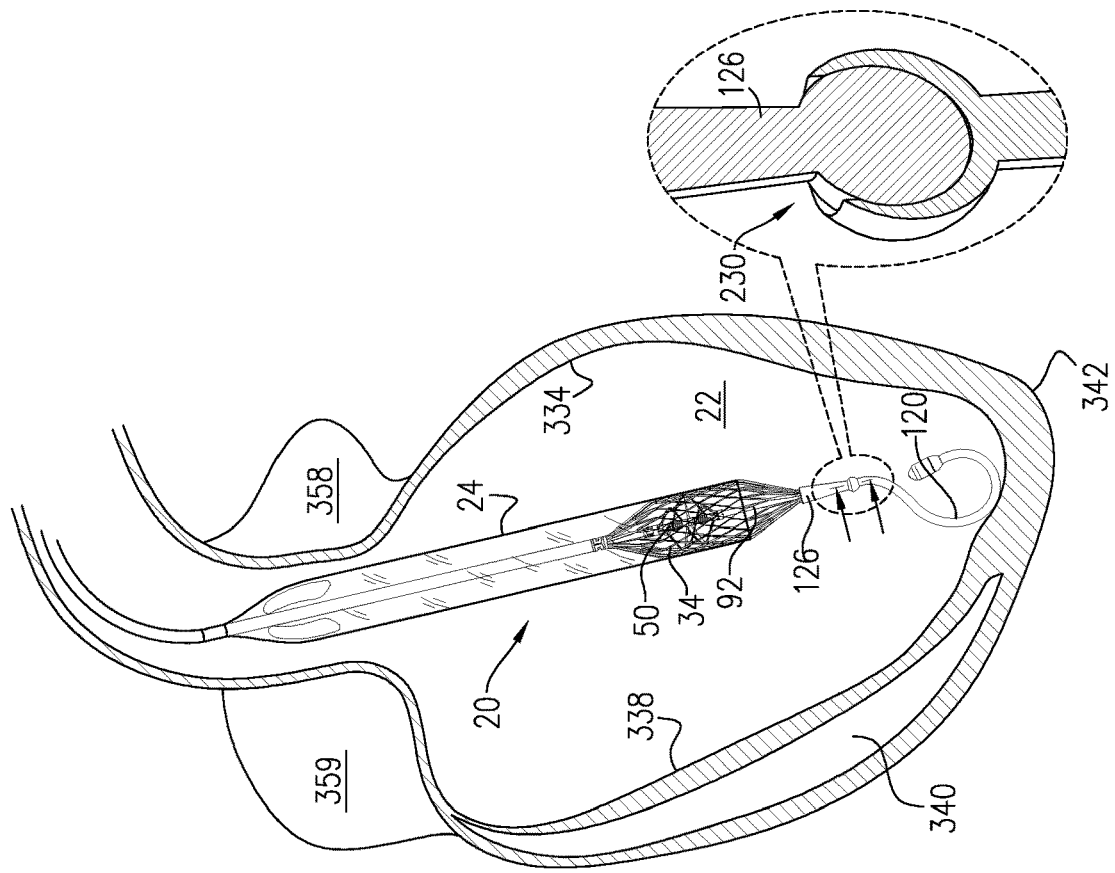
FIG. 17Bi

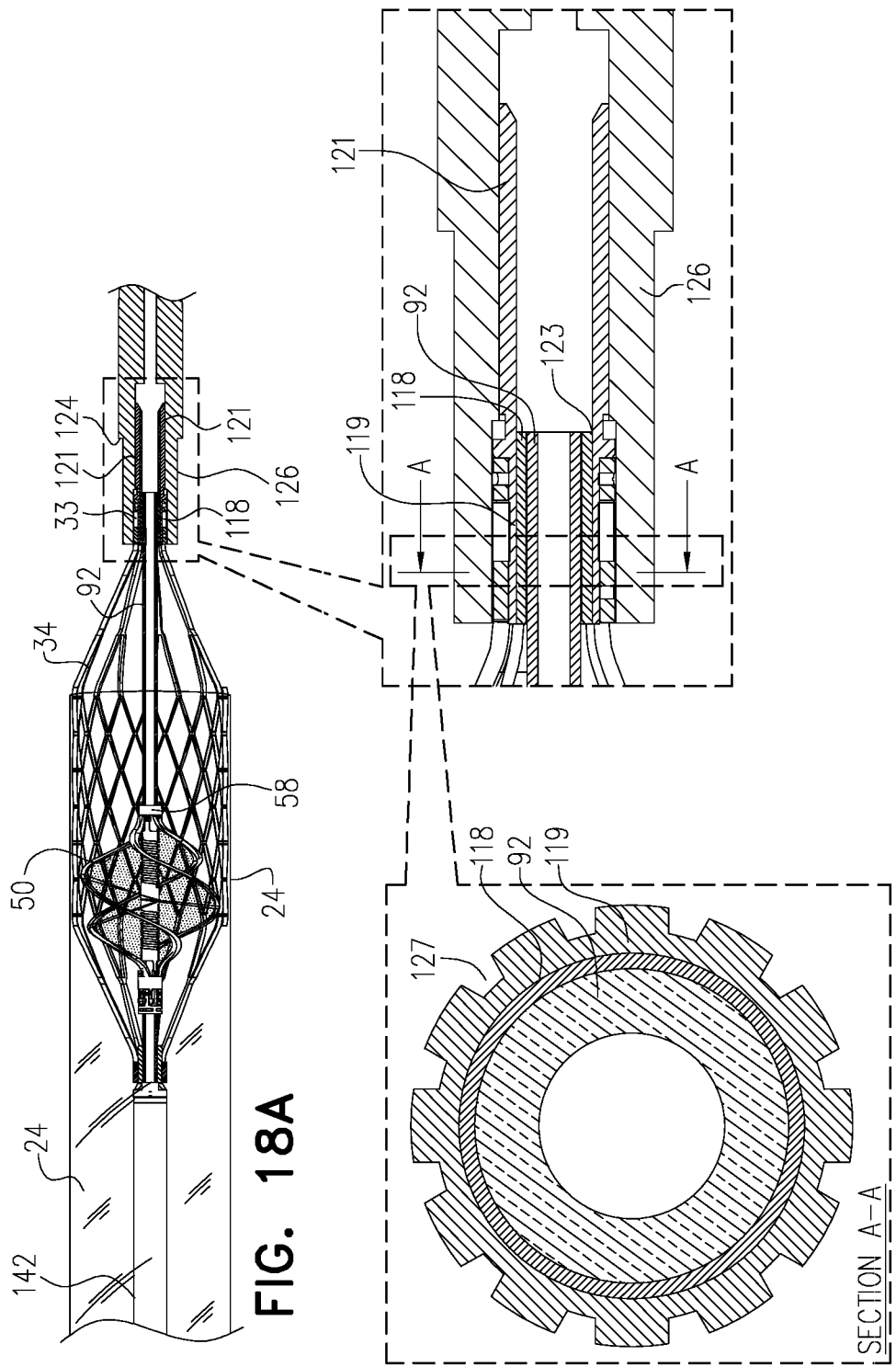

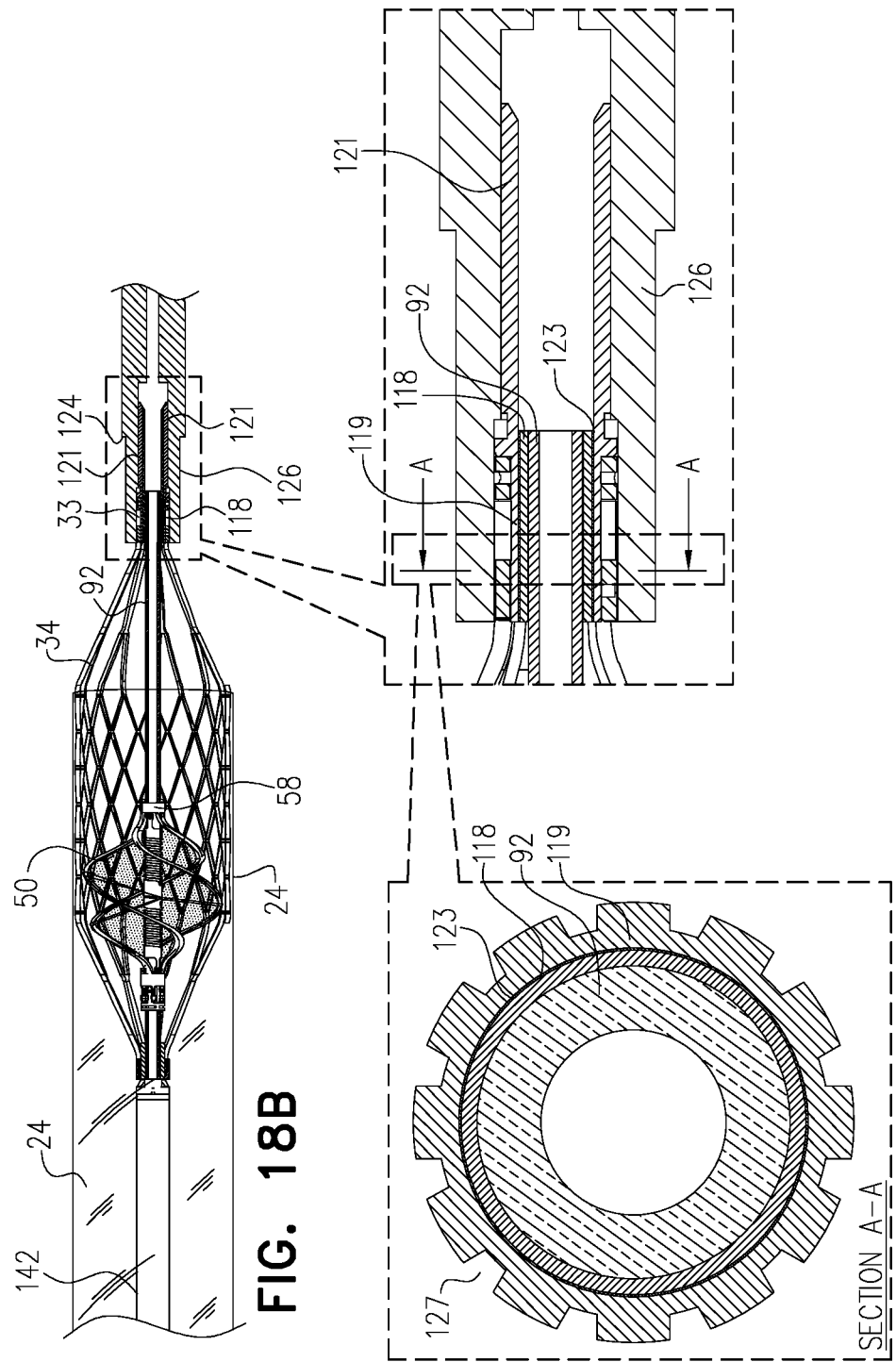

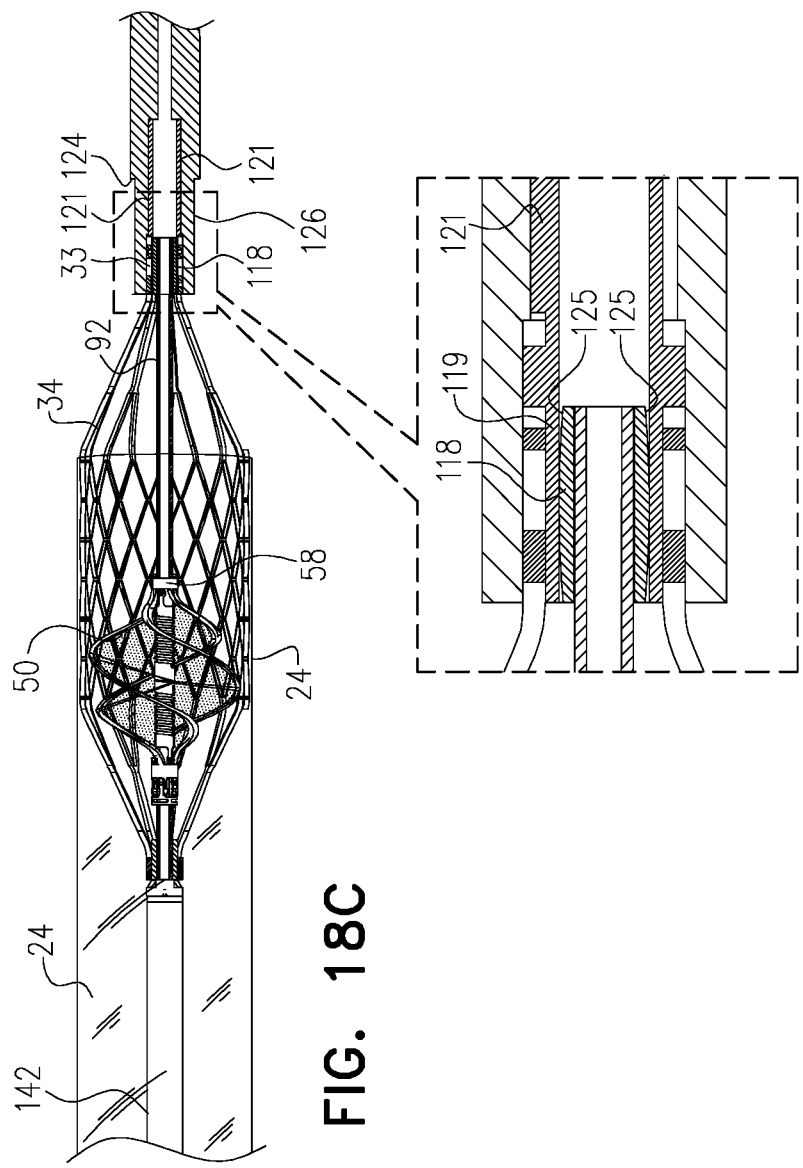

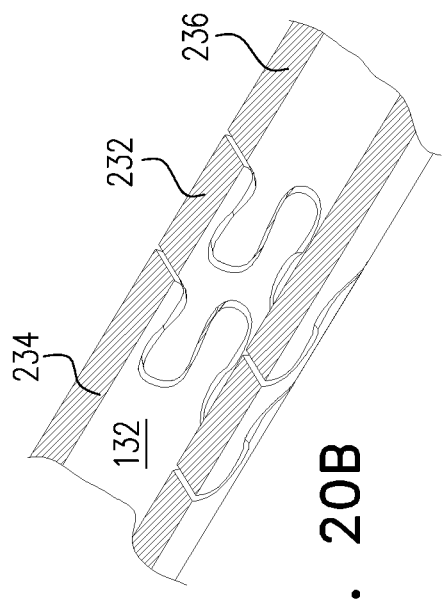
FIG. 20B
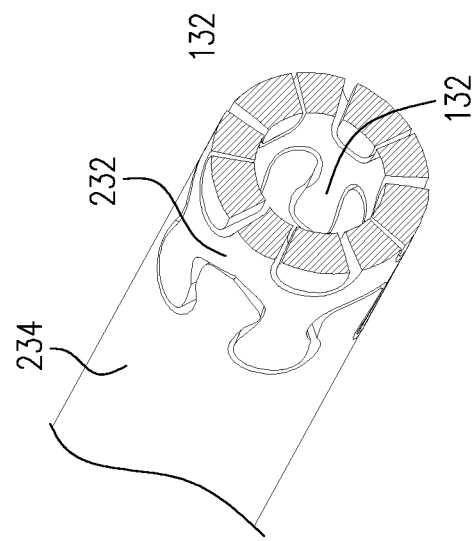
FIG. 20C
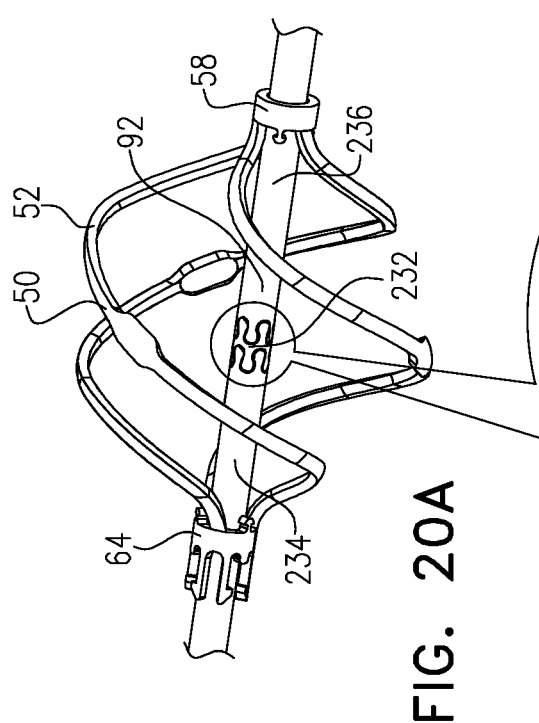
FIG. 20A
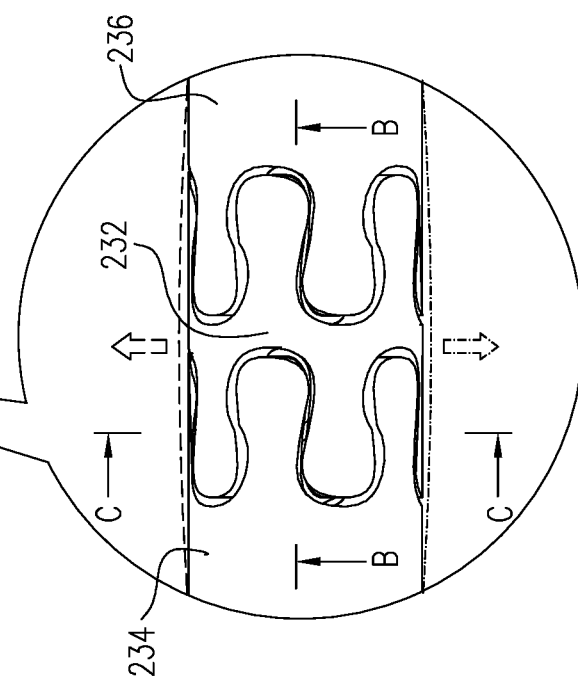

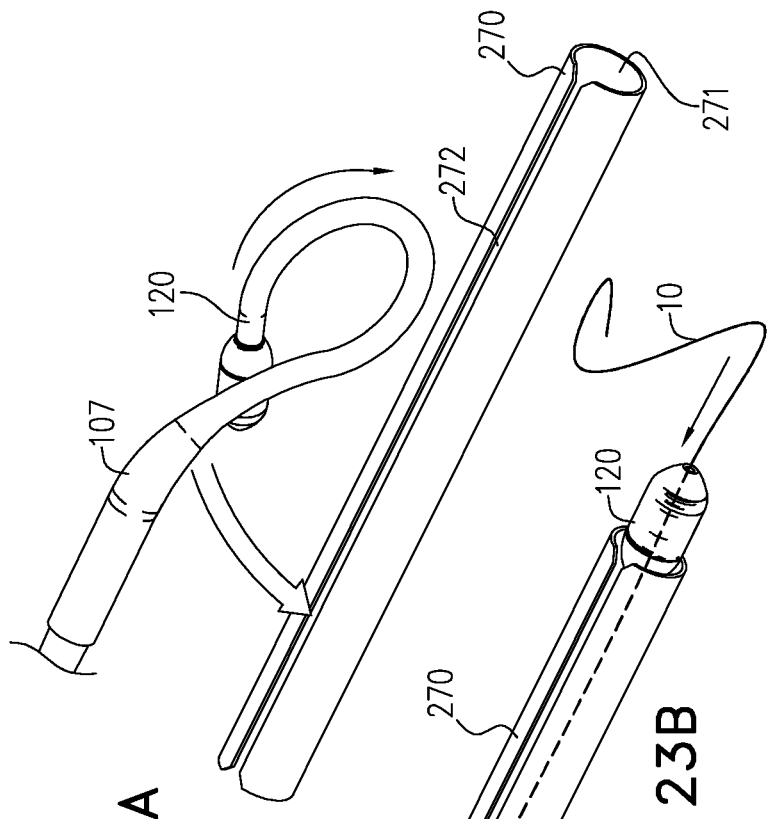
FIG. 23A
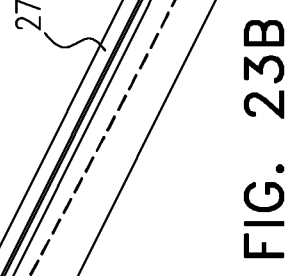
FIG. 23B
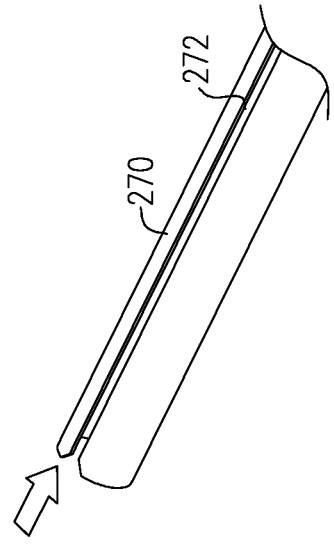
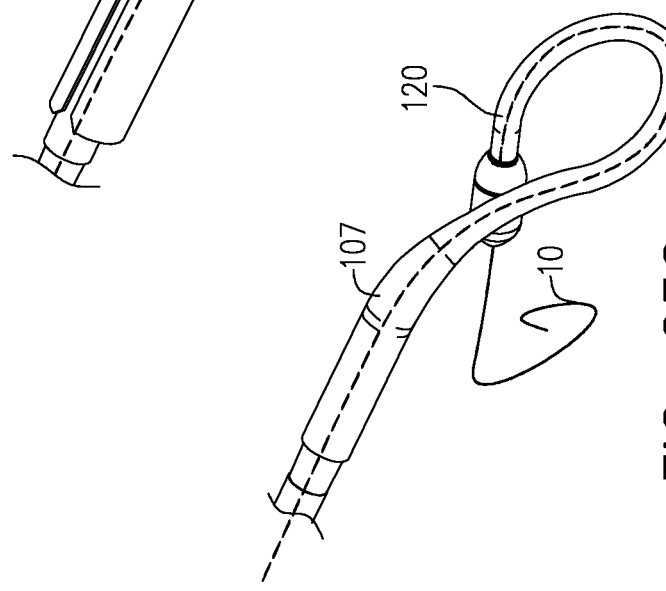
FIG. 23C

MANUFACTURE OF AN IMPELLER

CROSS-REFERENCES TO RELATED APPLICATIONS

The present application is a continuation of U.S. application Ser. No. 17/609,589 to Tuval filed Nov. 8, 2021, which is a US national phase application of PCT Application No. PCT/IB2021/052857 to Tuval (published as WO 21/205346), filed Apr. 6, 2021, which claims priority from:

U.S. Provisional Patent Application No. 63/006,122 to Tuval, entitled "Ventricular assist device," filed Apr. 7, 2020;

U.S. Provisional Patent Application No. 63/114,136 to Tuval, entitled "Ventricular assist device," filed Nov. 16, 2020; and U.S. Provisional Patent Application No. 63/129,983 to Tuval, entitled "Ventricular assist device," filed Dec. 23, 2020.

Each of the above-referenced U.S. Provisional applications is incorporated herein by reference.

FIELD OF EMBODIMENTS OF THE INVENTION

Some applications of the present invention generally relate to medical apparatus. Specifically, some applications of the present invention relate to a ventricular assist device and methods of use thereof.

BACKGROUND

Ventricular assist devices are mechanical circulatory support devices designed to assist and unload cardiac chambers in order to maintain or augment cardiac output. They are used in patients suffering from a failing heart and in patients at risk for deterioration of cardiac function during percutaneous coronary interventions. Most commonly, a left-ventricular assist device is applied to a defective heart in order to assist left-ventricular functioning. In some cases, a right-ventricular assist device is used in order to assist right-ventricular functioning. Such assist devices are either designed to be permanently implanted or mounted on a catheter for temporary placement.

SUMMARY OF EMBODIMENTS

In accordance with some applications of the present invention, a blood pump includes an impeller. The impeller includes proximal and distal bushings, and two or more helical elongate elements (and typically three helical elongate elements) that extend from the proximal bushing to the distal bushing. An axial structure (e.g., a cylindrical axial structure, such as a spring) is disposed inside of the two or more helical elongate elements, and along an axis around which the helical elongate elements wind. A film of material is supported between the helical elongate elements and the axial structure such that each of the helical elongate elements with the film of material coupled thereto defines a respective blade of the impeller. An impeller-overexpansion-prevention element is disposed within the impeller. The impeller-overexpansion-prevention element is a single integrated structure comprising a ring disposed around the axial structure, and a plurality of elongate elements. Each of the elongate elements extends from the ring to a respective helical elongate element and is coupled to the respective helical elongate element so as to prevent radial expansion of the impeller. Typically, the elongate elements are configured to not resist compression, and the elongate elements are configured to prevent the impeller from radially expanding by applying tensile force to the helical elongate elements.

For some applications, along at least a portion of the length of the impeller, as the film of material transitions from one impeller blade to an adjacent blade, the film of material forms a continuous U-shaped curved surface, with the U-shaped curvature of the film of material being substantially unbroken at the axial structure. For some applications, when viewed from a distal end of the impeller, the pressure side of each of the blades of the impeller (i.e., the side that is configured to push the blood during operation of the impeller), is convex in a distal region of the impeller and is concave in a proximal region of the impeller. Typically, the pressure side of each of the blades of the impeller transforms to being substantially radially oriented in a region of the elongate element within the impeller blade.

For some applications, an impeller is manufactured by forming a structure having first and second bushings at proximal and distal ends of the structure, the first and second bushings being connected to one another by at least one elongate element. The at least one elongate element is made to radially expand and form at least one helical elongate element, at least partially by axially compressing the structure. The at least one helical elongate element is coated with a coupling agent, the coupling agent being configured to enhance bonding between the helical elongate element and an elastomeric layer. The coated helical elongate element is then coated with the elastomeric layer. Subsequently, an elastomeric film is coupled to the at least one helical elongate element, such that the at least one helical elongate element with the elastomeric film coupled thereto defines a blade of the impeller. For example, the helical elongate element may be dipped into an elastomeric material from which the elastomeric layer is made. For some applications, the elastomeric film comprises an elastic material having an ultimate elongation of more than 300 percent, having a melt flow index of at least 4, and/or having an ultimate tensile strength of more than 6000 psi.

For some applications, the impeller is driven to rotate by one or more drive magnets (which are coupled to a motor) driving one or more driven magnets to rotate, with the driven magnet being coupled to the impeller via a drive cable. In accordance with some applications of the invention, a magnetic phase difference between the driven magnet(s) and the drive magnet(s) is measured, and a physiological parameter of the subject is determined, at least partially in response thereto. For example, at least partially based upon variations in the phase difference, a computer processor may determine the difference between a subject's left-ventricular pressure and the subject's aortic pressure, the subject's left ventricular pressure, an event in the subject's cardiac cycle, the subject's cardiac afterload, and/or a different physiological parameter. For some applications, the physiological parameter is determined based upon the phase difference measurements in combination with one or more additional measurements, such as magnetic flux amplitude measurements, power consumed by the motor, and/or current consumed by the motor. Typically, such measurements are combined in a mathematical model, such as a linear regression model, and/or a space state model.

For some applications of the present invention, during operation of a ventricular assist device that functions as a blood pump, the subject's arterial pulsatility is measured and a parameter is derived from the subject's arterial pulsatility. Typically, as the rotation rate of the impeller increases, the flow rate that is generated by the blood pump increases.

Typically, flow that is generated by the blood pump is non-pulsatile, since the blood pump is a continuous-flow blood pump rather than a pulsatile blood pump. As such, it is typically the case that are the rotation rate of the impeller increases and the flow rate that is generated by the blood pump increases, the subject's arterial pulsatility decreases. For some applications, the subject's arterial pulsatility is measured as the rotation rate of the impeller changes. Based upon the aforementioned measurements, a relationship between the arterial pulsatility and the impeller rotation rate and/or the pump flow rate is derived. For some applications, based upon the aforementioned relationship, the subject's native cardiac output is derived. For some such applications, the relationship between the subject's arterial pulsatility and the pump flow rate is extrapolated to determine what the pump flow rate would be when the subject's arterial pulsatility reaches zero. It is hypothesized that, at this value, the blood pump is replacing the native function of the heart and that the flow rate that is generated by the pump at this value provides an approximation of the subject's native cardiac output.

There is therefore provided, in accordance with some applications of the present invention, apparatus including:
  a blood pump configured to be placed inside a body of subject, the blood pump including:
    an impeller including:
      proximal and distal bushings;
      two or more helical elongate elements that extend from the proximal bushing to the distal bushing;
      an axial structure that is disposed inside of the two or more helical elongate elements, and along an axis around which the helical elongate elements wind; and
      a film of material supported between the helical elongate elements and the axial structure such that each of the helical elongate elements with the film of material coupled thereto defines a respective blade of the impeller; and
    an impeller-overexpansion-prevention element, the impeller-overexpansion-prevention element being a single integrated structure including a ring disposed around the axial structure, and a plurality of elongate elements,
    each of the elongate elements extending from the ring to a respective helical elongate element and being coupled to the respective helical elongate element so as to prevent radial expansion of the impeller.

In some applications, the impeller includes three helical elongate elements, such that the three helical elongate elements with the film of material coupled thereto defines three blades of the impeller, and a respective elongate element extends from the ring to each of the three helical elongate elements, such that there is a respective elongate element within each of the three blades of the impeller.

In some applications, the elongate elements are configured to not resist compression, and the elongate elements are configured to prevent the impeller from radially expanding by applying tensile force to the helical elongate elements.

In some applications, along at least a portion of the length of the impeller, as the film of material transitions from one impeller blade to an adjacent blade, the film of material forms a continuous U-shaped curved surface, with the U-shaped curvature of the film of material being substantially unbroken at the axial structure.

In some applications, when viewed from a distal end of the impeller, a pressure side of each of the blades of the impeller, which is configured to push the blood during operation of the impeller, is convex in a distal region of the impeller and is concave in a proximal region of the impeller. In some applications, the pressure side of each of the blades of the impeller transforms to being substantially radially oriented in a region of the elongate element within the impeller blade.

In some applications, the helical elongate elements are coated with a coupling agent that is configured to enhance bonding between the helical elongate element and the film of material. In some applications, the film of material includes an elastomeric material, and the coupling agent includes at least two functional groups that are configured to bond respectively with the helical elongate elements and with the elastomeric material. In some applications, the coupling agent includes a silane compound.

In some applications, the apparatus further includes a layer of an elastomer disposed between the film of material and the coupling agent. In some applications, the layer of the elastomer is configured to round the helical elongate elements. In some applications, the film of material is made of the elastomer. In some applications, the elastomer includes a polycarbonate-based thermoplastic polyurethane.

In some applications, the axial structure includes a spring. In some applications, the spring includes a tube at an intermediate location along a length of the spring and the ring is disposed around the tube.

There is therefore provided, in accordance with some applications of the present invention, a method, including:
  manufacturing an impeller by:
    forming a structure having first and second bushings at proximal and distal ends of the structure, the first and second bushings being connected to one another by at least one elongate element;
    causing the at least one elongate element to radially expand and form at least one helical elongate element, at least partially by axially compressing the structure;
    coating the at least one helical elongate element with a coupling agent, the coupling agent configured to enhance bonding between the helical elongate element and an elastomeric layer;
    coating the coated helical elongate element with the elastomeric layer; and
    subsequently, coupling an elastomeric film to the at least one helical elongate element, such that the at least one helical elongate element with the elastomeric film coupled thereto defines a blade of the impeller.

In some applications, coupling the elastomeric film to the at least one helical elongate element, such that the at least one helical elongate element with the elastomeric film coupled thereto defines a blade of the impeller includes dipping the helical elongate element into an elastomeric material from which the elastomeric film is made.

In some applications, the elastomeric film includes an elastic material having an ultimate elongation of more than 300 percent. In some applications, the elastomeric film includes an elastic material having a melt flow index of at least 4. In some applications, the elastomeric film includes an elastic material having an ultimate tensile strength of more than 6000 psi.

In some applications, coating the at least one helical elongate element with the coupling agent includes coating the at least one helical elongate element with a silane compound containing a first functional group which is configured to bond with the helical elongate element, and a second functional group which is configured to bond with the elastomeric layer.

In some applications, the elastomeric layer is made of a given elastomeric material and the elastomeric film is made of the given elastomeric material. In some applications, the elastomeric layer is made of a first elastomeric material and the elastomeric film is made of a second elastomeric material that is different from the first elastomeric material.

In some applications, coating the coated helical elongate element with the elastomeric layer includes spraying an elastomer onto the coated helical elongate element. In some applications, coating the coated helical elongate element with the elastomeric layer includes at least partially rounding the coated helical elongate element.

In some applications, coating the coated helical elongate element with the elastomeric layer includes coating the coated helical elongate element with the elastomeric layer within a given time period of coating the at least one helical elongate element with the coupling agent. In some applications, coating the coated helical elongate element with the elastomeric layer further includes spraying additional elastomeric material onto the coated helical elongate element subsequent to coating the coated helical elongate element with the elastomeric layer within the given time period of coating the at least one helical elongate element with the coupling agent.

There is further provided, in accordance with some applications of the present invention, apparatus including:
 a ventricular assist device including:
  an impeller configured to be placed inside a left ventricle of a subject;
  a motor;
  at least one driving magnet coupled to the motor and configured to be rotated by the motor;
  at least one driven magnet magnetically coupled to the driving magnet and being configured to be rotated by the driving magnet;
  a drive cable extending form the driven magnet and configured to impart rotational motion from the driven magnet to the impeller;
  a set of sensors configured to detect a magnetic phase difference between the driven magnet and the drive magnet; and
  a computer processor configured to receive the detected magnetic phase difference and to determine a physiological parameter of the subject, at least partially in response thereto.

In some applications, the set of sensors is additionally configured to measure a magnetic flux amplitude signal, and computer processor is configured to determine the physiological parameter of the subject at least partially based upon a combination of the magnetic flux amplitude signal and the detected magnetic phase difference.

In some applications, the computer processor is configured to determine a pressure difference between the subject's left ventricle and an aorta of the subject at least partially in response to the magnetic phase difference between the driven magnet and the drive magnet. In some applications, the computer processor is configured to determine left ventricular pressure of the subject at least partially in response to the magnetic phase difference between the driven magnet and the drive magnet. In some applications, the computer processor is configured to determine an event in a cardiac cycle of the subject at least partially in response to the magnetic phase difference between the driven magnet and the drive magnet.

In some applications, the set of sensors includes a first magnetometer configured to measure magnetic phase of the driven magnet, and a second magnetometer configured to measure magnetic phase of the driven magnet. In some applications, the second magnetometer is configured to measure the magnetic phase of the driven magnet by measuring a magnetic phase of the motor.

In some applications, the computer processor is configured to receive a signal indicative of current consumption by the motor and is configured to determine the physiological parameter of the subject at least partially based upon a combination of the current consumption by the motor and the detected magnetic phase difference. In some applications, the set of sensors is additionally configured to measure a magnetic flux amplitude signal, and computer processor is configured to determine the physiological parameter of the subject at least partially based upon a combination of the current consumption by the motor, the magnetic flux amplitude signal, and the detected magnetic phase difference.

There is further provided, in accordance with some applications of the present invention, apparatus including:
 a ventricular assist device including an impeller configured to be placed inside a left ventricle of a subject and to pump blood from the subject's left ventricle to an aorta of the subject;
 a blood pressure sensor configured to measure aortic pressure of the subject;
 a computer processor configured to:
  derive arterial pulsatility of the subject, based upon the measured aortic pressure; and
  estimate native cardiac output of the subject at least partially based upon the arterial pulsatility.

There is further provided, in accordance with some applications of the present invention, apparatus including:
 a left-ventricular assist device configured to assist left-ventricular functioning of a subject, the left-ventricular assist device including:
  an impeller;
  a frame disposed around the impeller;
  a rigid axial shaft extending from a proximal end of the frame to a distal end of the frame, the impeller being coupled to the rigid axial shaft, and the rigid axial shaft including a proximal portion and a distal portion which are coupled to each other via a joint, the proximal portion and a distal portion being configured to flex with respect to each other via the joint.

For some applications, the frame has a length of more than 25 mm.

There is further provided, in accordance with some applications of the present invention, apparatus including:
 an impeller including:
  proximal and distal bushings;
  a plurality of helical elongate elements;
  an axial structure disposed inside of the helical elongate elements and along an axis around which the helical elongate elements wind; and
  a film of elastomeric material supported between the helical elongate elements and the axial structure, such that each of the helical elongate elements with the film of elastomeric material coupled thereto defines a respective blade of the impeller,
 along at least a portion of the length of the impeller, as the film of elastomeric material transitions from one impeller blade to an adjacent blade, the elastomeric film forms a continuous U-shaped curvature, with the U-shaped curvature of the elastomeric film of material being substantially unbroken at the axial structure.

In some applications, the axial structure includes a cylindrical axial structure. In some applications, the cylindrical axial structure includes a spring.

There is further provided, in accordance with some applications of the present invention, a method including:
  inserting a ventricular assist device through an arterial incision and into a subject's vasculature via an introducer sheath, the ventricular assist device including a delivery catheter, a drive cable and an outer tube surrounding the drive cable;
  removing the introducer sheath while the ventricular assist device remains within subject's vasculature; and
  maintaining sterility of the arterial incision, while permitting movement of the outer tube relative to the delivery catheter, using a sterile sleeve disposed between the outer tube and the delivery catheter.

There is further provided, in accordance with some applications of the present invention, apparatus including:
  a blood pump including:
    an axial shaft;
    an impeller disposed on the axial shaft;
    a motor unit including a motor that is configured to drive the impeller to pump blood from a distal end of the impeller to a proximal end of the impeller, by rotating the impeller in a given direction of rotation;
    a drive cable configured to extend from to the motor unit to the axial shaft, the drive cable being configured to impart rotational motion from the motor to the impeller by rotating,
      at least a portion of the drive cable including two or more layers, each of which includes a plurality of wires,
      the plurality of wires of each of the two or more layers being disposed in coiled configurations that are such that, in response to the drive cable rotating in the given direction of rotation, the wires of each of the layers at least partially unwind, such that the portion of the drive cable shortens axially, and
      the drive cable being maintained in a state of pretension, such that the drive cable is stretched relative to its rest state, even when the impeller is at rest.

There is further provided, in accordance with some applications of the present invention, apparatus including:
  a blood pump including:
    an axial shaft;
    an impeller disposed on the axial shaft;
    a motor unit including a motor that is configured to drive the impeller to pump blood from a distal end of the impeller to a proximal end of the impeller, by rotating the impeller in a counterclockwise direction when viewed from the proximal end of the impeller to the distal end of the impeller;
    a drive cable configured to extend from to the motor unit to the axial shaft, the drive cable being configured to impart rotational motion from the motor to the impeller by rotating,
      at least a portion of the drive cable including two or more layers, each of which includes a plurality of wires,
      the plurality of wires of each of the two or more layers being disposed in a left-handed lay coiled configuration.

There is further provided, in accordance with some applications of the present invention, apparatus including:
  a blood pump including:
    an axial shaft;
    an impeller disposed on the axial shaft;
    a motor unit including a motor that is configured to drive the impeller to pump blood from a distal end of the impeller to a proximal end of the impeller, by rotating the impeller in a clockwise direction when viewed from the proximal end of the impeller to the distal end of the impeller;
    a drive cable configured to extend from to the motor unit to the axial shaft, the drive cable being configured to impart rotational motion from the motor to the impeller by rotating,
      at least a portion of the drive cable including two or more layers, each of which includes a plurality of wires, the plurality of wires of each of the two or more layers being disposed in a right-handed lay coiled configuration.

There is further provided, in accordance with some applications of the present invention, apparatus including:
  a blood pump including:
    an axial shaft;
    an impeller disposed on the axial shaft;
    a motor unit including a motor that is configured to drive the impeller to pump blood from a distal end of the impeller to a proximal end of the impeller, by rotating the impeller in a given direction of rotation;
    a drive cable configured to extend from the motor unit to the axial shaft, the drive cable being configured to impart rotational motion from the motor to the impeller by rotating,
      at least a portion of the drive cable including an inner layer and an outer layer which are coaxial with each other, and each of which includes a plurality of wires disposed in the coiled configuration,
      a ratio of a number of wires within the outer layer to a number of wires within the inner layer is between 2:3 and 2:5, and a ratio of a diameter of the wires within the outer layer to a diameter of the wires within the inner layer is between 3:2 and 5:2.

There is further provided, in accordance with some applications of the present invention, apparatus including:
  a blood pump including:
    an axial shaft;
    an impeller disposed on the axial shaft;
    a motor unit including a motor that is configured to drive the impeller to pump blood from a distal end of the impeller to a proximal end of the impeller, by rotating the impeller in a given direction of rotation;
    a drive cable configured to extend from the motor unit to the axial shaft, the drive cable being configured to impart rotational motion from the motor to the impeller by rotating; and
    a drive-cable bearing tube within which the drive cable is configured to rotate, at least a portion of the drive-cable bearing tube includes:
      an inner layer and an outer layer including respective materials that are different from each other; and
      a coiled wire embedded between the inner and outer layers, the coiled wire being configured to maintain a substantially circular cross-section for the drive-cable bearing tube, even within regions in which the drive-cable bearing tube undergoes a substantial curve.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

The present invention will be more fully understood from the following detailed description of embodiments thereof, taken together with the drawings, in which:

BRIEF DESCRIPTION OF THE DRAWINGS

FIGS. 1E and 1F are schematic illustrations of a ventricular assist device that includes a braided structure and/or a mesh in a distal region, the braided structure and/or the mesh being configured to separate blood-inlet openings of the ventricular assist device from internal structures of the ventricle, in accordance with some applications of the present invention;

FIGS. 3Gi and 3Gii are photographs of an impeller of a ventricular assist device, in accordance with some applications of the present invention;

FIGS. 6A and 6B are schematic illustrations of a ventricular assist device at respective stages of a motion cycle of the impeller of the ventricular assist device with respect to the frame of the ventricular assist device, in accordance with some applications of the present invention;

FIG. 6C is a schematic illustration of a distal-tip element that includes an axial-shaft-receiving tube and a distal-tip portion of a ventricular assist device, in accordance with some applications of the present invention;

FIGS. 6D and 6E are schematic illustrations of a coupling element for coupling to an impeller bushing, the coupling element being proximally-extended and functioning as a stopper, in accordance with some applications of the present invention;

FIGS. 9A, 9B, 9C, 9D, 9E, 9F, and 9G are schematic illustrations of a motor-unit support configured to support the motor unit on a patient's leg, in accordance with some applications of the present invention;

FIGS. 11A, 11B, 11C, 11D, and 11E are schematic illustrations of apparatus and a method for purging a drive cable, radial bearings, and/or an impeller bushing of a ventricular assist device, in accordance with some applications of the present invention;

FIGS. 17Ai and 17Aii are schematic illustrations of a ventricular assist device having a balloon disposed on its distal tip portion, the balloon being configured to facilitate movement of the axial shaft with respect to walls of the ventricle, in accordance with some applications of the present invention;

FIGS. 17Bi and 17Bii are schematic illustrations of a ventricular assist device having a joint that is configured to facilitate pivoting of its distal tip portion with respect to its axial shaft, in accordance with some applications of the present invention;

FIGS. 18A, 18B, and 18C are schematic illustrations of a distal radial bearing of a ventricular assist device, in accordance with respective applications of the present invention;

FIGS. 20A, 20B, and 20C are schematic illustrations of a ventricular-assist device, an axial shaft of which includes a joint, such as a Cardan joint, in accordance with some applications of the present invention;

FIGS. 23A, 23B, and 23C are schematic illustrations a tip straightener that is used to straighten the distal tip of a ventricular assist device during insertion of a guidewire therethrough, in accordance with some applications of the present invention.

DETAILED DESCRIPTION OF EMBODIMENTS

Figure 1A:
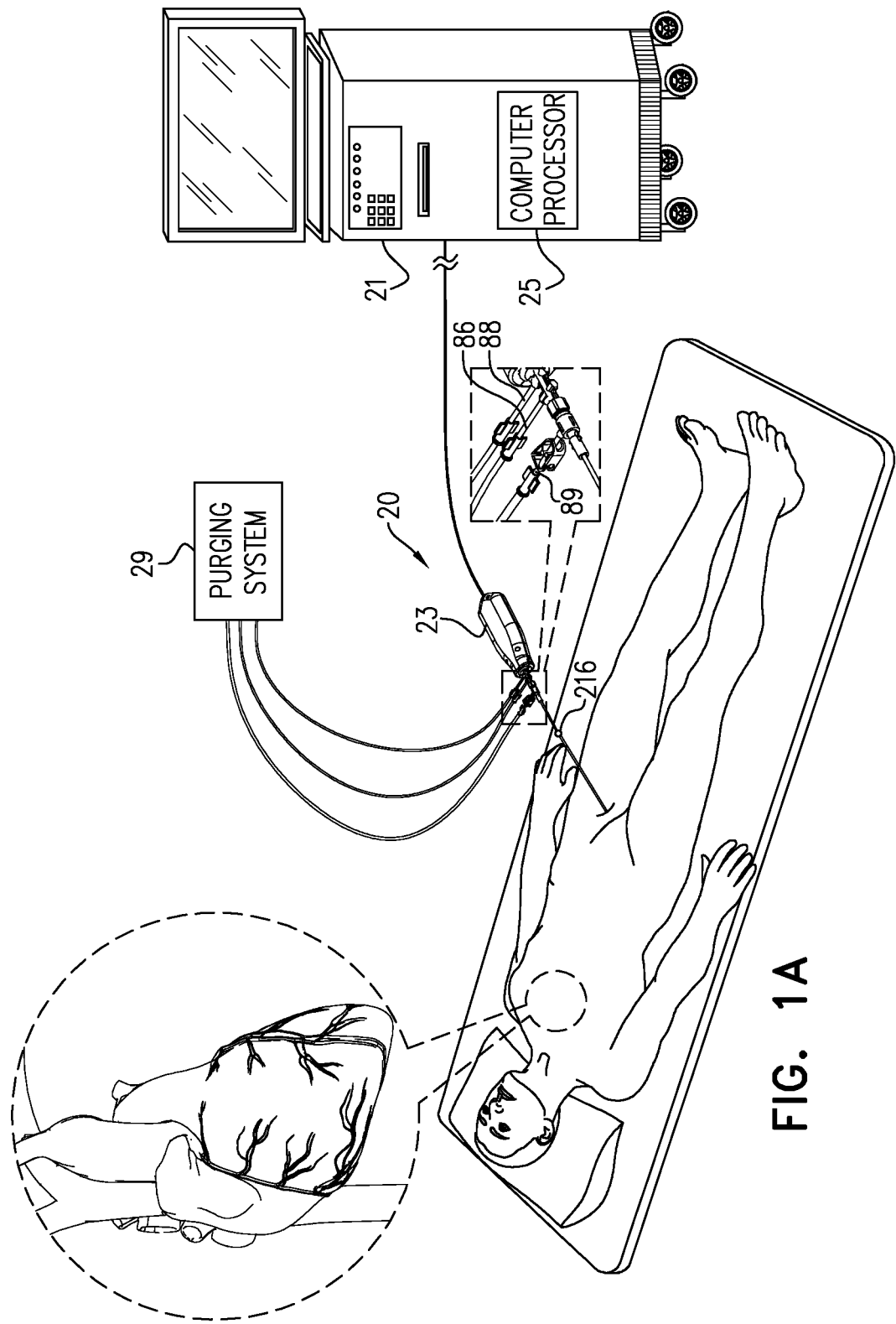
FIGS. 1A, 1B, 1C, and 1D are schematic illustrations of a ventricular assist device, a distal end of which is configured to be placed in a subject's left ventricle, in accordance with some applications of the present invention.
Figure 1B:
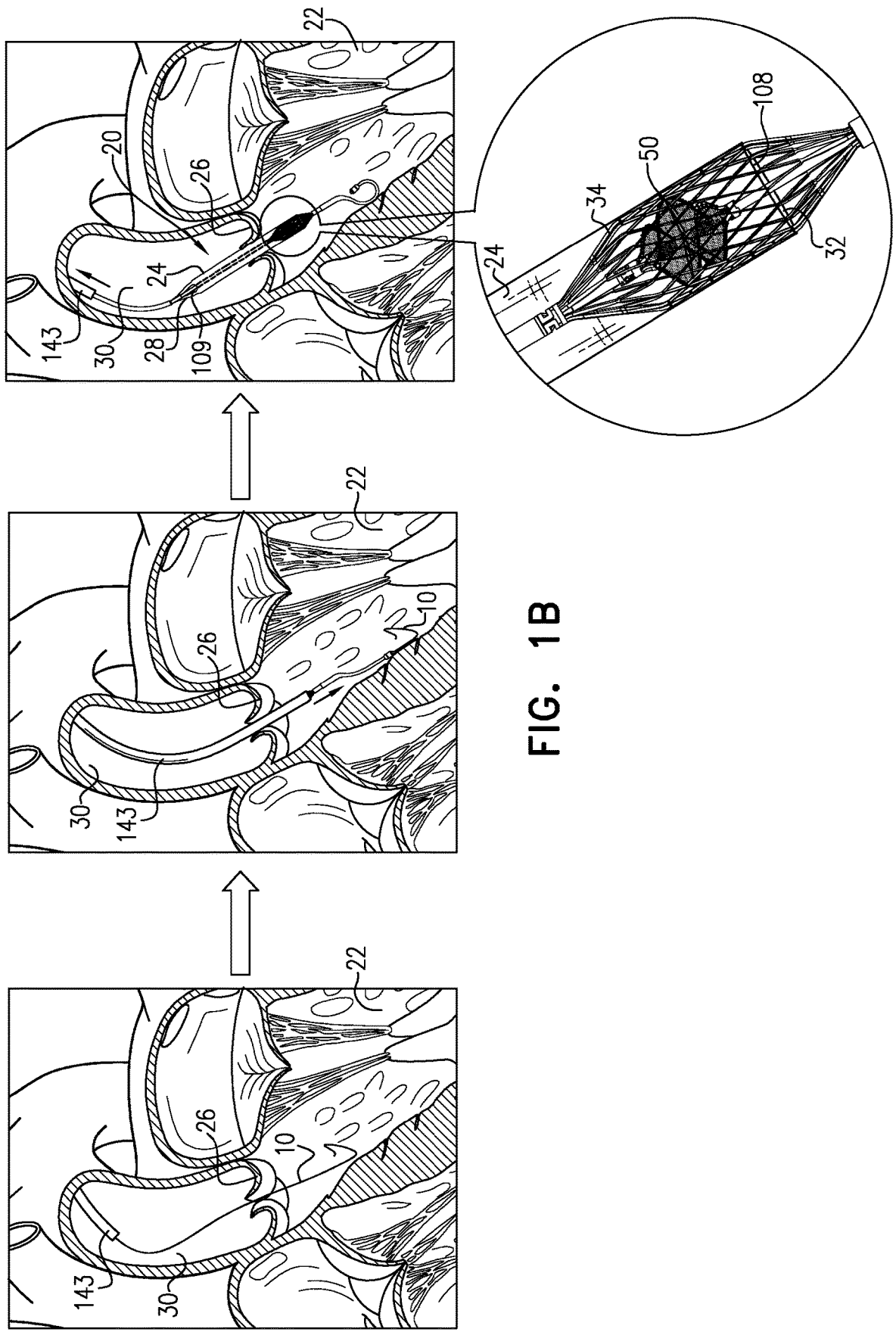
Figure 1C:
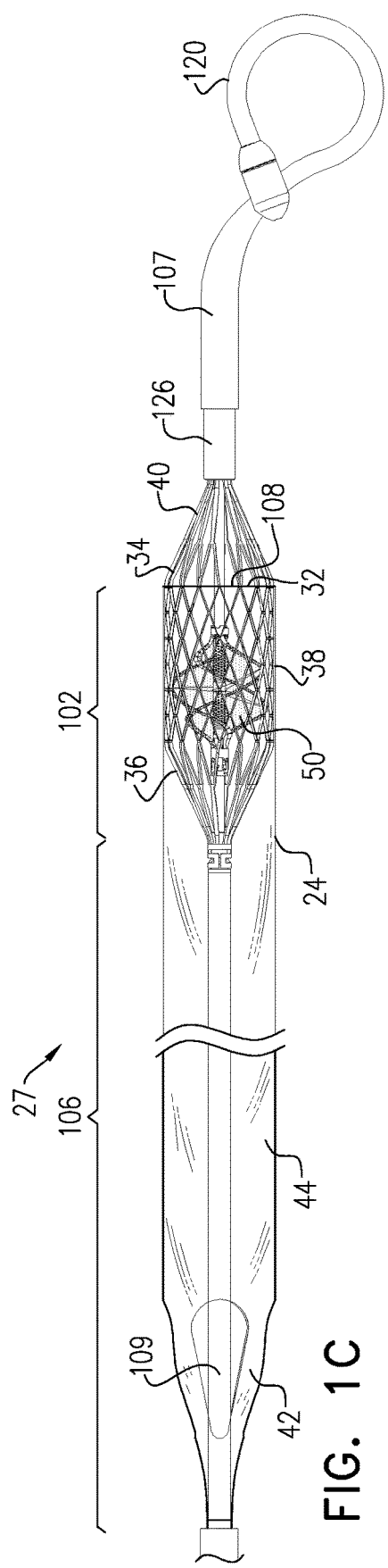

Reference is now made to FIGS. 1A, 1B, and 1C, which are schematic illustrations of a ventricular assist device 20, a distal end of which is configured to be disposed in a subject's left ventricle 22, in accordance with some applications of the present invention. FIG. 1A shows an overview of the ventricular assist device system including a control console 21, and a motor unit 23. (As described hereinbelow, the motor unit is typically a handle that houses a motor.) FIG. 1B shows the ventricular assist device being inserted into the subject's left ventricle, and FIG. 1C shows a pump portion 27 of the ventricular assist device in greater detail. The ventricular assist device includes a pump-outlet tube 24, which traverses an aortic valve 26 of the subject, such that a proximal end 28 of the pump-outlet tube is disposed in an aorta 30 of the subject and a distal end 32 of the pump-outlet tube is disposed within left ventricle 22. Pump-outlet tube 24 is typically an elongate tube, an axial length of the pump-outlet tube typically being substantially larger than its diameter. The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

For some applications, the ventricular assist device is used to assist the functioning of a subject's left ventricle during a percutaneous coronary intervention. In such cases, the ventricular assist device is typically used for a period of up to 10 hours (e.g., up to six hours), during a period in which there is risk of developing hemodynamic instability (e.g., during or immediately following the percutaneous coronary intervention). Alternatively or additionally, the ventricular assist device is used to assist the functioning of a subject's left ventricle for a longer period (e.g., for example, 2-20 days, e.g., 4-14 days) upon a patient suffering from cardiogenic shock, which may include any low-cardiac-output state (e.g., acute myocardial infarction, myocarditis, cardiomyopathy, post-partum, etc.). For some applications, the ventricular assist device is used to assist the functioning of a subject's left ventricle for yet a longer period (e.g., several weeks or months), e.g., in a "bridge to recovery" treatment. For some such applications, the ventricular assist device is permanently or semi-permanently implanted, and the impeller of the ventricular assist device is powered transcutaneously, e.g., using an external antenna that is magnetically coupled to the impeller.

As shown in FIG. 1B, which shows steps in the deployment of the ventricular assist device in the left ventricle, typically the distal end of the ventricular assist device is guided to the left ventricle over a guidewire 10. During the insertion of the distal end of the device to the left ventricle, a delivery catheter 143 is disposed over the distal end of the device. Once the distal end of the device is disposed in the left ventricle, the delivery catheter is typically retracted to the aorta, and the guidewire is withdrawn from the subject's body. The retraction of the delivery catheter typically causes self-expandable components of the distal end of the device to assume non-radially-constrained configurations, as described in further detail hereinbelow. Typically, the ventricular assist device is inserted into the subject's body in order to provide an acute treatment to the subject. For some applications, in order to withdraw the left ventricular device from the subject's body at the end of the treatment, the delivery catheter is advanced over the distal end of the device, which causes the self-expandable components of the distal end of the device to assume radially-constrained configurations. Alternatively or additionally, the distal end of the device is retracted into the delivery catheter which causes the self-expandable components of the distal end of the device to assume radially-constrained configurations.

For some applications (not shown), the ventricular assist device and/or delivery catheter 143 includes an ultrasound transducer at its distal end and the ventricular assist device is advanced toward the subject's ventricle under ultrasound guidance.

Referring now to FIG. 1C, which shows pump portion 27 of ventricular assist device 20 in greater detail. Typically, an impeller 50 is disposed within a distal section 102 of pump-outlet tube 24 and is configured to pump blood from the left ventricle into the aorta by rotating. The pump-outlet tube typically defines one or more blood inlet openings 108 at the distal end 32 of the pump-outlet tube, via which blood flows into the pump-outlet tube from the left ventricle, during operation of the impeller. For some applications, proximal section 106 of the pump-outlet tube defines one or more blood outlet openings 109, via which blood flows from the pump-outlet tube into the ascending aorta, during operation of the impeller.

For some applications, control console 21 (shown in FIG. 1A), which typically includes a computer processor 25, controls impeller rotation. For example, the computer processor may control a motor 74 (shown in FIG. 7A, for example), which is disposed within motor unit 23 (shown in FIG. 1A) and which drives the impeller to rotate via a drive cable 130 (shown in FIG. 7A, for example). For some applications, the computer processor is configured to detect a physiological parameter of the subject (such as left-ventricular pressure, cardiac afterload, rate of change of left-ventricular pressure, etc.) and to control rotation of the impeller in response thereto, as described in further detail hereinbelow. Typically, the operations described herein that are performed by the computer processor, transform the physical state of a memory, which is a real physical article that is in communication with the computer processor, to have a different magnetic polarity, electrical charge, or the like, depending on the technology of the memory that is used. Computer processor 25 is typically a hardware device programmed with computer program instructions to produce a special-purpose computer. For example, when programmed to perform the techniques described herein, computer processor 25 typically acts as a special-purpose, ventricular-assist computer processor and/or a special-purpose, blood-pump computer processor.

For some applications, a purging system 29 (shown in FIG. 1A) drives a fluid (e.g., a glucose solution) to pass through portions of ventricular assist device 20, for example, in order to cool portions of the device and/or in order to wash debris from portions of the device. Purging system 29 is described in further detail hereinbelow.

Typically, along distal section 102 of pump-outlet tube 24, a frame 34 is disposed within the pump-outlet tube around impeller 50. The frame is typically made of a shape-memory alloy, such as nitinol. For some applications, the shape-memory alloy of the frame is shape set such that at least a portion of the frame (and thereby distal section 102 of tube 24) assumes a generally circular, elliptical, or polygonal cross-sectional shape in the absence of any forces being applied to distal section 102 of tube 24. By assuming its generally circular, elliptical, or polygonal cross-sectional shape, the frame is configured to hold the distal portion of the pump-outlet tube in an open state. Typically, during operation of the ventricular assist device, the distal portion of the pump-outlet tube is configured to be placed within the subject's body, such that the distal portion of the pump-outlet tube is disposed at least partially within the left ventricle.

For some applications, along proximal section 106 of pump-outlet tube 24, the frame is not disposed within the pump-outlet tube, and the pump-outlet tube is therefore not supported in an open state by frame 34. Pump-outlet tube 24 is typically made of a blood-impermeable collapsible material. For example, pump-outlet tube 24 may include polyurethane, polyester, and/or silicone. Alternatively or additionally, the pump-outlet tube is made of polyethylene terephthalate (PET) and/or polyether block amide (e.g., PEBAX®). For some applications (not shown), the pump-outlet tube is reinforced with a reinforcement structure, e.g., a braided reinforcement structure, such as a braided nitinol tube. Typically, the proximal portion of the pump-outlet tube is configured to be placed such that it is at least partially disposed within the subject's ascending aorta. For some applications, the proximal portion of the pump-outlet tube traverses the subject's aortic valve, passing from the subject's left ventricle into the subject's ascending aorta, as shown in FIG. 1B.

As described hereinabove, the pump-outlet tube typically defines one or more blood inlet openings 108 at the distal end of the pump-outlet tube, via which blood flows into the pump-outlet tube from the left ventricle, during operation of the impeller. For some applications, the proximal portion of the pump-outlet tube defines one or more blood outlet openings 109, via which blood flows from the pump-outlet tube into the ascending aorta, during operation of the impeller. Typically, the pump-outlet tube defines a plurality of blood outlet openings 109, for example, between two and eight blood outlet openings (e.g., between two and four blood outlet openings). During operation of the impeller, the pressure of the blood flow through the pump-outlet tube typically maintains the proximal portion of the tube in an open state. For some applications, in the event that, for example, the impeller malfunctions, the proximal portion of the pump-outlet tube is configured to collapse inwardly, in response to pressure outside of the proximal portion of the pump-outlet tube exceeding pressure inside the proximal portion of the pump-outlet tube. In this manner, the proximal portion of the pump-outlet tube acts as a safety valve, preventing retrograde blood flow into the left ventricle from the aorta.

Referring again to FIG. 1C, for some applications, frame 34 is shaped such that the frame defines a proximal conical portion 36, a central cylindrical portion 38, and a distal conical portion 40. Typically, the proximal conical portion is such that the narrow end of the cone is proximal with respect to the wide end of the cone. Further typically, the distal conical portion is such that the narrow end of the cone is distal with respect to the wide end of the cone. For some applications, pump-outlet tube 24 extends to the distal end of cylindrical portion 38 (or slightly proximal or distal thereof), such that the distal end of the pump-outlet tube defines a single axially-facing blood inlet opening 108, as shown in FIG. 1C. For some applications, within at least a portion of frame 34, an inner lining 39 lines the frame, as described hereinbelow with reference to FIGS. 12A-B. In accordance with respective applications, the inner lining partially overlaps or fully overlaps with pump-outlet tube 24 over the portion of the frame that the inner lining lines. For such applications, the distal end of the inner lining defines a single axially-facing blood inlet opening 108. For some applications, the pump-outlet tube and the inner lining both terminate before the distal end of the cylindrical portion of the frame, such that a distal part of the cylindrical portion of the frame is uncovered, as described hereinbelow with reference to FIG. 13.

Typically, pump-outlet tube 24 includes a conical proximal portion 42 and a cylindrical central portion 44. (Typically, conical proximal portion 36 is disposed entirely within proximal section 106 described hereinabove, and the cylindrical central portion typically extends from within proximal section 106 to distal section 102.) The proximal conical portion is typically such that the narrow end of the cone is proximal with respect to the wide end of the cone. Typically, blood outlet openings 109 are defined by pump-outlet tube 24, such that the openings extend at least partially along proximal conical portion 42 of tube 24. For some such applications, the blood outlet openings are teardrop-shaped, as shown in FIG. 1C. Typically, the teardrop-shaped nature of the blood outlet openings in combination with the openings extending at least partially along the proximal conical section of tube 24 causes blood to flow out of the blood outlet openings along flow lines that are substantially parallel with the longitudinal axis of tube 24 at the location of the blood outlet openings.

For some applications (not shown), the diameter of pump-outlet tube 24 changes along the length of the central portion of the pump-outlet tube, such that the central portion of the pump-outlet tube has a frustoconical shape. For example, the central portion of the pump-outlet tube may widen from its proximal end to is distal end, or may narrow from its proximal end to its distal end. For some applications, at its proximal end, the central portion of the pump-outlet tube has a diameter of between 5 and 7 mm, and at its distal end, the central portion of the pump-outlet tube has a diameter of between 8 and 12 mm.

Again referring to FIG. 1C, the ventricular assist device typically includes a distal-tip element 107 that is disposed distally with respect to frame 34 and that includes an axial-shaft-receiving tube 126 and a distal-tip portion 120, both of which are described in further detail hereinbelow.

Figure 1D:
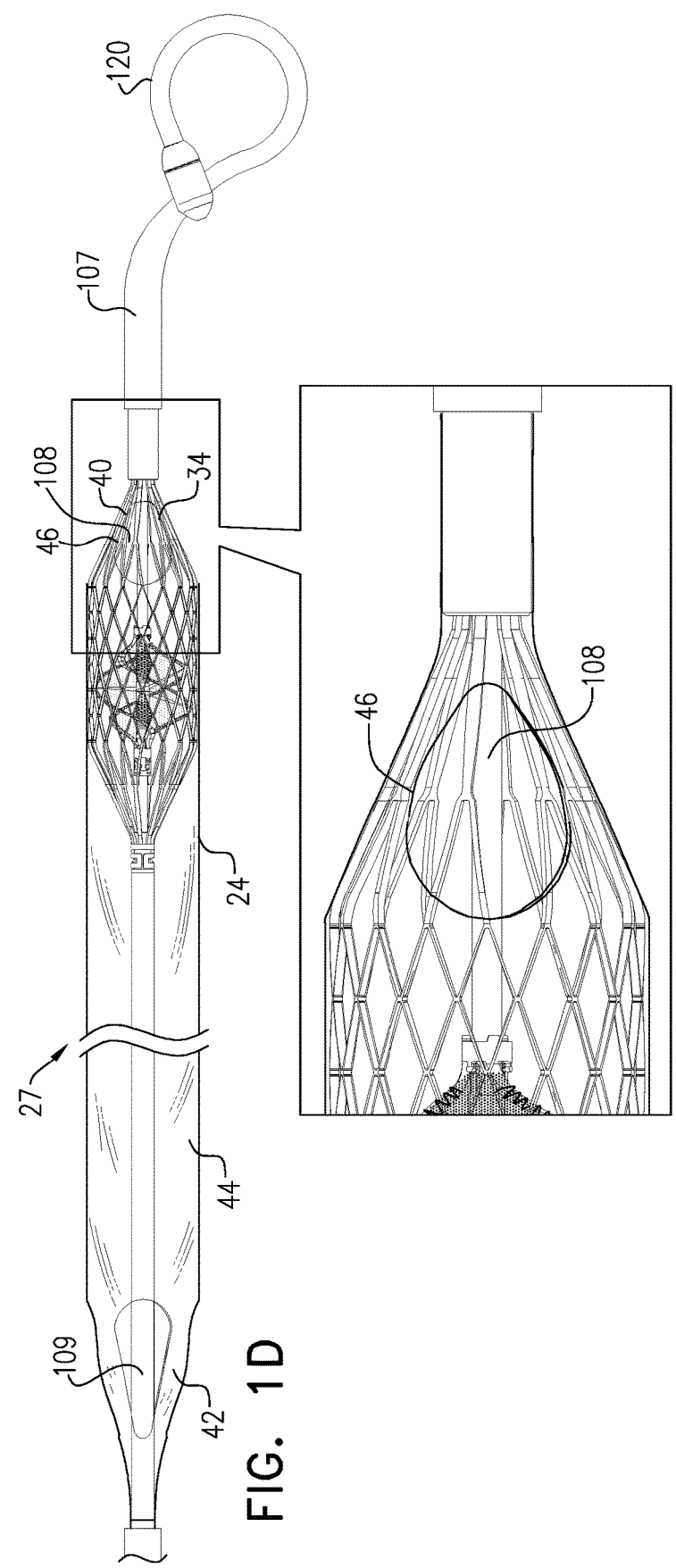

Reference is now made to FIG. 1D, which is a schematic illustration of ventricular assist device 20, in which pump-outlet tube 24 extends to the end of distal conical portion 40 of the frame, and the pump-outlet tube defines a plurality of lateral blood inlet openings 108, in accordance with some applications of the present invention. For such applications, the pump-outlet tube typically defines a distal conical portion 46, with the narrow end of the cone being distal with respect to the wide end of the cone. For some such applications, the pump-outlet tube defines two to four lateral blood inlet openings. Typically, for such applications, each of the blood inlet openings 108 defines an area of more than 20 square mm (e.g., more than 30 square mm), and/or less than 60 square mm (e.g., less than 50 square mm), e.g., 20-60 square mm, or 30-50 square mm. Alternatively or additionally, the outlet tube defines a greater number of smaller blood inlet openings (not shown), e.g., more than 10 small blood inlet openings, more than 50 small blood inlet openings, more than 100 small blood inlet openings, or more than 150 small blood inlet openings, e.g., 50-100 small blood inlet openings, 100-150 small blood inlet openings, or 150-200 small blood inlet openings. For some such applications, each of the small blood inlet openings defines an area of more than 0.1 square mm (e.g., more than 0.3 square mm), and/or less than 5 square mm (e.g., less than 1 square mm), e.g., 0.1-5 square mm, 0.2-0.5 square mm, or 0.3-1 square mm.

Typically, distal conical portion 46 of the pump-outlet tube is configured to reduce a risk of structures from the left ventricle (such as chordae tendineae, trabeculae carneae, and/or papillary muscles) entering into the frame and potentially being damaged by the impeller and/or an axial shaft upon which the impeller is mounted, and/or causing damage to the left ventricular assist device. Therefore, for some applications, the small blood-inlet openings are shaped such that in at least one direction the widths (or spans) of the openings are less than 1 mm, e.g., 0.1-1 mm, or 0.3-0.8 mm. By defining such a small width (or span), it is typically the case that structures from the left ventricle (such as chordae tendineae, trabeculae carneae, and/or papillary muscles) are blocked from entering into the frame. For some applications, the small blood inlet openings define generally rectangular (or elliptical) shapes. For some such applications, the ratio of the lengths to the widths of the small blood inlet openings is between 1.1:1 and 4:1, e.g., between 3:2 and 5:2. For some applications, by having such shapes, the small blood-inlet openings are configured (a) to block structures from the left ventricle (such as chordae tendineae, trabeculae carneae, and/or papillary muscles) from entering into the frame, but (b) to provide the portion of the pump-outlet tube that defines the small blood inlet openings with a relatively high porosity. Typically, the portion of the pump-outlet tube that defines the small blood inlet openings has a porosity of more than 40 percent, e.g., more than 50 percent (where porosity is defined as the percentage of the area of this portion that is porous to blood flow).

Reference is now made to FIGS. 1E and 1F, which are schematic illustrations of ventricular assist device 20, the ventricular assist device that includes a braided structure 260 and/or a mesh 282 in a distal region of the device, the braided structure and/or mesh being configured to separate blood-inlet openings of the ventricular assist device from internal structures of the ventricle, in accordance with some applications of the present invention. Braided structure 260 is typically generally similar to braided structure 260 described with respect to FIG. 20B of US 2019/0209758 to Tuval, which is incorporated herein by reference. Mesh 282 is generally similar to mesh 282 described with respect to FIG. 21D of US 2019/0209758 to Tuval, which is incorporated herein by reference.

Referring to FIG. 1E, for some applications, braided structure 260 (e.g., a braided metal or alloy, such as a shape-memory alloy (e.g., nitinol)) is disposed at a distal region of the device. For example, the braided material may be disposed at the distal end of the device. Alternatively or additionally, the device may include distal-tip element 107 (which is typically as described with reference to FIGS. 14-16B), and the braided material is disposed around a portion of the device, such as to cover a portion of the distal-tip element. For some applications, the braided material is disposed over at least a portion of frame 34. For example, the braided material may surround a portion of the frame extending distally from at least a longitudinal location along the frame at which blood-outlet tube 24 ends and/or at which inner lining 39 ends until a distal end of the frame. For some applications, the braided structure is disposed such as to cover blood-inlet openings 108.

As shown in FIG. 1F, for some applications, the outer surface of distal-tip element 107 includes a radially-expandable mesh 282, which is configured to self-expand when distal-tip element 107 is disposed inside the subject's left ventricle. For some applications, the device includes a distal-tip element that is generally as described with reference to FIGS. 14-16B, and the mesh is disposed around a portion of the device, such as to cover a portion of the distal-tip element. For some applications, the mesh is disposed over at least a portion of frame 34. For example, the mesh may surround a portion of the frame extending distally from at least a longitudinal location along the frame at which blood-outlet tube 24 ends and/or at which inner lining 39 ends until a distal end of the frame. For some applications, the mesh is disposed such as to cover blood-inlet openings 108.

Typically, braided structure 260 and/or mesh 282 separates the one or more blood inlet openings 108 from inner structures of the left ventricle in three dimensions. In this manner, braided structure 260 and/or mesh 282 separates one or more blood inlet openings 108 from the interventricular septum, chordae tendineae, papillary muscles, trabeculae carneae, and/or the apex of the left ventricle. As an alternative or in addition to the braided structure and/or the mesh being used to separate the one or more blood inlet openings 108 from inner structures of the left ventricle, cells of frame 34 in the vicinity of blood inlet openings 108 are configured to define openings that are smaller than those in other portions of the frame. For example, the cells in the distal conical portion of the frame may define openings that are smaller than openings defined by cells in the proximal conical portion of the frame. Alternatively or additionally, the cells in the distal conical portion of the frame may define openings that are smaller than openings defined by cells in the cylindrical portion of the frame.

Figure 2:
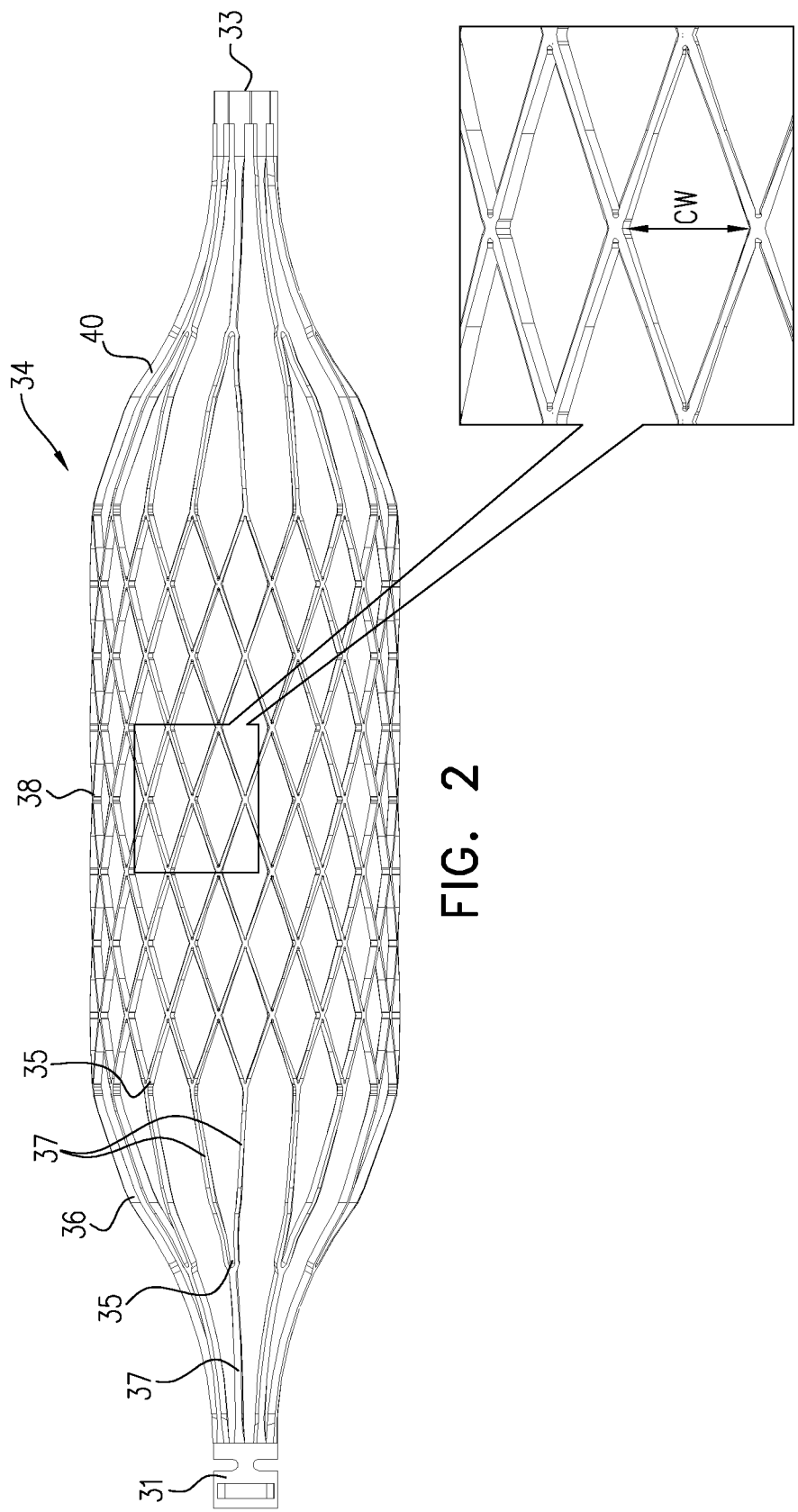
FIG. 2 is a schematic illustration of a frame that houses an impeller of a ventricular assist device, in accordance with some applications of the present invention.

Reference is now made to FIG. 2, which is a schematic illustration of frame 34 that houses an impeller of ventricular assist device 20, in accordance with some applications of the present invention. As described hereinabove, frame 34 is typically made of a shape-memory alloy, such as nitinol, and the shape-memory alloy of the frame is shape set such that the frame (and thereby tube 24) assumes a generally circular, elliptical, or polygonal cross-sectional shape in the absence of any forces being applied to pump-outlet tube 24 and/or frame 34. By assuming its generally circular, elliptical, or polygonal cross-sectional shape, the frame is configured to hold the distal portion of the tube in an open state.

Typically, the frame is a stent-like frame, in that it comprises struts that, in turn, define cells. Further typically, the frame is covered with pump-outlet tube 24, and/or covered with an inner lining 39, described hereinbelow, with reference to FIGS. 12A-B. As described hereinbelow, for some applications impeller 50 undergoes axial back-and-forth motion with respect to frame 34. Typically, over the course of the motion of the impeller with respect to the frame the location of the portion of the impeller that defines the maximum span of the impeller is disposed within cylindrical portion 38 of frame 34. In some cases, if the cells of the cylindrical portion 38 of frame 34 are too large, then pump-outlet tube 24, and/or inner lining 39 gets stretched between edges of the cells, such that the pump-outlet tube 24, and/or inner lining 39 does not define a circular cross-section. For some applications, if this occurs in the region in which the portion of the impeller that defines the maximum span of the impeller is disposed, this results in a non-constant gap between the edges of the impeller blades and tube 24 (and/or inner lining) at that location, over the course of a rotation cycle of the impeller. For some applications, this may lead to increased hemolysis relative to if there were a constant gap between the edges of the impeller blades and tube 24 (and/or inner lining) at that location, over the course of the rotation cycle of the impeller.

Referring to FIG. 2, at least partially in view of the issues described in the above paragraph, within cylindrical portion 38 of frame 34, the frame defines a large number of relatively small cells. Typically, when the frame is disposed in its non-radially-constrained configuration, the maximum cell width CW of the each of the cells (i.e., the distance from the inner edge of the strut at the central junction on one side of the cell to the inner edge of the strut at the central junction on the other side of the cell, as measured around the circumference of cylindrical portion 38) within the cylindrical portion of the frame is less than 2 mm, e.g., between 1.4 mm and 1.6 mm, or between 1.6 and 1.8 mm. Since the cells are relatively small, the pump-outlet tube 24 (and/or inner lining) defines a substantially circular cross-section within the cylindrical portion of the frame.

Still referring to FIG. 2, and starting from the proximal end of the frame (which is to the left of the figure), typically the frame defines the following portions (a) coupling portion 31 via which the frame is coupled to a proximal bearing 116 (shown in FIG. 4) of the ventricular assist device, (b) proximal conical portion 36, (c) cylindrical portion 38, (d) distal conical portion 40, and (e) distal strut junctions 33. As illustrated, as the frame transitions from a proximal end of the frame toward the center of the frame (e.g., as the frame transitions through coupling portion 31, through proximal conical portion 36, and to cylindrical portion 38), struts 37 of the frame pass through junctions 35, at which the two struts branch from a single strut, in a Y-shape. As described in further detail hereinbelow, typically frame 34 is placed in a radially-constrained (i.e., crimped) configuration within delivery catheter 143 by the frame being axially elongated. Moreover, the frame typically transmits its radial narrowing to the impeller, and the impeller becomes radially constrained by becoming axially elongated within the frame. For some applications, the struts of the frame being configured in the manner described above facilitates transmission of axial elongation from the delivery catheter (or other device that is configured to crimp the frame) to the frame, which in turn facilitates transmission of axial elongation to the impeller. This is because the pairs of struts that branch from each of junctions 35 are configured to pivot about the junction and move closer to each other such as to close.

Still referring to FIG. 2, for some applications distal strut junctions 33 are not circumferentially connected and are typically configured to be maintained in open states when the frame is coupled to axial shaft 92 (shown in FIG. 4), in order for the impeller to be placed within the frame via the distal end of the frame. Subsequently, the distal strut portions are closed around the outside of a distal bearing 118, as described in further detail hereinbelow with reference to FIGS. 5A-B. For some applications, a proximal end of distal-tip element 107 (shown in FIG. 1C) holds the distal strut portions in their closed configurations around the outside of distal bearing 118.

Typically, when disposed in its non-radially constrained configuration, frame 34 has a total length of more than 25 mm (e.g., more than 30 mm), and/or less than 50 mm (e.g., less than 45 mm), e.g., 25-50 mm, or 30-45 mm. Typically, when disposed in its radially-constrained configuration (within delivery catheter 143), the length of the frame increases by between 2 and 5 mm. Typically, when disposed in its non-radially constrained configuration, the cylindrical portion of frame 34 has a length of more than 10 mm (e.g., more than 12 mm), and/or less than 25 mm (e.g., less than 20 mm), e.g., 10-25 mm, or 12-20 mm. For some applications, a ratio of the length of the cylindrical portion of the frame to the total length of the frame is more than 1:4 and/or less than 1:2, e.g., between 1:4 and 1:2.

Figure 3A:
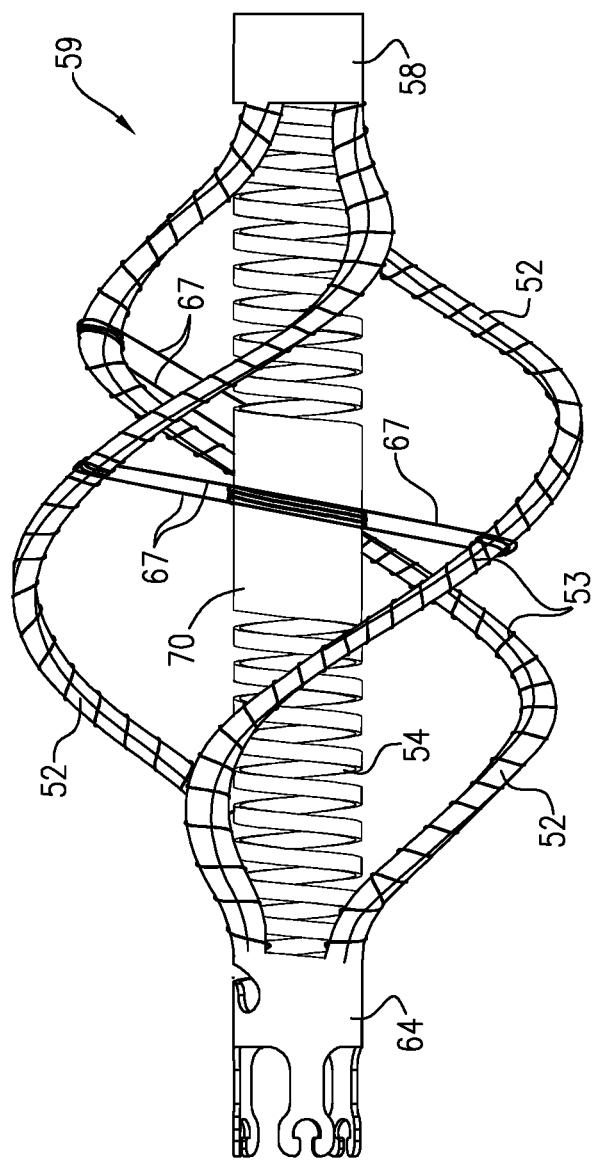
FIGS. 3A, 3B, 3C, 3D, 3E, and 3F are schematic illustrations of an impeller of a ventricular assist device or portions thereof, in accordance with some applications of the present invention.
Figures 3B, 3C:
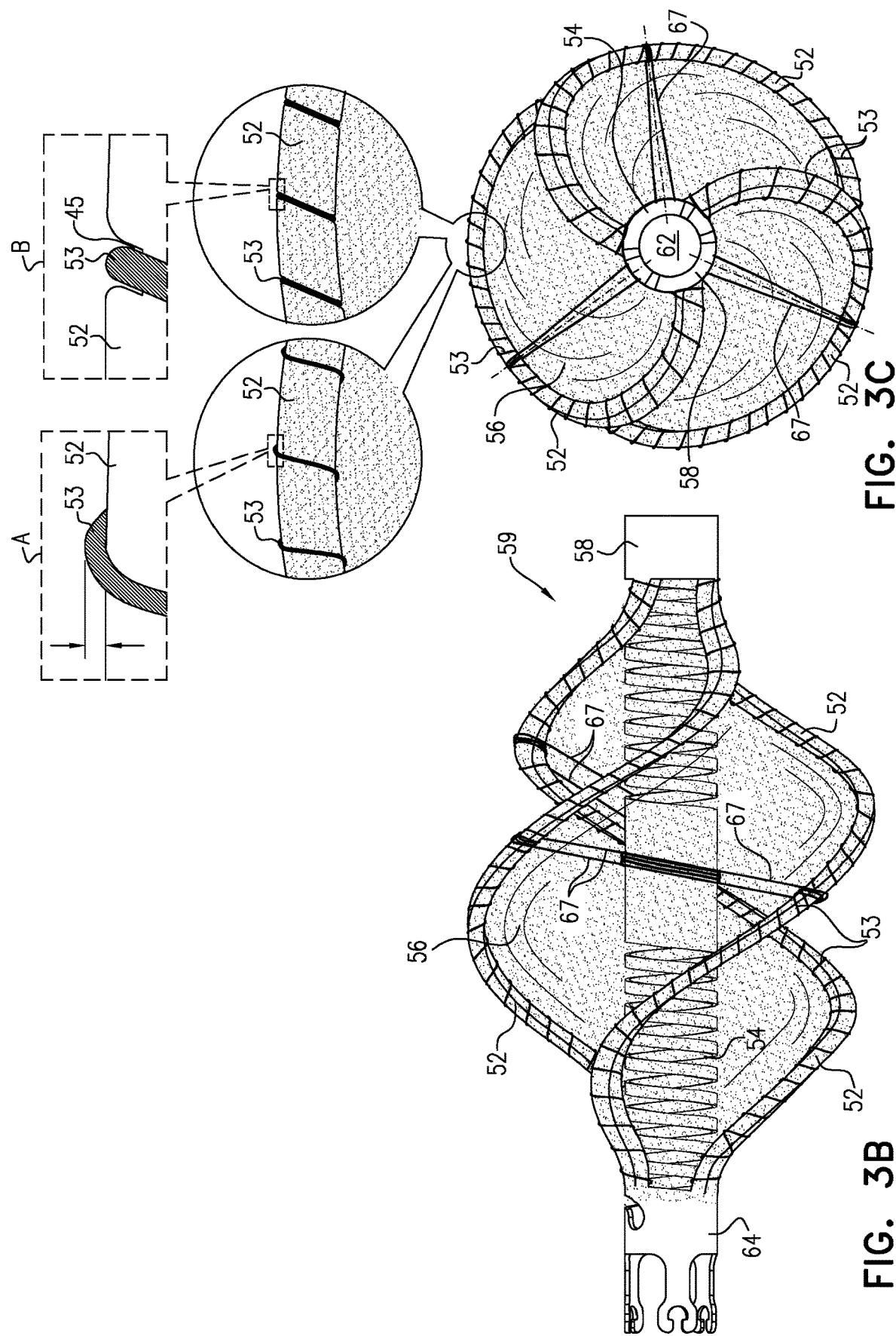

Reference is now made to FIGS. 3A-C, which are schematic illustrations of impeller 50 or portions thereof, in accordance with some applications of the present invention. Typically, the impeller includes at least one outer helical elongate element 52, which winds around a central axial spring 54, such that the helix defined by the helical elongate element is coaxial with the central axial spring. (As described in further details herein below, typically central axial spring includes a tube 70 at an intermediate location along its length. Also, as described hereinbelow, the scope of the present application includes using other axial structure in place of a spring. Therefore, in some places, the present application refers to "axial structure 54".) Typically, the impeller includes two or more helical elongate elements (e.g., three helical elongate elements, as shown in FIGS. 3A-C). For some applications, the helical elongate elements and the central axial spring are made of a shape-memory material, e.g., a shape-memory alloy such as nitinol. Typically, each of the helical elongate elements and the central axial spring support a film 56 of a material (e.g., an elastomer, such as polyurethane, and/or silicone) therebetween. For some applications, the film of material includes pieces of nitinol embedded therein, for example in order to strengthen the film of material. For illustrative purposes, the impeller is shown in the absence of the film of material in FIG. 3A. FIGS. 3B and 3C show respective views of the impeller with the film of material supported between the helical elongate elements and the spring.

Each of the helical elongate elements, together with the film extending from the helical elongate element to the spring, defines a respective impeller blade, with the helical elongate elements defining the outer edges of the blades, and the axial spring defining the axis of the impeller. Typically, the film of material extends along and coats the spring. For some applications, sutures 53 (e.g., polyester sutures, shown in FIGS. 3B and 3C) are wound around the helical elongate elements, e.g., as described in U.S. Pat. No. 10,864,310 to Schwammenthal, which is incorporated herein by reference. Typically, the sutures are configured to facilitate bonding between the film of material (which is typically an elastomer, such as polyurethane, or silicone) and the helical elongate element (which is typically a shape-memory alloy, such as nitinol). For some applications, sutures (e.g., polyester sutures, not shown) are wound around spring 54. Typically, the sutures are configured to facilitate bonding between the film of material (which is typically an elastomer, such as polyurethane, or silicone) and the spring (which is typically a shape-memory alloy, such as nitinol).

Enlargements A and B of FIG. 3C show two alternative ways in which the sutures are tied around helical elongate elements 52. For some applications, the sutures are tied around the outer surface of the helical elongate elements, as shown in enlargement A. Alternatively, the helical elongate elements define grooves 45 on their outer surfaces, and the sutures are embedded within the grooves, as shown in enlargement B. By embedding the sutures within the grooves, the sutures typically do not add to the outer profile of the impeller, and the outer profile of the impeller is defined by the outer surfaces of the helical elongate elements.

Typically, proximal ends of spring 54 and helical elongate elements 52 extend from a proximal bushing (i.e., sleeve bearing) 64 of the impeller, such that the proximal ends of spring 54 and helical elongate elements 52 are disposed at approximately the same point and have a similar radial distance from the longitudinal axis of the impeller. Similarly, typically, distal ends of spring 54 and helical elongate elements 52 extend from a distal bushing 58 of the impeller, such that the distal ends of spring 54 and helical elongate elements 52 are disposed at approximately the same point and have a similar radial distance from the longitudinal axis of the impeller. Typically, spring 54, as well as proximal bushing 64 and distal bushing 58 of the impeller, define a lumen therethrough, such that the impeller defines a continuous lumen 62 therethrough (shown in FIG. 3C).

Figure 4:
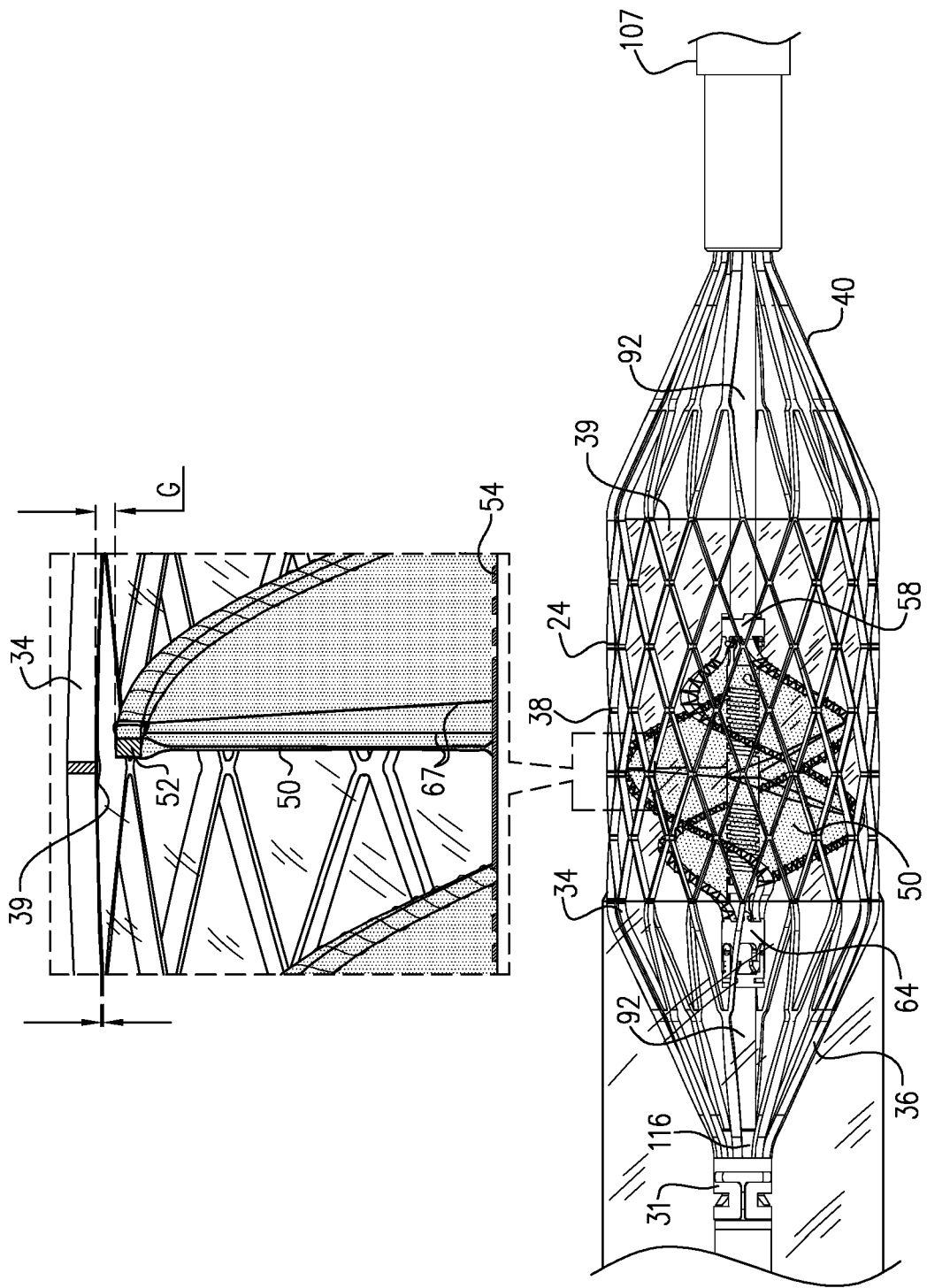
FIG. 4 is a schematic illustration of an impeller disposed inside a frame of a ventricular assist device, in accordance with some applications of the present invention.

Reference is now made to FIG. 4, which is a schematic illustration of impeller 50 disposed inside frame 34 of ventricular assist device 20, in accordance with some applications of the present invention. For some applications, within at least a portion of frame 34, an inner lining 39 lines the frame, as described hereinbelow with reference to FIGS. 12A-B. In accordance with respective applications, the inner lining partially overlaps or fully overlaps with pump-outlet tube 24 over the portion of the frame that the inner lining lines. For some applications, the pump-outlet tube and the inner lining both terminate before the distal end of cylindrical portion 38 of the frame, such that a distal part of the cylindrical portion of the frame is uncovered, as described hereinbelow with reference to FIG. 13. For some applications, the pump-outlet tube continues to cover the distal conical portion of the frame, as described with reference to FIG. 1D. In the application shown in FIG. 4, the inner lining lines the inside of the cylindrical portion of the frame and pump-outlet tube 24 does not cover the cylindrical portion of the frame. However, the scope of the present application includes applying the apparatus and methods described with reference to FIG. 4 to any one of the applications described hereinbelow with reference to FIGS. 1D, 12A-B or FIG. 13.

As shown in FIG. 4, typically there is a gap G, between the outer edge of impeller 50 and inner lining 39, even at a location at which the span of the impeller is at its maximum. For some applications, it is desirable that the gap between the outer edge of the blade of the impeller and the inner lining 39 be relatively small, in order for the impeller to efficiently pump blood from the subject's left ventricle into the subject's aorta. However, it is also desirable that a gap between the outer edge of the blade of the impeller and the inner surface of frame 34 be maintained substantially constant throughout the rotation of the impeller within frame 34, for example, in order to reduce the risk of hemolysis.

For some applications, when the impeller and frame 34 are both disposed in non-radially-constrained configurations, gap G between the outer edge of the impeller and the inner lining 39, at the location at which the span of the impeller is at its maximum, is greater than 0.05 mm (e.g., greater than 0.1 mm), and/or less than 1 mm (e.g., less than 0.4 mm), e.g., 0.05-1 mm, or 0.1-0.4 mm. For some applications, when the impeller is disposed in its non-radially-constrained configurations, the outer diameter of the impeller at the location at which the outer diameter of the impeller is at its maximum is more than 7 mm (e.g., more than 8 mm), and/or less than 10 mm (e.g., less than 9 mm), e.g., 7-10 mm, or 8-9 mm. For some applications, when frame 34 is disposed in its non-radially-constrained configuration, the inner diameter of frame 34 (as measured from the inside of inner lining 39 on one side of the frame to the inside of inner lining on the opposite side of the frame) is greater than 7.5 mm (e.g., greater than 8.5 mm), and/or less than 10.5 mm (e.g., less than 9.5 mm), e.g., 7.5-10.5 mm, or 8.5-9.5 mm. For some applications, when the frame is disposed in its non-radially-constrained configuration, the outer diameter of frame 34 is greater than 8 mm (e.g., greater than 9 mm), and/or less than 13 mm (e.g., less than 12 mm), e.g., 8-13 mm, or 9-12 mm.

Typically, an axial shaft 92 passes through the axis of impeller 50, via lumen 62 of the impeller. Further typically, the axial shaft is rigid, e.g., a rigid tube. (For some applications, a portion of the axial shaft is at least partially flexible, e.g., as described with reference to FIGS. 20A-C.) For some applications, proximal bushing 64 of the impeller is coupled to the shaft such that the axial position of the proximal bushing with respect to the shaft is fixed, and distal bushing 58 of the impeller is slidable with respect to the shaft. The axial shaft itself is radially stabilized via a proximal radial bearing 116 and a distal radial bearing 118. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller.

Referring again to FIGS. 3A-C, for some applications, the impeller includes a plurality of elongate elements 67 extending radially from central axial spring 54 to outer helical elongate elements 52. Elongate elements 67 are typically flexible but are substantially non-stretchable along the axis defined by elongate elements 67. Further typically, each of elongate elements 67 is configured to substantially not resist compression. Rather, each elongate element 67 is configured to exert a tensile force upon helical elongate element 52 that prevents helical elongate element 52 from moving radially outward, such that (in the absence of elongate element 67) a separation between helical elongate element 52 and central axial spring 54 would be greater than a length of elongate element 67. For example, elongate elements 67 may include strings (such as polyester, and/or another polymer or a natural material that contains fibers) and/or wires (such as nitinol wires, and/or wires made of a different alloy, or a metal). In this manner, the elongate elements prevent the impeller from radially expanding by applying tensile force to the helical elongate elements.

For some applications, elongate elements 67 maintain helical elongate element 52 (which defines the outer edge of the impeller blade) within a given distance with respect to central axial spring 54. In this manner, elongate elements 67 are configured to prevent the outer edge of the impeller from being forced radially outward due to forces exerted upon the impeller during the rotation of the impeller. In other words, elongate elements 67 act as impeller-expansion-prevention elements. Elongate elements 67 are thereby configured to maintain the gap between the outer edge of the blade of the impeller and the inner surface of frame 34, during rotation of the impeller. Typically, more than one (e.g., more than two) and/or fewer than eight (e.g., fewer than four) elongate elements 67 are used in the impeller, with each of elongate elements 67 typically being doubled (i.e., extending radially from central axial spring 54 to an outer edge of helical elongate element 52, and then returning from the helical elongate element back to the central axial spring). For some applications, a plurality of elongate elements 67, each of which extends from the spring to a respective helical elongate element 52 and back to central axial spring 54, are formed from a single piece of string or a single wire.

For some applications, the impeller is manufactured in the following manner. Proximal bushing 64, distal bushing 58, and helical elongate elements 52 are cut from a tube of shape-memory material, such as nitinol. The cutting of the tube, as well as the shape setting of the shape-memory material, is typically performed such that the helical elongate elements and the bushings are defined by a tube of shape-memory material that is cut and shape set, e.g., using generally similar techniques to those described in U.S. Pat. No. 10,039,874 to Schwammenthal. Typically, spring 54 is inserted into the cut and shape-set tube, such that the spring extends along the length of the tube from at least the proximal bushing to the distal bushing. For some applications, the spring is inserted into the cut and shape-set tube while the spring is in an axially compressed state, and the spring is configured to be held in position with respect to the tube, by exerting a radial force upon the proximal and distal bushings. Alternatively or additionally, portions of the spring are welded to the proximal and distal bushings. For some applications, the spring is cut from a tube of a shape-memory material, such as nitinol. For some such applications, the spring is configured such that, when the spring is disposed in a non-radially-constrained configuration (in which the spring is typically disposed during operation of the impeller), there are substantially no gaps between windings of the spring and adjacent windings thereto.

For some applications, subsequent to spring 54 being inserted into the cut and shape-set tube, elongate elements 67, as described hereinabove, are placed such as to extend between the spring and one or more of helical elongate elements 52, for example, in the following manner. A mandrel (e.g., a polyether ether ketone (PEEK) and/or a polytetrafluoroethylene (PTFE) mandrel) is inserted through the lumen defined by the spring and the bushings. A string or a wire is then threaded such that it passes (a) from the mandrel to a first one of the helical elongate elements 52, (b) back from the first of the helical elongate elements 52 to the mandrel, (c) around the mandrel, and to a second one of the helical elongate elements 52, (d) back from the second one of the helical elongate elements 52 to the mandrel, etc. Once the string or the wire has been threaded from the mandrel to each of helical elongate elements 52 and back again, the ends of the string or the wire are coupled to each other, e.g., by tying them to each other. For some applications, a separate string or wire is used for each of the helical elongate elements 52. Typically, each string or wire passes from the helical elongate element around the mandrel and back to the helical elongate element, with the two ends of the string being tied to each other. For some applications, at a longitudinally-central location of spring 54, the spring is shaped to define a tube 70 (i.e., at this location the spring does not define windings), as shown, and the string or the wire is wound around the tube. For some applications, the string or the wire is not wound around the tube, and does not cross the longitudinal axis of the impeller. Rather, the string or the wire is secured with respect to tube 70 via a securing element 75 (such as a ring), as described in further detail hereinbelow with reference to FIG. 3F.

For some applications, at this stage, sutures 53 (e.g., polyester sutures) are wound around helical elongate elements 52, in order to facilitate bonding between the film of material (which is typically an elastomer, such as polyurethane, or silicone) and helical elongate elements 52 (which is typically a shape-memory alloy, such as nitinol), in a subsequent stage of the manufacture of the impeller. For some applications, sutures (e.g., polyester sutures, not shown) are wound around spring 54. Typically, the sutures are configured to facilitate bonding between the film of material (which is typically an elastomer, such as polyurethane, or silicone) and the spring (which is typically a shape-memory alloy, such as nitinol), in the subsequent stage of the manufacture of the impeller.

Typically, at this stage, a structure 59 has been assembled that is as shown in FIG. 3A. The structure includes the cut and shape-set tube that defines the proximal and distal bushings, the helical elongate elements, and the spring (and, optionally, the elongate elements, and the sutures). This structure is dipped into the material that defines film 56. For some applications, the assembled structure is dipped into the material with the mandrel disposed through the lumen defined by the spring and the bushings, although it is noted that the mandrel is not shown in FIG. 3A. Typically, the material from which the film is made is silicone and/or polyurethane (and/or a similar elastomer), and the assembled structure is dipped into the material, while the material is in an uncured, liquid state. Subsequently, the material is cured such that it solidifies, e.g., by being left to dry. For some applications, while the material is drying the assembled structure is rotated, which typically facilitates the formation of a film of material having a substantially uniform thickness within each of the impeller blades. Once the material has dried, the mandrel is typically removed from the lumen defined by the bushings and the spring.

The result of the process described above is typically that there is a continuous film of material extending between each of the helical elongate elements to the spring, and also extending along the length of the spring, such as to define a tube, with the spring embedded within the tube. The portions of the film that extend from each of the helical elongate elements to the spring define the impeller blades. For applications in which the impeller includes elongate elements 67, the elongate elements are typically embedded within these portions of film.

Typically, elongate elements 67 are configured to limit the radial expansion of the blades of the impeller, as described in detail hereinabove. For some applications, the span to which the elongate elements allow the impeller blades to expand is set using the following technique. As described in the above paragraph, the two ends of the string or the wire within respective blades are tied to each other. Typically, the ends of the string or the wire in each of the blade are tied such that the spans of the impeller blades are set to less than the span of the impeller that is desired, and such that there is some slack in the knots via which the two ends of the strings or the wires are tied to each other. Subsequently, the outer edges of the impeller blades are pulled apart from each other, such as to increase the spans of the impeller blades, by tightening the knots between the ends of the strings or the wires within the respective blades. The process is repeated and the spans of the impeller blades are measured, until the desired span of the impeller blades has been achieved. Subsequently, structure 59 with the string or wires tied thereto is dipped in an elastomeric material from which film 56 is made, and the elastomeric material is allowed to dry, such that the strings or the wires are maintained with the ends tied to each other at the desired span of the impeller blades.

Typically, impeller 50 is inserted into the left ventricle transcatheterally, while impeller 50 is in a radially-constrained configuration. In the radially-constrained configuration, both helical elongate elements 52 and central axial spring 54 become axially elongated, and radially constrained. Typically film 56 of the material (e.g., silicone and/or polyurethane) changes shape to conform to the shape changes of the helical elongate elements and the central axial spring, both of which support the film of material. Typically, using a spring to support the inner edge of the film allows the film to change shape without the film becoming broken or collapsing, due to the spring providing a large surface area to which the inner edge of the film bonds. For some applications, using a spring to support the inner edge of the film reduces a diameter to which the impeller can be radially constrained, relative to if, for example, a rigid shaft were to be used to support the inner edge of the film, since the diameter of the spring itself can be reduced by axially elongating the spring.

As described hereinabove, for some applications, proximal bushing 64 of impeller 50 is coupled to axial shaft 92 such that the axial position of the proximal bushing with respect to the shaft is fixed, and distal bushing 58 of the impeller is slidable with respect to the shaft. For some applications, when the impeller is radially constrained for the purpose of inserting the impeller into the ventricle or for the purpose of withdrawing the impeller from the subject's body, the impeller axially elongates by the distal bushing sliding along the axial shaft distally. Subsequent to being released inside the subject's body, the impeller assumes its non-radially-constrained configuration (in which the impeller is typically disposed during operation of the impeller), as shown in FIGS. 3A-C.

It is noted that, for illustrative purposes, in some of the figures, impeller 50 is shown without including all of the features of the impeller as shown and described with respect to FIGS. 3A-C. For example, some of the figures show the impeller not including sutures 53 and/or elongate elements 67. The scope of the present application includes using an impeller with any of the features shown and described with respect to FIGS. 3A-C in combination with any of the apparatus and methods described herein.

For some applications, the following technique is used to enhance bonding of the elastomeric material to the at least one helical elongate element in a manner that does not cause a protrusion from the effective edge of the impeller blade. Prior to being dipped in the elastomeric material, the helical elongate elements are coated with a coupling agent. Typically, a coupling agent is selected that has at least two functional groups that are configured to bond respectively with the helical elongate elements and with the elastomeric material. For example, a silane compound, such as n-(2-aminoethyl)-3-aminopropyltrimethoxysilane, may be used, with the silane compound containing a first functional group (e.g., (OH)) which is configured to bond with the helical elongate elements (which are typically made of an alloy, such a nitinol), and the silane compound containing a second functional group (e.g., (NH2)) which is configured to bond with the elastomeric material. Typically, the functional groups in the coupling agent are only active for a given time period (e.g., approximately an hour or less). Therefore, during this time period, a coat of elastomeric material is applied around the helical elongate elements. Typically, the coat of elastomeric material is the same elastomeric material or a similar elastomeric material to that used in film 56. For example, a polycarbonate-based thermoplastic polyurethane, such as Aromatic Carbothane™ (e.g., Aromatic Carbothane™ 75A) may be used in film 56, and the coating may be the same polycarbonate-based thermoplastic polyurethane, or a similar polycarbonate-based thermoplastic polyurethane, such as Pellethane® (e.g., Pellethane® 90A).

For some applications, subsequent to the coating having been applied to the helical elongate elements, the coated helical elongate elements are sprayed with a further layer of an elastomeric material. Typically, the elastomeric material that is sprayed is the same elastomeric material or a similar elastomeric material to that used as film 56. For example, a polycarbonate-based thermoplastic polyurethane, such as Aromatic Carbothane™ (e.g., Aromatic Carbothane™ 75A) may be used as film 56, and the sprayed material may be the same polycarbonate-based thermoplastic polyurethane, or a similar polycarbonate-based thermoplastic polyurethane, such as Pellethane® (e.g., Pellethane® 90A). For some applications, applying the spray to the helical elongate elements rounds the helical elongate elements. Typically, when the helical elongate element has a rounded cross section, the elastomeric material forms a layer having a substantially uniform thickness at the interface with the helical elongate element. For some applications, the step of applying the coat of elastomeric material, as described in the previous paragraph, at least partially rounds the helical elongate elements.

For some applications, subsequent to the spray having been applied to the helical elongate elements, structure 59 is dipped in the elastomer from which film 56 is made, e.g., as described hereinabove. For some applications, the material from which the film is made is an elastic material having an ultimate elongation of more than 300 percent, e.g., more than 400 percent. Typically, the material has a relatively low molecular weight. For some applications, the material has a melt flow index (which is an indirect measure of molecular weight) of at least 4, e.g., at least 4.3. For some applications, the material has an ultimate tensile strength of more than 6000 psi, e.g., more than 7000 psi, or more than 7500 psi. For some applications, the material is a thermoplastic polyurethane, e.g., a Carbothane™. For some applications, Aromatic Carbothane™ 75 A is used. Typically, such materials combine one or more of the following properties: no outer diameter loss caused during the dip process, resistance to fatigue, resistance to becoming misshaped by being crimped, and low outer diameter loss during crimping.

In accordance with the above description of the application of film 56 to the helical elongate elements, the scope of the present invention includes any technique whereby, prior to the helical elongate elements being dipped into the elastomeric material from which film 56 is made, additional layers of the same elastomeric material, a different elastomeric material, and/or a mediating material are applied to the helical elongate elements, whether by spraying, dipping, or a different coating method. For some applications, additional layers of elastomeric material are configured to round the helical elongate elements, and/or to act as mediators to enhance bonding between the helical elongate elements and film 56 of material. For some applications, a mediating material (such as silane) is configured to act as a mediator to enhance bonding between the helical elongate elements and film 56 of material.

Figure 3E:
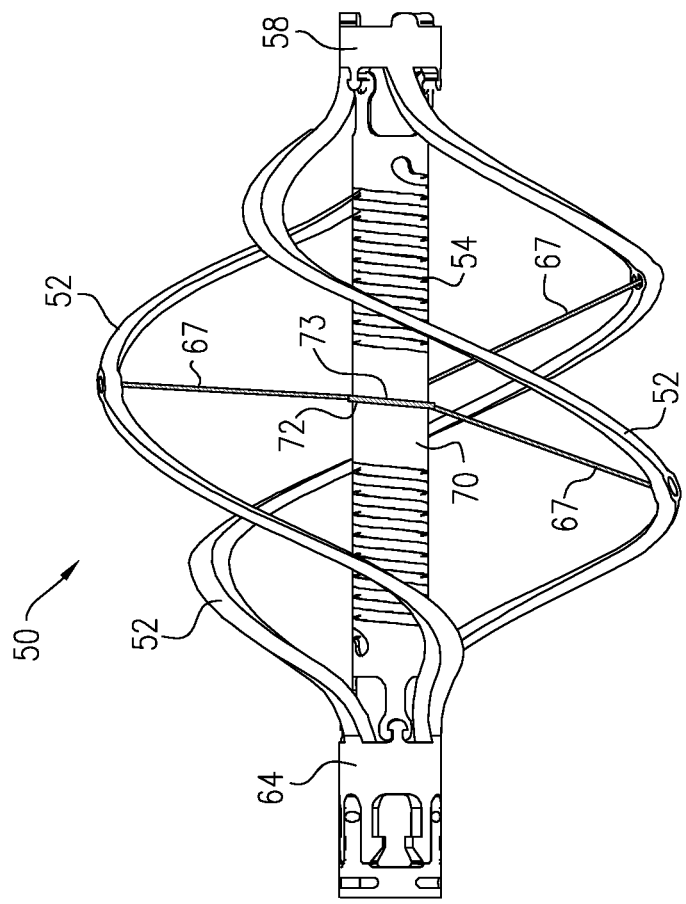
Figure 3D:
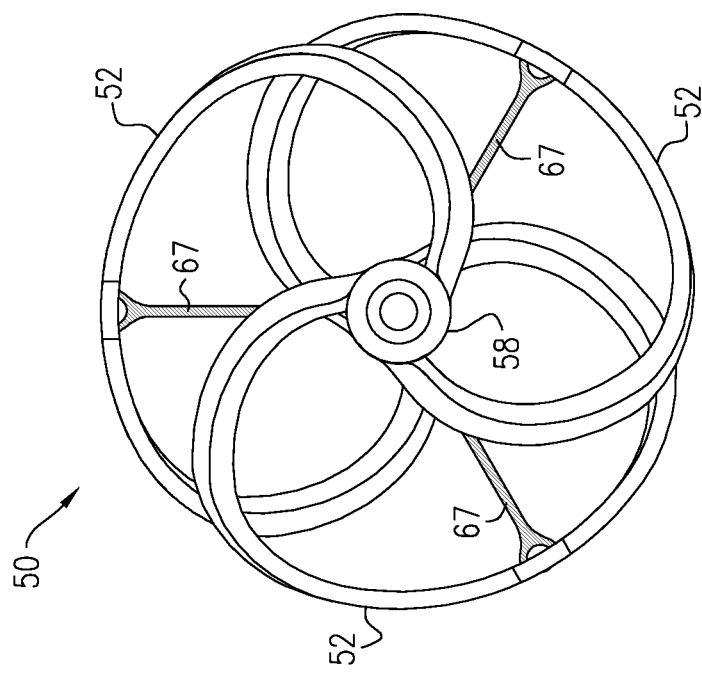

Reference is now made to FIGS. 3D and 3E, which are schematic illustrations of impeller 50, the impeller including a single integrated impeller-overexpansion-prevention element 72 that defines a plurality of elongate elements 67, in accordance with some applications of the present invention. FIGS. 3D and 3E show the impeller in the absence of the film 56 of material, for illustrative purposes. For some applications, element 72 defines a ring 73 and the plurality of elongate elements 67 extending radially from the ring. For some applications, rather than threading strings and/or wire around spring 54, ring 73 of element 72 is placed around the spring, e.g., by being placed around tube 70, which is typically disposed at the longitudinally-central location of the spring. The ends of respective elongate elements 67 are then coupled to respective helical elongate elements 52. As described hereinabove, elongate elements 67 are typically flexible but are substantially non-stretchable along the axis defined by the elongate elements. Further typically, each of elongate elements 67 is configured to substantially not resist compression. Rather, each elongate element 67 is configured to exert a tensile force upon helical elongate element 52 that prevents helical elongate element 52 from moving radially outward, such that (in the absence of elongate element 67) a separation between helical elongate element 52 and central axial spring 54 would be greater than a length of elongate element 67. When a force is acting upon the impeller that would cause the helical elongate element 52 to move radially outward (in the absence of elongate element 67), the impeller-overexpansion-prevention element is configured to prevent radial expansion of the impeller. Typically, a respective elongate element 67 is disposed within each one of the impeller blades and is configured to prevent the impeller blade from radially expanding. For some applications, element 72 is made of polyester, and/or another polymer or a natural material that contains fibers, and/or nitinol (or a similar shape-memory alloy).

It is noted that the scope of the present application includes using single integrated impeller-overexpansion-prevention element 72 with an impeller having a different construction from that shown in FIGS. 3D-E. For example, the single integrated impeller-overexpansion-prevention element 72 could be used with an impeller having a differently constructed axial structure than spring 54. Typically, the axial structure defines a lumen therethrough, such that the impeller defines lumen 62 therethrough.

Figure 3F:
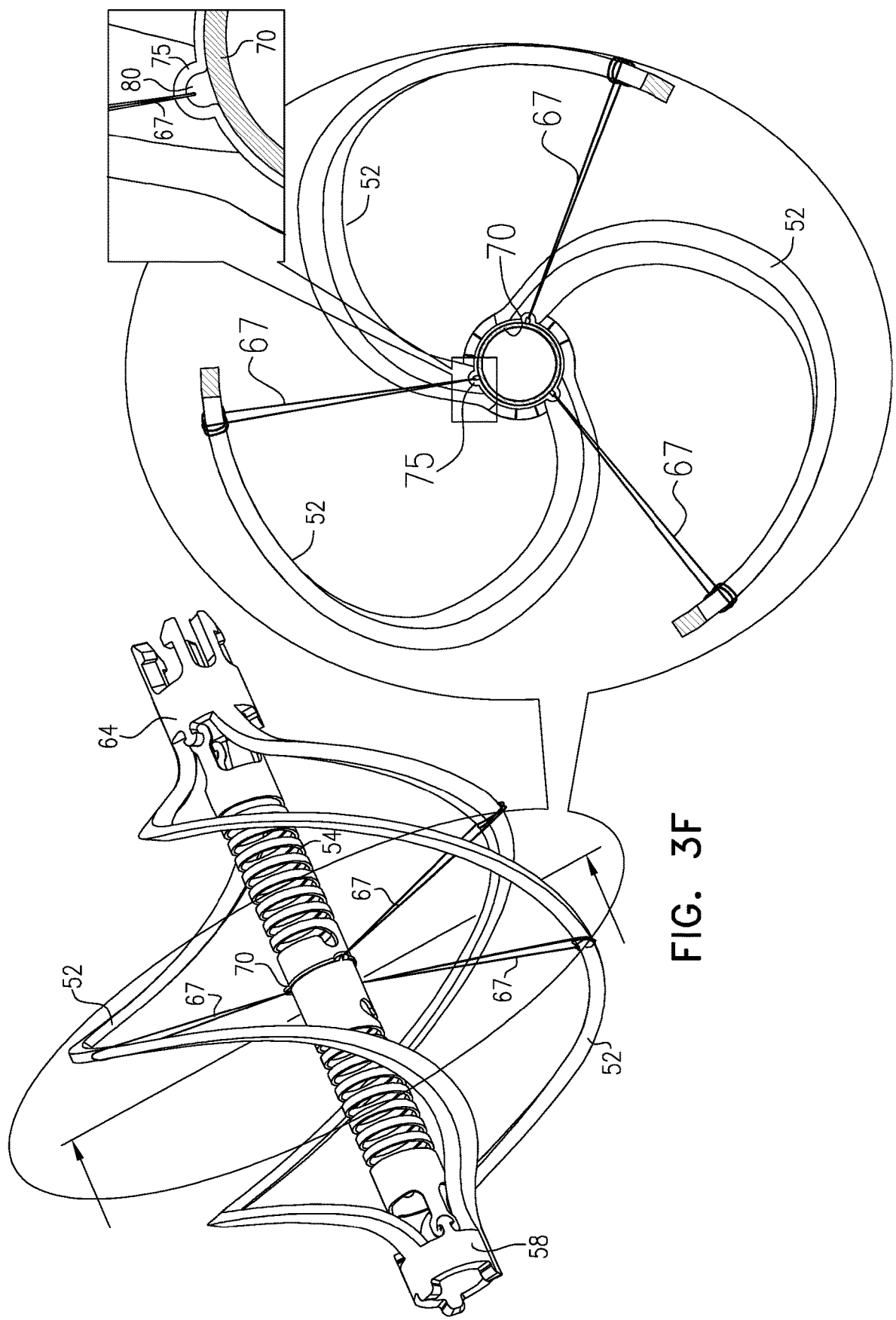

Reference is now made to FIG. 3F, which is a schematic illustration of impeller 50, the impeller including a securing element 75 that is configured to secure elongate elements 67 with respect to tube 70, in accordance with some applications of the present invention. For some applications, the string or the wire that comprises elongate element 67 is not wound around tube 70, and does not cross the longitudinal axis of the impeller. Rather, the string or the wire is secured with respect to tube 70 via securing element 75. Typically, the string or the wire is secured to the outer surface of tube 70 at a location on the outer surface of the tube that is closest to the maximum span of the helical elongate element to which the ends of the string or the wire are tied. For some applications, the securing element comprises a ring, as shown. For some such applications, the ring define small notches (or eyelets) 80 through which the string or the wire passes between the ring and tube 70.

Reference is now made to FIGS. 3Gi and 3Gii, which are photographs of impeller 50, in accordance with some applications of the present invention. As shown, for some applications, by manufacturing an impeller using the methods described hereinabove, adjacent blades 51 of impeller 50 becomes shaped such as to define a continuous U-shaped curved surface. As indicated by curve 55 which has been added to FIG. 3Gii, along at least a portion of the length of the impeller, as film 56 of the elastomeric material transition from one blade to an adjacent blade, the film forms a continuous U-shaped curve. It is noted that even at spring 54 which runs along the axis of the impeller, the curvature of the film of material is substantially unbroken. For some applications, by virtue of forming the impeller in the manner described hereinabove, the film of material assumes the above-described curvature. Typically, by virtue of defining continuous U-shaped curved surfaces, the impeller blades are configured to provide smooth flow lines along which blood flows through the impeller, thereby enhancing efficiency of blood pumping by the impeller and/or reducing a risk of hemolysis, relative to if the adjacent blades did not define a continuous curved surface (e.g., relative to if the curvature were to be broken at spring 54). For some applications, a generally similar impeller is used in which the impeller has an axial structure (e.g., a cylindrical axial structure) that is configured differently from spring 54. Typically, the axial structure defines a lumen therethrough, such that the impeller defines lumen 62 therethrough. Alternatively, the impeller includes spring 54 (which includes tube 70) as an axial structure, as shown.

When viewed from the distal end of the impeller, the pressure side of each of the blades of the impeller (i.e., the side that pushes the blood during operation of the impeller) is convex in the distal region of the impeller, transforms to being substantially radially oriented in the region of the elongate elements 67, and then is concave in the proximal region of the impeller. (For illustrative purposes, the opposite side to the pressure side of the impeller blades (i.e., the "non-pressure side") is indicated in FIG. 3Gii.) Thus, when in use, the blood that is pumped by the impeller is first pumped by a convex impeller surface and then pumped by a concave impeller surface. For some applications, elongate elements 67 are disposed approximately halfway along the length of the impeller blade and are configured to facilitate the transition of the film of material from having a convex curvature to having a concave curvature. Thus, typically, at the region of elongate element 67 within the impeller blade, the blade is substantially radially oriented. Typically, by defining a concave surface in the proximal region of the impeller, the pressure side of the blades of the impeller are configured to add flow and/or pressure to the blood even after blood has had flow and/or pressure applied to it within the distal region of the impeller. Alternatively (not shown), the pressure side of each of the blades of the impeller (i.e., the side that pushes the blood during operation of the impeller) is concave in the distal region of the impeller, transforms to being substantially radially oriented in the region of the elongate elements 67, and then is convex in the proximal region of the impeller.

Figure 5A:
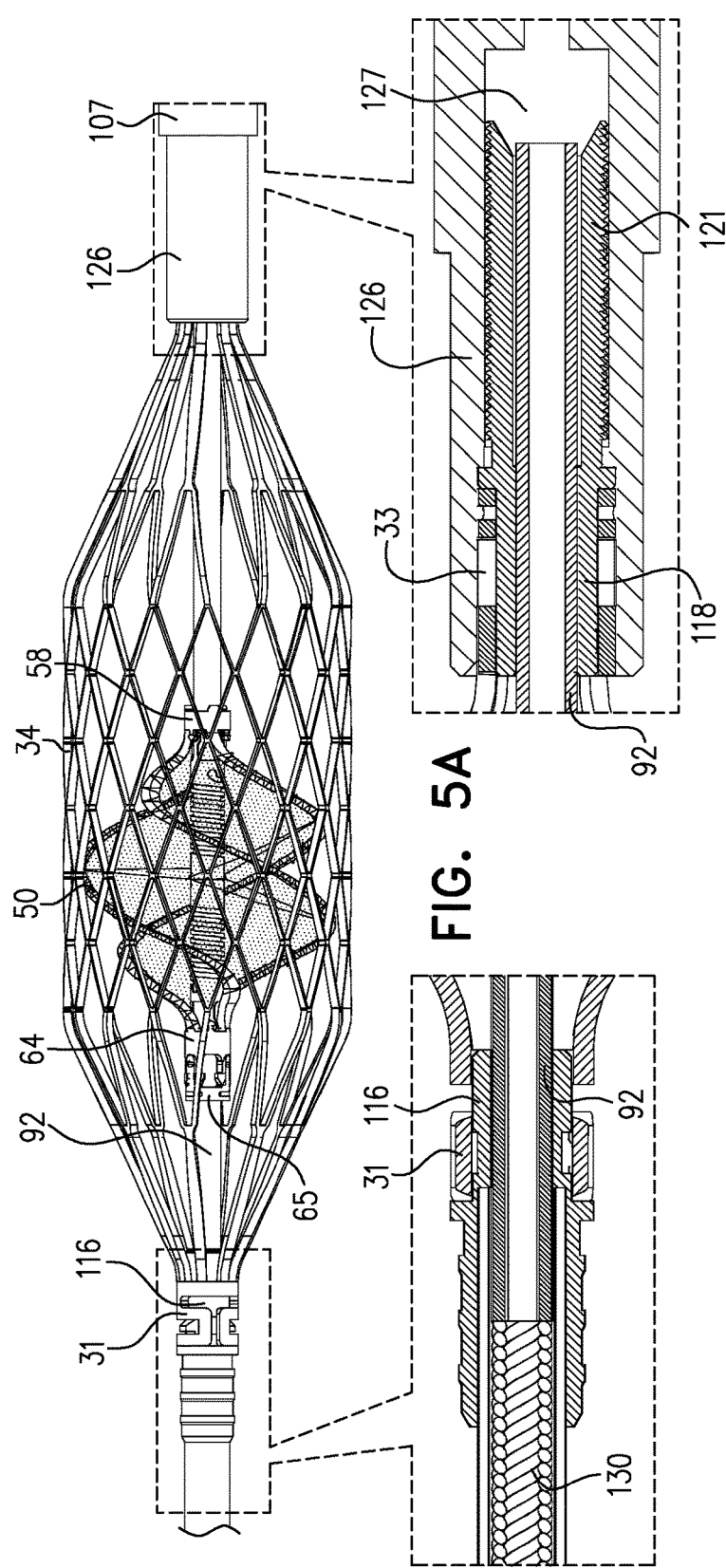
FIGS. 5A and 5B are schematic illustrations of the impeller and the frame of the ventricular assist device, respectively in non-radially-constrained and radially-constrained states thereof, in accordance with some applications of the present invention.
Figure 5B:
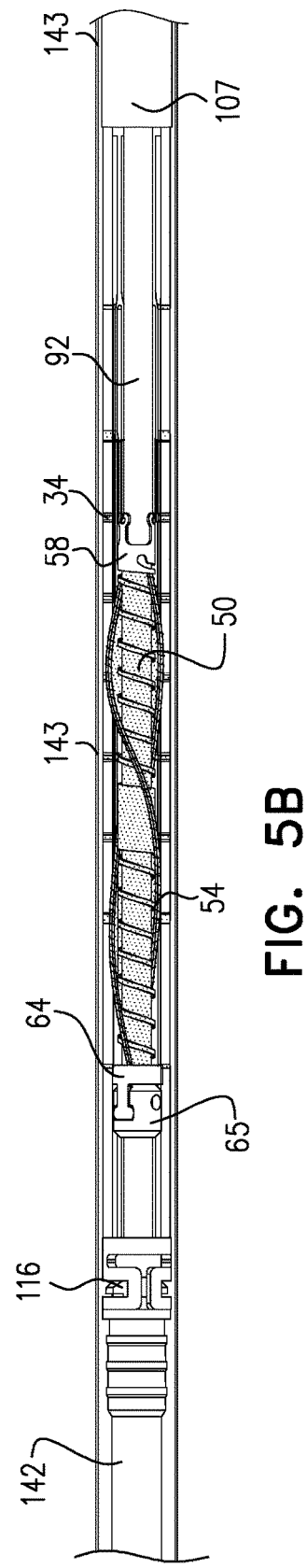

Reference is now made to FIGS. 5A and 5B, which are schematic illustrations of impeller 50 and frame 34 of ventricular assist device 20, respectively in non-radially-constrained and radially-constrained states thereof, in accordance with some applications of the present invention. The impeller and the frame are typically disposed in the radially-constrained states during the transcatheteral insertion of the impeller and the frame into the subject's body, and are disposed in the non-radially-constrained states during operation of the impeller inside the subject's left ventricle. As described hereinabove, typically pump-outlet tube 24 is disposed over at least some of the frame and extends proximally therefrom. However, for illustrative purposes, the frame and the impeller are shown in the absence of pump-outlet tube 24 in FIGS. 5A-B.

As indicated in FIG. 5B, the frame and the impeller are typically maintained in radially-constrained configurations by delivery catheter 143. Typically, in the radially-constrained configuration of the impeller the impeller has a total length of more than 15 mm (e.g., more than 20 mm), and/or less than 30 mm (e.g., less than 25 mm), e.g., 15-30 mm, or 20-25 mm. Further typically, in the non-radially constrained configuration of the impeller, the impeller has a length of more than 8 mm (e.g., more than 10 mm), and/or less than 18 mm (e.g., less than 15 mm), e.g., 8-18 mm, or 10-15 mm. Still further typically, when the impeller and frame 34 are disposed in radially constrained configurations (as shown in FIG. 5B), the impeller has an outer diameter of less than 2 mm (e.g., less than 1.6 mm) and the frame has an outer diameter of less than 2.5 mm (e.g., less than 2.1 mm).

As described hereinabove, typically, axial shaft 92 passes through the axis of impeller 50, via lumen 62 of the impeller (lumen 62 being shown in FIG. 3C). Typically, proximal bushing 64 of the impeller is coupled to the shaft via a coupling element 65 such that the axial position of the proximal bushing with respect to the shaft is fixed, and distal bushing 58 of the impeller is slidable with respect to the shaft. The axial shaft itself is radially stabilized via a proximal radial bearing 116 and a distal radial bearing 118.

Typically, coupling portion 31 of frame 34 is coupled to proximal radial bearing 116, for example, via snap-fit coupling, and/or via welding. Typically, at the distal end of frame 34 distal strut junctions 33 are placed into grooves defined by the outer surface of distal radial bearing 118, the grooves being shaped to conform with the shapes of the distal strut portions. The proximal end of distal-tip element 107 (which defines distal-tip portion 120) typically holds the distal strut portions in their closed configurations around the outside of distal radial bearing 118, as shown. For some applications, the device includes a distal extension 121 that extends distally from the distal radial bearing. Typically, the extension is configured to stiffen a region of the distal-tip element into which the distal end of shaft 92 moves (e.g., an axial-shaft-receiving tube 126, described hereinbelow, or a portion thereof).

As described above, axial shaft 92 is radially stabilized via proximal radial bearing 116 and distal radial bearing 118. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller, as described hereinabove. For some applications, axial shaft 92 is made of stainless steel, and proximal bearing 116 and/or distal bearing 118 are made of hardened steel. Typically, when crimping (i.e., radially constraining) the impeller and the frame for the purpose of inserting the impeller and the frame into the subject's body, distal bushing 58 of the impeller is configured to slide along the axial shaft in the distal direction, such that the impeller becomes axially elongated, while the proximal bushing remains in an axially fixed position with respect to the axial shaft. More generally, the impeller changes from its radially-constrained configuration to its non-radially-constrained configuration, and vice versa, by the distal bushing sliding over the axial shaft, while the proximal bushing remains in an axially fixed position with respect to the axial shaft.

Typically, the impeller itself is not directly disposed within any radial bearings or thrust bearings. Rather, bearings 116 and 118 act as radial bearings with respect to the axial shaft. Typically, pump portion 27 (and more generally ventricular assist device 20) does not include any thrust bearing that is configured to be disposed within the subject's body and that is configured to oppose thrust generated by the rotation of the impeller. For some applications, one or more thrust bearings are disposed outside the subject's body (e.g., within motor unit 23, shown in FIGS. 1A and 7A-Bii), and opposition to thrust generated by the rotation of the impeller is provided solely by the one or more thrust bearings disposed outside the subject's body. For some applications, a mechanical element and/or a magnetic element is configured to maintain the impeller within a given range of axial positions. For example, a magnet (e.g., magnet 82, described hereinbelow with reference to FIG. 7A) that is disposed at the proximal end of drive cable 130 (e.g., outside the subject's body) may be configured to impart axial motion to the impeller, and/or to maintain the impeller within a given range of axial positions.

Reference is now made to FIGS. 6A and 6B, which are schematic illustrations of ventricular assist device 20 at respective stages of a motion cycle of impeller 50 of the ventricular assist device with respect to frame 34 of the ventricular assist device, in accordance with some applications of the present invention. For some applications, while the impeller is pumping blood through tube 24 by rotating, axial shaft 92 (to which the impeller is fixated) is driven to move the impeller axially back-and-forth within frame 34, by the axial shaft moving in an axial back-and-forth motion, as described in further detail hereinbelow with reference to FIG. 7A-Bii. Alternatively or additionally, the impeller and the axial shaft are configured to move axially back-and-forth within frame 34 in response to forces that are acting upon the impeller, and without requiring the axial shaft to be actively driven to move in the axial back-and-forth motion. Typically, over the course of the subject's cardiac cycle, the pressure difference between the left ventricle and the aorta varies from being approximately zero during ventricular systole (hereinafter "systole") to a relatively large pressure difference (e.g., 50-70 mmHg) during ventricular diastole (hereinafter "diastole"). For some applications, due to the increased pressure difference that the impeller is pumping against during diastole (and due to the fact that drive cable 130 is stretchable), the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller, in order to cause them to undergo this motion. FIG. 6A shows the impeller and axial shaft disposed at their typical systolic positions and FIG. 6B shows the impeller and axial shaft disposed at their typical diastolic positions.

For some applications, by moving in the axial back-and-forth motion, the portions of the axial shaft that are in contact with proximal bearing 116 and distal bearing 118 are constantly changing. For some such applications, in this manner, the frictional force that is exerted upon the axial shaft by the bearings is spread over a larger area of the axial shaft than if the axial shaft were not to move relative to the bearings, thereby reducing wear upon the axial shaft, ceteris paribus. Alternatively or additionally, by moving in the back-and-forth motion with respect to the bearing, the axial shaft cleans the interface between the axial shaft and the bearings from any residues, such as blood residues.

For some applications, when frame 34 and impeller 50 are in non-radially-constrained configurations thereof (e.g., when the frame and the impeller are deployed within the left ventricle), the length of the frame exceeds the length of the impeller by at least 2 mm (e.g., at least 4 mm, or at least 8 mm). Typically, the proximal bearing 116 and distal bearing 118 are each 2-4 mm (e.g., 2-3 mm) in length. Further typically, the impeller and the axial shaft are configured to move axially within the frame in the back-and-forth motion at least along the length of each of the proximal and distal bearings, or at least along twice the length of each of the bearings. Thus, during the back-and-forth axial movement of the axial shaft, the axial shaft is wiped clean on either side of each of the bearings.

For some applications, the range of the impeller motion is as indicated in FIGS. 6A-B, with FIG. 6A indicating the proximal-most disposition of the impeller over the course of the cardiac cycle (at which the impeller is typically disposed during systole) and FIG. 6B indicating the distal-most disposition of the impeller over the course of the cardiac cycle (at which the impeller is typically disposed during diastole). As shown in FIG. 6A, for some applications, at its proximal-most position the proximal end of the impeller is disposed at location Ip, which is within the proximal conical section of frame 34. As shown in FIG. 6B, for some applications, at its distal-most position the distal end of the impeller is disposed at location Id, which is at the distal end of the cylindrical section of frame 34. For the purpose of the present application, the entire section of the frame from Ip to Id may be considered as housing the impeller, since this entire section of the frame typically houses at least a portion of the impeller over at least a portion of the cardiac cycle. Typically, over the course of the entire cardiac cycle, the section of the impeller at which the span of the impeller is at its maximum is disposed within the cylindrical portion of the frame 34. However, a proximal portion of the impeller is typically disposed within the proximal conical section of the frame during at least a portion of the cardiac cycle.

Reference is again made to FIGS. 6A and 6B, and reference is also made to FIG. 6C, which is an enlarged schematic illustration of distal-tip element 107, which includes axial-shaft-receiving tube 126 and distal-tip portion 120 of ventricular assist device 20, in accordance with some applications of the present invention. Typically, distal-tip element 107 is a single integrated element that includes both axial-shaft-receiving tube 126 and distal-tip portion 120. For some applications, distal-tip element 107 is configured to be soft, such that the distal-tip portion is configured not to injure tissue of the subject, even if the distal-tip portion comes into contact with the tissue (e.g., tissue of the left ventricle). For example, distal-tip element 107 may be made of silicone, polyethylene terephthalate (PET) and/or polyether block amide (e.g., PEBAX®). For some applications, the distal-tip portion defines a lumen 122 therethrough. For some such applications, during insertion of the ventricular assist device into the left ventricle, guidewire 10 (FIG. 1B) is first inserted into the left ventricle, for example, in accordance with known techniques. The distal-tip portion of the ventricular assist device is then guided to the left ventricle by advancing the distal-tip portion over the guidewire, with the guidewire disposed inside lumen 122. For some applications, a duckbill valve 390 (or a different type of hemostasis valve) is disposed at the distal end of lumen 122 of distal-tip portion 120.

Typically, during the insertion of the ventricular assist device into the subject's ventricle, delivery catheter 143 is placed over impeller 50 and frame 34 and maintains the impeller and the frame in their radially-constrained configurations. For some applications, distal-tip element 107 extends distally from the delivery catheter during the insertion of the delivery catheter into the subject's ventricle. For some applications, at the proximal end of the distal-tip element, the distal-tip element has a flared portion 124 that acts as a stopper and prevents the delivery catheter from advancing beyond the flared portion.

Figure 15A:
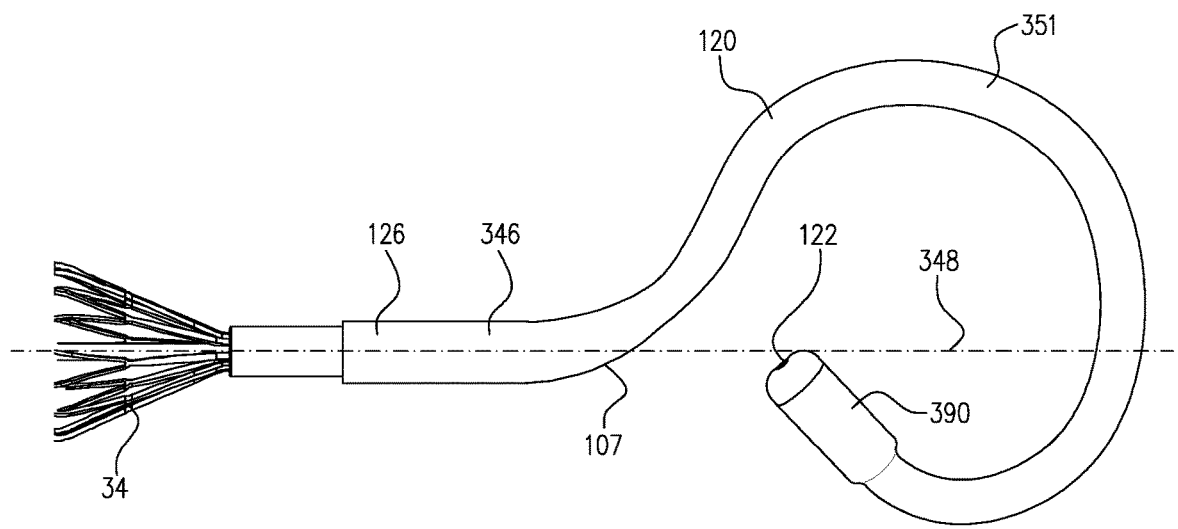
FIGS. 15A, 15B, 15C, and 15D are schematic illustrations of a distal-tip element of a ventricular assist device that is at least partially curved such as to define a question-mark shape or a tennis-racket shape, in accordance with some applications of the present invention.
Figure 15B:
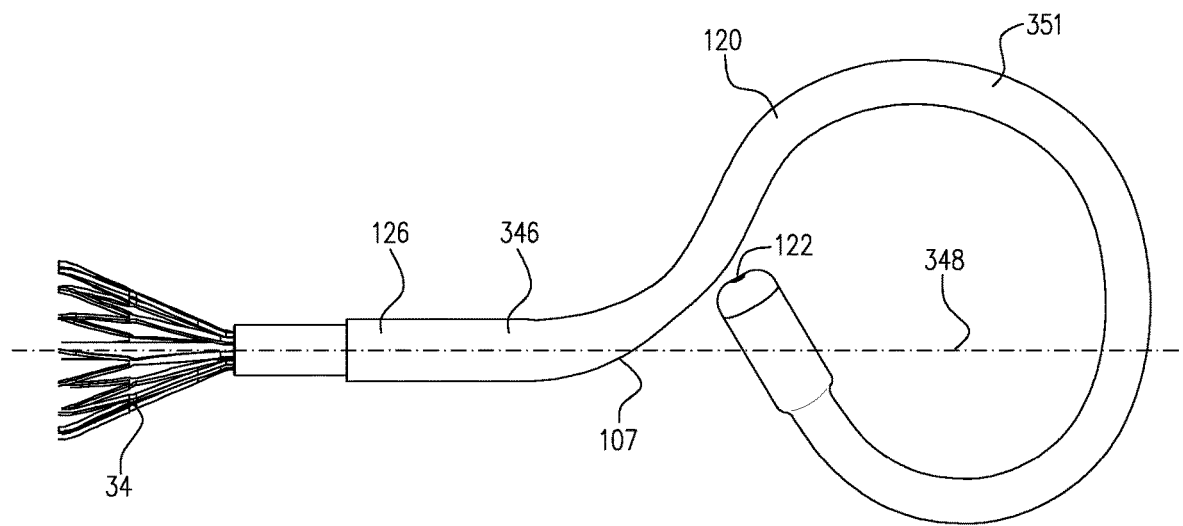
Figure 15C:
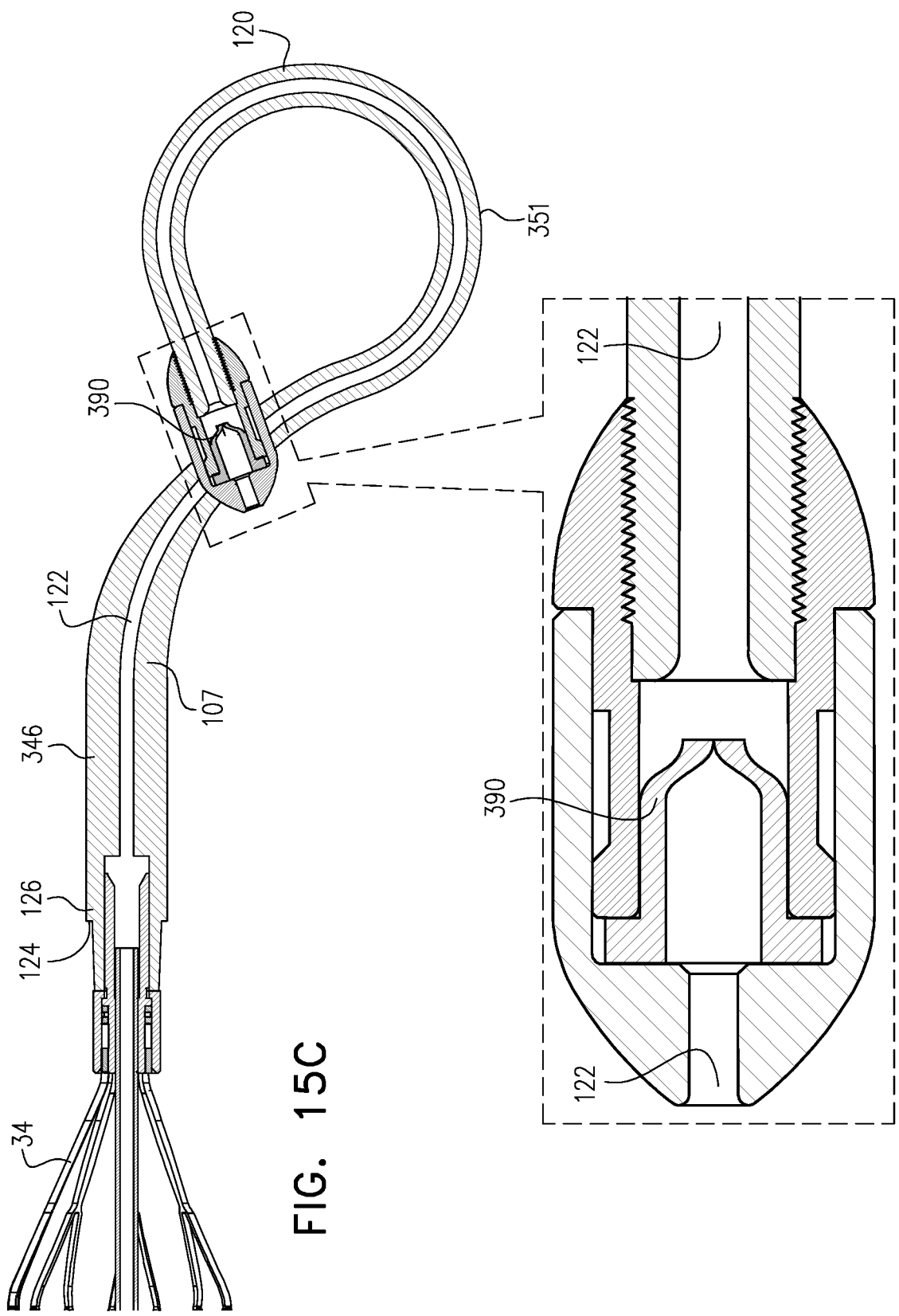
Figure 15D:
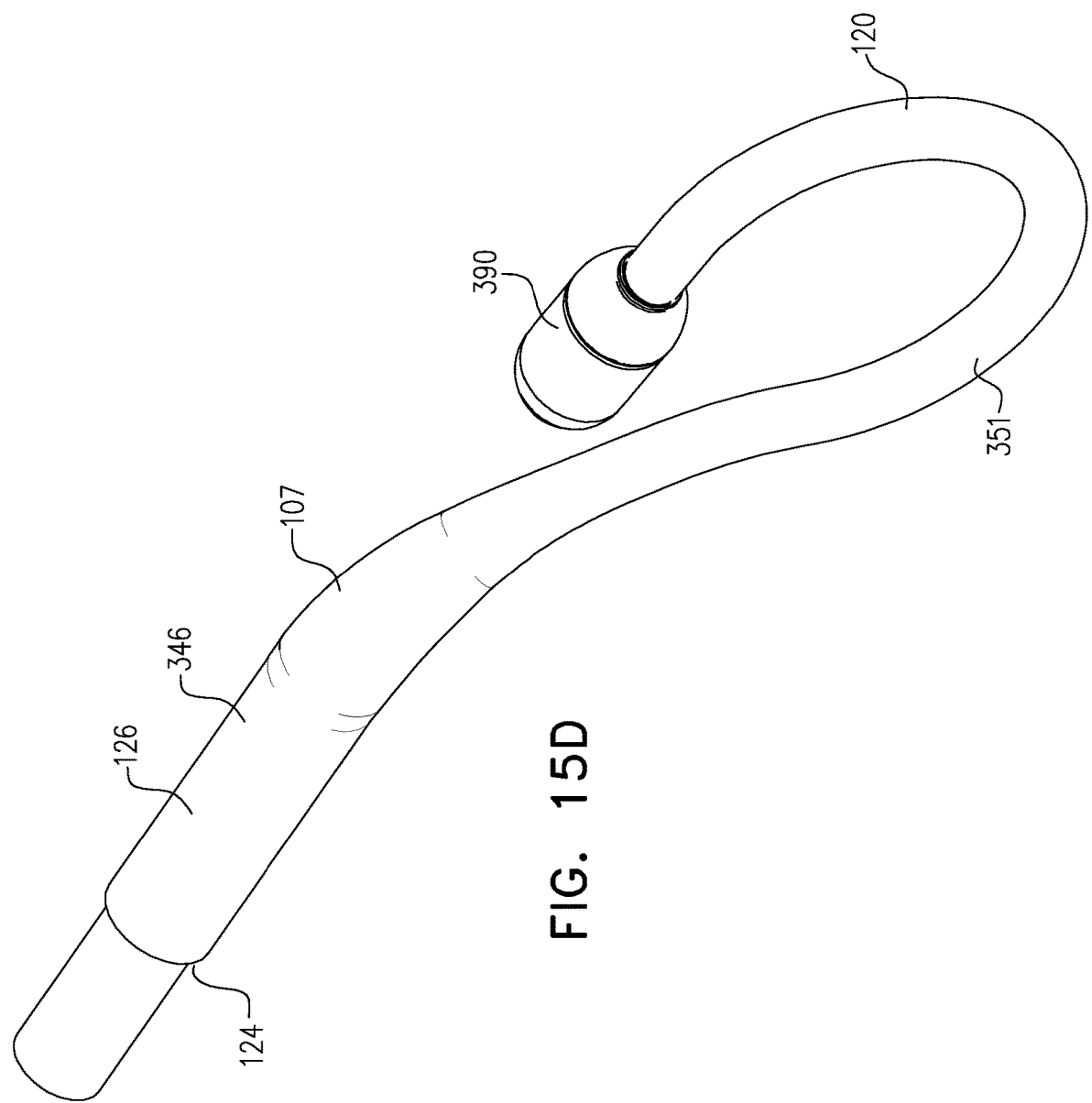
Figure 16B:
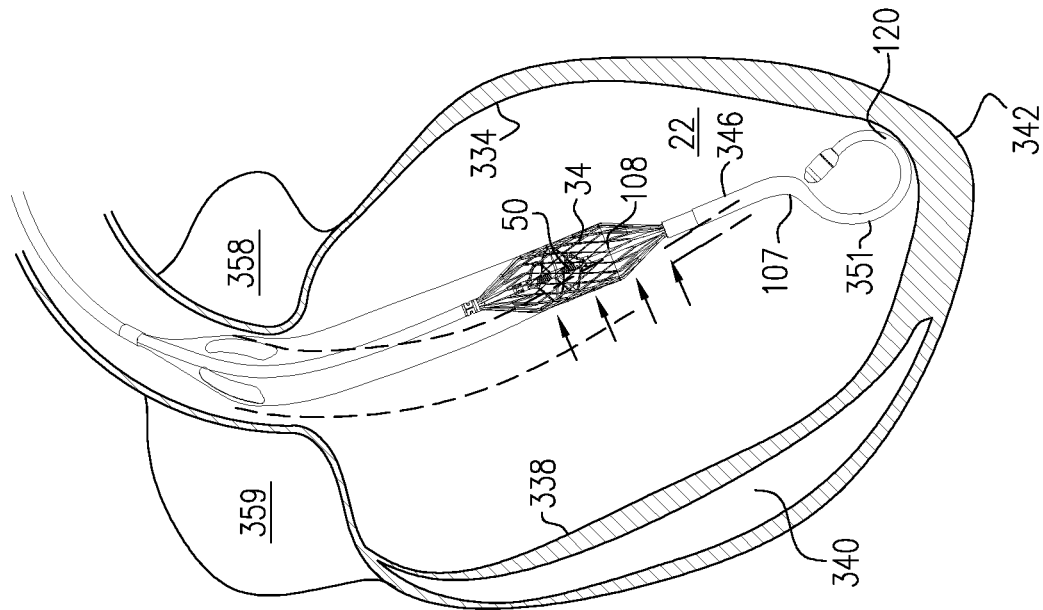
FIGS. 16A and 16B are schematic illustrations of the ventricular assist device of FIG. 15D disposed inside a subject's left ventricle, in accordance with some applications of the present invention.
Figure 16A:
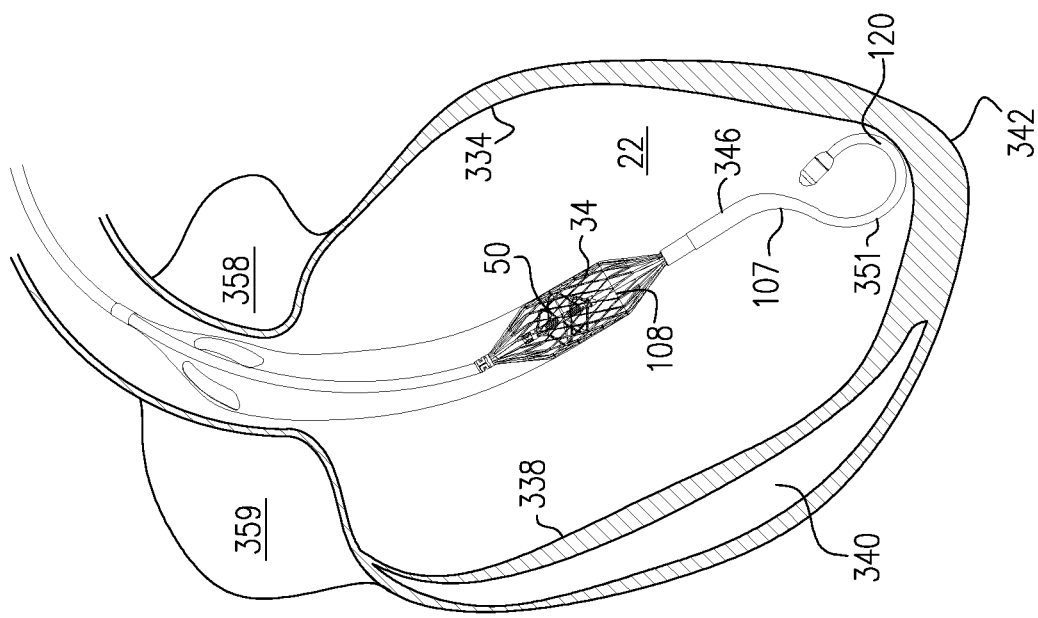

It is noted that the external shape of distal-tip portion in FIGS. 6A-C(as well as in some other figures) is shown as defining a complete loop, with the distal end of the distal-tip portion (within which duckbill valve 390 is disposed) crossing over a more proximal portion of the distal-tip portion. Typically, as a result of having had a guidewire inserted therethrough (during insertion of the ventricular assist device into the left ventricle), the distal-tip portion remains partially straightened, even after the removal of the guidewire from the distal-tip portion. Typically, the partial straightening of the distal-tip portion is such that, when the distal-tip portion is disposed within the left ventricle, in the absence of external forces acting upon the distal-tip portion, the distal-tip portion does not define a complete loop, e.g., as shown in FIG. 1B, 15D, and FIG. 16A. For some applications, in order to insert the guidewire through the distal-tip potion of straightening element 270 is used, as described in further detail hereinbelow, for example, with reference to FIGS. 23A-C. Other aspects of the shape of the distal-tip portion are described in further detail hereinbelow.

Reference is now made to FIGS. 6D and 6E, which are schematic illustrations of impeller 50, proximal bushing 64 of the impeller being coupled to a coupling element 65 that is proximally-extended such as to function as a stopper, in accordance with some applications of the present invention. FIG. 6D shows the impeller at the systolic phase of the motion cycle of the impeller and the FIG. 6E shows the impeller at the diastolic phase of its motion cycle. Typically, the coupling element is proximally-extended such as to prevent a central region of the impeller (at which the span of the impeller is at its maximum) from sliding proximally into the proximal conical portion of frame 34. For example, in the systolic phase of the impeller's motion cycle (shown in FIG. 6D), if the impeller were to slide further proximally by more than a given amount, the proximally-extended coupling element would contact proximal radial bearing 116, thereby preventing further proximal motion of the impeller. For some applications, the coupling element is proximally extended such that it has a total length of more than 1.5 mm, e.g., more than 4 mm. For some applications (not shown), as an alternative or in addition to the coupling element extending proximally, a separate stopper element is disposed upon axial shaft proximally with respect to the coupling element. Typically, the stopper is configured as described with reference to the proximally-extended coupling element. Namely, such that if the impeller were to slide further proximally by more than a given amount, the stopper element would contact proximal radial bearing 116, thereby preventing further proximal motion of the impeller.

Figure 7A:
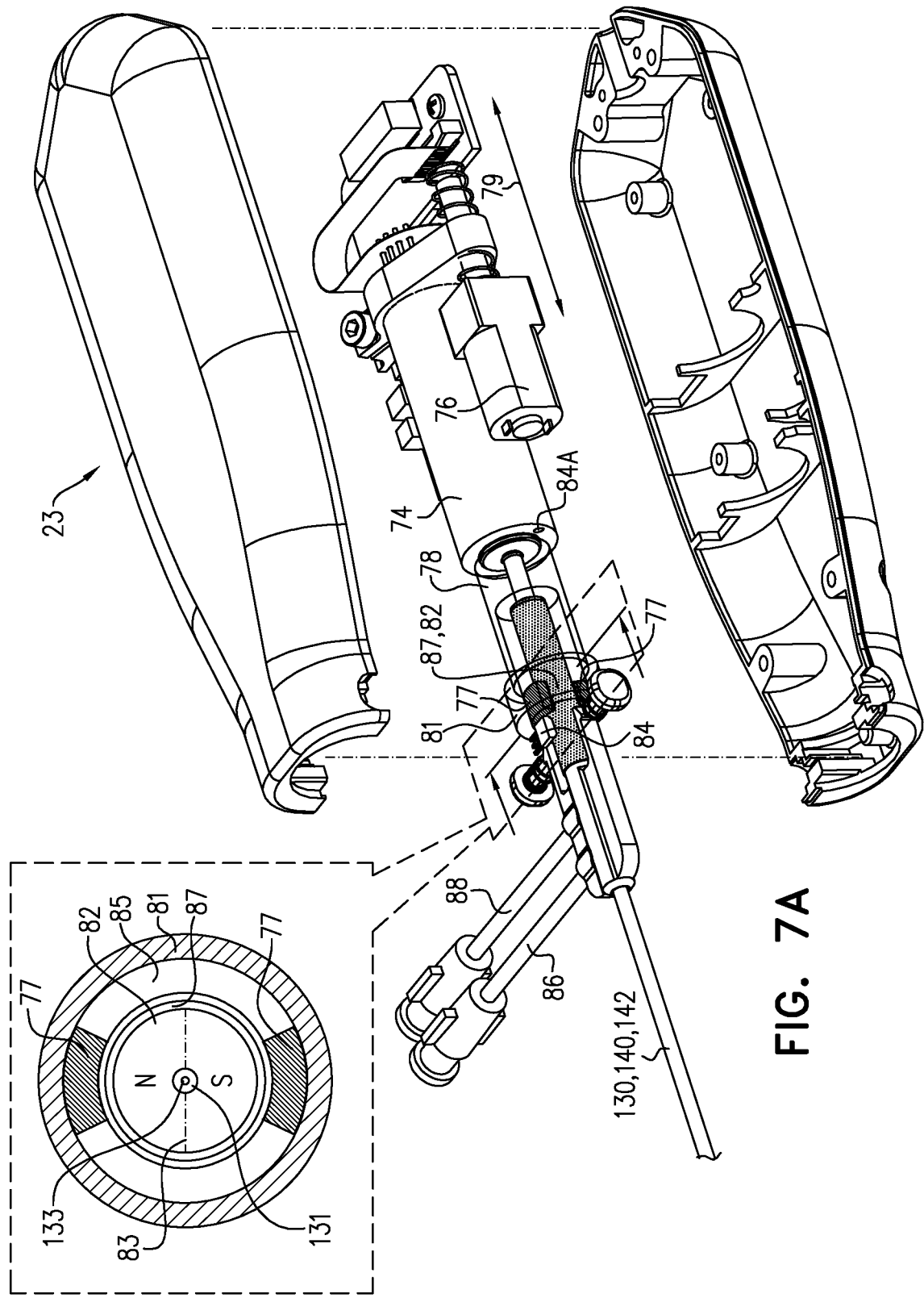
FIG. 7A is a schematic illustration of a motor unit of a ventricular assist device, in accordance with some applications of the present invention.

Reference is now made to FIG. 7A, which is a schematic illustration of an exploded view of motor unit 23 of ventricular assist device 20, in accordance with some applications of the present invention. As shown, the motor unit is typically a handle that is configured to be disposed outside the subject's body, and which houses a motor. As such, the motor unit may alternatively be referred to as a handle unit.

For some applications, computer processor 25 of control console 21 (FIG. 1A) that controls the rotation of impeller 50 is also configured to control the back-and-forth motion of the axial shaft. Typically, both types of motion are generated using motor unit 23. The scope of the present invention includes controlling the back-and-forth motion at any frequency. For some applications, an indication of the subject's cardiac cycle is detected (e.g., by detecting the subject's ECG), and the back-and-forth motion of the axial shaft is synchronized to the subject's cardiac cycle.

Typically, motor unit 23 includes a motor 74 that is configured to impart rotational motion to impeller 50, via drive cable 130. As described in further detail hereinbelow, typically, the motor is magnetically coupled to the drive cable. For some applications, an axial motion driver 76 is configured to drive the motor to move in an axial back-and-forth motion, as indicated by double-headed arrow 79. Typically, by virtue of the magnetic coupling of the motor to the drive cable, the motor imparts the back-and-forth motion to the drive cable, which it turn imparts this motion to the impeller. As described hereinabove and hereinbelow, for some applications, the drive cable, the impeller, and/or the axial shaft undergo axial back-and-forth motion in a passive manner, e.g., due to cyclical changes in the pressure gradient against which the impeller is pumping blood. Typically, for such applications, motor unit 23 does not include axial motion driver 76.

For some applications, the magnetic coupling of the motor to the drive cable is as shown in FIG. 7A. As shown in FIG. 7A, a least one more driving magnet 77 (e.g., two driving magnets 77) are coupled to the motor via a driving magnet housing 78. For some applications, the driving magnet housing includes ring 81 (e.g., a steel ring), and the driving magnets are adhered to an inner surface of the ring. For some applications, a spacer 85 is adhered to the inner surface of ring 81, between the two driving magnets, as shown. At least one driven magnet 82 is disposed between the driving magnets such that there is axial overlap between the driving magnets and the driven magnet. The driven magnet is coupled to a pin 131, which extends to beyond the distal end of driven magnet 82, where the pin is coupled to the proximal end of drive cable 130. For example, the driven magnet may be cylindrical and define a hole therethrough, and pin 131 may be adhered to an inner surface of the driven magnet that defines the hole. For some applications, the driven magnet is cylindrical, and the magnet includes a North pole and a South pole, which are divided from each other along the length of the cylinder along a line 83 that bisects the cylinder, as shown. For some applications, the driven magnet is housed inside a cylindrical housing 87. Typically, pin 131 defines a lumen 133, via which guidewire 10 is inserted through the pin.

It is noted that in the application shown in FIG. 7A, the driving magnets are disposed outside the driven magnet. However, the scope of the present application includes reversing the configurations of the driving magnets and the driven magnet, *mutatis mutandis*. For example, the proximal end of the drive cable may be coupled to two or more driven magnets, which are disposed around a driving magnet, such that there is axial overlap between the driven magnets and the driving magnet.

As described hereinabove, typically purging system 29 (shown in FIG. 1A) is used with ventricular assist device 20. Typically, motor unit 23 includes an inlet port 86 and an outlet port 88, for use with the purging system. For some applications, a purging fluid is continuously or periodically pumped into the ventricular assist device via inlet port 86 and out of the ventricular assist device via outlet port 88. Additional aspects of the purging system are described hereinbelow.

Typically, magnet 82 and pin 131 are held in axially relatively-fixed positions within motor unit 23. (For some applications, magnet 82 does have a small freedom of movement axially and/or rotationally relative to other components of the motor unit, such as the driving magnets 77. For some applications, such movement is measurable, as described in further detail hereinbelow.) The proximal end of the drive cable is typically coupled to pin 131 and is thereby held in an axially fixed position relative to the pin. Typically, drive cable 130 extends from pin 131 to axial shaft 92 and thereby at least partially fixes the axial position of the axial shaft, and in turn impeller 50. For some applications, the drive cable is somewhat stretchable. For example, the drive cable may be made of coiled wires that are stretchable, as described in further detail hereinbelow. The drive cable typically allows the axial shaft (and in turn the impeller) to assume a range of axial positions (by the drive cable becoming more or less stretched), but limits the axial motion of the axial shaft and the impeller to being within a certain range of motion (by virtue of the proximal end of the drive cable being held in an axially relatively-fixed position, and the stretchability of the drive cable being limited).

Figure 7B:
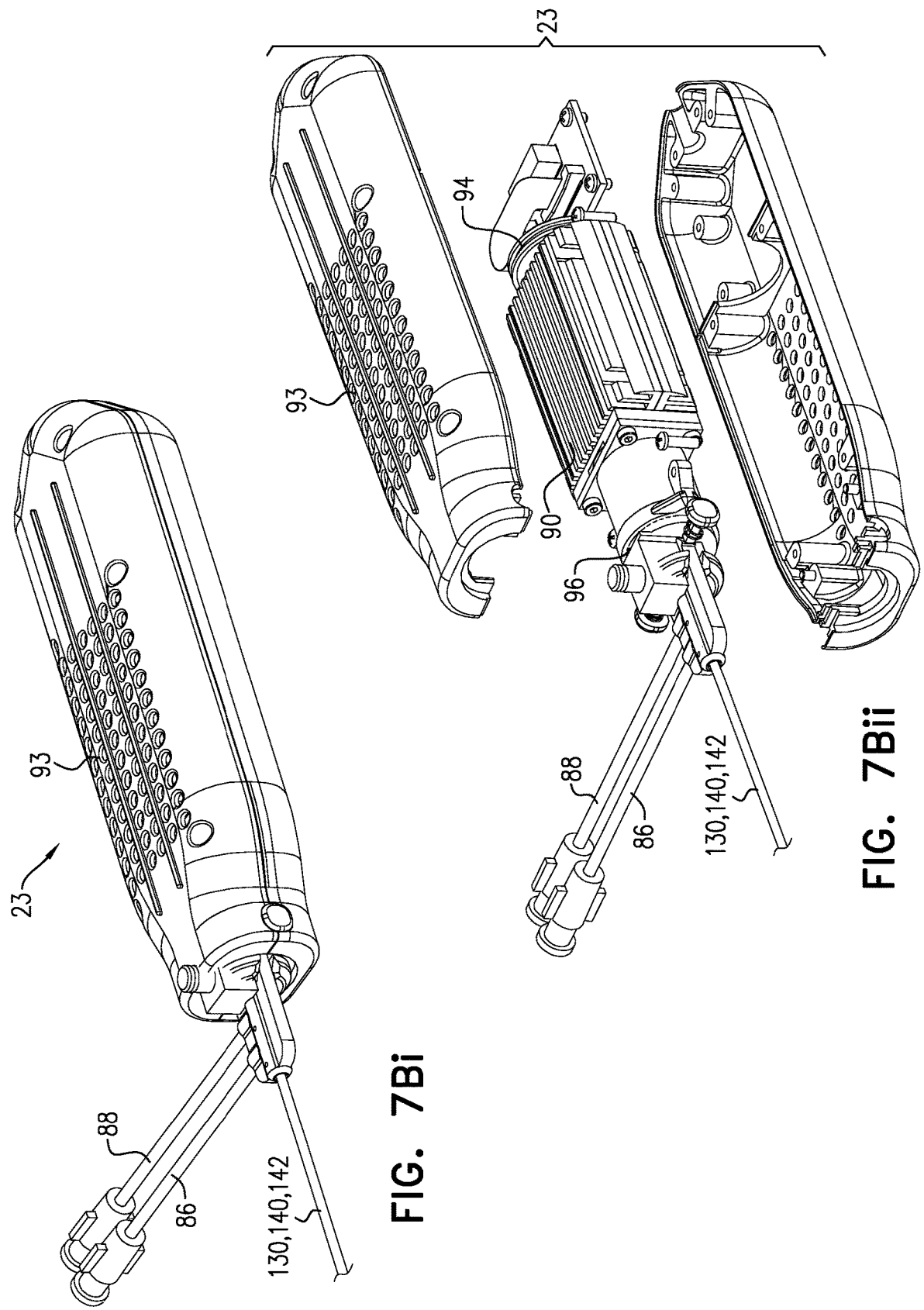
FIGS. 7Bi and 7Bii are schematic illustrations of a motor unit of a ventricular assist device, in accordance with some applications of the present invention.

Reference is now made to FIGS. 7Bi and 7Bii, which are schematic illustrations of motor unit 23, in accordance with some applications of the present invention. In general, motor unit 23 as shown in FIGS. 7Bi and 7Bii is similar to that shown in FIG. 7A, and, unless described otherwise, motor unit 23 as shown in FIGS. 7Bi and 7Bii contains similar components to motor unit 23 as shown in FIG. 7A. For some applications, the motor unit includes a heat sink 90 that is configured to dissipate heat that is generated by the motor. Alternatively or additionally, the motor unit includes ventilation ports 93 that are configured to facilitate the dissipation of heat that is generated by the motor. For some applications, the motor unit includes vibration dampeners 94 and 96 that are configured to dampen vibration of the motor unit that is caused by rotational motion and/or axial back-and-forth motion of components of the ventricular assist device.

As described hereinabove, for some applications, impeller 50 and axial shaft 92 are configured to move axially back-and-forth within frame 34 in response to forces that act upon the impeller, and without requiring the axial shaft to be actively driven to move in the axial back-and-forth motion. Typically, over the course of the subject's cardiac cycle, the pressure difference between the left ventricle and the aorta varies from being approximately zero during systole to a relatively large pressure difference (e.g., 50-70 mmHg) during diastole. For some applications, due to the increased pressure difference that the impeller is pumping against during diastole (and due to the drive cable being stretchable), the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller, in order to cause them to undergo this motion.

Figure 8A:
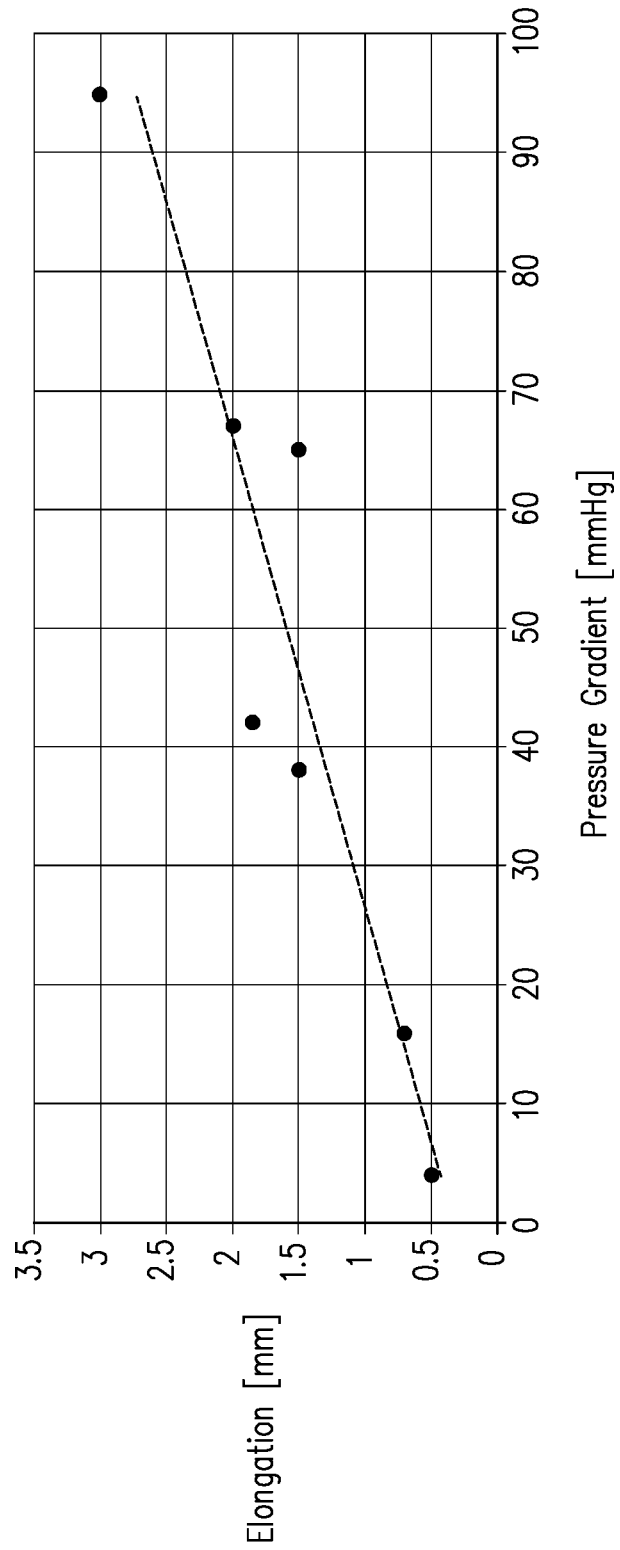
FIG. 8A is a graph indicating variations in the length of a drive cable of a ventricular assist device as a pressure gradient against which the impeller of the blood pump varies, as measured in experiments.

Reference is now made to FIG. 8A, which is a graph indicating variations in the length of a drive cable of a ventricular assist device, as a pressure gradient against which the impeller of the ventricular assist device varies, as measured in experiments. An impeller and a drive cable as described herein were used to pump a glycerin-based solution through chambers, with the chambers set up to replicate the left ventricle and the aorta, and the solution having properties (such as, density and viscosity) similar to those of blood. The pressure gradient against which the impeller was pumping was varied in a pulsatile manner to represent the pulsatility of the pressure gradient against which the impeller typically pumps when it is pumping blood from the left ventricle to the aorta. At the same time, movement of the drive cable was imaged and changes in the length of the drive cable were determined via analysis of the images. The graph shown in FIG. 8A indicates the changes in the length of the drive cable that were measured, as a function of the pressure gradient. As shown in FIG. 8A, as the pressure gradient against which the impeller pumped increased, the drive cable became increasingly elongated. As indicated by the results shown in FIG. 8A and as described hereinabove, it is typically the case that, in response to variations in the pressure against which the impeller is pumping blood (e.g., the pressure difference between the left ventricle and the aorta), the impeller moves back and forth with respect to frame 34. In turn, the movement of the impeller causes drive cable 130 to become more or less elongated.

For some applications, during operation of the ventricular assist device, computer processor 25 of control console 21 (FIG. 1A) is configured to measure an indication of the pressure exerted upon the impeller (which is indicative of the pressure difference between the left ventricle and the aorta), by measuring an indication of tension in drive cable 130, and/or axial motion of the drive cable. For some applications, based upon the measured indication, the computer processor detects events in the subject's cardiac cycle, determines the subject's left-ventricular pressure, and/or determines the subject's cardiac afterload. For some applications, the computer processor controls the rotation of the impeller, and/or the axial back-and-forth motion of the axial shaft in response thereto.

Referring again to FIG. 7A, for some applications, ventricular assist device 20 includes a sensor 84. For example, the sensor may include a magnetometer (e.g., a Hall sensor) that is disposed within motor unit 23, as shown in FIG. 7A. (In some cases, sensor 84 is referred to as magnetometer 84.) For some applications, it is the case that the axial back-and-forth motion of the impeller gives rise to a measurable back-and-forth motion of the inner, driven magnet 82 relative to the outer, one or more drive magnets 77, since the driven magnet is held in place with respect to the drive magnets via magnetic coupling, rather than rigid mechanical coupling. It is noted that typically the axial motion of the magnet is substantially less than that of the impeller, since the full range of motion of the impeller is not transmitted along the length of the drive cable. For some applications, the magnetometer measures variations in the magnetic field that is generated by one of the magnets in order to measure the axial motion of drive cable 130, and, in turn, to determine the pressure against which the impeller is pumping. For example, the inner, driven magnet 82 may be axially longer than the outer, driving magnets 77. Due to the inner magnet being longer than the outer magnets, there are magnetic field lines that emanate from the inner magnet that do not pass to the outer magnets, and the magnetic flux generated by those field lines, as measured by the magnetometer, varies as the drive cable, and, in turn, the inner magnet moves axially. During operation, motor 74 rotates, creating an AC signal in the magnetometer, which typically has a frequency of between 200 Hz and 800 Hz. Typically, as the tension in the drive cable changes due to the subject's cardiac cycle, this gives rise to a low frequency envelope in the signal measured by the magnetometer, the low frequency envelope typically having a frequency of 0.5-2 Hz. For some applications, the computer processor measures the low frequency envelope, and derives the subject's cardiac cycle from the measured envelope.

For some applications, the magnetometer measurements are initially calibrated, such that the change in magnetic flux per unit change in pressure against which the impeller is pumping (i.e., per unit change in the pressure difference between the left ventricle and the aorta, or per unit change in the pressure gradient) is known. It is known that, in most subjects, at systole, the left-ventricular pressure is equal to the aortic pressure. Therefore, for some applications, the subject's aortic pressure is measured, and the subject's left-ventricular pressure at a given time is then calculated by the computer processor, based upon (a) the measured aortic pressure, and (b) the difference between the magnetic flux measured by the magnetometer at that time, and the magnetic flux measured by the magnetometer during systole (when the pressure in the left ventricle is assumed to be equal to that of the aorta). For example, the subject's aortic pressure may be measured by measuring pressure in a channel 224 defined by delivery catheter 143, as described in further detail hereinbelow. For some applications, alternative or additional physiological parameters are determined using the above-described technique. For example, events in the subject's cardiac cycle and/or the subject's cardiac afterload may be determined.

For some applications, generally similar techniques to those described in the above paragraph are used, but as an alternative to or in addition to utilizing magnetometer measurements, a different parameter is measured in order to determine left ventricular blood pressure (and/or a different physiological parameter, e.g., events in the subject's cardiac cycle and/or the subject's cardiac afterload) at a given time. For example, it is typically the case that there is a relationship between the amount of power (and/or current) that is required to power the rotation of the impeller at a given rotation rate and the pressure difference that is generated by the impeller. (It is noted that some of the pressure difference that is generated by the impeller is used to overcome the pressure gradient against which the impeller is pumping, and some of the pressure difference that is generated by the impeller is used to actively pump the blood from the left ventricle to the aorta, by generating a positive pressure difference between the left ventricle and the aorta. Moreover, the relationship between the aforementioned components typically varies over the course of the cardiac cycle.) For some applications, calibration measurements are performed, such that the relationship between (a) power (and/or current) consumption by the motor that is required to rotate the impeller at a given rotation rate and (b) the pressure difference that is generated by the impeller, is known. For some applications, the subject's aortic pressure is measured, and the subject's left-ventricular pressure at a given time is then calculated by the computer processor, based upon (a) the measured aortic pressure, (b) the power (and/or current) consumption by the motor that is required to rotate the impeller at a given rotation rate at that time, and (c) the predetermined relationship between power (and/or current) consumption by the motor that is required to rotate the impeller at a given rotation rate and the pressure difference that is generated by the impeller. For some applications, the above-described technique is performed while maintaining the rotation rate of the impeller at a constant rate. Alternatively or additionally, the rotation rate of the impeller is varied, and the variation of the rotation rate of the impeller is accounted for in the above-described calculations. For some applications, alternative or additional physiological parameters are determined using the above-described technique. For example, events in the subject's cardiac cycle and/or the subject's cardiac afterload may be determined.

Typically, tube 24 has a known cross-sectional area (when the tube is in an open state due to blood flow through the tube). For some applications, the flow through tube 24 that is generated by the impeller is determined based on the determined pressure difference that is generated by the impeller, and the known cross-sectional area of the tube. For some applications, such flow calculations incorporate calibration parameters in order to account for factors such as flow resistance that are specific to the ventricular assist device (or type of ventricular assist device) upon which the calculations are performed. For some applications, the ventricular pressure-volume loop is derived, based upon the determined ventricular pressure.

Referring again to FIG. 7A, for some applications, in addition to magnetometer 84, which is configured to measure the magnetic flux density generated by the driven magnet, a second magnetometer 84A (e.g., a second Hall sensor) measures an indication of the magnetic flux density generated by the driving magnet. For some applications, the second magnetometer measures magnetic flux density of the motor, which is indicative of the flux density cycle of the driving magnet, since the motor directly drives the driving magnet to rotate. Typically, as the impeller rotates such as to pump blood, torque is generated upon the impeller. Further typically, the strength of the torque is dependent upon various parameters, such as the flow that is generated by the impeller, the rotational speed of the impeller, and/or the pressure gradient against which the impeller is pumping. For some applications, it is the case that the torque generated upon the impeller gives rise to a measurable torque on the inner, driven magnet 82 relative to the outer, drive magnets 77, since the driven magnet is held in place with respect to the drive magnets via magnetic coupling, rather than rigid mechanical coupling. It is noted that typically the torque generated upon the driven magnet is substantially less than that generated upon the impeller, since the torque that is generated upon the impeller is not transmitted along the length of the drive cable. However, it is typically the case that the torque that is generated upon the impeller is at least partially transmitted to the driven magnet via the drive cable.

The torque that is transmitted to the driven magnet typically gives rise to a phase difference between the signal that is measured by magnetometer 84 (which measures magnetic flux density of the driven magnet) and the signal that is measured by second magnetometer 84A (which measures magnetic flux density of the motor and/or the driving magnet). For some applications, as the torque upon the impeller varies, this gives rise to a variation in the phase difference between the signal that is measured by magnetometer 84 and the signal that is measured by second magnetometer 84A. For some applications, the computer processor detects the variation in the aforementioned phase difference, and determines a physiological parameter of the subject, at least partially in response thereto. For example, at least partially based upon variations in the phase difference, the computer processor may determine the difference between the subject's left-ventricular pressure and the subject's aortic pressure, the subject's left ventricular pressure, an event in the subject's cardiac cycle, the subject's cardiac afterload, and/or a different physiological parameter. For some applications, the technique described in the present paragraph is used as an alternative to the above-described technique for using magnetic flux density measurements and/or power consumption measurements to determine physiological parameters. Alternatively, two or more of these techniques are used in combination with each other. For example, the subject's physiological parameters may be determined based upon a mathematical model that incorporates two or more measurements, and/or one of the techniques may be used to validate estimations of the subject's physiological parameters that are made using another one of the techniques.

Figure 8B:
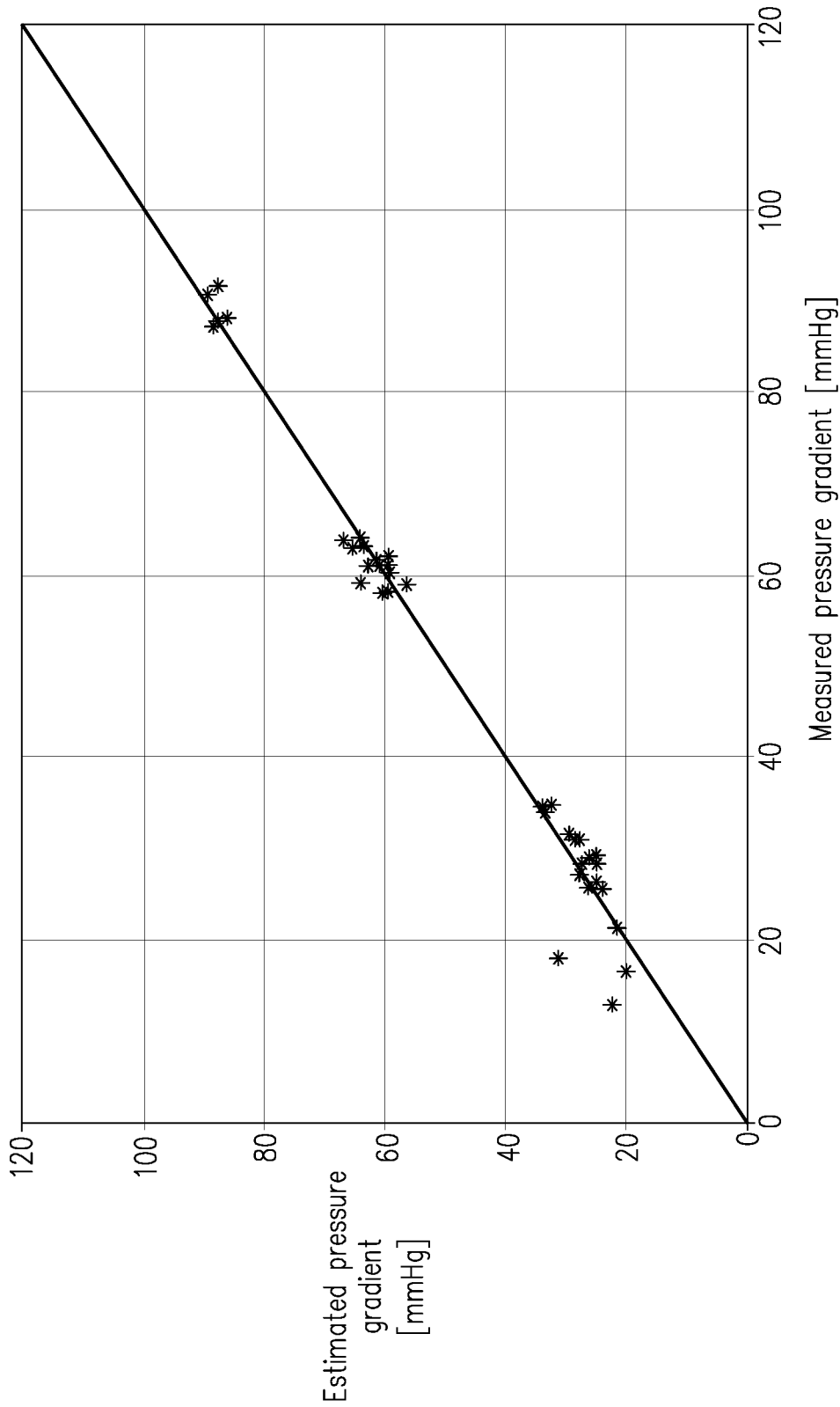
FIGS. 8B and 8C are graphs indicating variations magnetic phase measurements performed upon a blood pump as a pressure gradient against which the impeller of the blood pump varies, as measured in experiments.
Figure 8C:
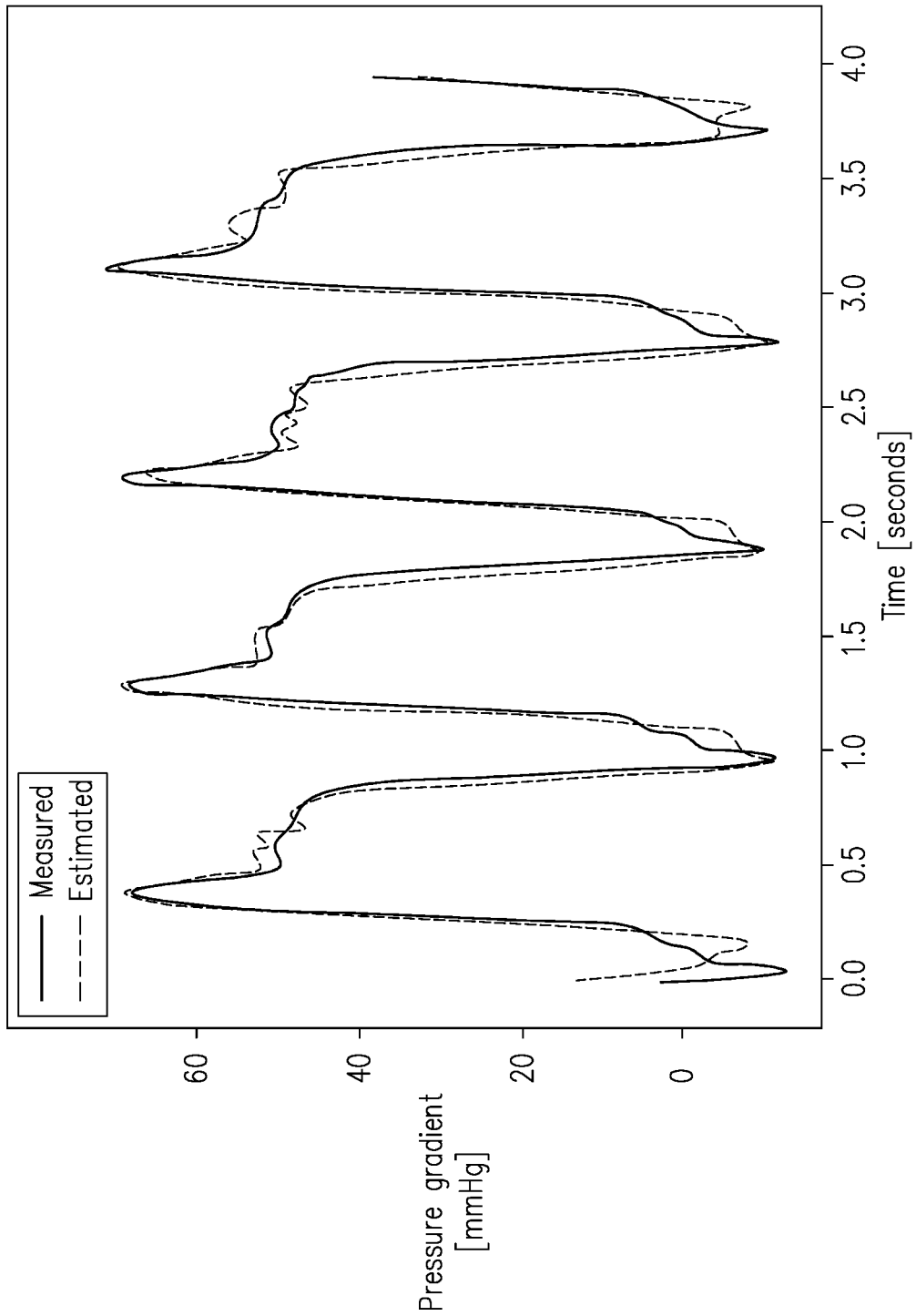

Reference is now made to FIGS. 8B and 8C, which are graphs that demonstrate the correlation between the phase difference signal and the pressure gradient against which impeller 50 pumps, in accordance with some applications of the present invention.

The graph shown in FIG. 8B shows the results of an experiment in which a ventricular assist device as described herein was used to pump blood against respective pressure gradients within a static in vitro system (i.e., in which when each measurement was taken, the pressure gradient was constant). A linear regression model was used to estimate the pressure gradient against which the impeller was pumping based upon a combination of the phase difference signal the magnetic flux amplitude signal, and the current consumed by the motor. The graph shown in FIG. 8B shows the estimated pressure gradient versus the measured pressure gradient. As shown the linear regression model which incorporates phase difference measurements provides a reliable method for estimating the pressure gradient against which the impeller is pumping.

The graph shown in FIG. 8C shows the results of an experiment in which a ventricular assist device as described herein was used to pump blood against respective pressure gradients within a pulsatile in vitro system (i.e., in which the pressure gradient was varied in a pulsatile manner). A space state model was used to estimate the pressure gradient against which the impeller was pumping based upon a combination of the phase difference signal the magnetic flux amplitude signal, and the current consumed by the motor. The graph shown in FIG. 8C shows the estimated pressure gradient overlaid upon the measured pressure gradient. As shown a space state model which incorporates phase difference measurements provides a reliable method for estimating the pressure gradient against which the impeller is pumping.

In accordance with the above, and in accordance with some applications of the invention, a magnetic phase difference between the one or more driven magnets and the one or more drive magnets is measured, and a physiological parameter of the subject is determined, at least partially in response thereto. For example, at least partially based upon variations in the phase difference, the computer processor may determine the difference between the subject's left-ventricular pressure and the subject's aortic pressure, the subject's left ventricular pressure, an event in the subject's cardiac cycle, the subject's cardiac afterload, and/or a different physiological parameter. For some applications, the physiological parameter is determined based upon the phase difference measurements in combination with one or more additional measurements, such as magnetic flux amplitude measurements, power consumed by the motor, and/or current consumed by the motor. Typically, such measurements are combined into a mathematical model, such as a linear regression model, and/or a space state model.

Reference is now made to FIGS. 9A-G, which are schematic illustrations of respective views of a motor-unit support 170 configured to support motor unit 23 on a patient's leg 172, in accordance with some applications of the present invention. For some applications, the ventricular assist device is inserted into the patient's body via a femoral access point 173, and the motor-unit support is configured to be placed on the patient's upper leg below the femoral access point, as shown. Typically, the motor unit support is configured to at least partially isolate the patient's leg from vibrations and/or heat that is generated by the motor unit, during operation of the motor unit.

For some applications, the motor-unit support comprises a curved base 176, which is configured to be placed on the patient's upper leg, as well as a motor-unit dock 178, upon which the motor unit is docked. Typically, there is a gap 179 between the motor-unit dock and the curved base of the motor-unit support, such that the patient's leg is separated from the motor unit by the gap, with the gap serving to at least partially isolate the patient's leg from vibrations and/or heat that is generated by the motor unit, during operation of the motor unit. For some applications, the motor-unit support is configured to receive a strap 174 through the gap, the strap being used to strap the motor-unit support to the patient leg. Typically the strap is elasticated and/or is adjustable to fit the patient's leg.

Figure 9A:
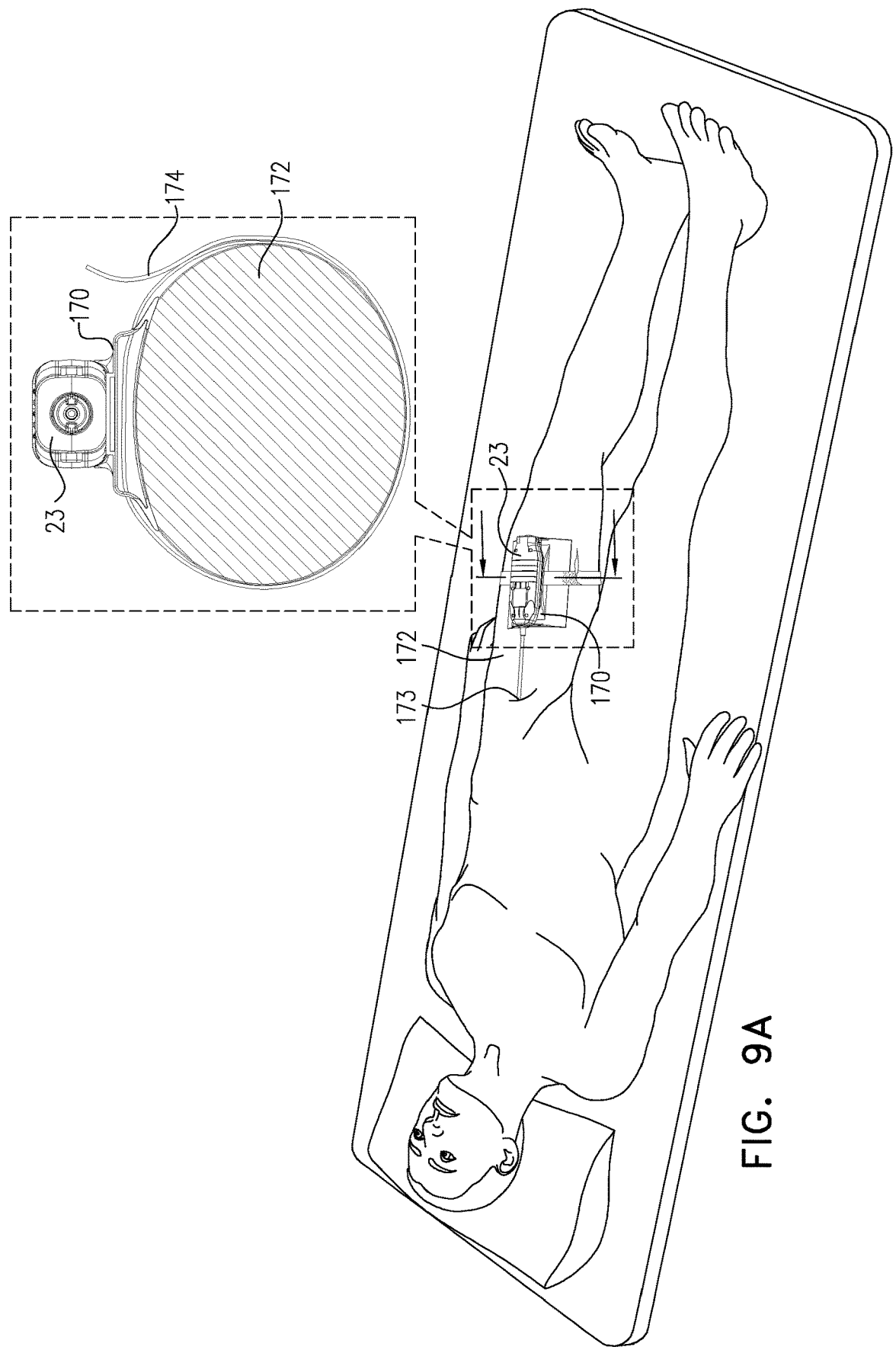
Figure 9B:
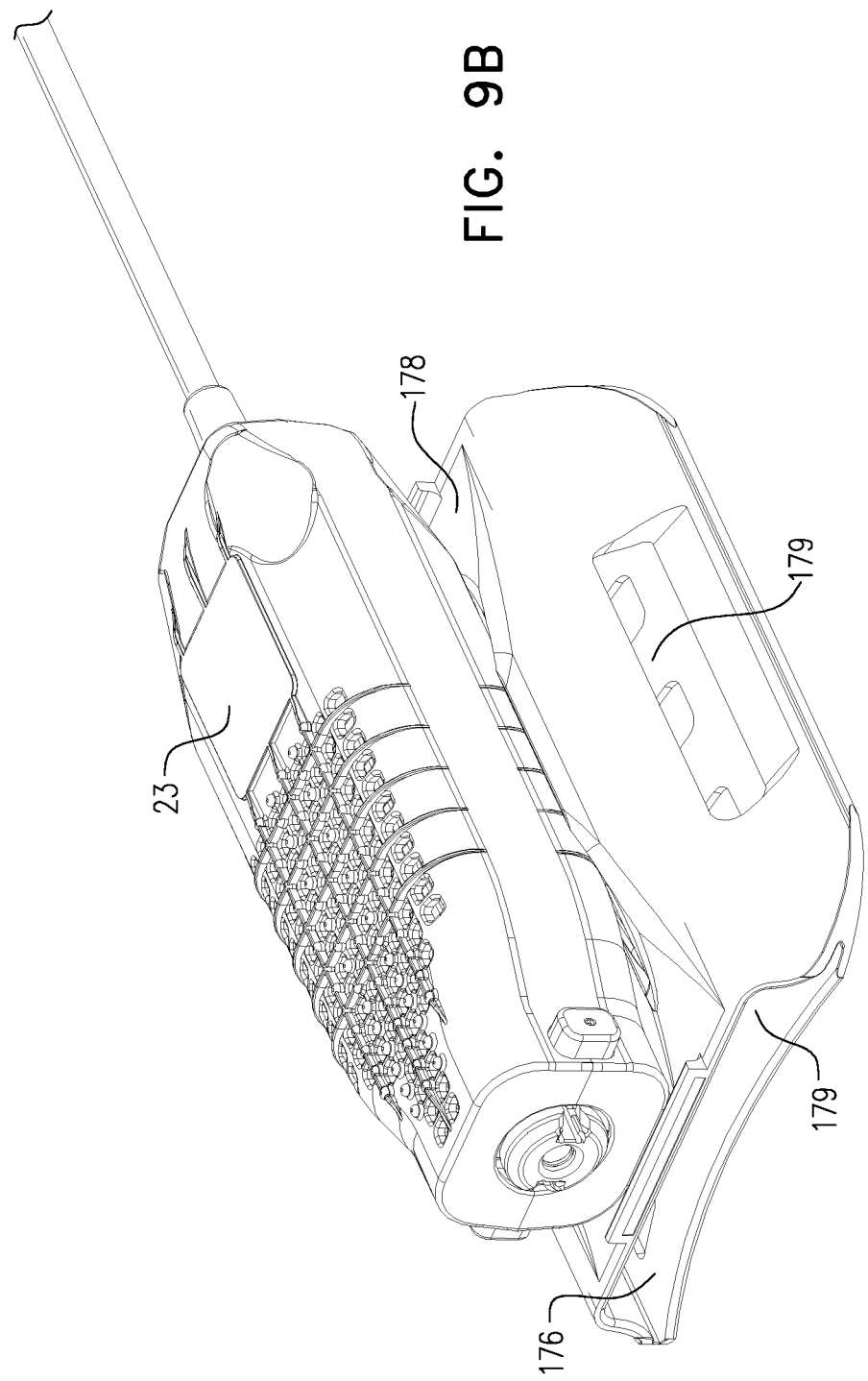
Figure 9C:
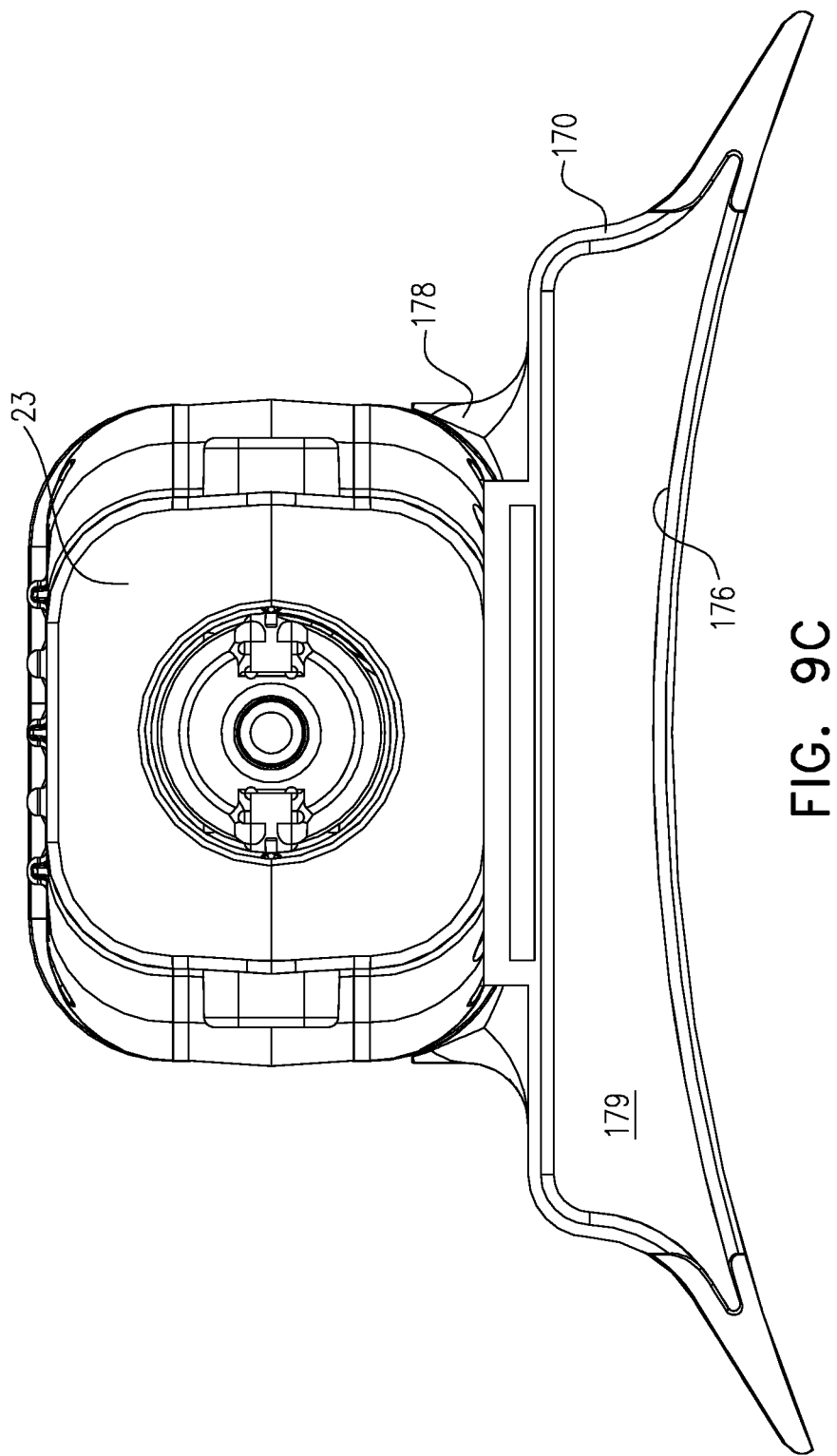
Figure 9E:
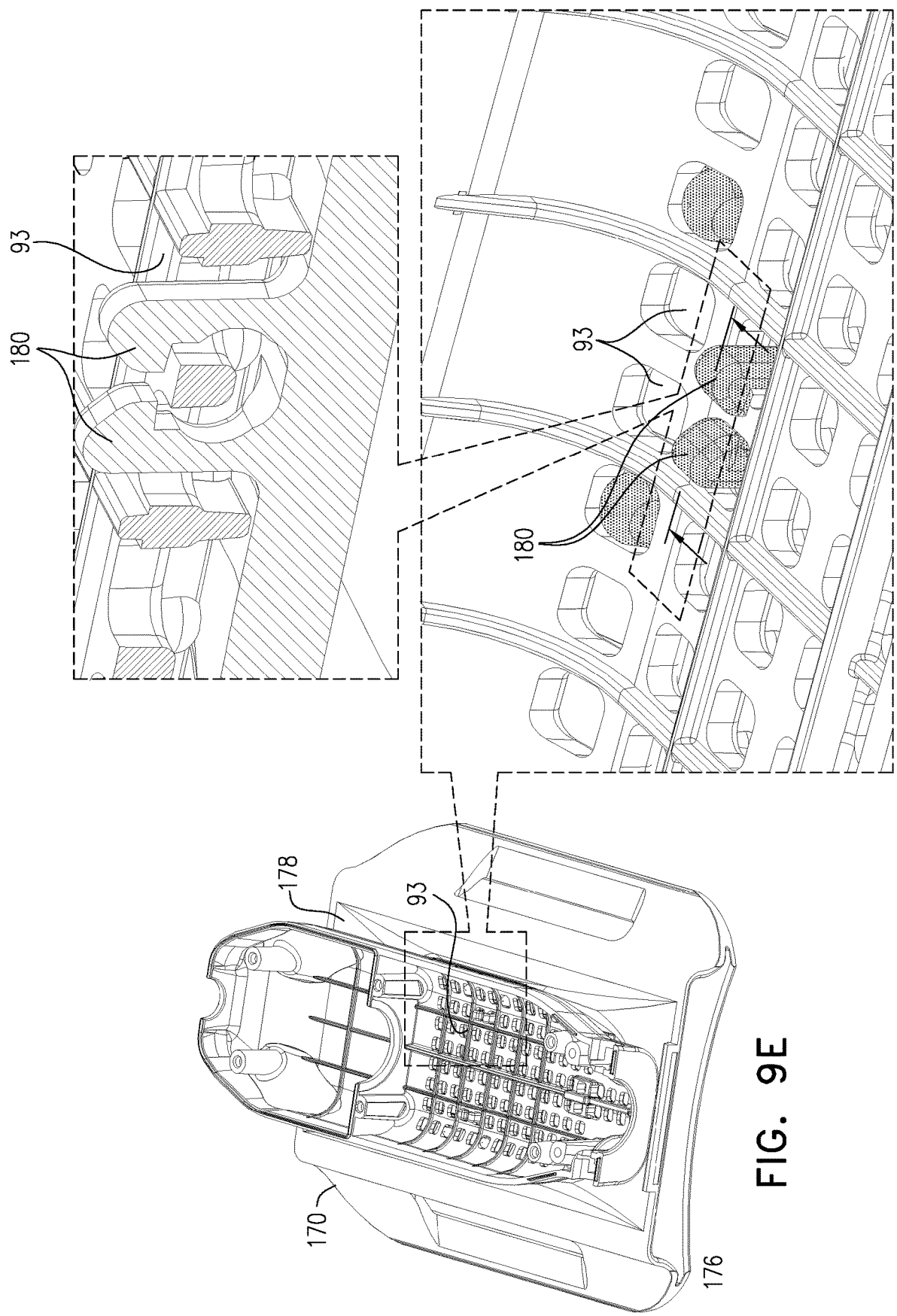

Typically, the motor-unit support includes coupling elements 180 for coupling the motor-unit dock to the motor unit (shown in FIG. 9D, for example). As described hereinabove, for some applications, the motor unit includes ventilation ports 93 that are configured to facilitate the dissipation of heat that is generated by the motor. For some such applications, the coupling elements comprise snap-fit coupling elements that are configured to couple the motor-unit dock to the motor unit by the coupling elements snapping into ventilation ports of the motor unit, as shown in FIG. 9E, for example. For some applications, the motor unit includes ventilation ports on both sides of the motor unit such that either side of the motor unit can be coupled to the motor-unit dock.

Figure 10A:
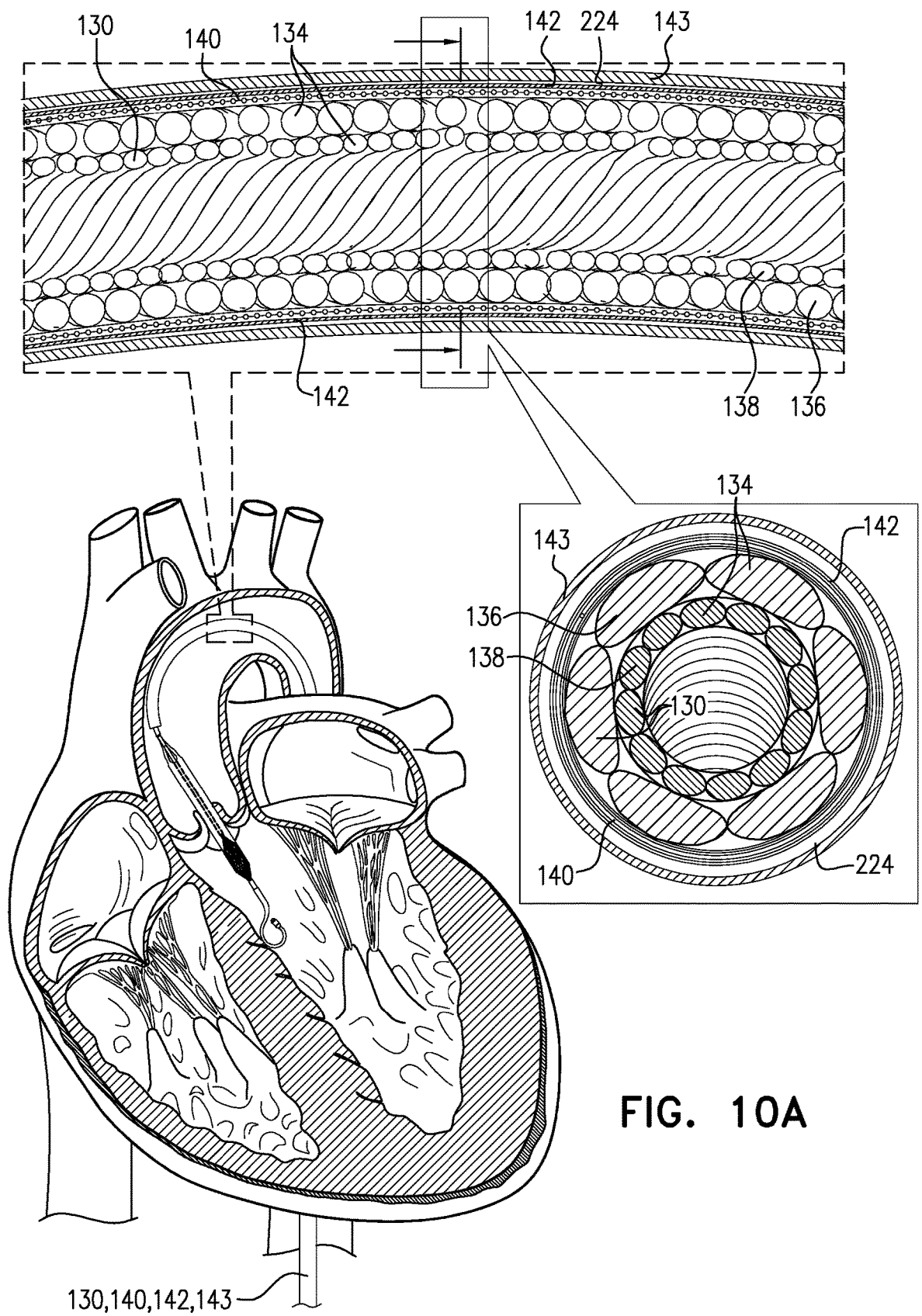
FIGS. 10A, 10B, and 10C are schematic illustrations of a drive cable of a ventricular assist device, in accordance with some applications of the present invention.
Figure 10B:
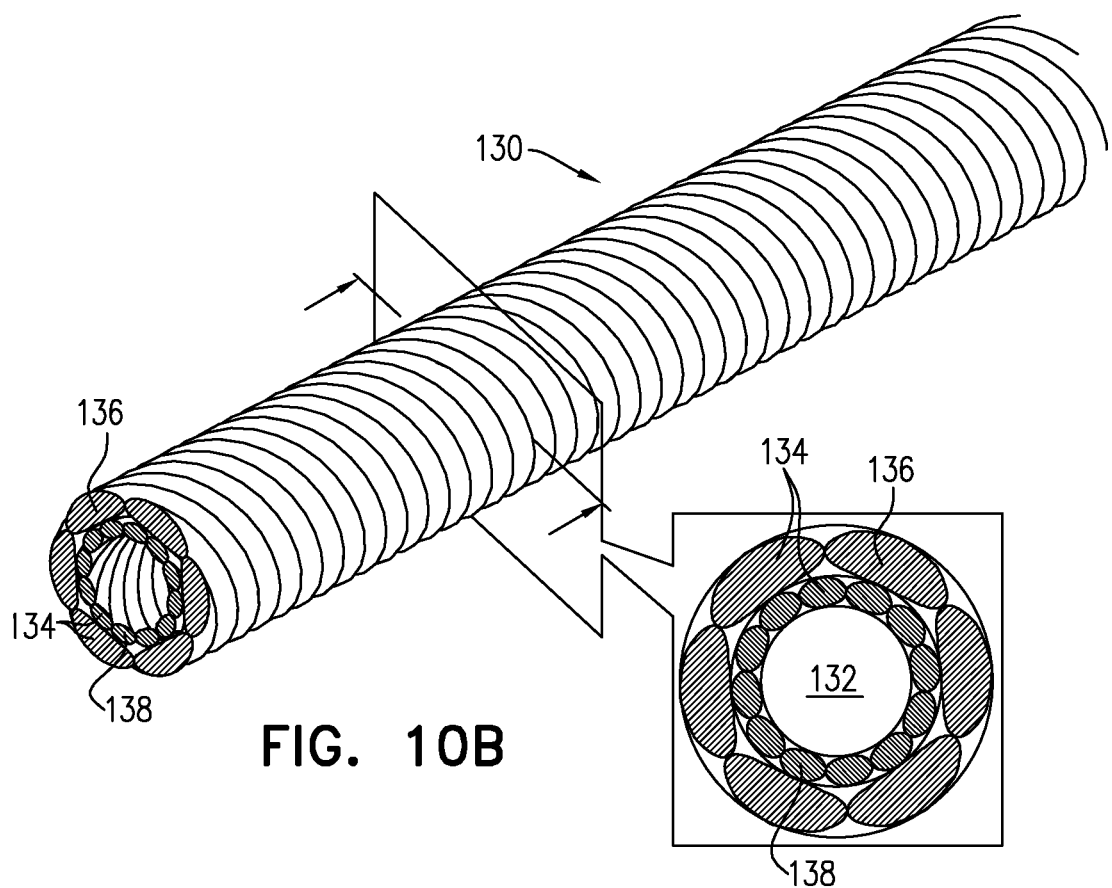
Figure 10C:
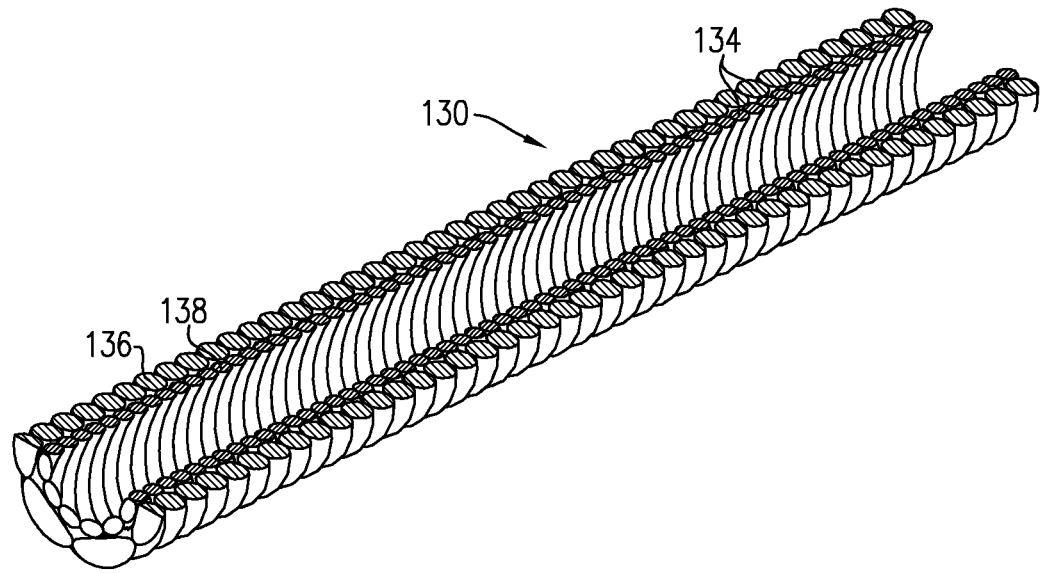

Reference is now made to FIGS. 10A, 10B, and 10C, which are schematic illustrations of drive cable 130 of ventricular assist device 20, in accordance with some applications of the present invention. Typically, the rotational motion of the of the motor is transmitted to the axial shaft via the drive cable. Typically, the drive cable extends from motor unit 23 (which is typically disposed outside the subject's body) to the proximal end of axial shaft 92 (with the connection between the distal end of the drive cable and the proximal end of the axial shaft being shown in the left enlarged portion of FIG. 5A for example). For some applications, the drive cable includes a plurality of wires 134 that are disposed in a coiled configuration in order to impart sufficient strength and flexibility to the drive cable, such that a portion of the cable is able to be maintained within the aortic arch (i.e., the portion corresponding to arrow 145 in FIG. 10A), while the cable is rotating and moving in the axial back-and-forth motion. For some applications, the drive cable includes a plurality of coaxial layers of coiled wires. For example, as shown in FIGS. 10A-C, the drive cable may include an outer layer 136 and an inner layer 138, which are coaxial with each other and each of which comprises coiled wires.

The drive cable is typically disposed within a first outer tube 140, which is configured to remain stationary while the drive cable undergoes rotational and/or axial back-and-forth motion. The first outer tube is configured to effectively act as a bearing tube for the drive cable, along the length of the drive cable. As such, first outer tube is also referred to herein as the drive-cable bearing tube. The drive-cable bearing tube is described in further detail hereinbelow with reference to FIG. 10D. For some applications, the drive-cable bearing tube is disposed within a second outer tube 142, which is typically made of a material having greater flexibility than that of the drive-cable bearing tube (e.g., nylon, and/or polyether block amide), and typically has a thickness that is greater than that of the drive cable bearing tube.

Typically, during insertion of the impeller and the frame into the left ventricle, impeller 50 and frame 34 are maintained in a radially-constrained configuration by delivery catheter 143. As described hereinabove, in order for the impeller and the frame to assume non-radially-constrained configurations, the delivery catheter is retracted. For some applications, as shown in FIG. 10A, the delivery catheter remains in the subject's aorta during operation of the left ventricular device, and outer tube 142 is disposed inside the delivery catheter. (Although FIG. 10A shows the distal end of the delivery catheter disposed within the aortic arch, for some application, the distal end of the delivery catheter is disposed within the descending aorta during operation of the left ventricular device.) For some applications, during operation of the left ventricular device, a channel 224 is defined between delivery catheter 143 and outer tube 142. (It is noted that the channel as shown in FIG. 10A is not to scale, for illustrative purposes.) For some such applications, the subject's aortic blood pressure is measured by measuring the pressure of blood within channel 224. For example, pressure sensor 216 (illustrated schematically in FIG. 1A) may be in fluid communication with channel 224, and may be configured to measure the subject's aortic pressure by measuring the pressure of blood within channel 224. Typically, in order to retract the left ventricular device from the subject's body, the delivery catheter is advanced over the impeller and the frame, such that the impeller and the frame assume their radially-constrained configurations. The catheter is then withdrawn from the subject's body.

For some applications, drive cable 130 is made up of a plurality of coaxial layers each of which comprises plurality of coiled wires 134. For example, as shown in FIGS. 10A-C, the drive cable includes outer layer 136 and inner layer 138, each of which comprises coiled wires. Typically, if the direction of rotation of the impeller is such that rotation of the drive cable in this direction results in the coiled wires of the drive cable at least partially tightening, then this would also cause the impeller to advance with respect to the frame when the rotation of the impeller is initiated, due to the coiled wires tightening (i.e., becoming wound up such that the radius of the coil decreases), and thereby axially elongating. For some applications, at least a portion of the drive cable is configured such that (a) in response to the impeller pumping blood from the left ventricle to the aorta, by rotating in a predefined direction of rotation, (b) rotation of the drive cable in this direction results in the coiled wires of the drive cable along the portion of the drive cable at least partially unwinding, such that the portion of the drive cable axially shortens (i.e., becoming unwound such that the radii of the coils increase). For some applications, the impeller is configured to rotate in the counterclockwise direction when viewed from the proximal end of the impeller to the distal end of the impeller, and the coiled wires in each of the layers of the drive cable are configured in a left-handed lay. As the impeller rotates in the counterclockwise direction, the counterpressure exerted on the coiled wires of each of the layers of the drive cable causes them to partially unwind, thereby shortening each of the layers of the drive cable. Alternatively, the impeller is configured to rotate in the clockwise direction when viewed from the proximal end of the impeller to the distal end of the impeller, and the coiled wires in each of the layers of the drive cable are configured in a right-handed lay.

Reference is again made to FIGS. 6A and 6B, which show the range of axial back- and forth motion of the impeller within frame 34 over the course of the cardiac cycle, in accordance with some applications of the present invention. As described hereinabove, FIG. 6A indicates the proximal-most disposition of the impeller over the course of the cardiac cycle (at which the impeller is typically disposed during systole) and FIG. 6B indicates the distal-most disposition of the impeller over the course of the cardiac cycle (at which the impeller is typically disposed during diastole). As shown in FIG. 6A, for some applications, at its proximal-most position the proximal end of the impeller is disposed at location Ip, which is within the proximal conical section of frame 34. As shown in FIG. 6B, for some applications, at its distal-most position the distal end of the impeller is disposed at location Id, which is at the distal end of the cylindrical section of frame 34.

Referring again to FIGS. 10A-C and to the configuration of the drive cable described with reference to these figures, typically, by configuring the drive cable in the aforementioned manner, the length of frame 34 does not need to accommodate distal movement of the impeller resulting from the drive cable axially elongating as a result of the device cable tightening, as the impeller and the drive cable begin to rotate. It is noted that, for some applications, due to drive cable bearing tube 140 limiting the extent to which the drive cable is able to unwind and thereby axially shorten (and/or due to other reasons), the drive cable does not shorten. In addition, for some applications, although, in theory, the drive cable would shorten if the impeller were to be rotated in the absence of any fluid, in practice, when the impeller is rotated within the subject's blood stream the drive cable does not shorten. This because, when the impeller is rotated within the subject's blood stream, the unwinding of the drive cable (which would result in the drive cable shortening) is offset by the impeller being pushed distally by virtue of the counterpressure of the blood that the impeller is pumping. For some applications, during diastole, the drive cable does in fact become elongated relative to when the impeller is at rest, due to the pressure gradient against which the impeller is pumping increasing relative to during systole. Typically, even in such applications, at least during systole, the drive cable is configured not to become elongated relative to when the impeller is at rest, due to the windings of the coil being configured as described hereinabove.

For some applications, in addition to configuring the directions of the coiled wires within the drive cable in the above-described manner, the drive cable is initially held within frame 34 in a preloaded (i.e., pretensioned) state, such that even before the drive cable and the impeller start to rotate, it is already stretched. That is to say that, even before the drive cable and the impeller start to rotate, the drive cable is in a stretched state relative to the drive cable rest state (i.e., the state of the drive cable in the absence of any external forces acting upon the drive cable.) For example, coupling element 65 (which in some applications is proximally-extended, as described hereinabove with reference to FIGS. 6D-E) may engage proximal bearing 116, such as to hold the drive cable in a preloaded state. Typically, (a) by virtue of the directions of the coiled wires within the drive cable being configured in the above-described manner, and/or (b) by virtue of the drive cable being held within frame 34 in a preloaded state, it is the case that, when the impeller and the drive cable start to rotate, the drive cable does not become stretched even during diastole (e.g., even when the impeller is pumping against a pressure gradient of 50-70 mmHg). For some applications, the drive cable does not become stretched even during diastole until the impeller is rotating at a rotation speed of more than 6,000 RPM, or more than 8,000 RPM. For some applications, by virtue of configuring the drive cable in this manner, the amount that the drive cable becomes elongated over the course of the cardiac cycle is limited to less than 5 mm (and typically less than 4 mm), even when the impeller is rotating at more than 20,000 RPM. Furthermore, for some applications, by virtue of configuring the drive cable in this manner, the widest portion of the impeller (which is typically located at the center of the length of the impeller) is disposed within the proximal half of frame 34 for more than 50 percent of the duration of the cardiac cycle, even when the impeller is rotating at more than 20,000 RPM.

For some applications, ventricular assist device is configured such that, even during diastole, even when the impeller is rotating at more than 20,000 RPM, there is an axial distance between the location of the impeller at which the impeller is at its maximum diameter and the blood inlet opening. For example, the ventricular assist device is configured such that, during diastole, even when the impeller is rotating at more than 20,000 RPM, there is an axial distance of more than 3 mm (e.g., more than 5 mm) between the location of the impeller at which the impeller is at its maximum diameter and the blood inlet opening. For some such applications, this reduces hemolysis (relative to if there were a smaller axial distance or no axial distance between the location of the impeller at which the impeller is at its maximum diameter and the blood inlet opening) and/or enhances the efficacy of the impeller by reducing turbulence, by allowing flow lines of the blood that enters the blood inlet opening to become at least partially aligned with the longitudinal axis of the impeller prior to being pumped by the impeller.

Typically, within outer layer 136 of the drive cable, there are fewer coiled wires than within inner layer 138, and each of the wires is wider than in those within the inner layer. For example, the ratio of the number of wires within the outer layer to those within the inner layer may be between 2:3 and 2:5. For some application, the outer layer contains 4-8 wires, and the inner layer contains 10-14 wires. For some applications, the ratio of the diameter of the wires within the outer layer to the diameter of the wires within the inner layer is between 3:2 and 5:2. For some applications, the diameters of the wires within the outer layer are between 0.15 mm and 0.2 mm, and the diameters of the wires within the outer layer are between 0.075 mm and 0.125 mm. Typically, the coiled wires of both layers are made of an alloy. For some applications, the inner diameter of the drive cable (i.e., the diameter of lumen 132) is between 0.4 mm and 0.7 mm. Further typically, the outer diameter of the drive cable (defined by outer layer 138) is between 1 mm and 1.2 mm. For some applications, drive cable 130 has a total length of more than 1 m (e.g., more than 1.1 m), and/or less than 1.4 m (e.g., less than 1.3 m), e.g., 1-1.4 m, or 1.1-1.3 m. Typically, the diameters of lumen 122 and lumen 133 are generally similar to that of lumen 132.

For some applications, the drive cable includes first (distal) and second (proximal) portions. Typically, the first portion is configured to be disposed in the subject's aortic arch, and the second portion is configured to be disposed along the descending aorta, and typically to extend until motor unit 23, outside the subject's body. Typically, at locations at which drive cable 130 undergoes substantial curvature, such as the aortic arch, it is desirable for the drive cable to be relatively flexible. However, a drive cable having greater flexibility is typically also more axially stretchable than a drive cable having less flexibility. Therefore, for some applications, there is a tradeoff between wanting the drive cable being flexible enough to conform to the curvature of the aortic arch, but on the other hand not wanting the drive cable to undergo substantial axial stretching (which may result in a loss of control over the axial positions of the impeller). For some applications, the respective portions of the drive cable have respective levels of flexibility. For example, the first portion of the drive cable that is configured to be disposed in the aortic arch may have a first flexibility, while the second portion of the drive cable that is configured to be disposed in the descending aorta may have a second flexibility, the first flexibility being greater than the second flexibility.

For some applications, the distal portion of the drive cable is configured to have greater flexibility than the proximal portion, by virtue of the coils of wires 134 in the distal portion having different parameters than those that are used in the proximal portion. For some applications, the distal portion has generally similar parameters to those described hereinabove (i.e., with inner and outer layers). For some applications, the proximal portion of the guidewire comprises a single layer of coiled wires. Typically, there are fewer coiled wires within the proximal portion of the drive cable than within even the outer layer of the distal portion of the drive cable. Typically, the ratio of the number of the wires within the outer layer of the distal portion of the drive cable to those within the proximal portion of the drive cable is between 3:2 and 5:2. For some application, there are between 3 and 6 wires in the proximal portion of the drive cable. Typically, the diameter of the coiled wires within the proximal portion of the drive cable is greater than that of the coiled wires within even the outer layer of the distal portion of the drive cable. For some applications, the ratio of the diameter of the wires within the proximal portion to the diameter of the wires within the outer layer of the distal portion is between 3:2 and 5:2. For some applications, the diameters of the wires within the distal portion of the drive cable are between 0.2 mm and 0.35 mm. Typically, the inner and outer diameters of both the distal and proximal portions of the drive cable are similar (or identical) to each other, and are typically as described hereinabove.

Figure 10D:
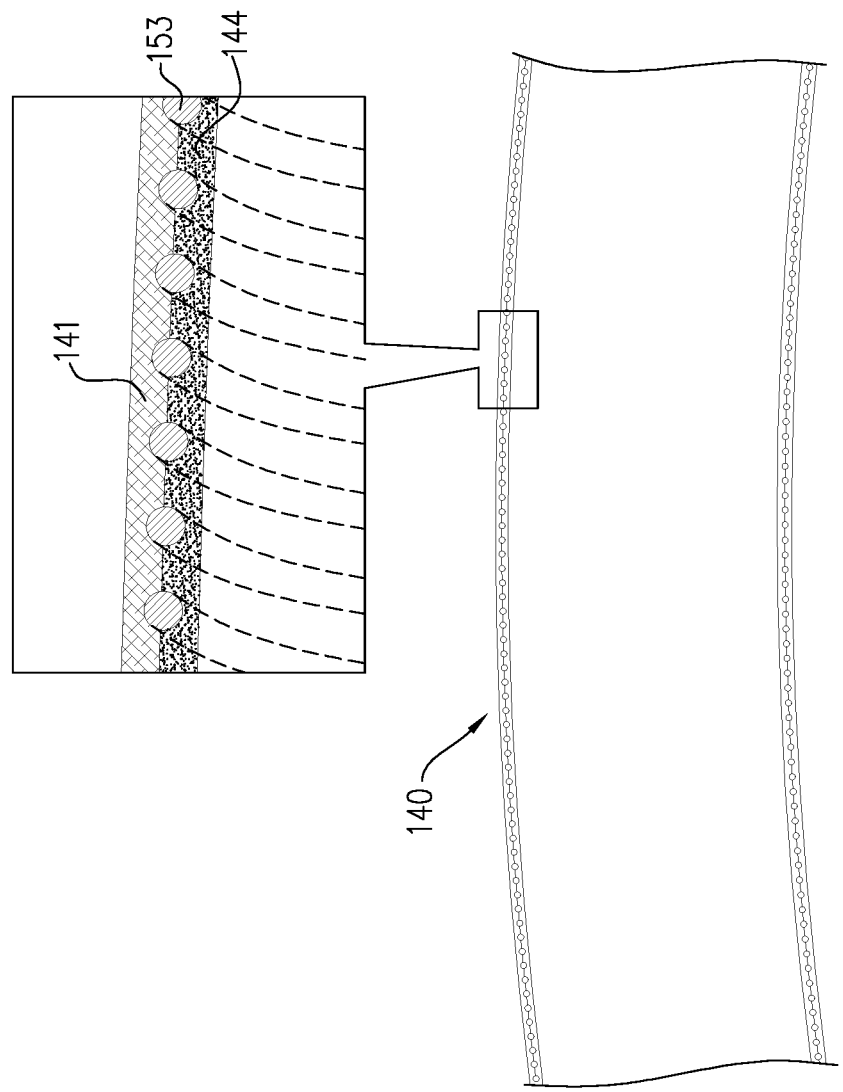
FIG. 10D is a schematic illustrations of a drive cable bearing tube, in accordance with some applications of the present invention.

Reference is now made to FIG. 10D, which is a schematic illustration of first outer tube 140, which acts as a drive-cable bearing tube, in accordance with some applications of the present invention. For some applications, the drive-cable bearing tube includes an outer layer 141 and inner layer 144, each of which is typically made of a biocompatible polymeric material, and a coil 153 embedded between the outer and inner layers. For some applications, outer layer 141 is made of Pebax, inner layer 144 is made of PTFE and/or polyimide (e.g., a mixture of PTFE and/or polyimide), and the coil is made of an alloy, such as stainless steel. Typically, the inner layer includes materials that are configured to provide low levels of friction and high wear resistance. Further typically, the outer layer is configured to provide additional strength to the drive-cable bearing tube, while still providing the drive-cable bearing tube with sufficient flexibility that it is able to conform with the curvature of the aortic arch, for example. Typically, the coil is configured such as to maintain a substantially circular cross-section for the drive-cable bearing tube, even within regions in which the drive-cable bearing tube undergoes a substantial curve (e.g., within the aortic arch). Typically, in the absence of the coil, the drive-cable bearing tube would have a tendency to flatten and form an elliptical cross-section within such regions.

Reference is now made to FIGS. 11A, 11B, 11C, 11D, and 11E, which are schematic illustrations of apparatus and a method for purging drive cable 130, radial bearings 116, 118, and/or an impeller bushing 58 of ventricular assist device 20, in accordance with some applications of the present invention.

Figure 11A:
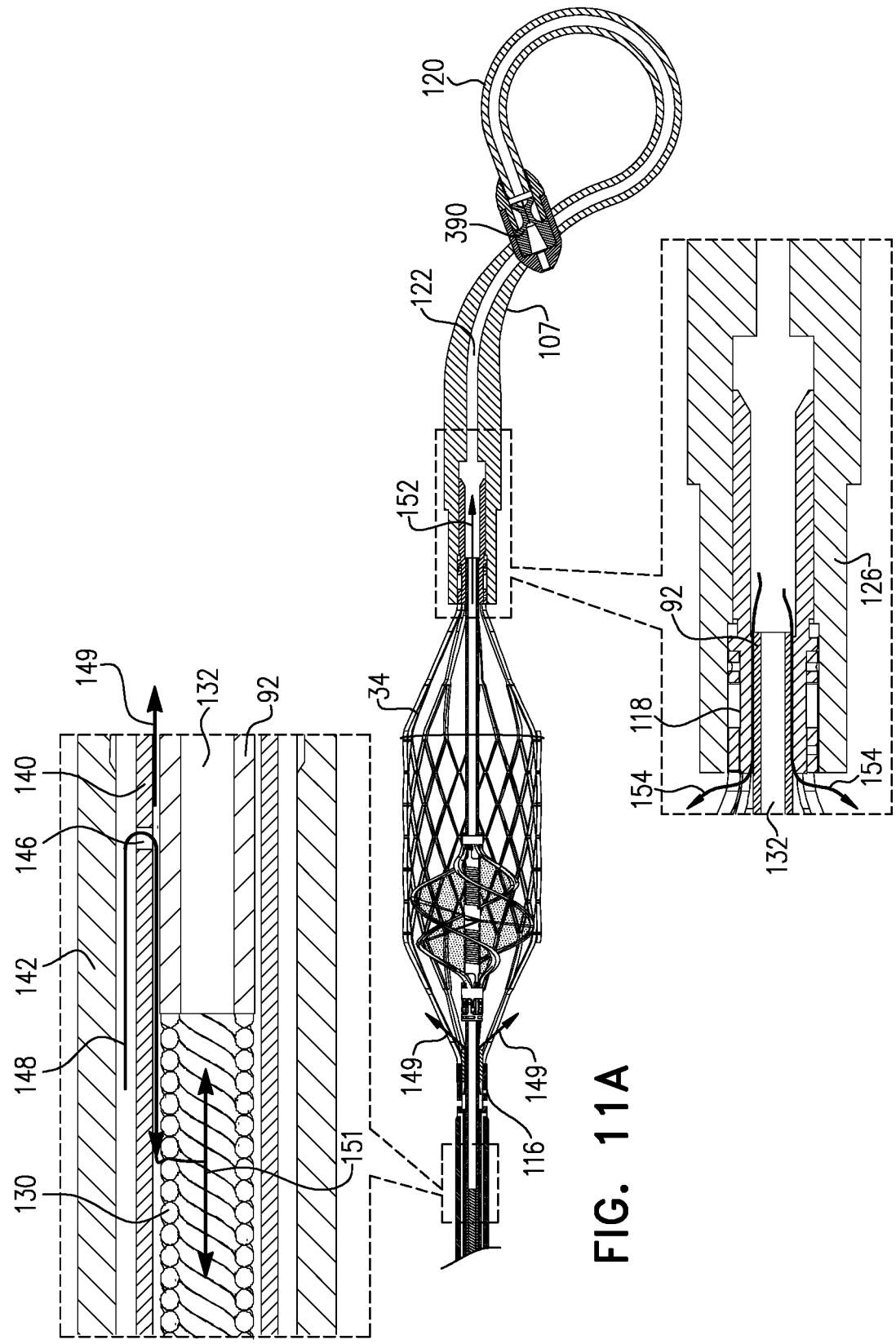

First, referring to FIG. 11A, typically, the axial shaft and the drive cable define a continuous lumen 132 therethrough. For some applications, the left ventricular device is guided to the aorta and to the left ventricle by placing the axial shaft and the cable over guidewire 10 (described hereinabove), such that the guidewire is disposed inside lumen 132. Typically, the guidewire is inserted through duckbill valve 390 (or other hemostasis valve) disposed at the distal end of distal tip portion of distal-tip element 107. The guidewire passes through lumen 122 (of the distal-tip portion), and then passes into lumen 132 which is defined by the axial shaft at that point. The guidewire then continues to pass through lumen 132 all the way until the proximal end of the drive cable. From the proximal end of the drive cable, the guidewire passes through lumen 133 defined by pin 131, which is disposed outside of the subject's body even after insertion of the distal end of ventricular assist device 20 into the subject's left ventricle. Typically, when the distal end of the ventricular assist device is disposed inside the subject's left ventricle, the guidewire is retracted from the subject's body by pulling the guidewire out of the proximal end of lumen 133. Subsequently, the axial position of driven magnet 82 (within which pin 131 is disposed) is fixed such as to be disposed between driving magnets 77, as shown in FIG. 7A. For example, a portion of motor unit 23 in which the driven magnet is disposed may be coupled to a portion of the motor unit in which driving magnets 77 are disposed using click-lock element 150 (shown in FIG. 11B). For some applications, techniques as described hereinbelow with reference to FIGS. 23A-C are used for inserting the guidewire into distal-tip element 107. For some applications, by using lumen 132 of the axial shaft and the cable in the above-described manner, it is not necessary to provide an additional guidewire guide to be used during insertion of left-ventricular assist device 20.

For some applications, lumen 132 is additionally used by purging system 29 (shown in FIG. 1A) of the ventricular assist device. Typically, both the first and second outer tubes 140, 142 remain stationary, during rotation of the drive cable. For some applications, purging system 29 controls the flow of a purging fluid (e.g., a fluid containing glucose or dextrose) via inlet port 86 and outlet port 88 (shown in FIGS. 7A-Bii, 11B, and 11C). The fluid is configured to remove air from the space between the drive cable and the outer tube, and/or to reduce frictional forces between drive cable 130 (which rotates), and outer tube 140 (which remains stationary, during rotation of the drive cable), and/or to reduce frictional forces between axial shaft 92 and proximal bearing 116 and/or distal bearing 118.

Referring again to FIG. 11A, for some applications, the purging fluid is pumped between the first and second outer tubes 140, 142, and there is an opening 146 within the first outer tube in the vicinity of the proximal bearing. For some applications, the purging fluid is pumped via a purging-fluid channel 226 defined between the first and second outer tubes, as described in further detail hereinbelow with reference to FIG. 21. For some applications, the purging fluid flows between first outer tube 140 and drive cable 130 via opening 146, as indicated by purging-fluid-flow arrow 148 in FIG. 11A. In this manner, the interface between drive cable 130 (which rotates), and outer tube 140 (which acts as the drive-cable bearing tube and remains stationary, during rotation of the drive cable) is purged. For some applications, some of the purging fluid additionally flows to the interface between the axial shaft and proximal bearing 116, thereby purging the interface (and/or reducing frictional forces at the interface), as indicated by purging-fluid-flow arrows 149 in FIG. 11A. Typically, the flow of the purging fluid in the direction of arrows 149 also prevents blood from flowing into the interface between the axial shaft and the proximal bearing.

As described hereinabove (with reference to FIGS. 10A-C) typically the drive cable includes a plurality of coiled wires. For some applications, purging fluid passes into lumen 132 defined by the drive cable via gaps in the coiled wires. Once the purging fluid is disposed within lumen 132 it flows in both proximal and distal directions, as indicated by arrow 151 of FIG. 11A. The purging fluid that flows in the distal direction typically flows out of the distal end of lumen 132 and toward lumen 122 defined by distal-tip portion, as indicated by arrow 152 of FIG. 11A. At the end of distal-tip portion, the purging fluid is typically prevented from flowing out of the distal-tip portion by duckbill valve 390. Therefore, some of the purging fluid typically flows to the interface between the axial shaft and distal bearing 118, thereby purging the interface (and/or reducing frictional forces at the interface), as indicated by purging-fluid-flow arrows 154 in FIG. 11A. Typically, the flow of the purging fluid in the direction of arrows 154 also prevents blood from flowing into the interface between the axial shaft and the distal bearing.

Figure 11B:
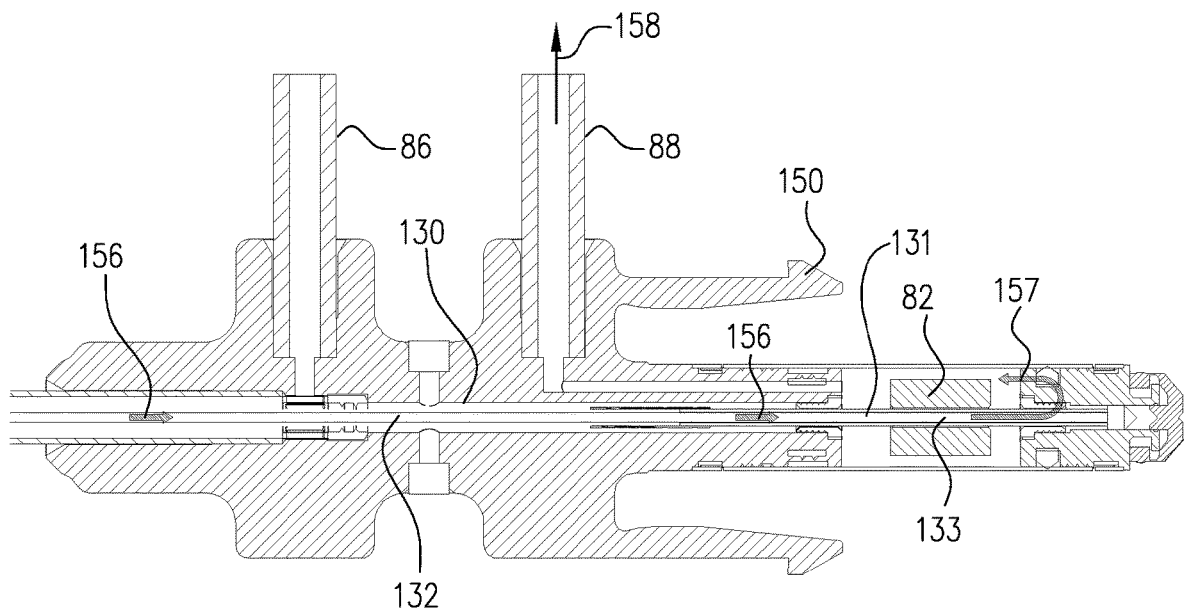

As described above, once the purging fluid is disposed within lumen 132 it flows in both proximal and distal directions, as indicated by arrow 151 of FIG. 11A. Referring now to FIG. 11B, typically, at the proximal end of ventricular assist device 20, the purging fluid flows in the direction of arrows 156 out of the proximal end of lumen 132 and then out of the proximal end of lumen 133 defined by pin 131. For some applications, the purging fluid then flows in the direction of arrow 157 and around driven magnet 82, such as to reduce frictional forces that the driven magnet is exposed to. For some applications, the purging fluid then flows out of outlet port 88, in the direction of arrow 158. Typically, the purging fluid is then disposed of. Alternatively, the purging fluid is pumped back into the device, via inlet port 86.

With reference to the above description of the purging procedure that is typically used with ventricular assist device 20, it is noted that lumens 122, 132, and 133 (which were previously used to facilitate insertion of the device over guidewire 10, as described hereinabove), are typically used as flow channels for purging fluid, during use of the ventricular assist device.

Figure 11C:
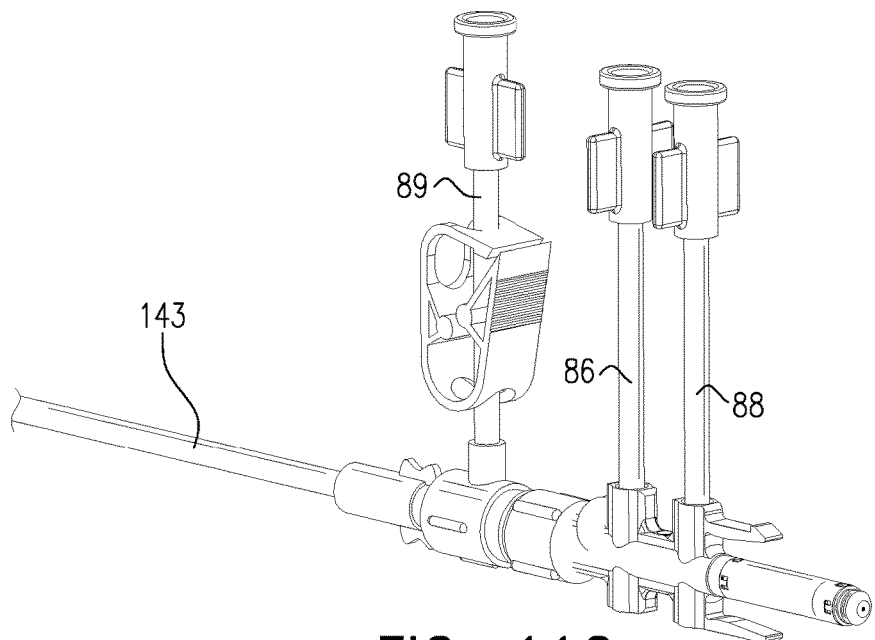

Referring now to FIG. 11C, for some applications, ventricular assist device includes an additional purging fluid inlet port 89, which is typically used to pump purging fluid into channel 224 between delivery catheter 143 and outer tube 142. For some applications, the purging fluid is pumped into this channel at a low enough pressure, that it is still possible to detect aortic blood pressure via this channel, as described elsewhere in this application. For some applications, rather than continuously pumping purging fluid into channel 224, fluid is pumped into this channel periodically in order to flush the channel. For some applications, port 89 and channel 224 are used for aortic pressure sensing. For example, pressure sensor 216 (which is illustrated schematically in FIG. 1A) may be disposed within channel 224, within port 89, and/or at a different location that is in fluid communication with channel 224.

Referring to FIGS. 11D and 11E, for some applications, axial shaft 92 includes purging fluid holes that are configured to allow the flow of the purging fluid from out of lumen 132, which is defined by axial shaft 92. For some applications, the axial shaft defines purging fluid holes 190 in the vicinity of distal bushing 58 of impeller 50. As described hereinabove, for some applications, the distal bushing is configured to be slidable with respect to the axial shaft. For some such applications, the interface between the distal bushing and the axial shaft is purged by the purging fluid flowing out of purging fluid holes 190. For some applications, the axial shaft defines holes 192 in the vicinity of distal radial bearing 118. For some such applications, the interface between the distal radial bearing and the axial shaft is purged by the purging fluid flowing out of purging fluid holes 192. For some applications, the axial shaft defines holes 194 in the vicinity of proximal radial bearing 116. For some such applications, the interface between the distal radial bearing and the axial shaft is purged by the purging fluid flowing out of purging fluid holes 194.

Figure 12A:
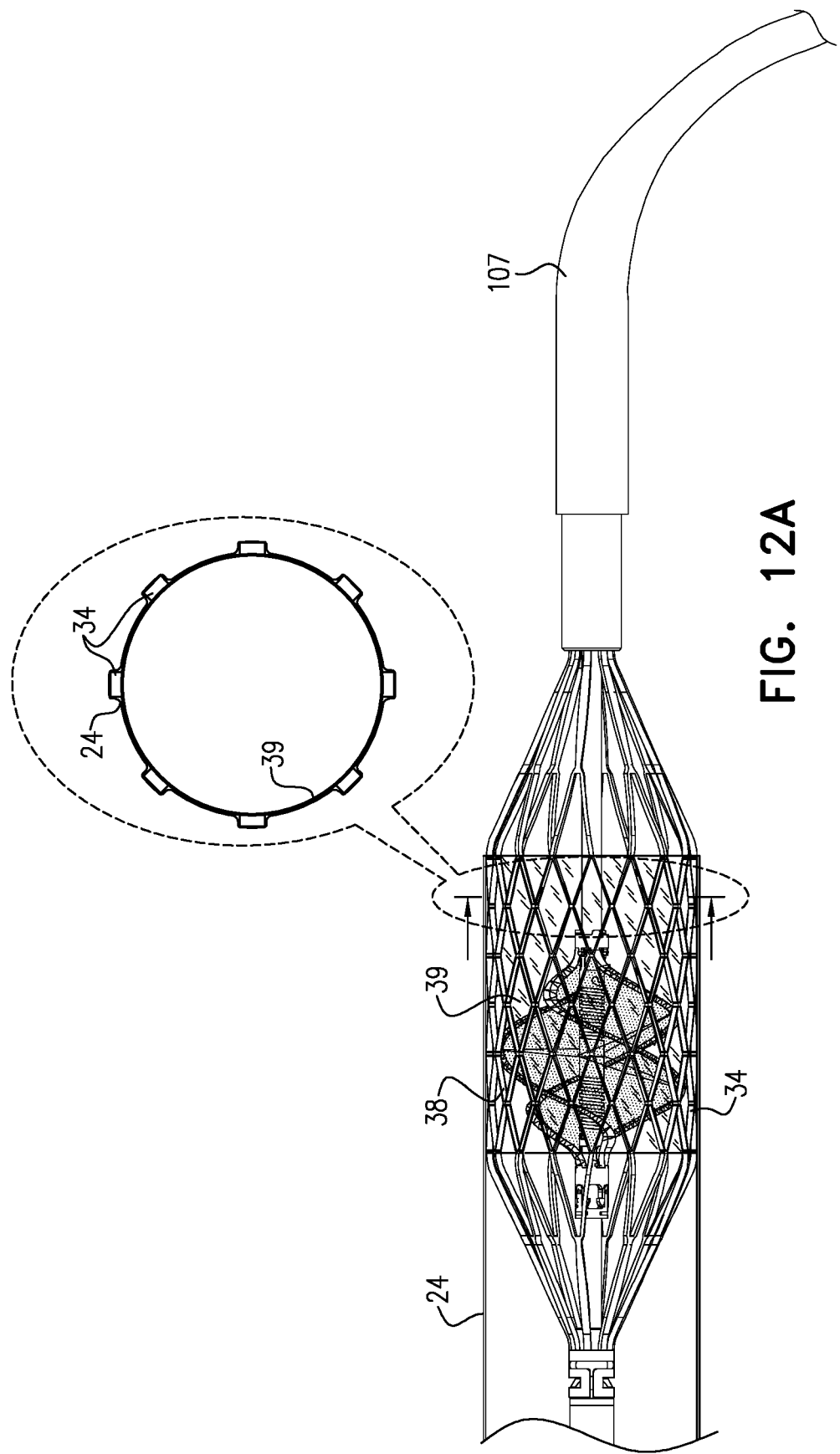
FIGS. 12A and 12B are schematic illustrations of a ventricular assist device that includes an inner lining on the inside of the frame that houses the impeller, in accordance with some applications of the present invention.
Figure 12B:
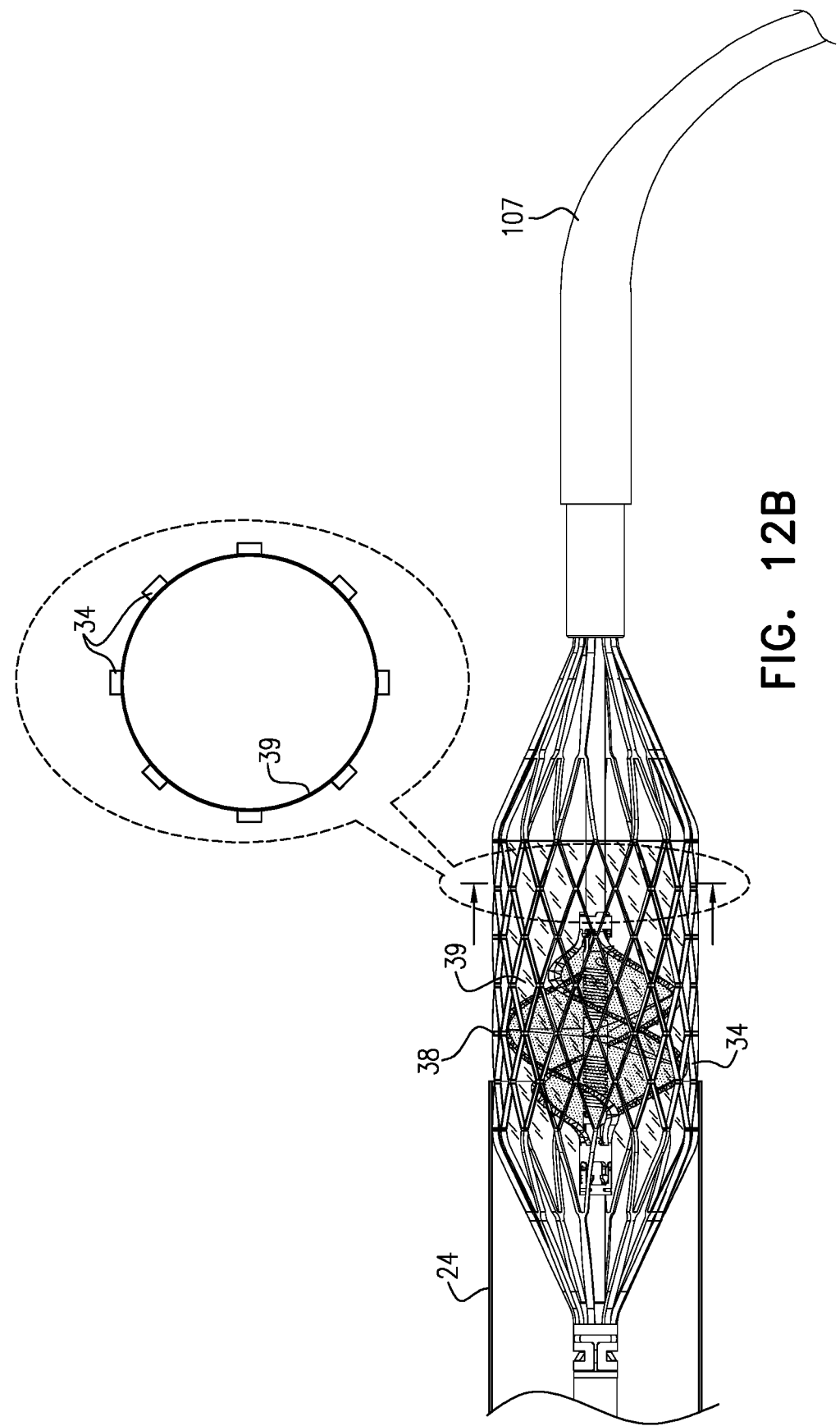

Reference is now made to FIGS. 12A and 12B, which are schematic illustrations of ventricular assist device 20, the device including inner lining 39 that lines the inside of frame 34 that houses impeller 50, in accordance with some applications of the present invention. (For illustrative purposes, inner lining 39 and pump-outlet tube 24 on the side of the device facing out of the page are shown as transparent in FIGS. 12A-B.) For some applications, inner lining 39 is disposed inside frame 34, in order to provide a smooth inner surface through which blood is pumped by impeller. Typically, by providing a smooth surface, the covering material reduces hemolysis that is caused by the pumping of blood by the impeller, relative to if the blood were pumped between the impeller and struts of frame 34. For some applications, inner lining includes polyurethane, polyester, and/or silicone. Alternatively or additionally, the inner lining includes polyethylene terephthalate (PET) and/or polyether block amide (PEBAX®).

Typically, the inner lining is disposed over at least the inner surface of the cylindrical portion of frame 34 (the cylindrical portion being indicated in FIGS. 2A-C, for example). For some applications, pump-outlet tube 24 also covers the cylindrical portion 38 of frame 34, around the outside of the frame, for example, such that pump-outlet tube 24 and inner lining 39 overlap over at least 50 percent of the length of the inner lining, for example, over the entire length of the cylindrical portion of frame 34, e.g., as shown in FIG. 12A. For some applications, there is only partial overlap between pump-outlet tube 24 and inner lining 39, e.g., as shown in FIG. 12B. For example, pump-outlet tube 24 may overlap with inner lining along less than 50 percent (e.g., along less than 25 percent) of the length of the inner lining. For some such applications, during insertion of ventricular assist device 20 into the subject's body, the impeller is advanced distally within frame 34, such that the impeller is not disposed within the area of overlap between the pump-outlet tube and the inner lining, such that there is no longitudinal location at which the impeller, pump-outlet tube 24, frame 34, and inner lining 39 all overlap with each other. As described hereinabove, with reference to FIG. 1D, for some applications, pump-outlet tube 24 extends to the end of distal conical portion 40 of the frame, and the pump-outlet tube defines a plurality of lateral blood inlet openings. For some such applications, the cylindrical portion of the frame is lined with inner lining 39.

Typically, over any area of overlap between inner lining 39 and pump-outlet tube 24, the inner lining is shaped to form a smooth surface (e.g., in order to reduce hemolysis, as described hereinabove), and pump-outlet tube 24 is shaped to conform with the struts of frame 34 (e.g., as shown in the cross-section in FIG. 12A). Typically, over the area of overlap between inner lining 39 and pump-outlet tube 24, the pump-outlet tube and the inner lining are coupled to each other, e.g., via vacuum, via an adhesive, and/or using a thermoforming procedure, for example as described hereinbelow.

For some applications, inner lining 39 and pump-outlet tube 24 are made of different materials. For example, the inner lining may be made of polyurethane, and the pump-outlet tube may be made of polyether block amide (PEBAX®). Typically, the material from which the inner lining is made has a higher thermoforming temperature than that of the material from which the pump-outlet tube is made. For some applications in which the inner lining and the pump-outlet tube overlap along at least a portion of frame 34 (e.g., along the cylindrical portion of frame 34), the pump-outlet tube and the inner lining are bonded to each other and/or the frame in the following manner. Initially, the inner lining is placed over a mandrel. The frame is then placed over the inner lining. Subsequently, pump-outlet tube 24 is placed around the outside of the frame. For some applications, in order to mold pump-outlet tube 24 to conform with the struts of frame 34, without causing the inner lining to deform, the frame is heated to a temperature that is above the thermoforming temperature of pump-outlet tube 24 but below the thermoforming temperature of inner lining 39. Typically, the frame is heated from inside the frame, using the mandrel. Typically, while the frame is heated to the aforementioned temperature, an outer tube (which is typically made from silicone) applies pressure to pump-outlet tube 24 that causes pump-outlet tube 24 to be pushed radially inwardly, in order to cause the pump-outlet tube to conform with the shapes of the struts of the frame, as shown in the cross-section of FIG. 12A. For some applications, the combination of the frame, the inner lining, and the portion of pump-outlet tube 24 disposed around the frame is subsequently shape set to a desired shape and dimensions using shape setting techniques that are known in the art.

For some applications (not shown), a density of struts of the frame at the distal end of the cylindrical portion of the frame is greater than the density of the struts within other parts of the cylindrical portion of the frame. For some such applications, the increased density of the struts of the frame at the distal end of the cylindrical portion of the frame facilitates bonding of the inner lining and/or the pump-outlet tube to the frame. For some applications, the inner lining and/or the pump-outlet tube does not extend all the way to the end of the cylindrical portion of the frame, e.g., as described with reference to FIG. 13. For some such applications, at the longitudinal location along the cylindrical portion of the frame at which the inner lining and/or the pump-outlet tube ends, the density of the struts of the frame is increased relative to at other locations along the cylindrical portion of the frame.

Figure 13:
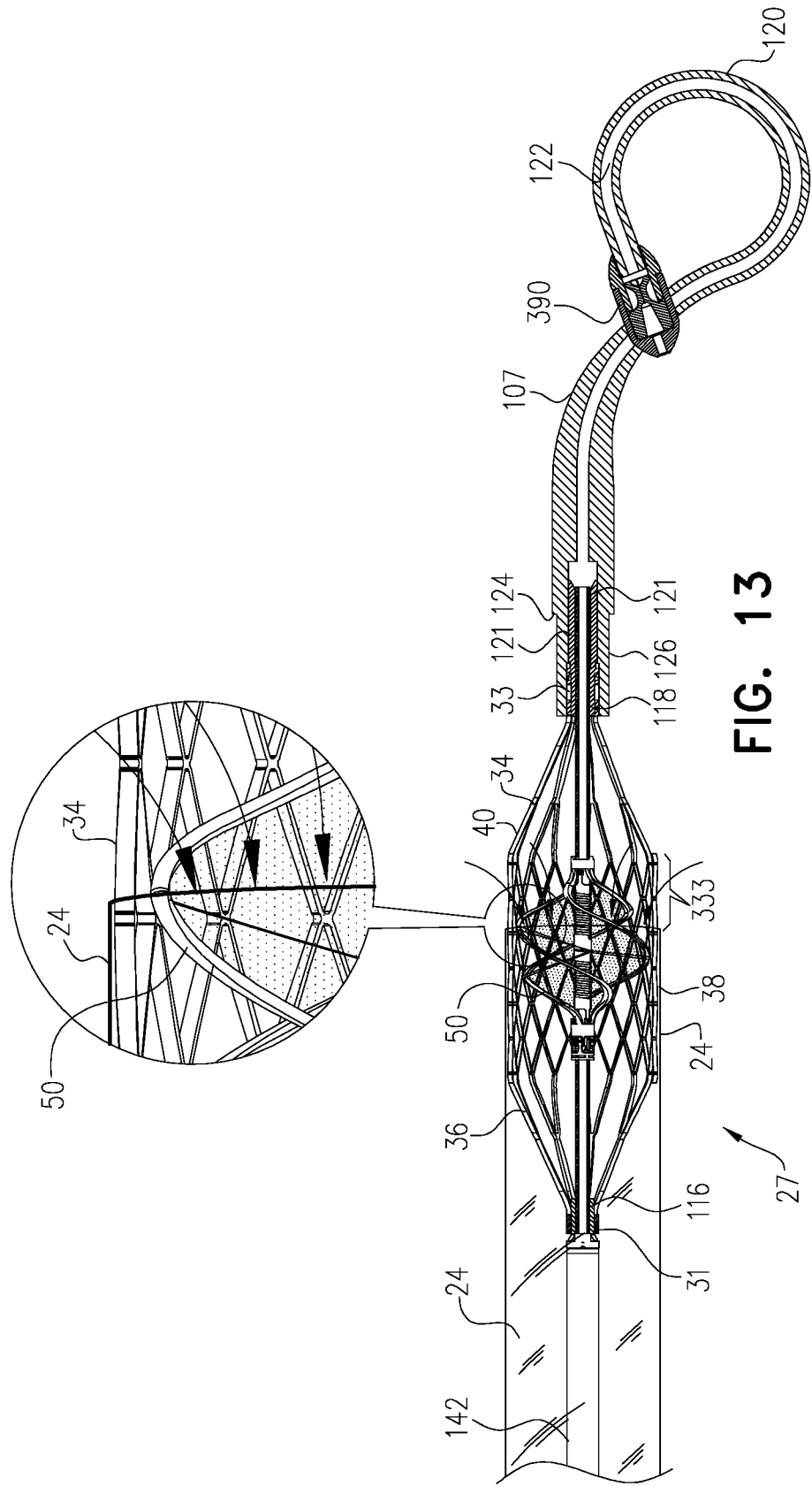
FIG. 13 is a schematic illustration of a ventricular assist device having a frame that houses an impeller, the frame defining a cylindrical portion at least a distal part of which is uncovered, in accordance with some applications of the present invention.

Reference is now made to FIG. 13, which is a schematic illustration of ventricular assist device 20, in which at least a distal part 333 of cylindrical portion 38 of frame 34 is uncovered, in accordance with some applications of the present invention. For some applications, over the course of the axial back-and-forth motion cycle of the impeller, even when the impeller is disposed at its most distal location within frame 34, the part of the impeller at which the span of the impeller is at its maximum does not advance beyond a given location within the cylindrical portion of the frame (e.g., as described hereinabove with reference to FIGS. 10A-C). For some applications, part of the frame that is disposed distally beyond this location is not covered by either pump-outlet tube 24 or inner lining 39. (It is noted that the frame is shown in the absence of inner lining 39 for illustrative purposes. However, for some applications, the frame is lined with inner lining 39. Typically, even in such applications, distal part 333 of the cylindrical portion of the frame is not covered by either pump-outlet tube 24 or inner lining 39.)

For some applications, the uncovered distal part of the cylindrical portion of the frame functions as a virtual widened inlet, since (as indicated by the blood flow arrows in FIG. 13) blood flows into the cylindrical portion of the frame from the sides of the cylindrical portion of the frame. For some applications, this reduces hemolysis that is generated by the impeller pumping blood. Alternatively or additionally, by having a part of the cylindrical portion of the frame be uncovered, the diameter of pump portion 27, when the pump portion is in its radially-constrained configuration, may be reduced. For example, the pump portion may be radially constrained such that the widest portion of the impeller overlaps with the uncovered part of the cylindrical portion of the frame in order to reduce the diameter of the pump portion of the ventricular assist device (relative to if the widest portion of the impeller overlaps with a covered part of the cylindrical portion of the frame, such that the widest portion of the impeller overlaps with the frame as well as covering material).

For some applications, ventricular assist device is configured such that, even during diastole, there is an axial distance between the location of the impeller at which the impeller is at its maximum diameter and the blood inlet opening. For example, the ventricular assist device is configured such that, during diastole, there is an axial distance of more than 3 mm (e.g., more than 5 mm) between the location of the impeller at which the impeller is at its maximum diameter and the blood inlet opening (e.g., as described hereinabove with reference to FIGS. 10A-C). For some such applications, this reduces hemolysis (relative to if there were a smaller axial distance or no axial distance between the location of the impeller at which the impeller is at its maximum diameter and the blood inlet opening) and/or enhances the efficacy of the impeller by reducing turbulence, by allowing flow lines of the blood that enters the blood inlet opening to become at least partially aligned with the longitudinal axis of the impeller prior to being pumped by the impeller.

Figure 14:
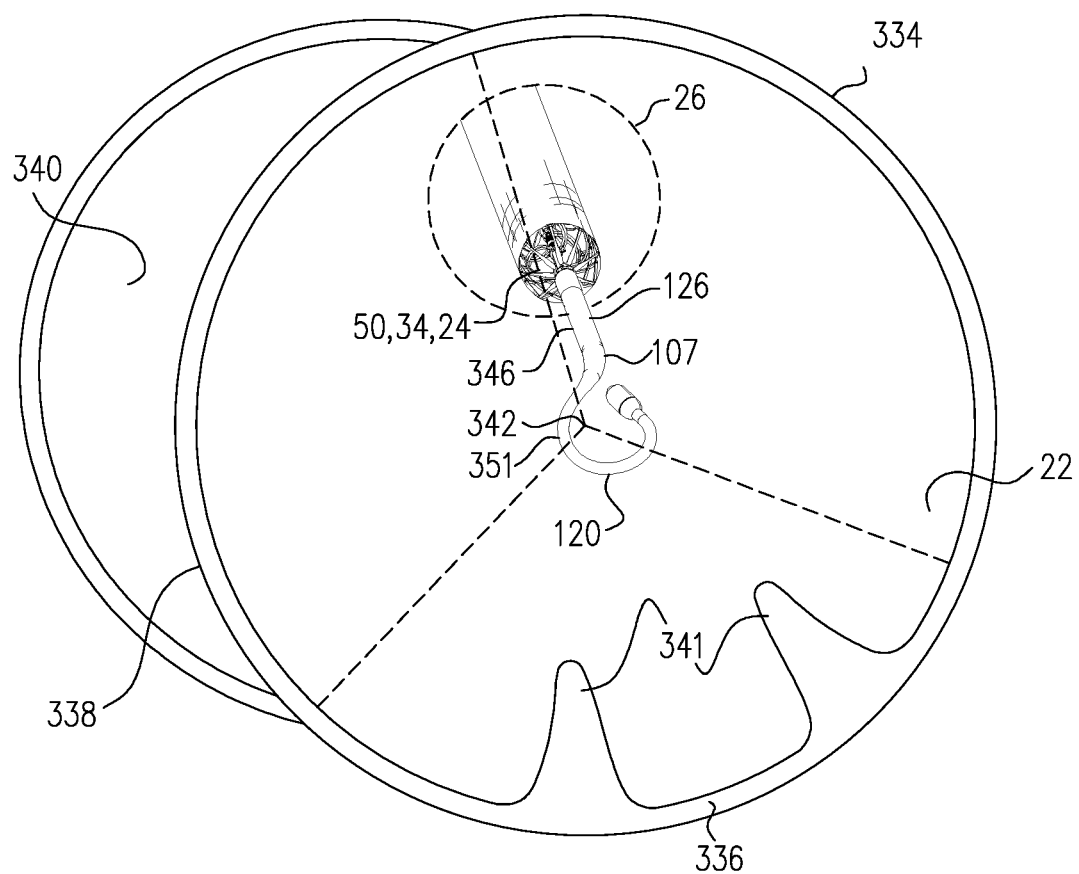
FIG. 14 is a schematic illustration of a ventricular assist device being placed inside a subject's left ventricle, with a transverse cross-sectional view of the left ventricle being illustrated, in accordance with some applications of the present invention.

Reference is now made to FIG. 14, which is a schematic illustration of ventricular assist device 20 being placed inside a subject's left ventricle 22 (a transverse cross-sectional view of the left ventricle being illustrated), in accordance with some applications of the present invention. (FIG. 14 shows aortic valve 26 overlaid on the transverse cross-section of the left ventricle even though the aortic valve lies in a different plane from the plane of the main cross-sectional view, for illustrative purposes.) Reference is also made to FIGS. 15A-D, which are schematic illustrations of distal-tip element 107 of the ventricular assist device that is at least partially curved such as to define a curvature that is similar to that of a question mark, in accordance with some applications of the present invention, and to FIGS. 16A and 16B, which are schematic illustrations of the ventricular assist device of FIGS. 15C-D disposed inside a subject's left ventricle, in accordance with some applications of the present invention.

For some applications, the ventricular assist device is guided by the guidewire over which it is inserted toward apex 342 of the left ventricle. The walls of the left ventricle may be thought of as being made up of the septal wall 338 (which separates the left ventricle from the right ventricle 340), the posterior wall 336 (from which the papillary muscles 341 protrude, and above which the mitral apparatus is disposed), and the free wall 334, each of these three walls occupying approximately one third of the circumference of the left ventricle (as illustrated by the dashed lines, which trisect the left ventricle in FIG. 14). Typically, it is undesirable for the distal-tip element (or any other portions of the ventricular assist device) to come into contact with the septal wall, since there is a risk that this can give rise to arrythmias. Further typically, it is desirable to maintain a distance between the distal-tip element (and any other portions of the ventricular assist device) from the posterior wall, in order not to interfere with the mitral apparatus, and in order to prevent the mitral apparatus from interfering with the functioning of the ventricular assist device. Therefore, the ventricular assist device is typically guided toward the apex, in such a manner that, if and when the distal-tip element contacts the inner wall of the left ventricle, it contacts free wall 334, as shown in FIGS. 14 and 16A-B.

Typically, the ventricular assist device is introduced into the subject's ventricle over a guidewire, as described hereinabove. Distal-tip portion 120 defines lumen 122, such that the distal-tip portion is held in a straightened configuration during the introduction of the ventricular assist device into the subject's ventricle. For some applications, upon the guidewire being removed, distal-tip portion is configured to assume its curved shape. It is noted that FIGS. 15A-D illustrate the shape of distal-tip portion 120 as it is initially formed. Typically, as a result of having the guidewire inserted through lumen 122 (thereby temporarily straightening the distal-tip portion), upon being deployed within the subject's left ventricle, the curvature of the distal-tip portion is less than that shown in at least some of FIGS. 15A-D. For example, FIG. 15C shows that the curved portion of the distal-tip portion is such that the curved portion of the distal-tip portion forms a complete loop. However, the distal-tip portion of FIG. 15C is shown in FIG. 16A within the subject's left ventricle and it does not form a complete loop.

As described hereinabove, distal-tip portion 120 typically forms a portion of distal-tip element 107 which also includes axial-shaft receiving tube 126. Typically, distal-tip element 107 is configured such that in its non-constrained configuration (i.e., in the absence of any forces acting upon the distal-tip portion), the distal-tip element is at least partially curved. For some applications, within a given plane, distal-tip element 107 has a proximal, straight portion 346 (at least a portion of which typically comprises axial-shaft-receiving tube 126). The proximal straight portion of distal-tip element 107 defines a longitudinal axis 348. The curved portion of distal-tip element 107 curves away from longitudinal axis 348 in a first direction, and then passes through an inflection point and curves in the opposite direction with respect to longitudinal axis 348. For example, as shown in FIGS. 15A-B, within the plane of the page, the distal-tip element first curves to the top of the page, then curves to the bottom of the page, and as shown in FIGS. 15C-D, within the plane of the page, the distal-tip element first curves to the bottom of the page, then curves to the top of the page. Typically, when shaped as shown in FIGS. 15A-D, the distal-tip element defines an overall curvature that is similar to that of a question mark or a tennis-racket, the distal-tip element defining a bulge 351 on one side of the longitudinal axis of the straight proximal straight portion of the distal-tip element. For some applications, the bulge is generally shaped as a semi-ellipse. (It is noted that in this context the term "semi-ellipse" includes a semi-circle. It is further noted that is some cases, the tip does not define a precise semi-ellipse, but rather a bulged shape that is substantially similar to a semi-ellipse.)

As shown in FIGS. 15A-B, for some applications, after passing through the inflection point the distal-tip element continues to curve such that the distal-tip element crosses back over longitudinal axis 348. FIG. 15A shows an example in which the end of the distal-tip element does not cross back over the longitudinal axis yet again, and there is a larger gap between the distal end of the distal-tip element and the proximal end of the curved portion. FIG. 15B shows an example in which the end distal-tip element does cross back over the longitudinal axis yet again, and there is a smaller gap between the distal end of the distal-tip element and the proximal end of the curved portion. As shown in FIGS. 15C-D (which are, respectively, cross-sectional and isometric views of the same shaped distal-tip element), for some applications, after passing through the inflection point the tip does not curve such that the distal-tip element crosses back over longitudinal axis 348. Rather, all of the curvature of the curved portion of the distal-tip element occurs on one side of longitudinal axis 348.

Referring to FIG. 15C, typically, a hemostasis valve (e.g., duckbill valve 390) is disposed within a distal section of distal-tip portion 120, and is configured to prevent blood flow into lumen 122. Typically, the duckbill valve has a maximum width of less than 3 mm, e.g., less than 2 mm. Typically, the entire duckbill valve is disposed within a distal section of the distal-tip portion that is disposed within the distal-most 10 mm, e.g., the distal most 5 mm of the distal-tip portion. For some applications, the duckbill valve is proximally facing (i.e., such that the wide inlet of the valve faces the distal end of distal-tip portion and such that the narrow tip of the valve faces away from the distal end of distal-tip portion 120). Typically, upon being deployed within the subject's left ventricle, the curvature of the curved portion of distal-tip element 107 is configured to provide an atraumatic tip to ventricular assist device 20. Further typically, the distal-tip element is configured to space the inlet openings 108 of the ventricular assist device from walls of the left ventricle.

Referring now to FIGS. 16A and 16B, it is first noted that these figures show a cross-sectional view of the left ventricle 22 in which septal wall 338 is disposed on the left of the page and free wall 334 is disposed on the right of the page. In this view, the left atrium 359, and left atrial appendage 358 are visible above the left ventricle, and right ventricle 340 is visible to the left of the left ventricle. It is noted that the view of the aorta and the left ventricle as shown in FIGS. 16A-B (as well as in FIGS. 17Ai-17D) is different to that shown, for example, in FIG. 1B. FIG. 1B is a schematic illustration, provided for illustrative purposes, and does not properly depict the scale and orientation of the ventricular assist device with respect to the anatomy.

For some applications, distal-tip element 107 is configured to separate the blood inlet opening from a posterior wall of the subject's left ventricle when the distal-tip element is placed against the apex of the subject's left ventricle. Typically, the distal-tip element is configured to separate the blood-inlet opening from a septal wall of the subject's left ventricle as the distal-tip element contacts the apex of the subject's left ventricle.

Typically, distal-tip element 107 is inserted into the left ventricle, such that bulge 351 bulges toward the septal wall 338. When disposed in this configuration, in response to distal-tip element 107 being pushed against the apex (e.g., due to a physician advancing the device or in response to movement of the left ventricle), blood inlet opening 108 typically gets pushed in the direction of free wall 334 and away from the septal wall 338 (in the direction of the arrows shown in FIG. 16B. Typically, this is due to proximal straight portion 346 pivoting about the curved portion of the question mark shape, as shown. By contrast, other shapes of tips, if disposed in a similar orientation may result in the blood inlet opening being pushed toward the septal wall. For example, if the distal-tip element were to have a pigtail tip (in which the tip curves in a single direction of curvature) that is oriented such that the pigtail curve is on the free wall side of the longitudinal axis of the straight portion of the distal-tip element, then pushing the tip distally would typically cause the blood inlet openings toward the septal wall due to the loop of the pigtail curve tightening.

With reference to all of FIGS. 14-16B it is noted that the scope of the present invention includes using a question-mark or tennis-racket shaped distal-tip element in combination with any ventricular assist device, and even in the absence of other features and/or portions of distal-tip element 107 (such as, axial-shaft-receiving tube 126). It is further noted that, typically, the curvatures of the distal-tip portion are all within a single plane.

Reference is now made to FIGS. 17Ai and 17Aii, which are schematic illustrations of ventricular assist device 20, the device having a balloon 220 disposed on its distal-tip element 107, the balloon being configured to facilitate movement of axial shaft 92 with respect to walls of the ventricle, in accordance with some applications of the present invention.

As described hereinabove, axial shaft 92 typically passes through the axis of impeller 50, via lumen 62 of the impeller. Further typically, the axial shaft is rigid, e.g., a rigid tube. The axial shaft itself is radially stabilized via proximal radial bearing 116 and distal radial bearing 118. In turn, the axial shaft, by passing through lumen 62 defined by the impeller, radially stabilizes the impeller with respect to the inner surface of frame 34. For some applications, the axial shaft passes into axial-shaft-receiving tube 126 of distal-tip element 107. Typically, friction between the axial shaft and the distal and radial bearings is increased if the axial shaft is bent. Therefore, it is typically desirable for the axial shaft to be maintained in a straight configuration. For some applications, balloon 220 provides the distal end of the distal-tip element with freedom of movement with respect to the walls of the left ventricle is a manner that does not cause the proximal end of the distal tip portion (which defines the axial-shaft-receiving tube) to undergo substantial movement. For example, as indicated by the arrows in the vicinity of apex 342 in FIGS. 17Ai and 17Aii, the balloon may rotate with respect to the apex without causing substantial movement of the axial-shaft receiving tube. Thus, even if the balloon undergoes movement with respect to the apex (as shown in the transition from FIG. 17Ai to FIG. 17Aii), the axial shaft is maintained in a substantially straight configuration. For some applications, balloon 220 is inflated using purging fluid, e.g., using a technique as described with reference to FIG. 13D of US 2020/0237981 to Tuval, which is incorporated herein by reference.

Reference is now made to FIGS. 17Bi and 17Bii, which are schematic illustrations of ventricular assist device 20, the device having a joint 230 that is configured to facilitate pivoting of its distal tip portion 120 with respect to its axial shaft, in accordance with some applications of the present invention. As described hereinabove, for some applications, distal-tip element 107 includes axial-shaft-receiving tube 126, as well as distal-tip portion 120. For some applications, joint 230 allows distal-tip portion 120 to move with respect to axial-shaft receiving tube 126. For example, joint 230 may be a ball-and-socket joint as shown, and/or it may be a swivel joint, and/or a Cardan joint. Thus, even if the distal-tip portion undergoes movement with respect to apex 342 of the left ventricle (as shown in the transition from FIG. 17Bi to FIG. 17Bii), axial shaft 92 is maintained in a substantially straight configuration. For some such applications, distal-tip portion 120 is shaped as described hereinabove.

Figure 17D:
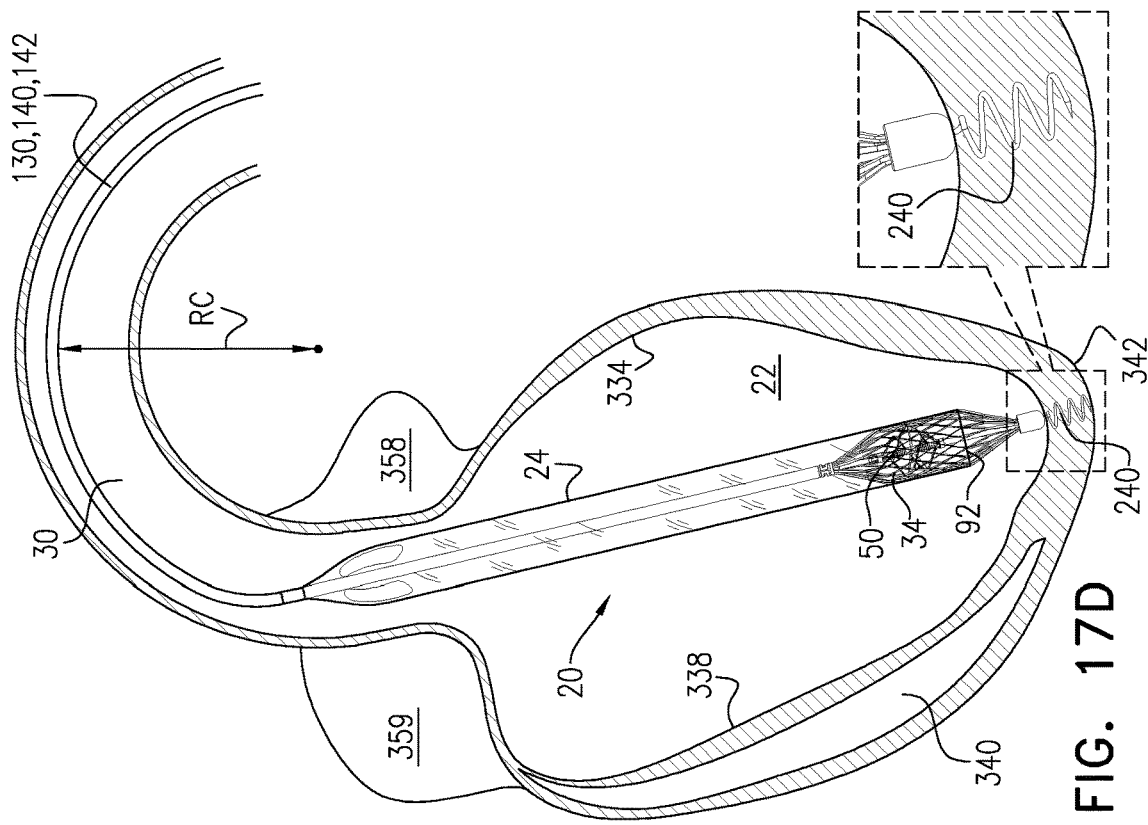
FIG. 17D is a schematic illustration of a ventricular assist device having a distal tip that is configured to be anchored to tissue of the left ventricular apex.
Figure 17C:
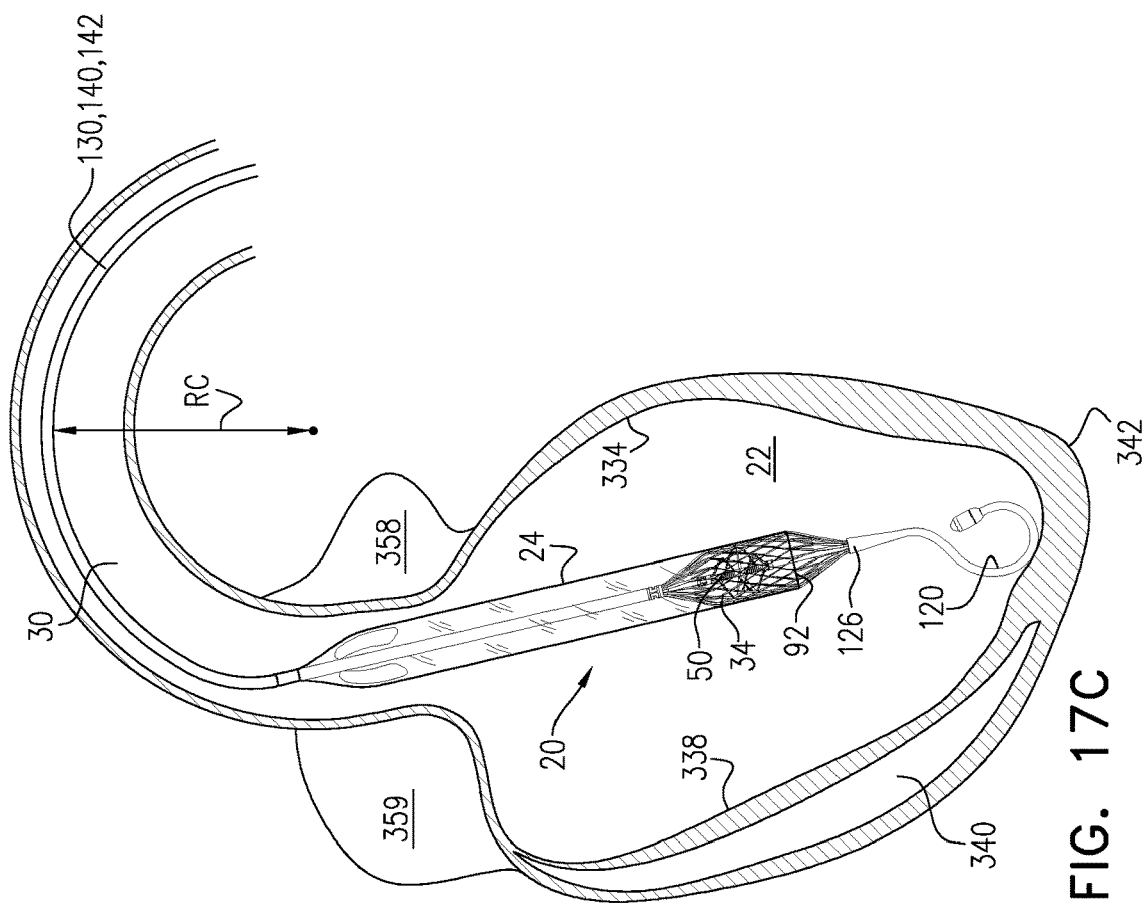
FIG. 17C is a schematic illustration of a ventricular assist device, an outer tube of which is shaped to a predefined curvature, such that the axial shaft of the ventricular assist device is maintained in a substantially straight configuration, when the axial shaft is disposed inside the subject's left ventricle, in accordance with some applications of the present invention.

Reference is now made to FIG. 17C, which is a schematic illustration of a ventricular assist device, an outer tube 140 and/or 142 of which is shaped to a predefined curvature, such that axial shaft 92 of the ventricular assist device is maintained in a substantially straight configuration when the axial shaft is disposed inside the subject's left ventricle 22, in accordance with some applications of the present invention.

As described hereinabove with reference to FIGS. 10A-C, for some applications, drive cable 130 is disposed within a first outer tube 140, which is configured to act a drive-cable bearing tube, first outer tube 140 remaining stationary while the drive cable undergoes rotational and/or axial back-and-forth motion. The first outer tube is configured to effectively act as a bearing along the length of the drive cable. For some applications first outer tube 140 is disposed within second outer tube 142. For some applications, at least one of the first and second outer tubes is shaped such that a portion of the outer tube that is disposed within the aortic arch has a predefined radius of curvature RC of more than 18 mm and/or less than 32 mm (e.g., less than 24 mm), e.g., 18-32 mm or 18-24 mm. For some applications, by defining such a radius of curvature the axial shaft enters the left ventricle at such an angle that when the distal tip portion of the ventricular assist device is disposed in the vicinity of apex 342, the axial shaft is in a substantially straight configuration.

Reference is now made to FIG. 17D, which is a schematic illustration of ventricular assist device 20 having a distal tip 240 that is configured to be anchored to tissue of the left ventricular apex 342, in accordance with some applications of the present invention. For some applications, distal tip 240 is a screw-shaped element (e.g., a corkscrew-shaped element as shown), and the distal tip is configured to be screwed into tissue of the apex, in order to anchor the distal end of the ventricular assist device to the apex. Typically, anchoring the distal tip the apex reduces movement of pump portion 27 with respect to inner structures of the left ventricle, and thereby reduces a risk of damage to the inner structure of the left ventricle that may be caused by such movement.

Reference is now made to FIGS. 18A, 18B, and 18C, which are schematic illustrations of a distal radial bearing 118 of a ventricular assist device, in accordance with respective applications of the present invention.

Referring to FIG. 18A, for some applications, the radial bearing is disposed inside a bearing housing 119. For some such applications, the radial bearing and the bearing housing are made of respective, different materials from each other. For example, the radial bearing may be made of a first material that has a relatively high hardness, such as ceramic, and the bearing housing may be made of a second material that is relatively easy to shape into a desired shaped, such as a metal or an alloy (e.g., stainless steel, cobalt chromium, and/or nitinol). For some applications, proximal radial bearing 116 is also disposed inside a bearing housing, with the proximal radial bearing and the bearing housing being made of respective, different materials from each other (in a generally similar manner to that described with reference to distal radial bearing 118). As described hereinabove, for some applications, the ventricular assist device includes a distal extension 121 that is configured to stiffen a region of the distal-tip element into which the distal end of shaft 92 moves (e.g., axial-shaft-receiving tube 126, described hereinbelow, or a portion thereof). For applications in which distal radial bearing 118 is disposed inside bearing housing 119, distal extension 121 typically comprises an extension from bearing housing 119 rather than from the distal radial bearing itself. As described hereinabove, typically, at the distal end of frame 34 distal strut junctions 33 are placed into grooves defined by the outer surface of distal radial bearing 118, the grooves being shaped to conform with the shapes of the distal strut portions. For some applications, the outer surface of the bearing housing (rather than that of the bearing) is shaped to define such grooves (the grooves being indicated by reference numeral 127 in FIGS. 18A and 18B).

Referring now to FIG. 18B, for some applications, a layer of material 123 is disposed between radial bearing 118 and bearing housing 119. For some applications, the material is configured to allow some movement of the radial bearing with respect to the bearing housing, and/or to cushion such movement. For example, the layer of material may include a layer of elastomeric material. For some applications, proximal radial bearing 116 has a similar configuration, with a material (e.g., an elastomeric material) being disposed between the radial bearing and the bearing housing that is configured to allow some movement of the radial bearing with respect to the bearing housing, and/or to cushion such movement. For some such applications, by allowing movement between the radial bearings and the bearing housings, the material layers permit some movement of the rigid axial shaft with respect to frame 34. For some applications, in this manner, axial shaft 92 is permitted to become slightly misaligned with the longitudinal axis of the frame.

Referring to FIG. 18C, for some applications, an outer surface 125 of distal radial bearing 118, which abuts the inner surface of bearing housing 119, has a convex curve. For some applications, the convexly curved outer surface of the bearing is configured to allow some movement of the radial bearing with respect to the bearing housing. For some applications (not shown), the inner radial surface of the bearing housing (which abuts the outer surface of the bearing) has a convex curve, such as to allow some movement of the radial bearing with respect to the bearing housing. For some applications, proximal radial bearing 116 has a similar configuration, with the outer surface of the bearing and/or the inner radial surface of the bearing housing having a convex curve. For some such applications, by allowing movement between the radial bearings and the bearing housings, the above-described shapes of the bearing and/or bearing housings allows movement of the rigid axial shaft with respect to frame 34. For some applications, in this manner, the axial shaft is permitted to become slightly misaligned with the longitudinal axis of the frame.

For some applications, the lengths of the radial bearings are such as to allow movement of the rigid axial shaft with respect to frame 34, such that the axial shaft is permitted to become slightly misaligned with the longitudinal axis of the frame. For example, the lengths of each of the proximal and distal radial bearings may be less than 2 mm, less than 1.5 mm, or less than 1 mm, for example, 0-1.5 mm, or 0.5-1 mm.

Figure 19A:
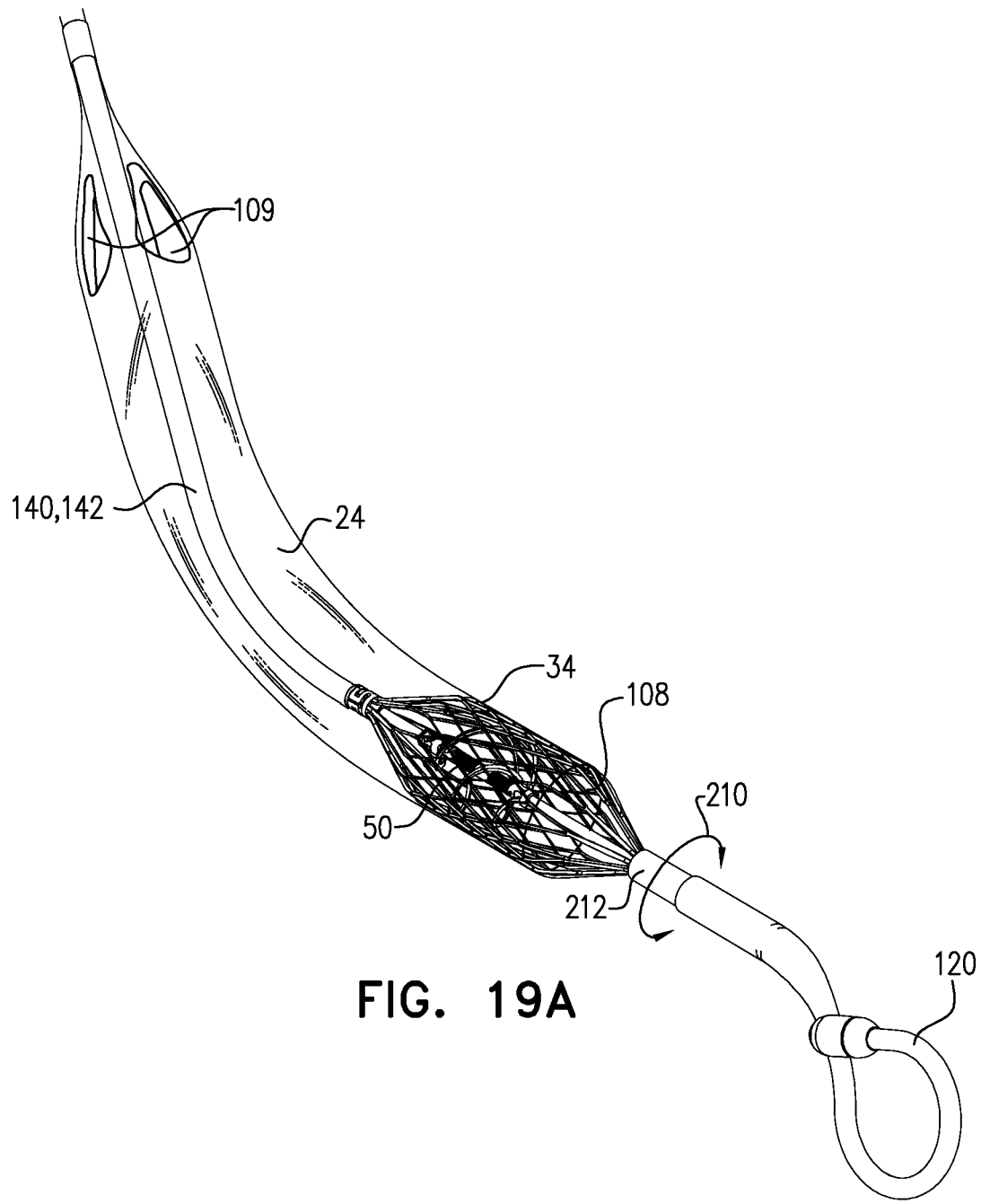
FIGS. 19A, 19B, 19C, 19D, and 19E are schematic illustrations of a ventricular assist device that includes a pump-outlet tube that is configured to become curved when blood is pumped through the pump-outlet tube, the pump-outlet tube being rotatable with respect to a distal-tip portion of the ventricular assist device, in accordance with some applications of the present invention.
Figure 19B:
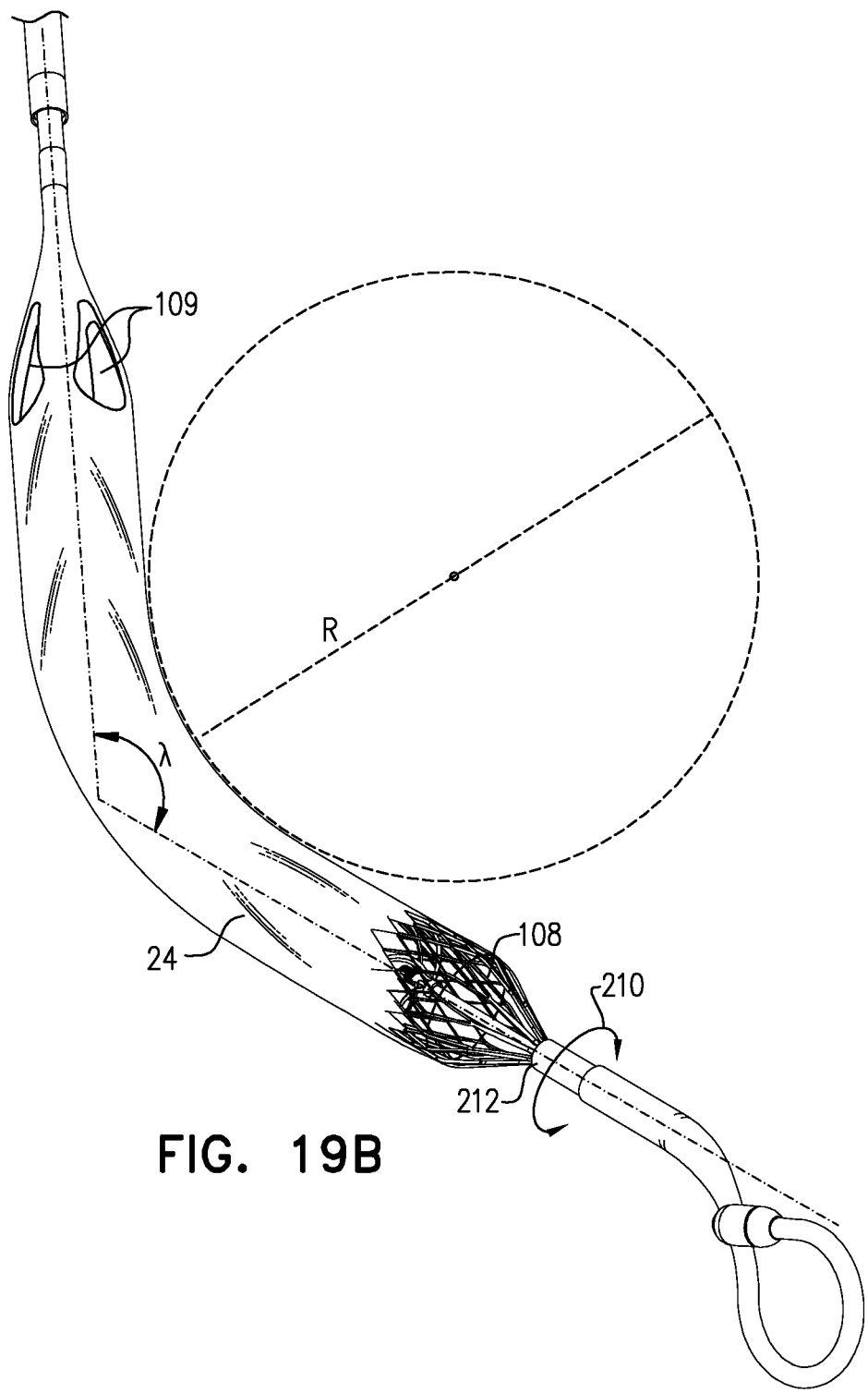
Figure 19C:
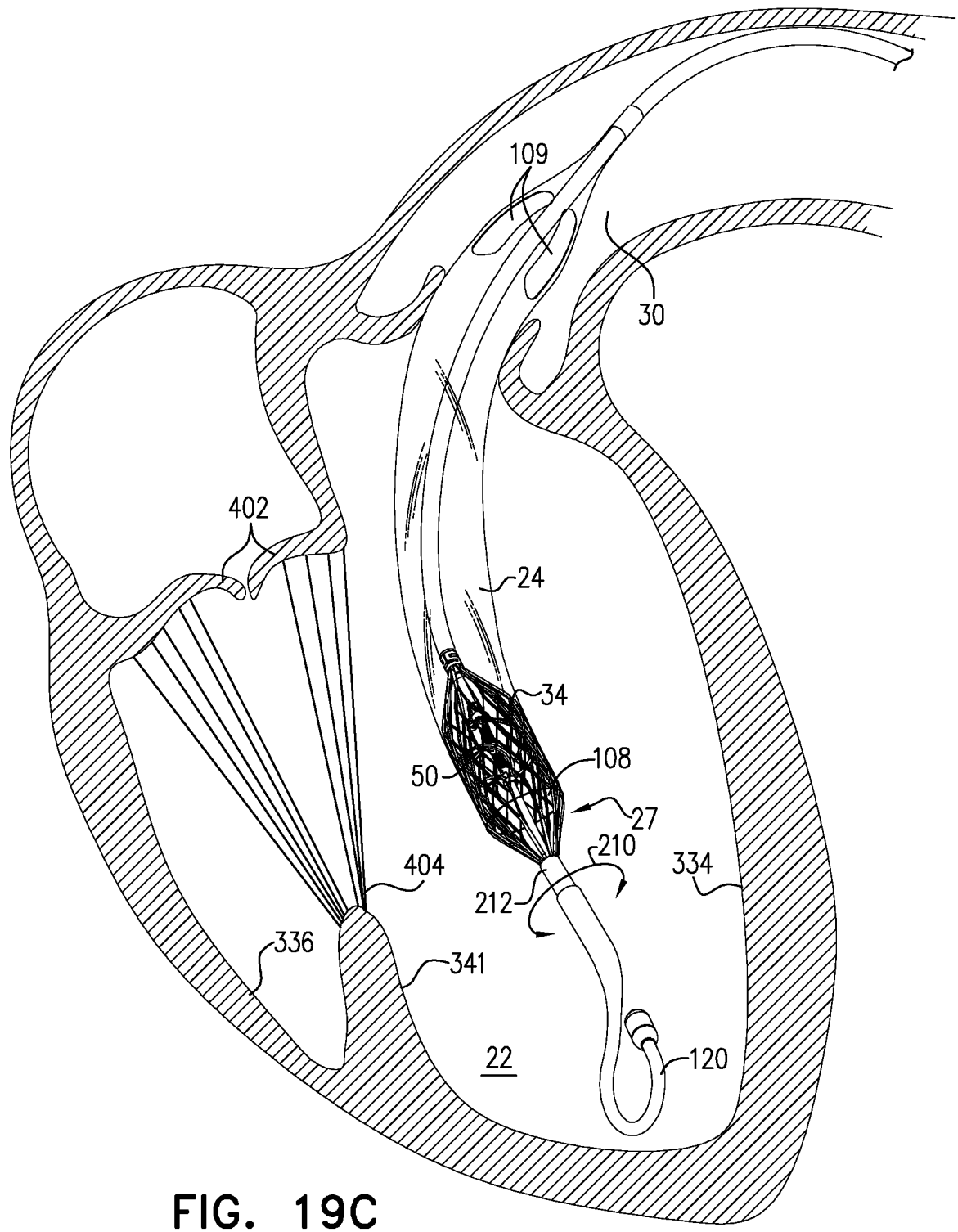

Reference is now made to FIG. 19A, which is a schematic illustration of ventricular assist device 20, pump-outlet tube 24 of the device being configured to become curved when blood is pumped through the pump-outlet tube, and the pump-outlet tube being rotatable with respect to distal-tip portion 120 of the ventricular assist device, in accordance with some applications of the present invention. Reference is also made to FIG. 19B, which is a schematic illustration of pump-outlet tube 24 of FIG. 19A, in the absence of other components of the ventricular assist device, in accordance with some applications of the present invention. Reference is additionally made to FIG. 19C, which is a schematic illustration of ventricular assist device 20 of FIGS. 19A-B disposed inside a subject's aorta 30 and left ventricle 22, in accordance with some applications of the present invention. It is noted that the view of the aorta and the left ventricle as shown in FIG. 19C is different to that shown, for example, in FIG. 1B. FIG. 1B is a schematic illustration, provided for illustrative purposes, and does not properly depict the scale and orientation of the ventricular assist with respect to the anatomy. It is further noted that the view of the aorta and the left ventricle as shown in FIG. 19C is different to that shown, for example, in FIGS. 16A-B, and 17Ai-17D. FIG. 19C shows a cross-sectional view of the left ventricle in which the posterior wall 336 is disposed on the left of the page and the free wall 334 is disposed on the right of the page.

As described hereinabove, for some applications, along a proximal portion of pump-outlet tube 24, frame 34 is not disposed within the tube, and the tube is therefore not supported in an open state by frame 34. Tube 24 is typically made of a blood-impermeable, collapsible material. For example, tube 24 may include polyurethane, polyester, and/or silicone. Alternatively or additionally, the tube is made of polyethylene terephthalate (PET) and/or polyether block amide (PEBAX®). Typically, the proximal portion of the tube is configured to be placed such that it is at least partially disposed within the subject's ascending aorta. For some applications, the proximal portion of the tube traverses the subject's aortic valve, passing from the subject's left ventricle into the subject's ascending aorta, as shown in FIG. 1B. As described hereinabove, the tube typically defines one or more blood inlet openings 108 at the distal end of the tube, via which blood flows into the tube from the left ventricle, during operation of the impeller. For some applications, the proximal portion of the tube defines one or more blood outlet openings 109, via which blood flows from the tube into the ascending aorta, during operation of the impeller. During operation of the impeller, the pressure of the blood flow through the tube typically maintains the proximal portion of the tube in an open state.

For some applications, pump-outlet tube 24 is pre-shaped such that, during operation of the impeller, when the pressure of the blood flow through the tube maintains the proximal portion of the tube in an open state, the tube is curved. Typically, the curvature is such that when the proximal end of the tube is disposed within the aorta, at least a portion of the tube is disposed within the left ventricle and curving away from the posterior wall of the left ventricle, toward the apex of the left ventricle and/or toward the free wall. Further typically, the curvature is such that when the proximal end of the tube is disposed within the aorta, at least a portion of the tube is disposed within the left ventricle and curving away from the septal wall of the left ventricle, toward the apex of the left ventricle and/or toward the free wall. For some applications, the curvature of the tube is such that a separation is maintained between blood inlet openings 108 and posterior wall 336 of the left ventricle, mitral valve leaflets 402 and/or subvalvular components of the mitral valve (such as chordae tendineae 404, trabeculae carneae, and/or papillary muscles 341), as shown in FIG. 19C.

Typically, tube 24 is pre-shaped using blow molding in a curved mold, or using a shaping mold after a blow-molding process or a dipping process. Typically, the distal portion of the tube, within which frame 34, impeller 50 and axial shaft 92 are disposed, is maintained in a straight and open configuration by frame 34. The portion of the tube, which is proximal to frame 34 and which is disposed within the left ventricle, is typically shaped to define the above-described curvature. For some applications, the curvature is such that an angle gamma between the longitudinal axis of the tube at the proximal end of the tube, and the longitudinal axis of the tube at the distal end of the tube is greater than 90 degrees (e.g., greater than 120 degrees, or greater than 140 degrees), and/or less than 180 degrees (e.g., less than 160 degrees, or less than 150 degrees), e.g., 90-180 degrees, 90-160 degrees, 120-160 degrees, or 140-150 degrees. For some applications, the curvature of the tube is such that the surface of the tube that is at the inside of the curve defines a radius of curvature R that is greater than 10 mm, e.g. greater than 20 mm, and/or less than 200 mm (e.g., 100 mm), e.g., 10-200 mm, or 20-100 mm. (A dashed circle with a dashed line across its diameter is shown in FIG. 19B, in order to indicate how radius of curvature R is measured.)

It is noted that pump-outlet tube 24, as described with reference to FIGS. 19A-C is configured such that (a) in the absence of blood flowing through the tube, the tube typically collapses in response to pressure outside the tube exceeding pressure inside the tube, and (b) when blood flows through the tube at a sufficient rate that pressure within the tube exceeds pressure outside the tube, then the tube assumes its pre-shaped, curved configuration. It is further noted that when tube 24 assumes its curved configuration, the tube typically causes the portion of drive cable 130 that is disposed within the curved portion of the tube to also become curved, as shown in FIGS. 19A and 19C. That is to say that it is the pre-shaping of the tube itself that typically causes the tube and the drive cable to curve, rather than the drive cable (or a different element disposed inside the tube) that causes the tube to curve. Alternatively, outer tube 140 and/or 142 (which is disposed around the drive cable) is shaped to define the curve, and the outer tube causes the drive cable and tube 24 to assume the curved shapes. For some applications, both outer tube 140 and/or 142 and tube 24 are shaped to define curved shapes.

Figure 19D:
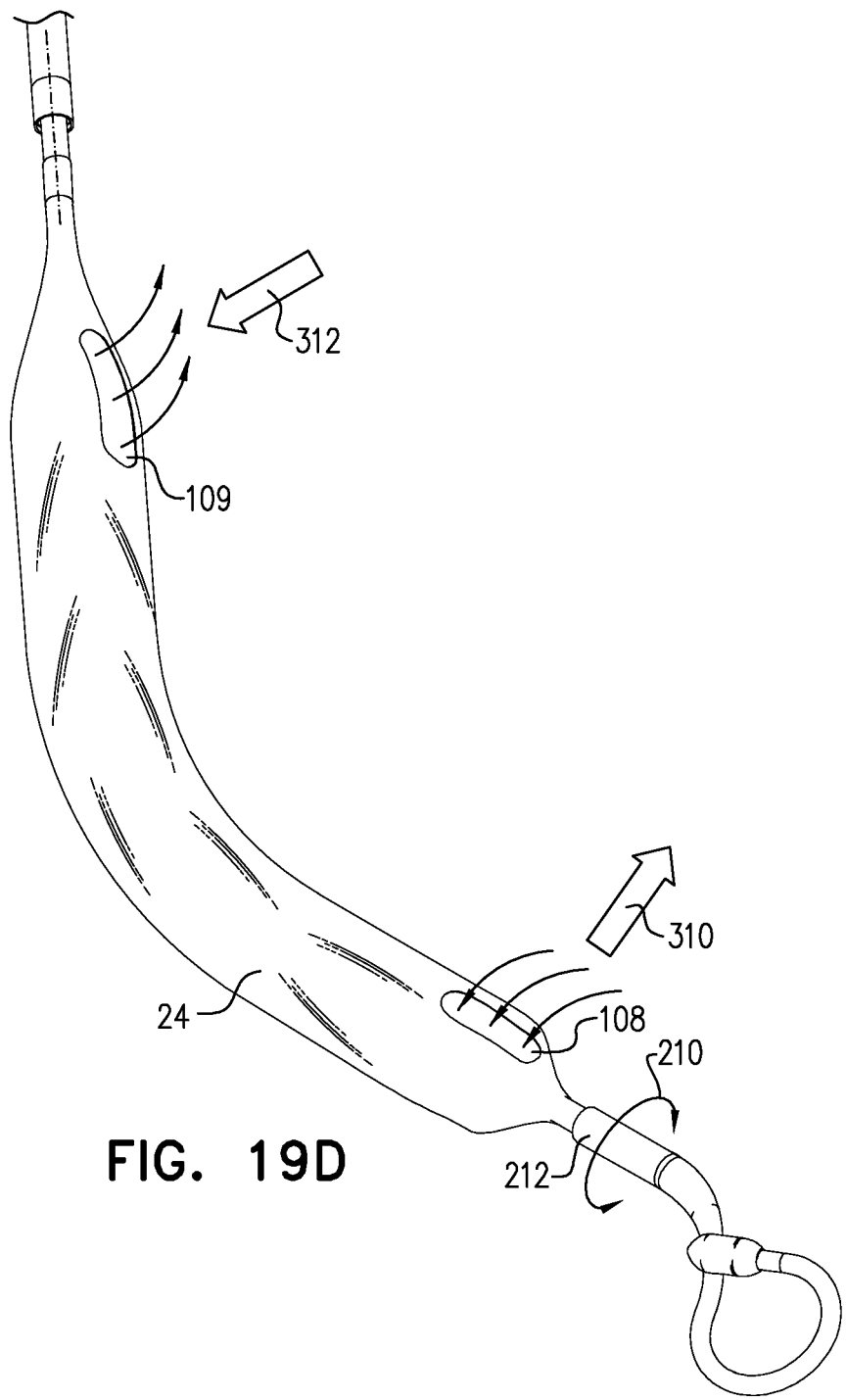
Figure 19E:
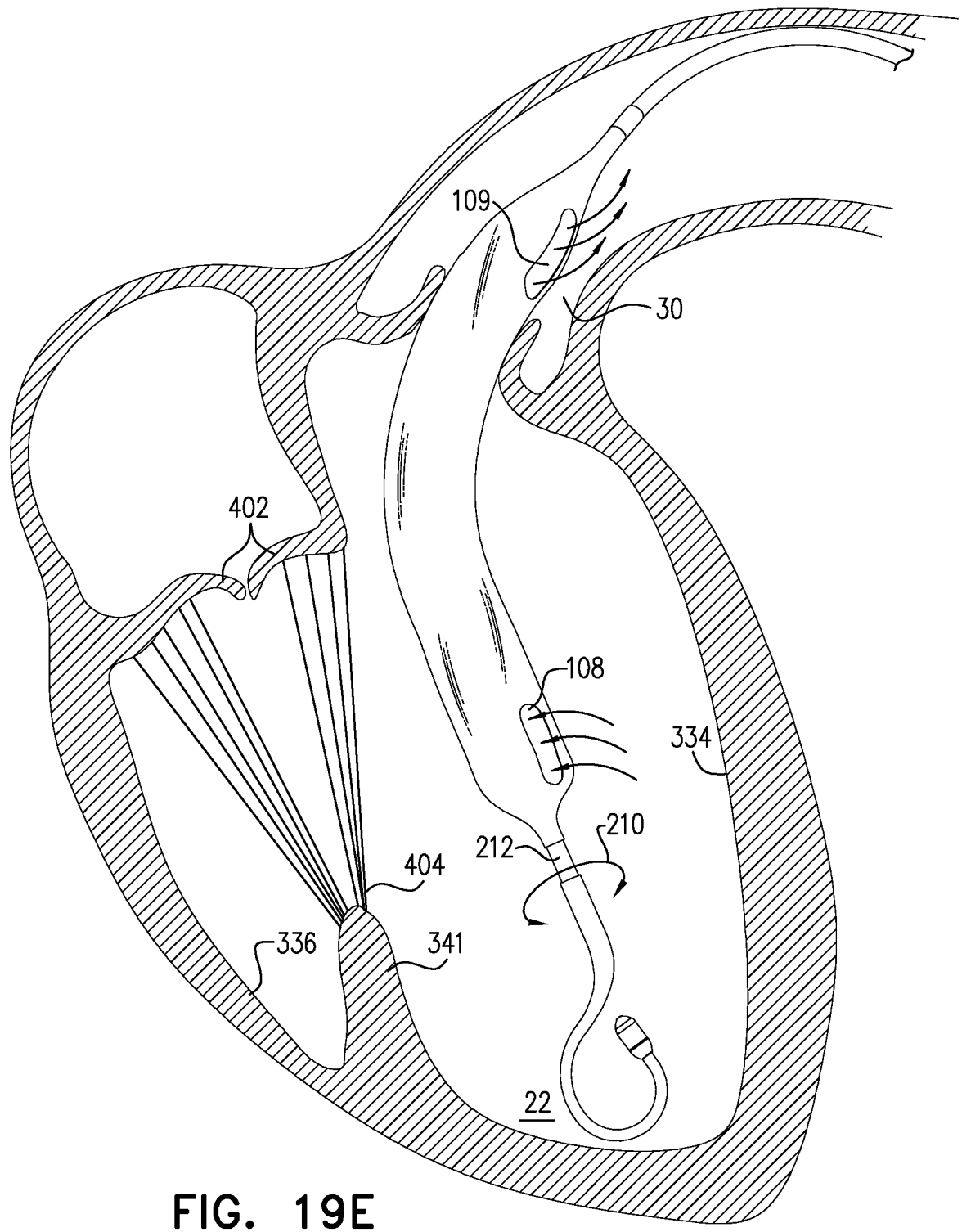

Reference is now made to FIGS. 19D-E, which are schematic illustrations of ventricular assist device 20, pump-outlet tube 24 of the device being configured to become curved when blood is pumped through the tube, in accordance with some applications of the present invention. In FIGS. 19D and 19E, tube 24 is shown in the absence of other components of the ventricular assist device (such as impeller 50, frame 34, etc.), for illustrative purposes. FIG. 19E is a schematic illustration of ventricular assist device 20 of FIG. 19D disposed inside a subject's aorta 30 and left ventricle 22, in accordance with some applications of the present invention. The view of the left ventricle shown in FIG. 19E is similar to that shown in FIG. 19C. For some applications, inlet openings 108 and/or outlet openings 109 are disposed in a non-axisymmetric configuration around tube 24. Typically, tube 24 defines the inlet openings and/or the outlet openings at locations that are such as to cause tube 24 to become curved and/or such as to maintain the curvature of tube 24 as described with reference to FIGS. 19A-C. For example, as shown, the blood inlet holes may be disposed on the side of tube 24 that is at the inside of the curve of the tube (or on the inside of the desired curve of the tube). As blood flows into the blood inlet opening, this lowers the pressure in the region above the blood inlet opening, and the distal end of tube 24 is then pulled toward this region (as indicated by arrow 310). Alternatively or additionally, the blood outlet openings 109 may be disposed on the side of tube 24 that is at the inside of the curve of the tube (or on the inside of the desired curve of the tube). As blood exits the blood outlet openings the blood impacts the wall of the aorta, which causes the proximal end of tube 24 to be pushed in the opposite direction, in the direction of arrow 312.

As described with reference to FIGS. 19A-C, typically, the curvature of the pump-outlet tube is such that a separation is maintained between blood inlet openings 108 and posterior wall 336 of the left ventricle, mitral valve leaflets 402 and/or subvalvular components of the mitral valve (such as chordae tendineae 404, trabeculae carneae, and/or papillary muscles 341), as shown in FIG. 19E. Typically, the curvature is such that when the proximal end of the tube is disposed within the aorta, at least a portion of the tube is disposed within the left ventricle and curving away from the posterior wall of the left ventricle, toward the apex of the left ventricle and/or toward the free wall. Further typically, the curvature is such that when the proximal end of the tube is disposed within the aorta, at least a portion of the tube is disposed within the left ventricle and curving away from the septal wall of the left ventricle, toward the apex of the left ventricle and/or toward the free wall.

For some applications, when deploying the ventricular assist device within the left ventricle, the distal-tip portion is deployed first. As described hereinabove, the distal-tip portion is typically deployed in a given orientation with respect to the left ventricular anatomy. Typically, after deploying the distal-tip portion, the pump-outlet tube is deployed. In some cases, having already deployed the distal-tip portion in the desired orientation with respect to the left ventricular anatomy, the curved portion of the tube is not disposed within the left ventricle in a desired orientation. Therefore, for some applications, the distal-tip portion is coupled (directly or indirectly) to the pump-outlet tube via a joint 212 that permits rotation of the pump-outlet tube with respect to a distal-tip portion of the ventricular assist device, as indicated by arrow 210 in FIGS. 19A-E. For example, the joint may be a swivel joint and/or a ball-and-socket joint (e.g., like ball-and-socket joint 230 shown in FIGS. 17Bi-Bii), and/or a Cardan joint (e.g., like joint 232 shown in FIGS. 20A-C). For some applications, the joint is disposed within a proximal portion of distal-tip element 107. Alternatively or additionally, the joint is disposed between distal-tip portion 120, and axial-shaft receiving tube 126 (e.g., as shown in FIGS. 17Bi-Bii).

Figure 19F:
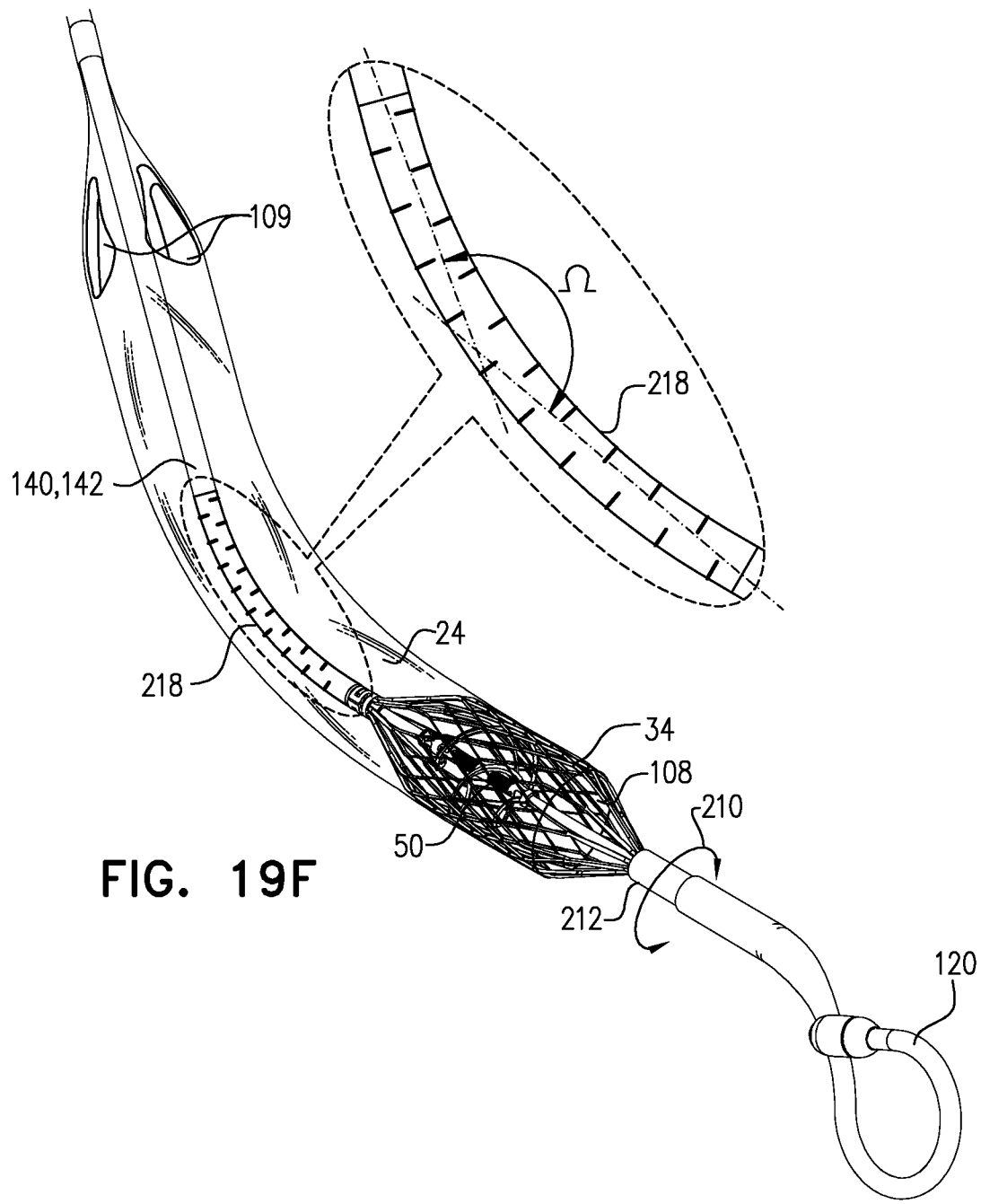
FIG. 19F is a schematic illustration of a ventricular assist device that includes a curved element that is made of a shape-memory material and that is configured to provide a portion of the ventricular assist device with a predefined curvature, the curved element being rotatable with respect to a distal-tip portion of the ventricular assist device, in accordance with some applications of the present invention.

Reference is now made to FIG. 19F, which is a schematic illustration of ventricular assist device 20, the ventricular assist device including a curved element 218 that is configured to provide tube 24 with a predefined curvature, in accordance with some applications of the present invention. For some applications, as an alternative or in addition to tube 24 itself being shaped to define a curve (e.g., as described with reference to FIGS. 19A-E), the ventricular assist device includes curved element 218. Typically, the curved element is made of a shape-memory material, e.g., a shape-memory alloy, such as nitinol. For some applications, the curved element is formed from a nitinol tube that is cut to define holes or slits, such that the tube is able to be pre-shaped in the desired curved shape. For example, the nitinol element may be what is known in the art as a nitinol "hypotube" (i.e., a nitinol tube with micro-engineered features along its length). Typically, curved element 218 is disposed around drive cable 130 along a longitudinal section of the drive cable that is proximal to (e.g., immediately proximal to) proximal radial bearing 116. For some applications, along this longitudinal section of the drive cable, the curved element is used in place of outer tube 142.

For some applications, the curved element is shape set to have a curvature that is generally similar to that described with respect to tube 24, with reference to FIGS. 19A-E. For some applications, the curvature is such that angle omega between the longitudinal axis of the curved element at the proximal end of the curved element, and the longitudinal axis of the curved element at the distal end of the curved element is greater than 90 degrees (e.g., greater than 120 degrees, or greater than 140 degrees), and/or less than 180 degrees (e.g., less than 160 degrees, or less than 150 degrees), e.g., 90-180 degrees, 90-160 degrees, 120-160 degrees, or 140-150 degrees. For some applications, the curvature of the tube is such that the surface of the curved element that is at the inside of the curve defines radius of curvature that is greater than 10 mm, e.g. greater than 20 mm, and/or less than 200 mm (e.g., 100 mm), e.g., 10-200 mm, or 20-100 mm. As described with reference to FIGS. 19A-C, typically, the curvature of the tube is such that a separation is maintained between blood inlet openings 108 and posterior wall 336 of the left ventricle, mitral valve leaflets 402 and/or subvalvular components of the mitral valve (such as chordae tendineae 404, trabeculae carneae, and/or papillary muscles 341), as shown in FIG. 19C. Typically, the curvature is such that when the proximal end of the tube is disposed within the aorta, at least a portion of the tube is disposed within the left ventricle and curving away from the posterior wall of the left ventricle, toward the apex of the left ventricle and/or toward the free wall. Further typically, the curvature is such that when the proximal end of the tube is disposed within the aorta, at least a portion of the tube is disposed within the left ventricle and curving away from the septal wall of the left ventricle, toward the apex of the left ventricle and/or toward the free wall.

For some applications, when deploying the ventricular assist device within the left ventricle, the distal-tip portion is deployed first. As described hereinabove, the distal-tip portion is typically deployed in a given orientation with respect to the left ventricular anatomy. Typically, after deploying the distal-tip portion, curved element 218 is deployed. In some cases, having already deployed the distal-tip portion in the desired orientation with respect to the left ventricular anatomy, curved element 218 is not disposed within the left ventricle in a desired orientation. Therefore, for some applications, the distal-tip portion is coupled (directly or indirectly) to the curved element 218 via a joint 212 that permits rotation of the pump-outlet tube with respect to a distal-tip portion of the ventricular assist device, as indicated by arrow 210 in FIGS. 19A-E. For example, the joint may be a swivel joint and/or a ball-and-socket joint (e.g., like ball-and-socket joint 230 shown in FIGS. 17Bi-Bii), and/or a Cardan joint (e.g., like joint 232 shown in FIGS. 20A-C). For some applications, the joint is disposed within a proximal portion of distal-tip element 107. Alternatively or additionally, the joint is disposed between distal-tip portion 120, and axial-shaft receiving tube 126 (e.g., as shown in FIGS. 17Bi-Bii).

With reference to FIGS. 19A-F, it is noted that for some applications tube 24 adopts a curved shape by virtue of outer tube 142 becoming anchored to the aorta and distal-tip portion 120 becoming anchored to the inner wall of the left ventricle (e.g., the free wall in the vicinity of the apex), as described hereinabove. It is further noted that the curvature of the tube shown in FIGS. 16A-B is less than that shown in FIGS. 19A-F because FIGS. 16A-B show a different view of the device. In the view shown in FIGS. 16A-B, the curvature is typically less pronounced than in the view shown in FIGS. 19A-F.

Reference is now made to FIGS. 20A-C, which are schematic illustrations of ventricular-assist device 20, axial shaft 92 of the device including a joint 232 (such as a Cardan joint, as shown), in accordance with some applications of the present invention. The joint is typically disposed within a portion of the axial shaft that is configured to be disposed between proximal bushing 64 and distal bushing 58 of the impeller, as shown. It is noted that in FIGS. 20A, portions of the impeller (such as film 56 of material and spring 54 are not shown, for illustrative purposes, and in order to provide visibility of the portion of the axial shaft that is typically disposed between proximal bushing 64 and distal bushing 58 of the impeller within lumen 62 defined by the impeller (lumen 62 being shown in FIGS. 3A-C, for example). Alternatively, the joint is disposed at a different location along axial shaft, such as proximal to the impeller or distal to the impeller.

For some applications, joint 232 is disposed between a proximal portion 234 of the axial shaft and a distal portion 236 of the axial shaft that are coupled to each other via the joint, such that the proximal and distal portion can flex with respect to each other via the joint. Typically, the joint allows the axial shaft to adopt a shape that conforms with the curvature of other portions of the left-ventricular device and/or the subject's anatomy. For some applications, the joint is configured to allow the axial shaft to conform with curvature of frame 34, such that even if frame 34 becomes slightly curved, the proximal portion of the axial shaft is disposed coaxially with respect to proximal bearing 116 and the distal portion of the axial shaft is disposed coaxially with respect to distal bearing 118.

Figure 21:
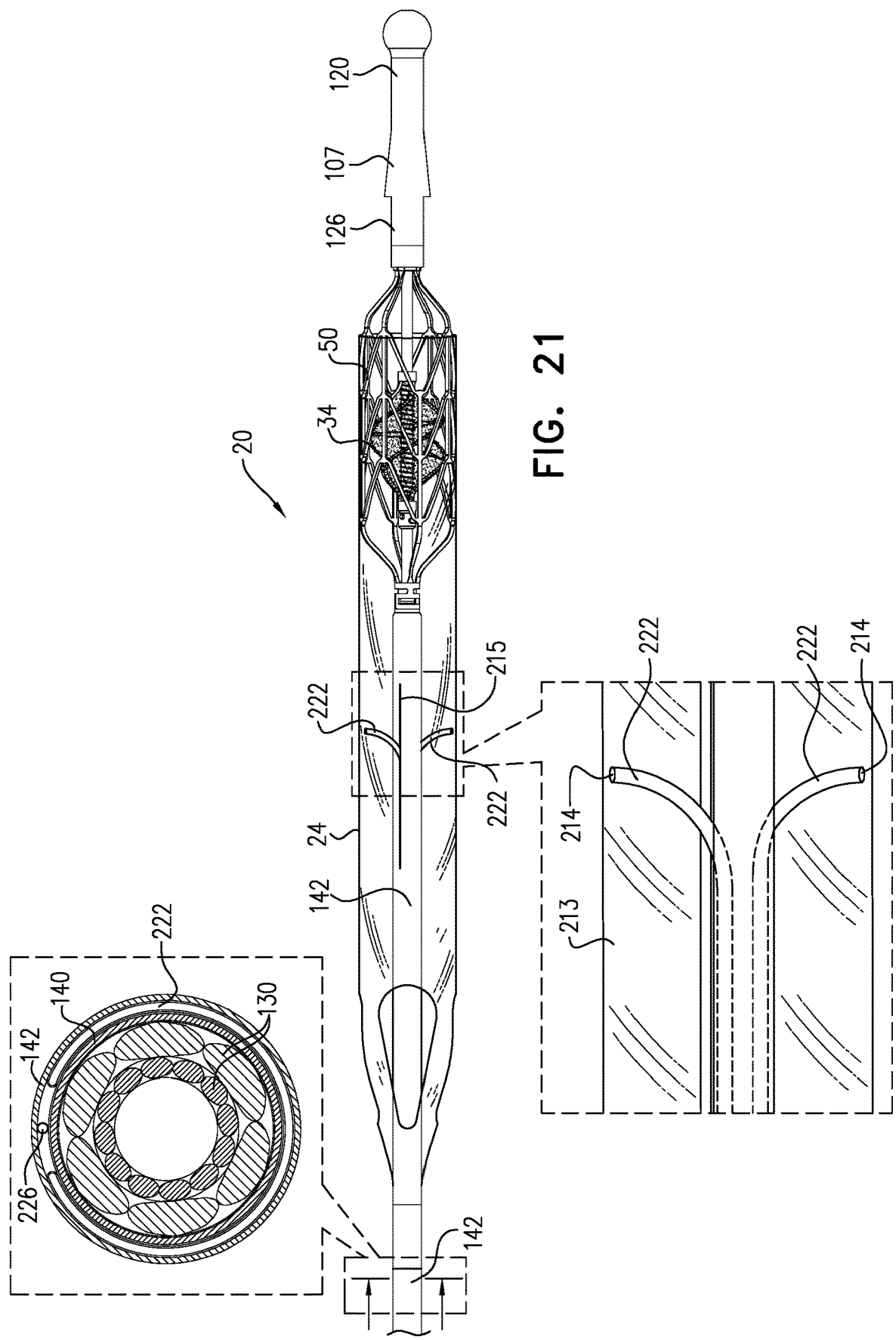
FIG. 21 is a schematic illustration of a ventricular assist device that includes one or more blood-pressure-measurement tubes, in accordance with some applications of the present invention.

FIG. 21 is a schematic illustration of a ventricular assist device that includes one or more blood-pressure-measurement tubes 222, in accordance with some applications of the present invention. As described hereinabove, typically, the ventricular assist device includes pump-outlet tube 24, which traverses the subject's aortic valve, such that a proximal end of the tube is disposed within the subject's aorta and a distal end of the tube is disposed within the subject's left ventricle. Typically, a blood pump (which typically includes impeller 50), is disposed within the subject's left ventricle within tube 24, and is configured to pump blood through tube 24 from the left ventricle into the subject's aorta. For some applications, ventricular blood-pressure-measurement tube 222 is configured to extend to at least an outer surface 213 of tube 24, such that an opening 214 at the distal end of the blood-pressure-measurement tube is in direct fluid communication with the patient's bloodstream outside tube 24. Typically, opening 214 is configured to be within the subject's left ventricle proximal to the blood pump (e.g., proximal to impeller 50). A pressure sensor 216 (illustrated schematically in FIG. 1A) measures pressure of blood within the ventricular blood-pressure-measurement tube. Typically, by measuring pressure of blood within the left ventricular blood-pressure-measurement tube, the pressure sensor thereby measures the subject's blood pressure outside tube 24 (i.e., left ventricular blood pressure). Typically, blood-pressure-measurement tube 222 extends from outside the subject's body to opening 214 at the distal end of the tube, and pressure sensor 216 is disposed toward a proximal end of the tube, e.g., outside the subject's body. For some applications, computer processor 25 (FIG. 1A), receives an indication of the measured blood pressure and controls the pumping of blood by the impeller, in response to the measured blood pressure.

For some applications, the ventricular assist device includes two or more such ventricular blood-pressure-measurement tubes 222, e.g., as shown in FIG. 21. For some applications, based upon the blood pressure as measured within each of the left ventricular blood-pressure-measurement tubes, computer processor 25 determines whether the opening of one of the two or more ventricular blood-pressure-measurement tubes is occluded. This may occur, for example, due to the opening coming into contact with the wall of the interventricular septum, and/or a different intraventricular portion. Typically, in response to determining that the opening of one of the two or more ventricular blood-pressure-measurement tubes is occluded, the computer processor determines the subject's left-ventricular pressure based upon the blood pressure measured within a different one of the two or more ventricular blood-pressure-measurement tubes.

For some applications, outer tube 142 defines a groove 215 in a portion of the outer surface of the outer tube that is configured to be disposed within tube 24. Typically, during insertion of the ventricular assist device into the subject's body, the portion of ventricular blood-pressure-measurement tube 222 that extends from within tube 24 to at least an outer surface of tube 24, is configured to be disposed within the groove, such that the portion of the ventricular blood-pressure-measurement tube does not protrude from the outer surface of the outer tube.

For some applications (not shown), distal portions of blood-pressure-measurement tubes 222 are disposed on the outside of pump-outlet tube 24. For example, blood-pressure-measurement tubes 222 may extend from outer tube 142 to the proximal end of pump-outlet tube 24, and thereafter the blood pressure measurement tubes may be built into the outer surface of tube pump-outlet tube 24, as shown in FIG. 16D of U.S. Pat. No. 10,881,770 to Tuval, which is incorporated herein by reference, for example.

As described hereinabove, for some applications, drive cable 130 extends from a motor outside the subject's body to axial shaft 92 upon which impeller 50 is disposed. Typically, the drive cable is disposed within first outer tube 140 and second outer tube 142, as described hereinabove. For some applications, a proximal portion of blood-pressure-measurement tube 222 comprises a channel between first outer tube 140 and second outer tube 142, as shown in the cross-section of FIG. 21. In this regard, it is noted that blood-pressure-measurement tube should be understood to refer to a continuous lumen extending from pressure sensor 216 to the outside of pump-outlet tube 24 within the subject's left ventricle, regardless of whether there are changes in the structure of the lumen along the length of the lumen. As described hereinabove, typically purging fluid is also pumped between outer tube 140 and outer tube 142, and for some applications, the purging fluid is pumped via channel 226. Typically, blood-pressure-measurement tube 222 occupies more of the cross-sectional area defined between outer tube 140 and outer tube 142 than purging fluid channel 226, as shown in FIG. 21. For example, the ratio of (a) the cross-sectional area defined between outer tube 140 and outer tube 142 that is occupied by blood-pressure-measurement tube to (b) the cross-sectional area defined between outer tube 140 and outer tube 142 that is occupied purging fluid channel 226 is typically more than 3:2, more than 3:1, or more than 5:1. For some applications, blood-pump-measurement tube occupies a relatively large proportion of the cross-sectional area defined between outer tube 140 and outer tube 142, in order for the blood pressure outside of pump-outlet tube 24 within the subject's left ventricle to be conveyed proximally to pressure sensor 216.

Figure 22A:
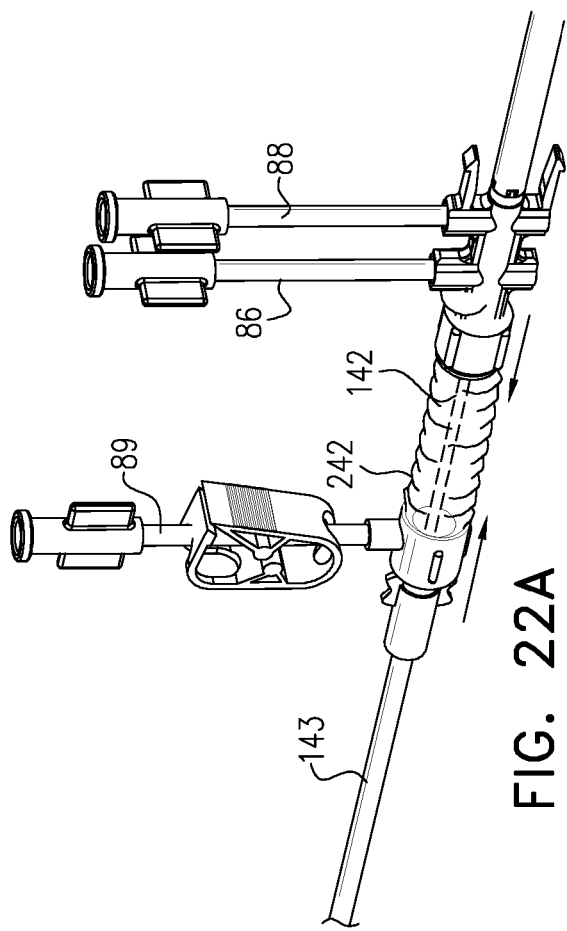
FIGS. 22A and 22B are schematic illustrations of a sterile sleeve configured to form a seal between a delivery catheter and an outer tube of a ventricular assist device, in accordance with some applications of the present invention.
Figure 22B:
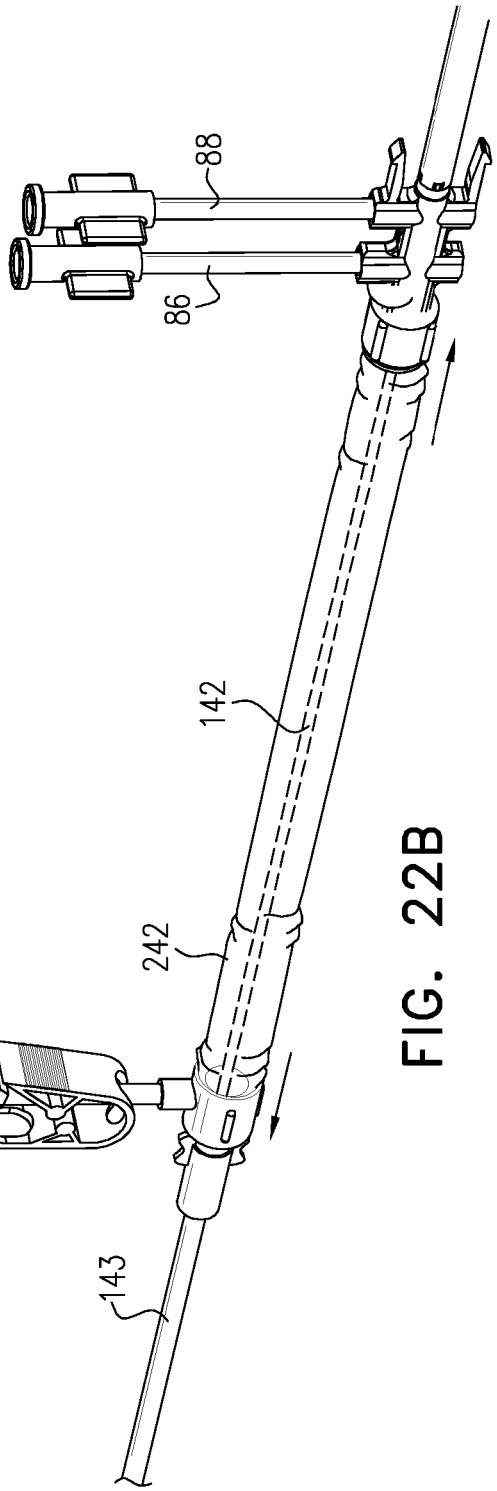

Reference is now made to FIGS. 22A and 22B, which are schematic illustrations of a sterile sleeve 242 configured to form a seal between delivery catheter 143 and outer tube 142 of ventricular assist device 20, in accordance with some applications of the present invention. For some applications (not shown), delivery catheter 143 is inserted into an artery of the subject (such as a femoral artery or a radial artery) via an introducer sheath (not shown) that is inserted into an incision in the artery and that typically remains in place within the artery throughout the operation of the ventricular assist device. For such applications, a sterile sleeve (that is generally similar to that shown in FIGS. 22A-B) is typically disposed between delivery catheter 143 and the introducer sheath (not shown), in order to permit movement between the delivery catheter and the introducer sheath, while maintaining the sterility of the artery incision.

For some alternative applications, the ventricular assist device is initially inserted into the artery incision via an introducer sheath, which is subsequently removed for the remainder of the operation of the ventricular assist device. For example, the ventricular assist device may be inserted via a peel-away introducer sheath. Subsequently, the delivery catheter is typically in direct contact with the artery incision. Typically, this reduces the diameter of the devices that are disposed within the artery incision for the remainder of the procedure, relative to if the introducer sheath were to remain inside the artery incision throughout the operation of the ventricular assist device. For example, the outer diameter of the delivery catheter may be less than 3.3 mm (i.e., 10

French), and this is the diameter that passes through the incision once the introducer sheath has been removed. The inner diameter of the delivery catheter typically less than 3 mm (i.e., 9 French), for example, the inner diameter may be 2.7 mm (i.e., 8 French). In contrast, if an introducer sheath were to remain in place throughout the duration of the operation of the ventricular assist device, then this would increase the diameter that passes through the incision because the thickness of the walls of the introducer sheath must additionally be accommodated by the incision. For example, it may increase the diameter by 0.3-0.6 mm (i.e., approximately 1-2 French).

For some such applications, the delivery catheter is advanced until the distal end of the delivery catheter is disposed at a given location within the subject's aorta (e.g., within the ascending aorta). Subsequently, the pump portion 27 of the ventricular assist device is advanced relative to the distal end of the delivery catheter by outer tube 142 being advance relative to the delivery catheter. For such applications, sterile sleeve 242 forms a seal between delivery catheter 143 and outer tube 142 of ventricular assist device 20, such as to permit movement of the outer tube relative to the delivery catheter while maintaining sterility of the artery incision. For some such applications, the ventricular assist device is provided to a user in a kit that contains sterile sleeve 242 disposed in place between outer tube 142 and delivery catheter 143.

Reference is now made to FIGS. 23A-C, which are schematic illustrations of a tip straightening element 270 that is used to straighten distal-tip portion 120 of ventricular assist device 20 during insertion of guidewire 10 therethrough, in accordance with some applications of the present invention. As described hereinabove, typically ventricular assist device is inserted into the subject ventricle over guidewire 10, which the ventricular assist device is disposed in a radially constrained (i.e., crimped) configuration inside delivery catheter 143 (e.g., as schematically illustrated in FIG. 1B). Typically, the guidewire is first inserted into the ventricular assist device at the distal end of distal-tip element 107. For some applications, in order to facilitate insertion of the guidewire through the distal end of the distal-tip element (i.e., through distal-tip portion 120), tip straightening element 270 is placed around the distal-tip element, such as to hold the distal-tip element in a straightened configuration. Typically, the straightening element is a housing that defines a straight lumen 271. The straightening element is placed around the distal-tip element, such that the distal tip element is disposed in a straightened configuration within lumen 271, and the guidewire is inserted into the distal end of the distal-tip element (i.e., through distal-tip portion 120), e.g., as shown in FIG. 23B. For some applications, the straightening element is configured to be removable from the distal-tip element, while the guidewire is disposed in the distal-tip-element. For example, the straightening element may be scored, perforated, and/or have a slit 272 (as shown) that passes along its length such as to facilitate removal of the straightening element from the distal-tip element, e.g., as shown in FIG. 23C.

Figure 24A:
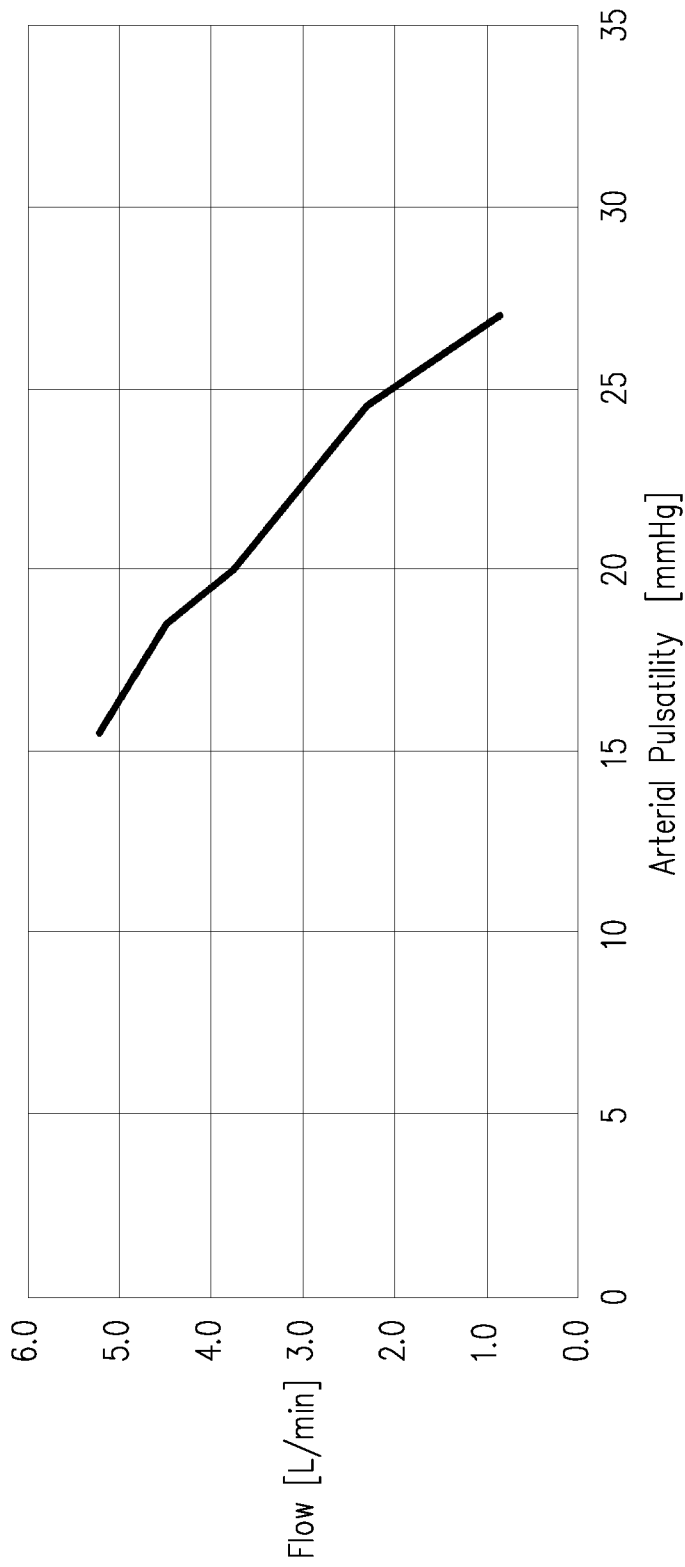
FIGS. 24A, 24B, and 24C are graphs showing measurements performed during the use of a left ventricular assist device, in accordance with some applications of the present invention.
Figure 24B:
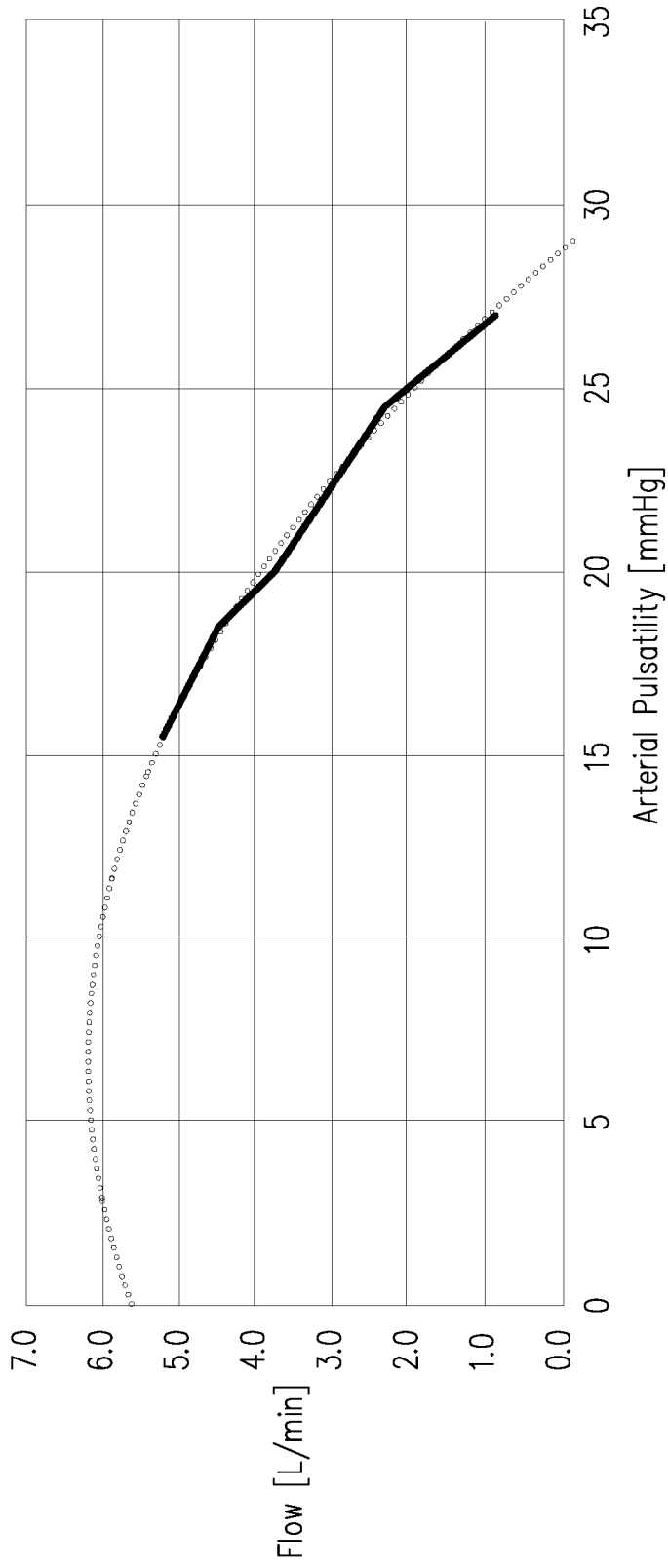
Figure 24C:
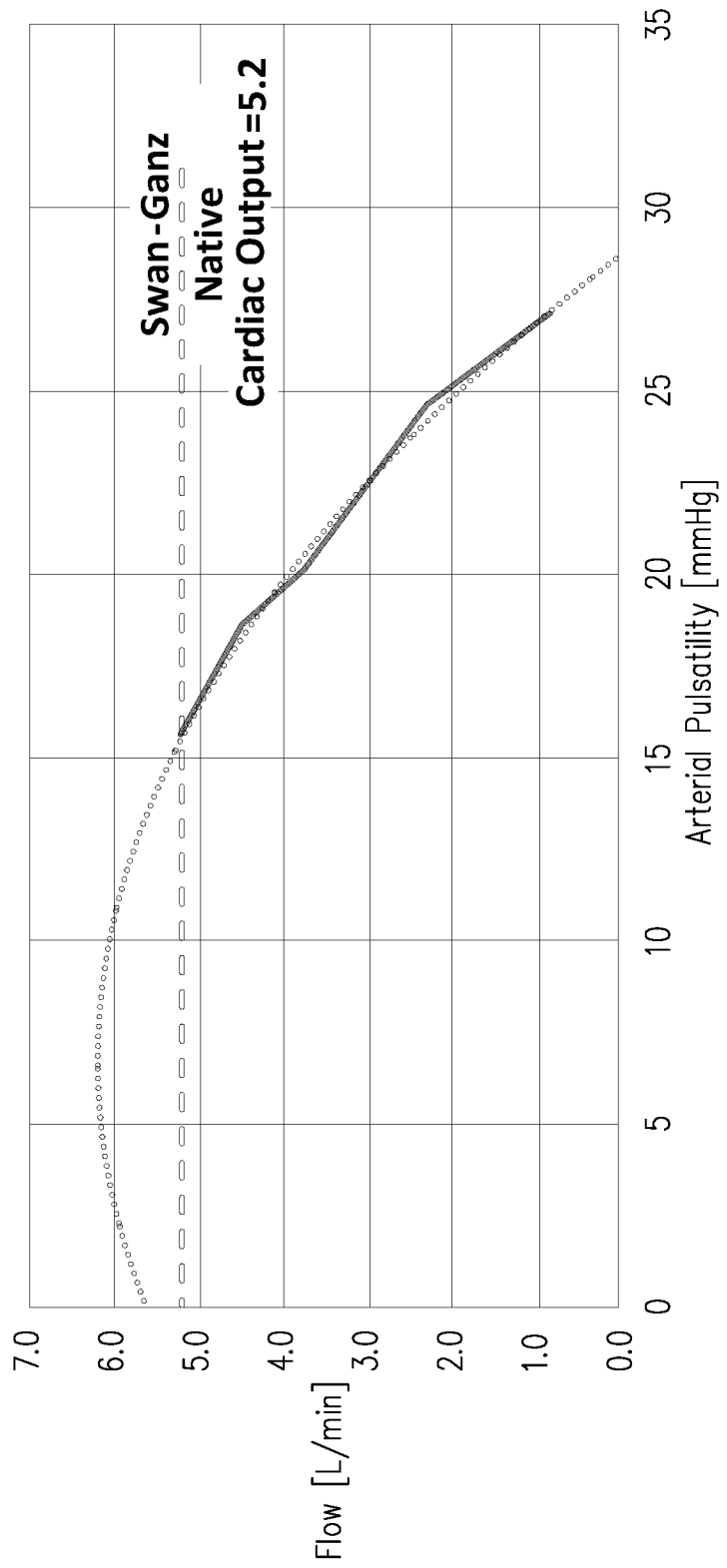

Reference is now made to FIGS. 24A, 24B, and 24C, which are graphs showing measurements performed during the use of a left-ventricular assist device, in accordance with some applications of the present invention. A left-ventricular assist device as described herein was deployed inside a pig heart. The pig's arterial pulsatility was measured using an intra-aortic pressure sensor, while the left-ventricular assist device was operated at respective rotation rates. Based upon in-vitro tests that had been performed upon the device, the device had been calibrated such that the flow generated by the device when the impeller rotates at respective rotation rates was known. FIG. 24A shows the plot of arterial pulsatility versus flow generated by the device, as measured in the experiment performed on the pig (and using the predetermined correspondence between impeller rotation rate and flow). The plot shown in FIG. 24A was then fitted to a curve, and the curve was extrapolated to the y-intercept (i.e., where arterial pulsatility is zero), as shown in FIG. 24B. As shown, the flow at an arterial pulsatility of zero was estimated to be 5.6 L/min, by extrapolation of the curve. On the same pig, a Swan-Ganz catheter was used to measure cardiac output when the left-ventricular assist device was not active. The Swan-Ganz catheter measured the pig's native cardiac output as 5.2 L/min, i.e., a similar value to the flow at an arterial pulsatility of zero as estimated by extrapolation of the flow/arterial-pulsatility curve. It is hypothesized, that, at an arterial pulsatility of zero, the left-ventricular device is largely replacing the native function of the heart and that the flow rate that is generated by the pump at this value provides a reasonable approximation of the subject's native cardiac output.

In accordance with the above-described experimental results, for some applications of the present invention, during operation of the ventricular assist device, the subject's arterial pulsatility is measured and a parameter is derived from the subject's arterial pulsatility. Typically, as the rotation rate of the impeller increases, the flow rate that is generated by the blood pump increases. Typically, flow that is generated by the blood pump is non-pulsatile, since the blood pump is a continuous-flow blood pump rather than a pulsatile blood pump. As such, it is typically the case that are the rotation rate of the impeller increases and the flow rate that is generated by the blood pump increases, the subject's arterial pulsatility decreases. For some applications, the subject's arterial pulsatility is measured as the rotation rate of the impeller changes. Based upon the aforementioned measurements, a relationship between the arterial pulsatility and the impeller rotation rate and/or the pump flow rate is derived. For some applications, based upon the aforementioned relationship, the subject's native cardiac output is derived. For some such applications, the relationship between the subject's arterial pulsatility and the pump flow rate is extrapolated to determine what the pump flow rate would be when the subject's arterial pulsatility reaches zero. In accordance with the above-described results, it is hypothesized that, at this value, the pump is replacing the native function of the heart and that the flow rate that is generated by the pump at this value provides an approximation of the subject's native cardiac output.

With regards to all aspects of ventricular assist device 20 described with reference to FIGS. 1A-24C, it is noted that, although FIGS. 1A and 1B show ventricular assist device 20 in the subject's left ventricle, for some applications, device 20 is placed inside the subject's right ventricle, such that the device traverses the subject's pulmonary valve, and techniques described herein are applied, *mutatis mutandis*. For some applications, components of device 20 are applicable to different types of blood pumps. For example, aspects of the present invention may be applicable to a pump that is used to pump blood from the vena cava and/or the right atrium into the right ventricle, from the vena cava and/or the right atrium into the pulmonary artery, and/or from the renal veins into the vena cava. Such aspects may include features of tube 24 (e.g., the curvature of the tube), impeller 50, features of pump portion 27, drive cable 130, etc. Alternatively or additionally, device 20 and/or a portion thereof (e.g., impeller 50, even in the absence of tube 24) is placed inside a different portion of the subject's body, in order to assist with the pumping of blood from that portion. For example, device 20 and/or a portion thereof (e.g., impeller 50, even in the absence of tube 24) may be placed in a blood vessel and may be used to pump blood through the blood vessel. For some applications, device 20 and/or a portion thereof (e.g., impeller 50, even in the absence of tube 24) is configured to be placed within the subclavian vein or jugular vein, at junctions of the vein with a lymph duct, and is used to increase flow of lymphatic fluid from the lymph duct into the vein, *mutatis mutandis*. Since the scope of the present invention includes using the apparatus and methods described herein in anatomical locations other than the left ventricle and the aorta, the ventricular assist device and/or portions thereof are sometimes referred to herein (in the specification and the claims) as a blood pump.

The scope of the present invention includes combining any of the apparatus and methods described herein with any of the apparatus and methods described in one or more of the following applications, all of which are incorporated herein by reference:

US 2020/0237981 to Tuval, entitled "Distal tip element for a ventricular assist device," filed Jan. 23, 2020, which claims priority from:

US Provisional Patent Application 62/796,138 to Tuval, entitled "Ventricular assist device," filed Jan. 24, 2019;

U.S. Provisional Patent Application 62/851,716 to Tuval, entitled "Ventricular assist device," filed May 23, 2019;

U.S. Provisional Patent Application 62/870,821 to Tuval, entitled "Ventricular assist device," filed Jul. 5, 2019; and U.S. Provisional Patent Application 62/896,026 to Tuval, entitled "Ventricular assist device," filed Sep. 5, 2019.

U.S. Pat. No. 10,881,770 to Tuval, which is a continuation of International Application No. PCT/IB2019/050186 to Tuval (published as WO 19/138350), entitled "Ventricular assist device, filed Jan. 10, 2019, which claims priority from:

U.S. Provisional Patent Application 62/615,538 to Sohn, entitled "Ventricular assist device," filed Jan. 10, 2018;

U.S. Provisional Patent Application 62/665,718 to Sohn, entitled "Ventricular assist device," filed May 2, 2018;

U.S. Provisional Patent Application 62/681,868 to Tuval, entitled "Ventricular assist device," filed Jun. 7, 2018; and U.S. Provisional Patent Application 62/727,605 to Tuval, entitled "Ventricular assist device," filed Sep. 6, 2018;

US 2019/0269840 to Tuval, which is the US national phase of International Patent Application PCT/IL2017/051273 to Tuval (published as WO 18/096531), filed Nov. 21, 2017, entitled "Blood pumps," which claims priority from U.S. Provisional Patent Application 62/425,814 to Tuval, filed Nov. 23, 2016;

US 2019/0175806 to Tuval, which is a continuation of International Application No. PCT/IL2017/051158 to Tuval (published as WO 18/078615), entitled "Ventricular assist device," filed Oct. 23, 2017, which claims priority from U.S. 62/412,631 to Tuval filed Oct. 25, 2016, and U.S. 62/543,540 to Tuval, filed Aug. 10, 2017;

US 2019/0239998 to Tuval, which is the US national phase of International Patent Application PCT/IL2017/051092 to Tuval (published as WO 18/061002), filed Sep. 28, 2017, entitled "Blood vessel tube," which claims priority from U.S. Provisional Patent Application 62/401,403 to Tuval, filed Sep. 29, 2016;

US 2018/0169313 to Schwammenthal, which is the US national phase of International Patent Application PCT/IL2016/050525 to Schwammenthal (published as WO 16/185473), filed May 18, 2016, entitled "Blood pump," which claims priority from U.S. Provisional Patent Application 62/162,881 to Schwammenthal, filed May 18, 2015, entitled "Blood pump;"

U.S. Pat. No. 10,583,231 to Schwammenthal, which is the US national phase of International Patent Application PCT/IL2015/050532 to Schwammenthal (published as WO IL2015/177793), filed May 19, 2015, entitled "Blood pump," which claims priority from US Provisional Patent Application 62/000,192 to Schwammenthal, filed May 19, 2014, entitled "Blood pump;"

US Patent U.S. Pat. No. 10,039,874 to Schwammenthal, which is the US national phase of International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. Pat. No. 9,764,113 to Tuval, issued Sep. 19, 2017, entitled "Curved catheter," which claims priority from U.S. Provisional Patent Application 61/914,470 to Tuval, filed Dec. 11, 2013, entitled "Curved catheter;" and U.S. Pat. No. 9,597,205 to Tuval, which is the US national phase of International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   manufacturing an impeller by:
      forming a structure having first and second bushings at proximal and distal ends of the structure, the first and second bushings being connected to one another by at least one elongate element;
      causing the at least one elongate element to radially expand and form at least one helical elongate element, at least partially by axially compressing the structure;
      coating the at least one helical elongate element with a coupling agent, the coupling agent configured to enhance bonding between the helical elongate element and an elastomeric layer;
      subsequently, coating the coupling-agent-coated helical elongate element with the elastomeric layer; and
      subsequently, coupling an elastomeric film to the at least one helical elongate element, such that the at least one helical elongate element with the elastomeric film coupled thereto defines a blade of the impeller.

2. The method according to claim 1, wherein coupling the elastomeric film to the at least one helical elongate element, such that the at least one helical elongate element with the elastomeric film coupled thereto defines a blade of the impeller comprises dipping the helical elongate element into an elastomeric material from which the elastomeric film is made.

3. The method according to claim 1, wherein the elastomeric film comprises an elastic material having an ultimate elongation of more than 300 percent.

4. The method according to claim 1, wherein the elastomeric film comprises an elastic material having a melt flow index of at least 4.

5. The method according to claim 1, wherein the elastomeric film comprises an elastic material having an ultimate tensile strength of more than 6000 psi.

6. The method according to claim 1, wherein coating the at least one helical elongate element with the coupling agent comprises coating the at least one helical elongate element with a silane compound containing a first functional group which is configured to bond with the helical elongate element, and a second functional group which is configured to bond with the elastomeric layer.

7. The method according to claim 1, wherein the elastomeric layer is made of a given elastomeric material and wherein the elastomeric film is made of the given elastomeric material.

8. The method according to claim 1, wherein the elastomeric layer is made of a first elastomeric material and wherein the elastomeric film is made of a second elastomeric material that is different from the first elastomeric material.

9. The method according to claim 1, wherein coating the coupling-agent-coated helical elongate element with the elastomeric layer comprises spraying an elastomer onto the coupling-agent-coated helical elongate element.

10. The method according to claim 1, wherein coating the coupling-agent-coated helical elongate element with the elastomeric layer comprises at least partially rounding the coupling-agent-coated helical elongate element.

11. The method according to claim 1, wherein coating the coupling-agent-coated helical elongate element with the elastomeric layer comprises coating the coupling-agent-coated helical elongate element with the elastomeric layer within a given time period of coating the at least one helical elongate element with the coupling agent.

12. The method according to claim 11, wherein coating the coupling-agent-coated helical elongate element with the elastomeric layer further comprises spraying additional elastomeric material onto the coupling-agent-coated helical elongate element subsequent to coating the coupling-agent-coated helical elongate element with the elastomeric layer within the given time period of coating the at least one helical elongate element with the coupling agent.

13. The method according to claim 1, wherein coating the at least one helical elongate element with the coupling agent comprises coating the at least one helical elongate element with a coupling agent containing a first functional group which is configured to bond with the helical elongate element, and a second functional group which is configured to bond with the elastomeric layer.

* * * * *